US007900635B2

(12) United States Patent
Gunaratnam et al.

(10) Patent No.: US 7,900,635 B2
(45) Date of Patent: Mar. 8, 2011

(54) NASAL ASSEMBLY

(75) Inventors: Michael K. Gunaratnam, Marsfield (AU); Philip R. Kwok, Chatswood (AU); Robin G. Hitchcock, Carlingford (AU); Lee J. Veliss, West Ryde (AU); Memduh Guney, Killara (AU); Richard Sokolov, Earlwood (AU); Perry D. Lithgow, Moruya (AU); Donald Darkin, Dural (AU); Susan R. Lynch, Epping (AU)

(73) Assignee: ResMed Limited, Bella Vista (AU)

( * ) Notice: Subject to any disclaimer, the term of this patent is extended or adjusted under 35 U.S.C. 154(b) by 262 days.

(21) Appl. No.: 12/314,298

(22) Filed: Dec. 8, 2008

(65) Prior Publication Data

US 2009/0095298 A1    Apr. 16, 2009

Related U.S. Application Data

(60) Continuation of application No. 11/603,107, filed on Nov. 22, 2006, now Pat. No. 7,461,656, which is a division of application No. 10/781,929, filed on Feb. 20, 2004, now Pat. No. 7,318,437.

(60) Provisional application No. 60/529,696, filed on Dec. 16, 2003, provisional application No. 60/494,119, filed on Aug. 12, 2003, provisional application No. 60/448,465, filed on Feb. 21, 2003, provisional application No. 60/482,872, filed on Jun. 27, 2003, provisional application No. 60/488,810, filed on Jul. 22, 2003.

(51) Int. Cl.
*A61M 11/00* (2006.01)

(52) U.S. Cl. ............................... 128/207.18; 128/206.24

(58) Field of Classification Search ............. 128/205.25, 128/206.21, 206.24, 206.26, 206.11, 206.12, 128/206.15, 206.27, 206.28, 207.11, 207.13, 128/207.18
See application file for complete search history.

(56) References Cited

U.S. PATENT DOCUMENTS

| 781,516 | A | 1/1905 | Guthrie, Jr. |
| 1,081,745 | A | 12/1913 | Johnston et al. |
| 1,084,596 | A | 1/1914 | Alexander |
| 1,192,186 | A | 7/1916 | Greene |
| 1,610,793 | A | 12/1926 | Kaufman |
| 1,632,449 | A | 6/1927 | McKesson |

(Continued)

FOREIGN PATENT DOCUMENTS

DE        956 195 C      1/1957

(Continued)

OTHER PUBLICATIONS

Decision of Rejection filed in related Japanese Appln. No. 2006-501369, mailed Feb. 2, 2010.

(Continued)

*Primary Examiner* — Steven O Douglas
(74) *Attorney, Agent, or Firm* — Nixon & Vanderhye P.C.

(57) ABSTRACT

A nasal assembly for delivering breathable gas to a patient includes a frame having an integrally formed first connector portion. A nozzle assembly includes a gusset or base portion and a pair of nozzles. At least one inlet conduit is structured to deliver breathable gas into the frame and nozzle assembly for breathing by the patient. A pair of second connector portions are removably and rotatably connected to respective first connector portions of the frame and are in communication with respective inlet conduits, e.g., directly or via angle connectors. A headgear assembly is removably connected to the pair of second connector portions and/or the angle connectors so as to maintain the frame and the nozzle assembly in a desired adjusted position on the patient's face.

45 Claims, 109 Drawing Sheets

U.S. PATENT DOCUMENTS

| | | | |
|---|---|---|---|
| 1,706,601 A | 3/1929 | Drager | |
| 2,016,210 A | 10/1935 | Mann | |
| 2,259,817 A | 10/1941 | Hawkins | |
| 2,353,643 A | 7/1944 | Bulbulian | |
| 2,783,474 A | 3/1957 | Campagna | |
| 2,837,090 A | 6/1958 | Bloom et al. | |
| 2,868,199 A | 1/1959 | Hudson | |
| 2,931,356 A | 4/1960 | Schwarz | |
| 3,056,402 A | 10/1962 | Dickinson | |
| 3,234,940 A | 2/1966 | Morton, Jr. | |
| 3,513,844 A | 5/1970 | Smith | |
| 3,643,660 A | 2/1972 | Hudson et al. | |
| 3,682,171 A | 8/1972 | Dali et al. | |
| 3,752,157 A | 8/1973 | Malmin | |
| 3,792,702 A | 2/1974 | Delest | |
| 3,990,727 A | 11/1976 | Gallagher | |
| 4,018,221 A | 4/1977 | Rennie | |
| 4,156,426 A | 5/1979 | Gold | |
| 4,274,406 A | 6/1981 | Bartholomew | |
| 4,414,973 A | 11/1983 | Matheson et al. | |
| 4,454,880 A | 6/1984 | Muto et al. | |
| 4,535,767 A | 8/1985 | Tiep et al. | |
| 4,593,688 A | 6/1986 | Payton | |
| 4,665,566 A | 5/1987 | Garrow | |
| 4,744,358 A | 5/1988 | McGinnis | |
| 4,774,940 A | 10/1988 | Linder | |
| 4,774,946 A | 10/1988 | Ackerman | |
| 4,782,832 A | 11/1988 | Trimble et al. | |
| 4,821,736 A | 4/1989 | Watson | |
| 4,910,804 A | 3/1990 | Lidgren | |
| 4,915,105 A | 4/1990 | Lee | |
| 4,919,128 A | 4/1990 | Kopala et al. | |
| 4,944,310 A | 7/1990 | Sullivan | |
| 4,960,121 A | 10/1990 | Nelson | |
| 5,069,205 A | 12/1991 | Urso | |
| 5,069,222 A | 12/1991 | McDonald, Jr. | |
| 5,113,857 A | 5/1992 | Dickerman et al. | |
| 5,243,971 A | 9/1993 | Sullivan et al. | |
| 5,245,995 A | 9/1993 | Sullivan et al. | |
| 5,269,296 A | 12/1993 | Landis | |
| 5,311,862 A | 5/1994 | Blasdell et al. | |
| 5,349,949 A | 9/1994 | Schegerin | |
| 5,441,046 A | 8/1995 | Starr et al. | |
| 5,458,139 A | 10/1995 | Pearl | |
| 5,481,763 A | 1/1996 | Brostrom et al. | |
| 5,533,506 A | 7/1996 | Wood | |
| 5,535,739 A | 7/1996 | Rapoport et al. | |
| 5,570,689 A | 11/1996 | Starr et al. | |
| 5,657,752 A | 8/1997 | Landis et al. | |
| 5,687,715 A | 11/1997 | Landis et al. | |
| 5,697,363 A | 12/1997 | Hart | |
| 5,704,345 A | 1/1998 | Berthon-Jones | |
| 5,709,204 A | 1/1998 | Lester | |
| 5,724,965 A | 3/1998 | Handke et al. | |
| 5,884,624 A | 3/1999 | Barnett et al. | |
| 5,921,239 A | 7/1999 | McCall et al. | |
| 5,979,133 A | 11/1999 | Funkhouser | |
| 6,012,455 A | 1/2000 | Goldstein | |
| 6,019,101 A | 2/2000 | Cotner et al. | |
| 6,112,746 A | 9/2000 | Kwok et al. | |
| 6,119,689 A | 9/2000 | Korman | |
| 6,119,693 A | 9/2000 | Kwok et al. | |
| 6,119,694 A | 9/2000 | Correa et al. | |
| 6,192,886 B1 | 2/2001 | Rudolph | |
| 6,196,223 B1 | 3/2001 | Belfer et al. | |
| 6,269,814 B1 | 8/2001 | Blaszczykiewicz et al. | |
| 6,332,465 B1 | 12/2001 | Xue et al. | |
| 6,338,342 B1 | 1/2002 | Fecteau et al. | |
| 6,347,631 B1 | 2/2002 | Hansen et al. | |
| 6,357,441 B1 | 3/2002 | Kwok et al. | |
| 6,374,826 B1 | 4/2002 | Gunaratnam et al. | |
| 6,412,487 B1 | 7/2002 | Gunaratnam et al. | |
| 6,422,238 B1 | 7/2002 | Lithgow | |
| 6,431,172 B1 | 8/2002 | Bordewick | |
| 6,439,230 B1 | 8/2002 | Gunaratnam et al. | |
| 6,467,483 B1 | 10/2002 | Kopacko et al. | |
| 6,470,886 B1 | 10/2002 | Jestrabek-Hart | |
| 6,478,026 B1 | 11/2002 | Wood | |
| 6,490,737 B1 | 12/2002 | Mazzei et al. | |
| 6,491,034 B1 | 12/2002 | Gunaratnam et al. | |
| 6,494,207 B1 | 12/2002 | Kwok | |
| 6,513,526 B2 | 2/2003 | Kwok et al. | |
| 6,516,802 B2 | 2/2003 | Hansen et al. | |
| 6,532,961 B1 | 3/2003 | Kwok et al. | |
| 6,550,070 B2 | 4/2003 | Weigand | |
| 6,561,190 B1 | 5/2003 | Kwok | |
| 6,565,461 B1 | 5/2003 | Zatlin | |
| 6,595,215 B2 | 7/2003 | Wood | |
| 6,610,032 B1 | 8/2003 | Prody | |
| 6,619,288 B2 | 9/2003 | Demers et al. | |
| 6,637,434 B2 | 10/2003 | Noble | |
| 6,637,436 B2 | 10/2003 | Farrell | |
| 6,679,265 B2 | 1/2004 | Strickland et al. | |
| D486,907 S | 2/2004 | Guney et al. | |
| 6,691,314 B1 | 2/2004 | Grilliot et al. | |
| 6,691,707 B1 | 2/2004 | Gunaratnam et al. | |
| 6,776,162 B2 | 8/2004 | Wood | |
| 6,796,308 B2 | 9/2004 | Gunaratnam et al. | |
| 6,807,967 B2 | 10/2004 | Wood | |
| 6,860,268 B2 | 3/2005 | Bohn et al. | |
| 6,907,882 B2 | 6/2005 | Ging et al. | |
| 6,997,187 B2 | 2/2006 | Wood et al. | |
| 7,000,613 B2 | 2/2006 | Wood et al. | |
| 7,047,972 B2 | 5/2006 | Ging et al. | |
| 7,047,974 B2 | 5/2006 | Strickland et al. | |
| 7,152,599 B2 | 12/2006 | Thomas | |
| 7,156,097 B2 | 1/2007 | Cardoso | |
| 7,210,481 B1 | 5/2007 | Lovell et al. | |
| 7,318,437 B2 | 1/2008 | Gunaratnam et al. | |
| 7,461,656 B2 | 12/2008 | Gunaratnam et al. | |
| 2001/0020474 A1 | 9/2001 | Hecker et al. | |
| 2001/0032648 A1 | 10/2001 | Jestrabek-Hart | |
| 2002/0023649 A1 | 2/2002 | Gunaratnam et al. | |
| 2002/0023650 A1 | 2/2002 | Gunaratnam et al. | |
| 2002/0144684 A1 | 10/2002 | Moone | |
| 2003/0005931 A1 | 1/2003 | Jaffre et al. | |
| 2003/0172936 A1 | 9/2003 | Wilkie et al. | |
| 2003/0196656 A1 | 10/2003 | Moore et al. | |
| 2003/0196657 A1 | 10/2003 | Ging et al. | |
| 2003/0196658 A1 | 10/2003 | Ging et al. | |
| 2003/0196662 A1 | 10/2003 | Ging et al. | |
| 2004/0025882 A1 | 2/2004 | Madaus et al. | |
| 2004/0045551 A1 | 3/2004 | Eaton et al. | |
| 2004/0065330 A1 | 4/2004 | Landis | |
| 2004/0067333 A1 | 4/2004 | Amarasinghe | |
| 2004/0182397 A1 | 9/2004 | Wood | |
| 2004/0226566 A1 | 11/2004 | Gunaratnam et al. | |
| 2005/0028821 A1 | 2/2005 | Wood et al. | |
| 2005/0028822 A1 | 2/2005 | Sleeper et al. | |
| 2005/0076913 A1 | 4/2005 | Ho et al. | |
| 2005/0155604 A1 | 7/2005 | Ging et al. | |
| 2005/0241644 A1 | 11/2005 | Gunaratnam et al. | |
| 2006/0081250 A1 | 4/2006 | Bordewick et al. | |
| 2006/0137690 A1 | 6/2006 | Gunaratnam et al. | |
| 2006/0150982 A1 | 7/2006 | Wood | |
| 2006/0162729 A1 | 7/2006 | Ging et al. | |
| 2006/0272645 A1 | 12/2006 | Ging et al. | |
| 2007/0062539 A1 | 3/2007 | Gunaratnam et al. | |
| 2007/0119458 A1 | 5/2007 | Ging et al. | |

FOREIGN PATENT DOCUMENTS

| | | |
|---|---|---|
| DE | 17 08 110 A1 | 4/1971 |
| DE | 19625337 | 1/1998 |

| | | |
|---|---|---|
| DE | 29923126 | 5/1999 |
| DE | 199 62 515 | 7/2001 |
| DE | 10035946 | 2/2002 |
| EP | 0658356 A2 | 6/1995 |
| EP | 0821978 A2 | 2/1998 |
| EP | 0958841 | 11/1999 |
| EP | 1027905 | 8/2000 |
| EP | 1099452 | 5/2001 |
| EP | 1118346 | 7/2001 |
| EP | 1258266 | 11/2002 |
| EP | 1314446 | 5/2003 |
| EP | 1334742 | 8/2003 |
| FR | 2618340 | 1/1989 |
| FR | 2720280 | 12/1995 |
| FR | 2735030 | 12/1996 |
| GB | 792 377 A | 3/1958 |
| GB | 799225 | 8/1958 |
| GB | 880942 | 10/1961 |
| GB | 2264646 | 9/1993 |
| GB | 2379886 | 3/2003 |
| WO | WO 84/01293 A1 | 4/1984 |
| WO | WO 87/01950 | 4/1987 |
| WO | WO 98/04310 | 2/1998 |
| WO | WO 98/12965 | 4/1998 |
| WO | WO 98/24499 | 6/1998 |
| WO | WO 99/04842 A1 | 2/1999 |
| WO | WO 99/06116 A | 2/1999 |
| WO | WO 99/61088 | 12/1999 |
| WO | WO 00/13751 | 3/2000 |
| WO | WO 00/69521 | 11/2000 |
| WO | WO 00/74758 | 12/2000 |
| WO | WO 00/78381 | 12/2000 |
| WO | WO 00/78383 | 12/2000 |
| WO | WO 00/78384 | 12/2000 |
| WO | WO 01/32250 | 5/2001 |
| WO | WO 01/62326 | 8/2001 |
| WO | WO 01/89381 | 11/2001 |
| WO | WO 01/97892 A1 | 12/2001 |
| WO | WO 02/07806 | 1/2002 |
| WO | WO 02/11804 | 2/2002 |
| WO | WO 02/47749 | 6/2002 |
| WO | WO 03/082406 | 10/2003 |
| WO | WO 03/090827 | 11/2003 |
| WO | WO 2004/041341 | 5/2004 |
| WO | WO 2004/073777 | 9/2004 |
| WO | WO 2004/073778 | 9/2004 |
| WO | WO 2005/014080 | 2/2005 |
| WO | WO 2005/016402 | 2/2005 |
| WO | WO 2005/016407 | 2/2005 |
| WO | WO 2005/018523 | 3/2005 |
| WO | WO 2005/063328 | 7/2005 |
| WO | WO 2005/079726 | 9/2005 |
| WO | WO 2005/097247 | 10/2005 |
| WO | WO 2006/044118 | 4/2006 |
| WO | WO 2006/044120 | 4/2006 |
| WO | WO 2006/096924 | 9/2006 |
| WO | WO 2006/130903 | 12/2006 |

OTHER PUBLICATIONS

Ging et al., U.S. Appl. No. 11/698,066, filed Jan. 26, 2007.
Gunaratnam et al., U.S. Appl. No. 11/967,346, filed Dec. 31, 2007.
Gunaratnam et al., U.S. Appl. No. 11/969,235, filed Jan. 4, 2008.
Gunaratnam et al., U.S. Appl. No. 11/960,040, filed Dec. 19, 2007.
Gunaratnam et al., U.S. Appl. No. 11/962,621, filed Dec. 21, 2007.
Gunaratnam et al., U.S. Appl. No. 11/964,783, filed Dec. 27, 2007.
Ging et al., U.S. Appl. No. 11/795,606, filed Jul. 19, 2007.
Ging et al., U.S. Appl. No. 12/010,475, filed Jan. 25, 2008.
Brochure for Adam® CPAP Circuits, Airway Delivery and Management, Puritan Bennett, Apr. 1993, 1 page.
Brochure for ComfortLite™ Nasal Mask, Part Number and Order Guide, Respironics®, Feb. 2004, 2 pages.
Specification Sheet for Infinity™ 481 Direct Nasal Mask, Fisher & Paykel Healthcare, 2004, 2 pages.
Specification Sheet for Opus Nasal Pillows Mask, Fisher & Paykel Healthcare, 2007, 2 pages.
Gunaratnam et al, U.S. Appl. No. 11/960,784, filed Dec. 20, 2007.
Gunaratnam et al., U.S. Appl. No. 10/546,305, filed Feb. 20, 2004.
U.S. Appl. No. 60/424,694, filed Nov. 8, 2002, Amarasinghe et al.
U.S. Appl. No. 60/488,810, filed Jul. 22, 2003, Gunaratnam et al.
U.S. Appl. No. 60/492,282, filed Aug. 5, 2003, Wood.
U.S. Appl. No. 60/493,325, filed Aug. 8, 2003, Wood.
U.S. Appl. No. 60/494,119, filed Aug. 12, 2003, Gunaratnam et al.
U.S. Appl. No. 60/496,059, filed Aug. 18, 2003, Ho.
U.S. Appl. No. 60/501,028, filed Sep. 9, 2003, Wood.
U.S. Appl. No. 60/529,696, filed Dec. 16, 2003, Lithgow et al.
U.S. Appl. No. 60/533,214, filed Dec. 31, 2003, Drew.
U.S. Appl. No. 60/560,610, filed Apr. 9, 2004, Gunaratnam.
U.S. Appl. No. 60/619,426, filed Oct. 15, 2004, Bordewick.
U.S. Appl. No. 60/632,193, filed Jun. 6, 2005, Lubke et al.
U.S. Appl. No. 60/687,453, filed Jun. 6, 2005, Lubke et al.
U.S. Appl. No. 60/702,581, filed Jul. 27, 2005, Lubke et al.
U.S. Appl. No. 60/795,562, filed Apr. 28, 2006, Lubke et al.

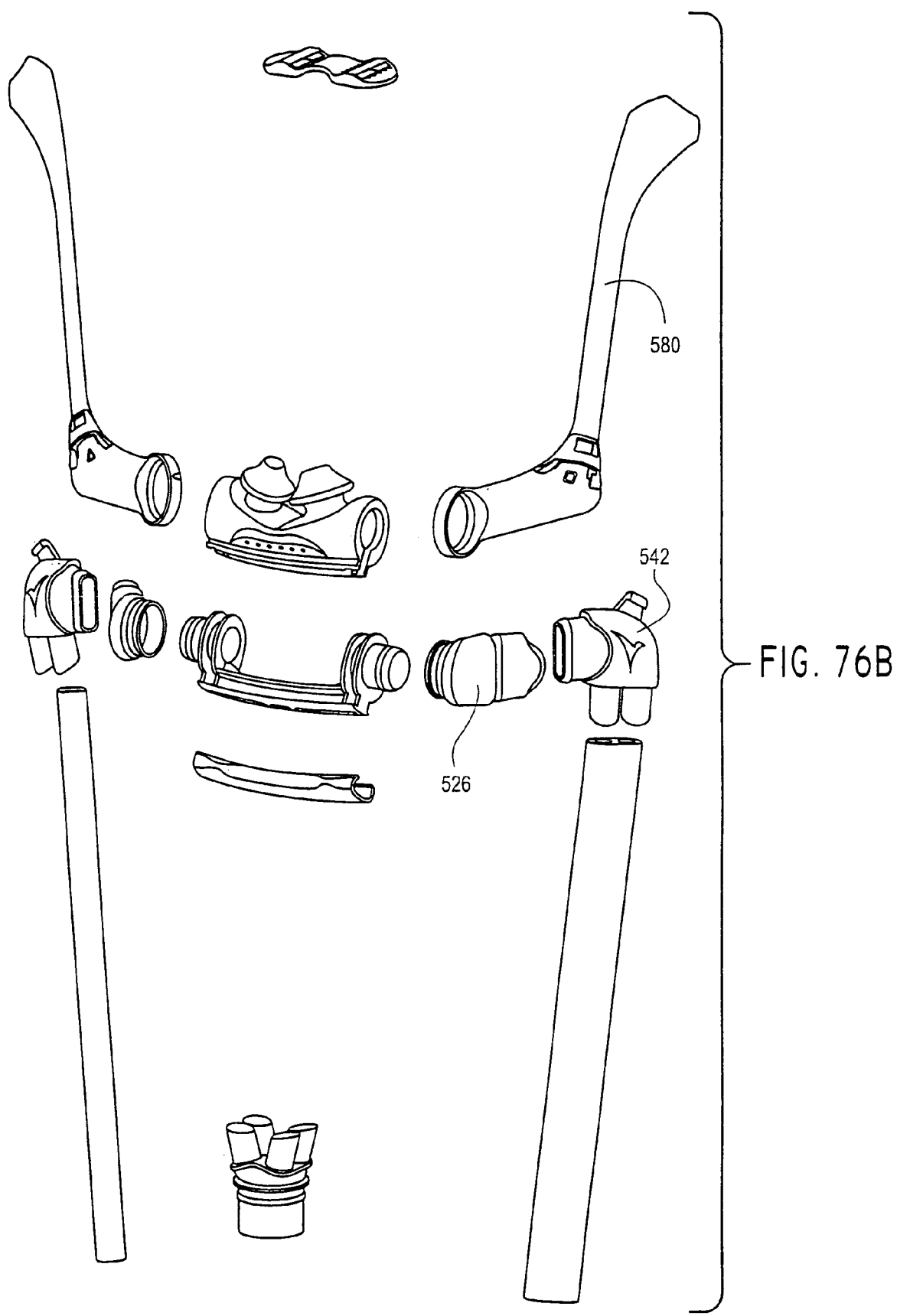

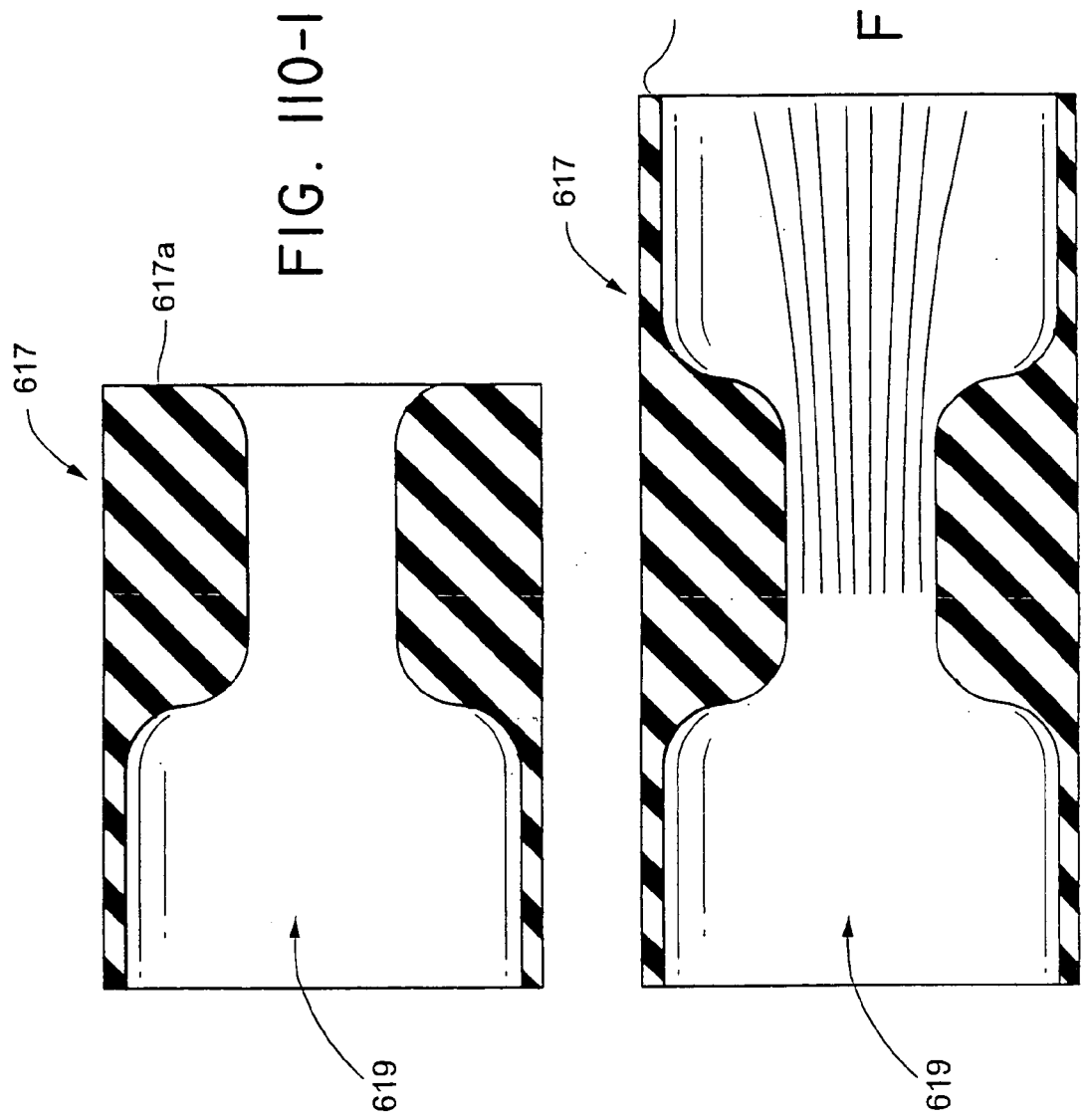

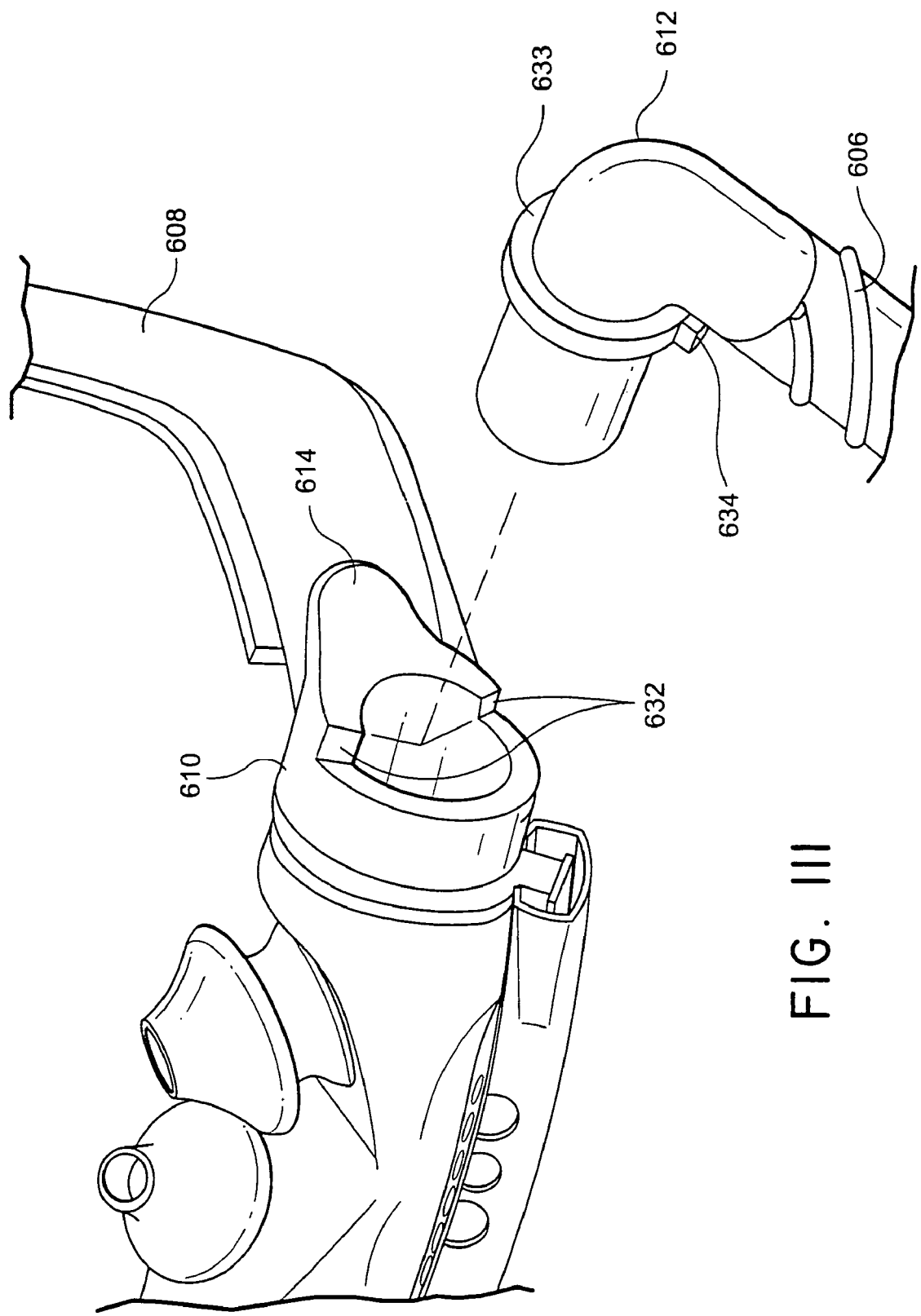
FIG. III

NASAL ASSEMBLY

CROSS-REFERENCE TO PRIORITY APPLICATIONS

This application is a continuation of U.S. application Ser. No. 11/603,107, filed Nov. 22, 2006, now U.S. Pat. No. 7,461, 656, which is a divisional of U.S. application Ser. No. 10/781, 929, filed Feb. 20, 2004, now U.S. Pat. No. 7,318,437, which claims the benefit of U.S. provisional applications Nos. 60/529,696, filed Dec. 16, 2003, 60/494,119, filed Aug. 12, 2003, 60/448,465, filed Feb. 21, 2003, 60/482,872, filed Jun. 27, 2003, and 60/488,810, filed Jul. 22, 2003, each of which is incorporated herein in its entirety.

FIELD OF THE INVENTION

The present invention relates to a nasal assembly used for treatment, e.g., of Sleep Disordered Breathing (SDB) with Continuous Positive Airway Pressure (CPAP) or Non-invasive Positive Pressure Ventilation (NPPV).

BACKGROUND OF THE INVENTION

Some nasal assemblies used in the treatment of SDB are designed for insertion into the nasal passages of the patient. Air or other breathable gas is supplied by a blower and passed along a flexible conduit to the nasal assembly.

The nasal assembly generally includes a relatively rigid shell, e.g., a frame, and a pair of nozzles (which may be in the form of nasal pillows, nasal prongs, cannula, or nasal puffs) that are mounted on the rigid shell and structured to be inserted into the nasal passages of the patient. The nozzles are usually held in place using a headgear assembly, the relatively rigid shell and headgear assembly being joined using some form of connector.

One form of known nasal assembly is described in U.S. Pat. No. 4,782,832 (Trimble et al.). Trimble discloses a nasal puff assembly 20 that includes a nasal puff 22 adapted to be worn adjacent the nose of a patient, together with a harness assembly 24 adapted to be worn over the head of the patient. The harness assembly 24 is designed to operatively hold puff 22 adjacent and partially within the nasal passages of the patient.

The puff 22 is in the form of a generally Y-shaped rigid hollow plenum chamber 28 together with a pair of laterally spaced apart nares elements 30. Adjustability of the nares elements 30 may be provided by rotatably mounting the elements 30 to the plenum chamber 28 and mounting the elements 30 in slots permitting selective lateral positioning of the elements 30 with respect to each other. Also, the harness assembly 24 may be adjusted to adjust the fit and seal of the nares elements 30 during use. That is, the force required to maintain a sufficient seal is directly associated with the force required to maintain a desired fit. Thus, adjustment of the fit or stability of the nasal assembly directly affects the seal, which can adversely affect patient comfort.

Other examples of nasal pillows or cannula mounted to rigid shells are disclosed in U.S. Pat. Nos. 5,724,965 and 6,431,172.

A nasal mask assembly manufactured by Viasys, i.e., Spiritus, includes a plenum chamber with a pair of adjacent or laterally spaced nares elements. A harness assembly is engaged with the plenum chamber to adjust the fit and seal of the nares elements during use. Similar to Trimble, adjustment of the fit or stability of the nasal assembly directly affects the seal, which can adversely affect patient comfort.

A nasal mask assembly manufactured by InnoMed, i.e., NasalAire, includes a plenum chamber with a pair of adjacent or laterally spaced nares elements. The nares elements are structured to engage within the mucosal surfaces or internal passages of the patient's nose to maintain the nasal mask assembly on the patient's face and to provide a seal. See, e.g., U.S. Pat. No. 5,533,506.

A nasal mask assembly manufactured by Stevenson Industries (see U.S. Pat. No. 6,012,455), i.e., CPAP-Pro, includes a dental anchor, a platform, and air supply tubes having nasal pads, wherein the platform supports the air supply tubes. The dental anchor is sized to be engaged between the teeth in the patient's mouth so as to retain the assembly in place.

PCT Application Publication No. WO 00/13751 discloses a device that includes gas delivery elements positioned into engagement with the patient's nose by a mouthpiece fitted to the patient's teeth.

A common problem with known nasal assemblies, such as those discussed above, is patient comfort. For example, the prongs tend to irritate the patient's nose due to the tension applied by the headgear assembly that pulls the rigid shell and prongs towards the patient's nose.

Another problem is achievement of a sealing fit with the patient's nasal passages without sacrificing patient comfort.

Another problem is irritation of the inside of the patient's nostrils caused by contact with the prongs, e.g., an edge thereof.

Another problem is irritation of the inside of the patient's nostrils caused by air jetting (air flow irritation) from the prongs.

Another problem is adjustment of the nasal assemblies relative to the nose and/or head of the patient so as to accommodate various shapes and angles of patient's noses.

Still another problem is the direct association between sealing and stability forces that can affect patient comfort.

SUMMARY OF THE INVENTION

One aspect of the invention is directed towards a nasal assembly that provides more comfort to the patient.

Another aspect of the invention is directed towards a nasal assembly that provides an effective seal with the patient's nasal passages. Preferably, the nasal assembly is a nozzle assembly including nozzles which comfortably come into contact with the external rim of the nares and avoid the sensitive internal passages (e.g., mucosal surfaces or internal passages) of the nasal passage.

Still another aspect of the invention is directed towards a nasal assembly that does not rely on tension from the headgear assembly to provide an effective seal between the nozzles and the patient's nasal passages.

Still another aspect of the invention is directed towards a nasal assembly that is unobtrusive.

Still another aspect of the invention is directed towards a nasal assembly that is easy to use.

Still another aspect of the invention is directed towards a nasal assembly that maintains a headgear adjustment setting.

Still another aspect of the invention is directed towards a nasal assembly that helps decouple sealing and stability forces. Specifically, one aspect of the invention is directed towards a nasal assembly that is structured such that the stability forces that act to maintain the nasal assembly on the patient's face are separated or at least better distinguished from the sealing forces that act to maintain a seal between the nasal assembly and the patient's face.

Yet another aspect of the invention is directed towards a nasal assembly that provides a greater range of movement for nozzles of the nasal assembly.

Another aspect of the invention provides a nasal assembly for delivering breathable gas to a patient. The nasal assembly includes a frame having a main body and a side frame member provided on each lateral side of the main body, each side frame member including an integrally formed first connector portion. A nozzle assembly includes a gusset or base portion and a pair of nozzles. The nozzle assembly is coupled with the main body of the frame with the pair of nozzles structured to sealingly engage with nasal passages of a patient's nose in use. A pair of inlet conduits are structured to deliver breathable gas into the frame and nozzle assembly for breathing by the patient. A pair of second connector portions are removably and rotatably connected to respective first connector portions of the frame. The second connector portions are in communication with the inlet conduits via angle connectors. A headgear assembly is removably connected to at least one of the second connector portions and the angle connectors so as to maintain the frame and the nozzle assembly in a desired adjusted position on the patient's face.

Other aspects, features and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 38B is a perspective view illustrating an inlet conduit and an inlet conduit and headgear connector of the nasal assembly shown in FIG. 38;

FIG. 76B is an exploded view of FIG. 76A;

FIG. 106 is a front perspective view illustrating the nasal assembly shown in FIG. 98 engaged with nasal passages of the patient;

FIG. 107 is a perspective view of another embodiment of a nasal assembly mounted to a patient's head;

FIG. 107-1 is a perspective view of yet another embodiment of the present invention;

FIG. 107-2 is a perspective view of yet another embodiment of the present invention;

FIGS. 107A-107C illustrate yet another alternative embodiment of the present invention;

FIGS. 107D and 107E illustrate still another embodiment according to the present invention;

FIG. 107F illustrates another alternative embodiment of the present invention;

FIGS. 107G and 107H illustrate another alternative embodiment of the present invention;

FIG. 107I illustrates still another embodiment of the present invention;

FIG. 107J illustrates yet another alternative embodiment of the present invention;

FIGS. 107K and 107L illustrate yet another embodiment of the present invention;

FIGS. 107M-107Q illustrate cross-sections of alternative nozzles according to the present invention;

Figure 1:
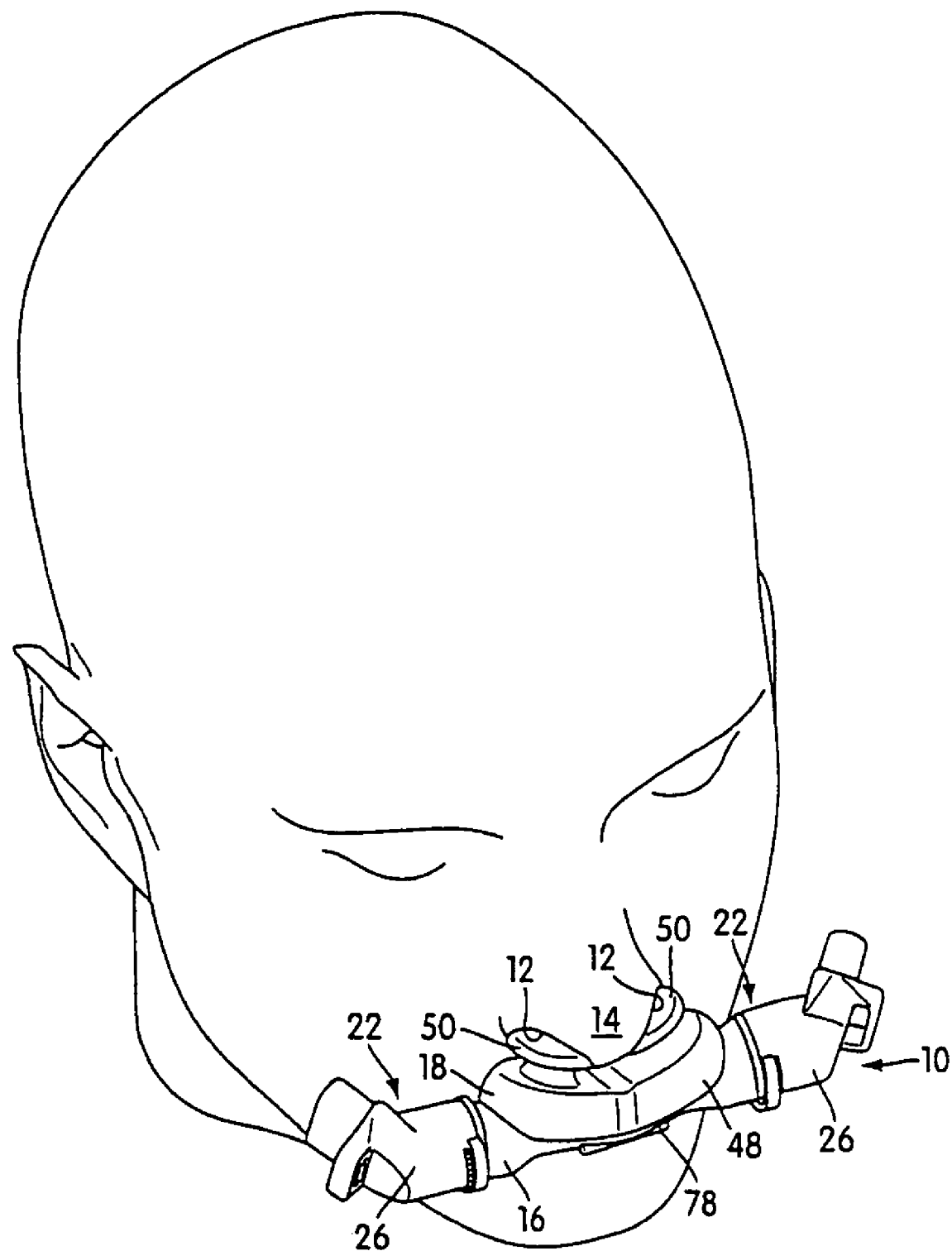
FIG. 1 is a perspective view illustrating a partial nasal assembly constructed in accordance with an embodiment of the invention mounted to a patient's head and engaged with nasal passages of the patient.
Figure 2:
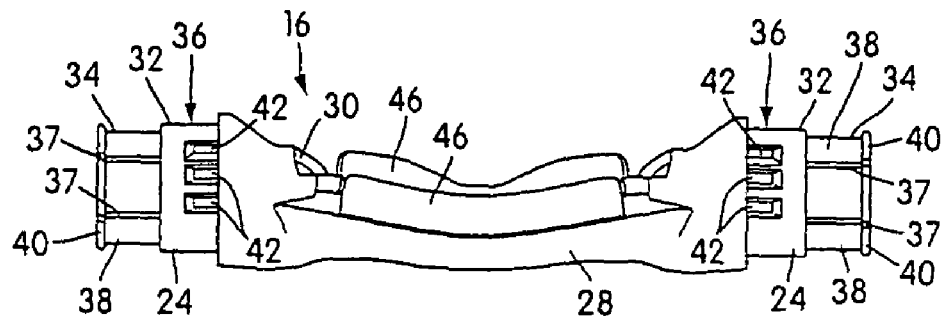
FIG. 2 is a front view of a frame of the nasal assembly shown in FIG. 1 with some parts removed for clarity.
Figure 107:
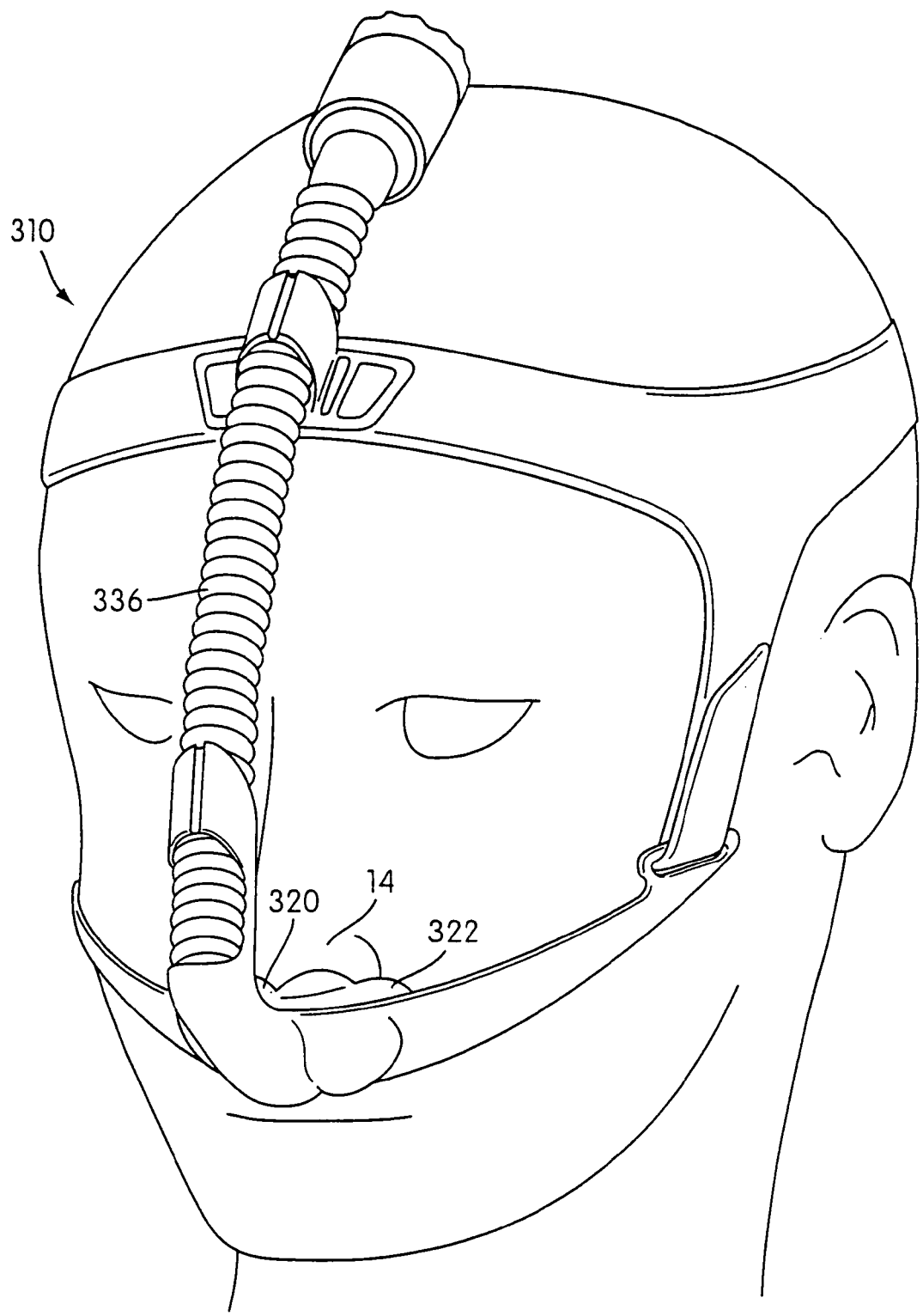
Figures 1, 107:
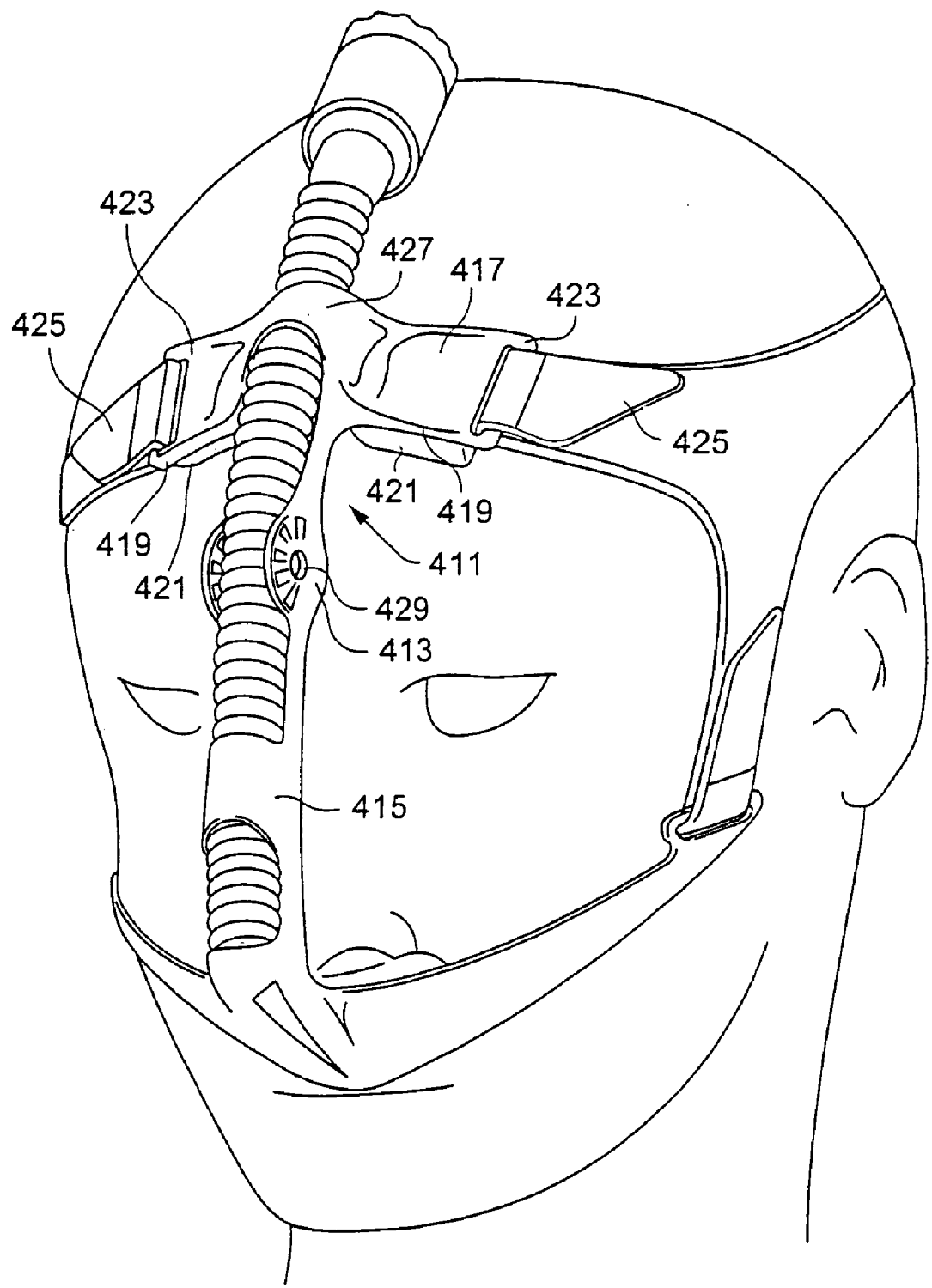
Figures 2, 107:
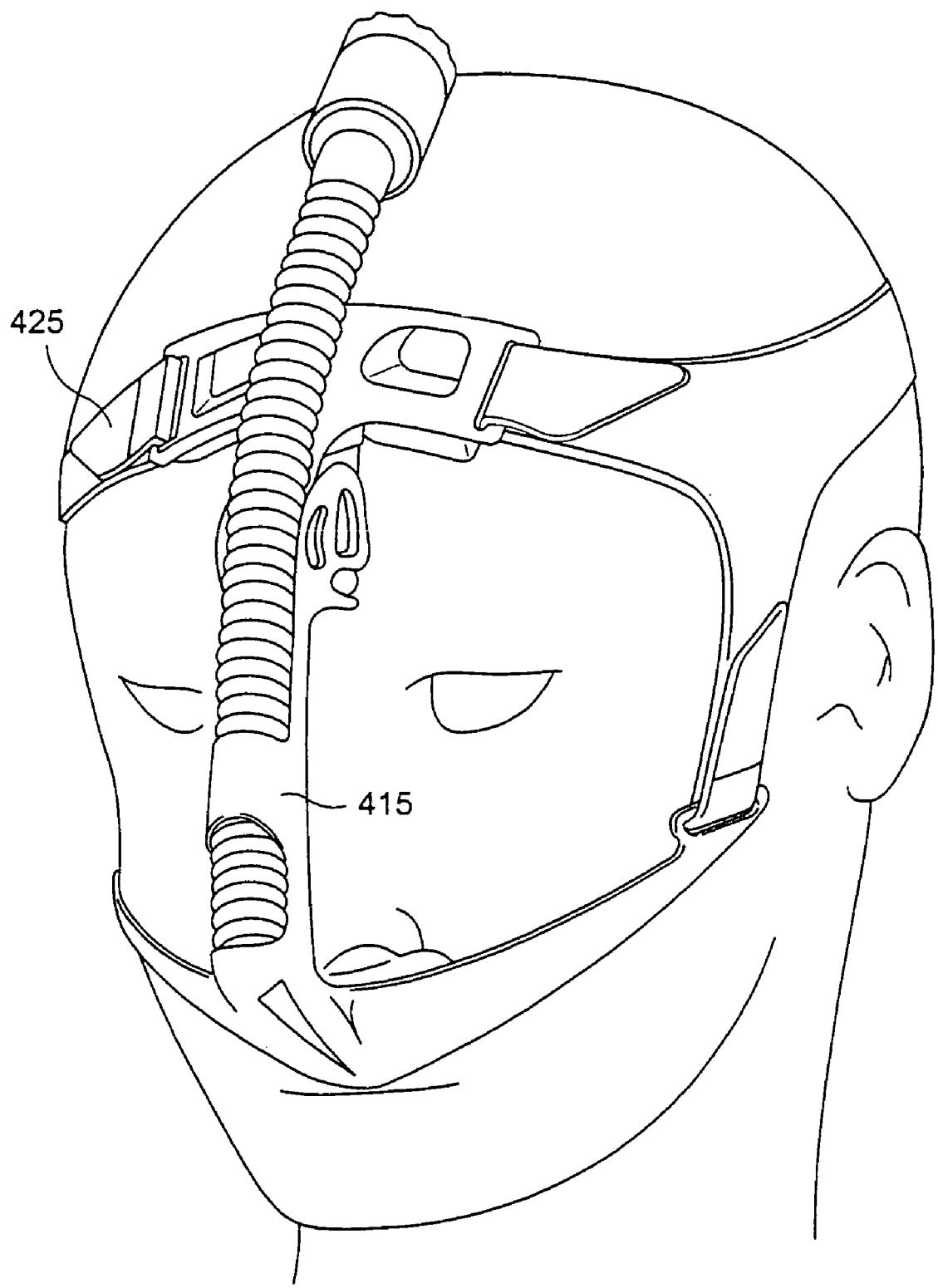
Figure 107A:
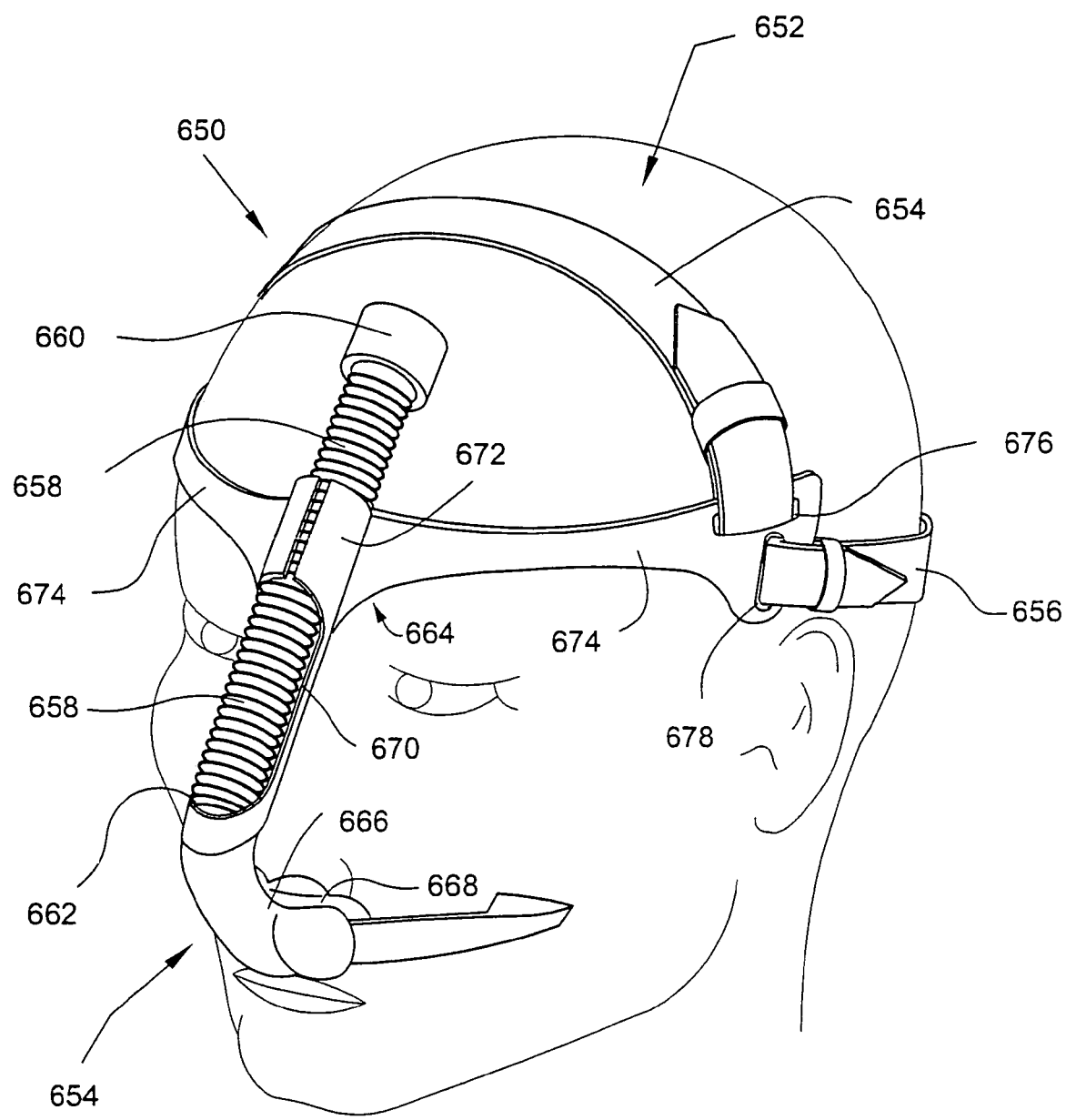
Figure 107B:
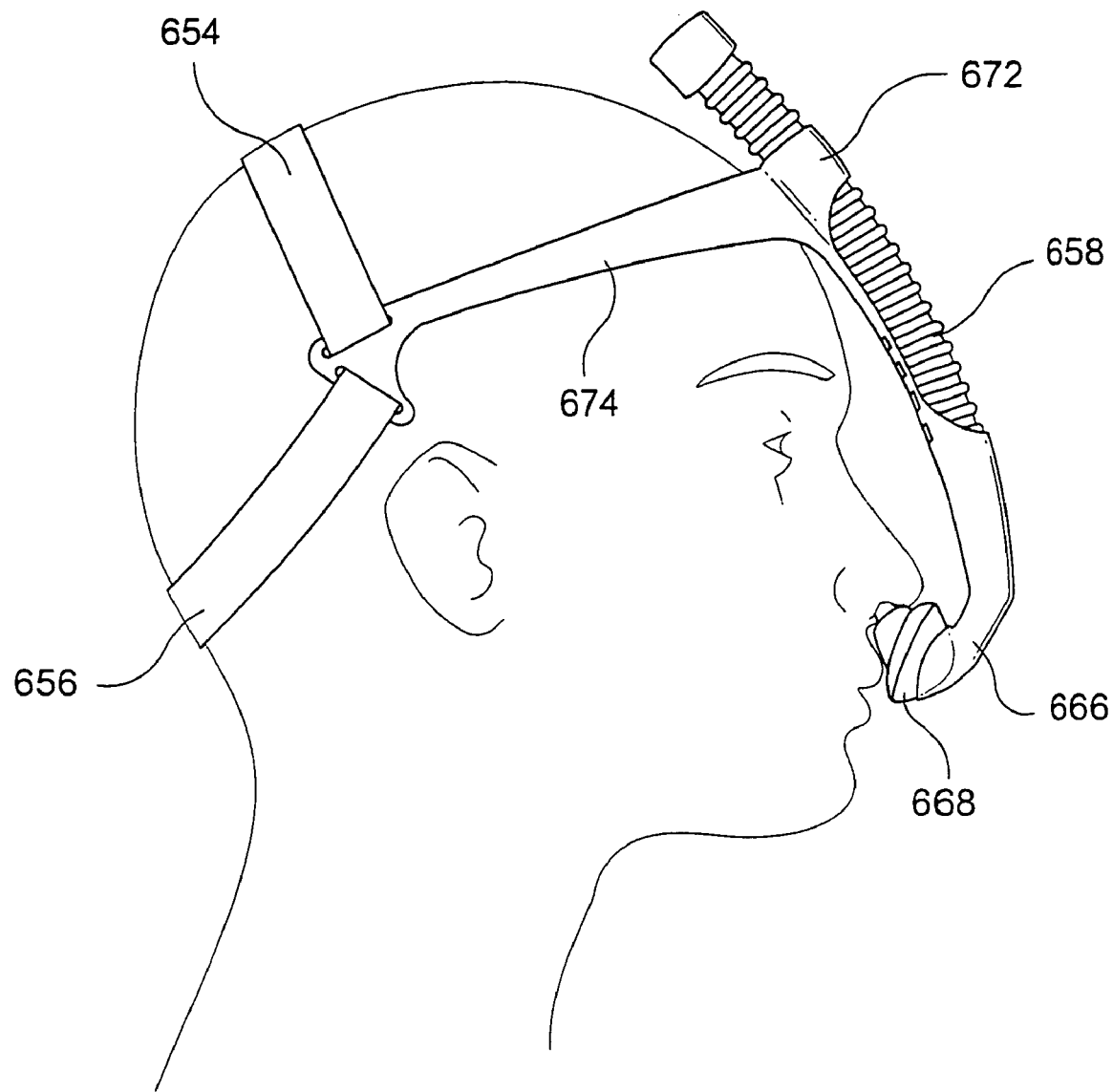
Figure 107C:
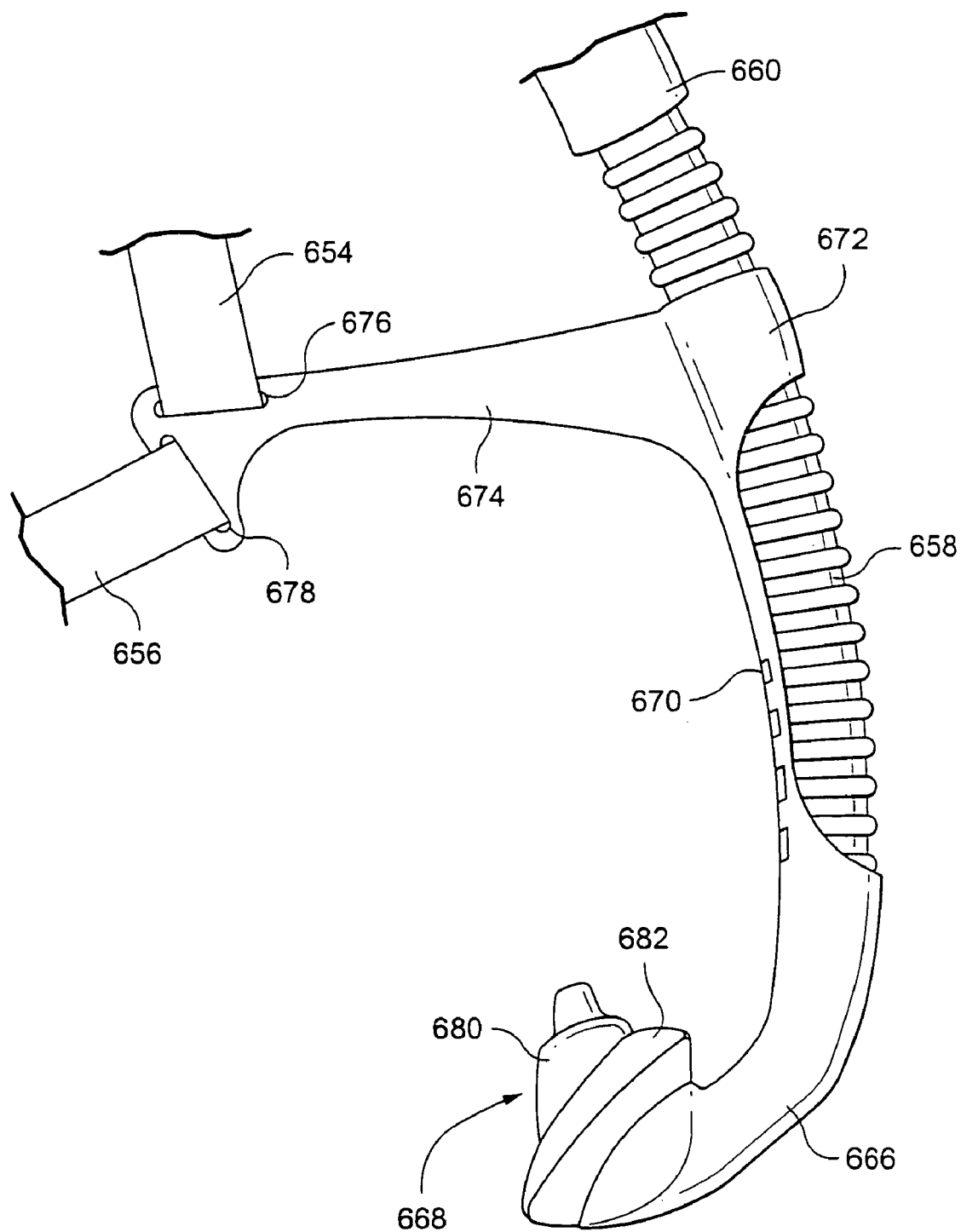
Figure 107D:
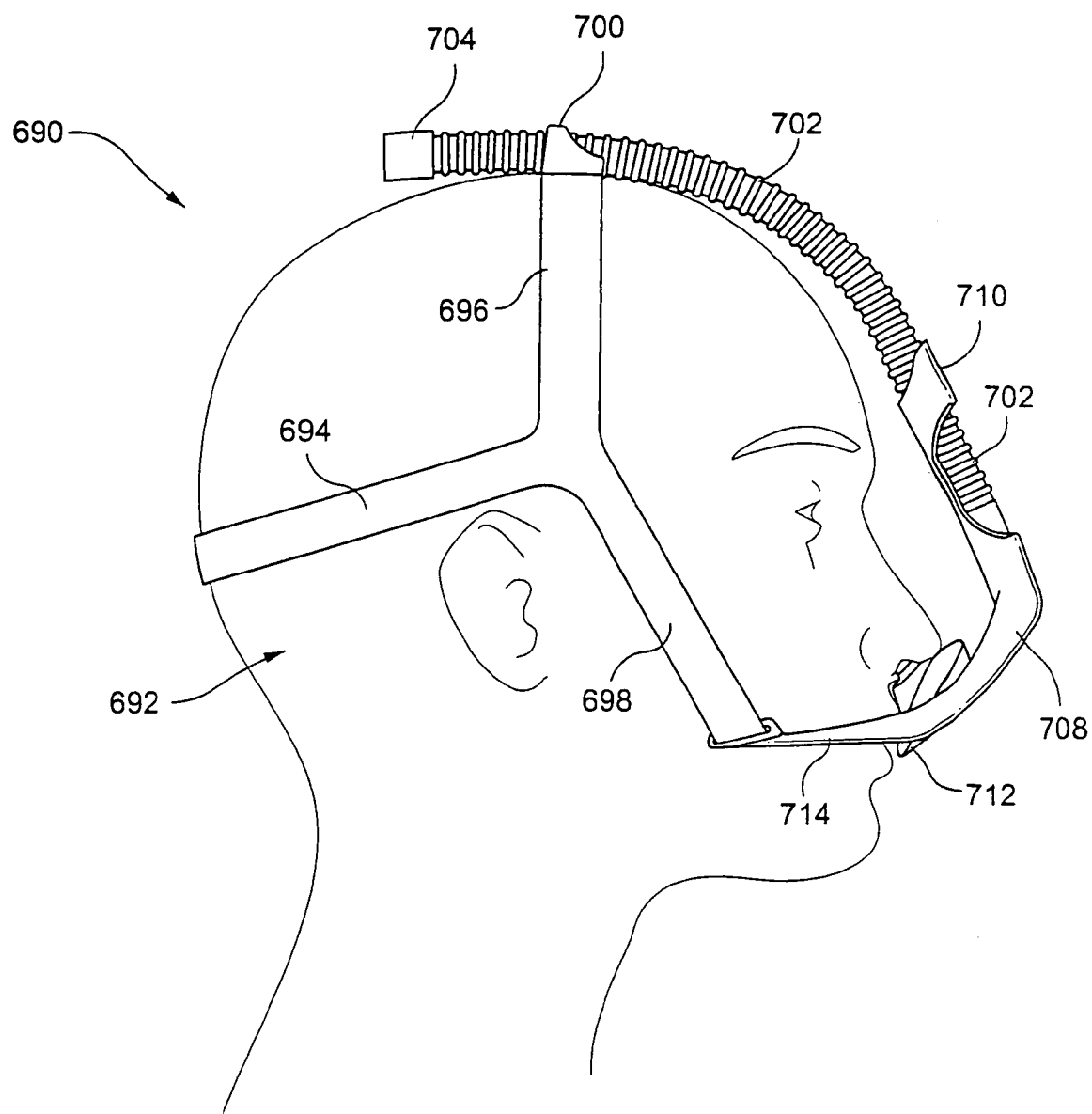
Figure 107E:
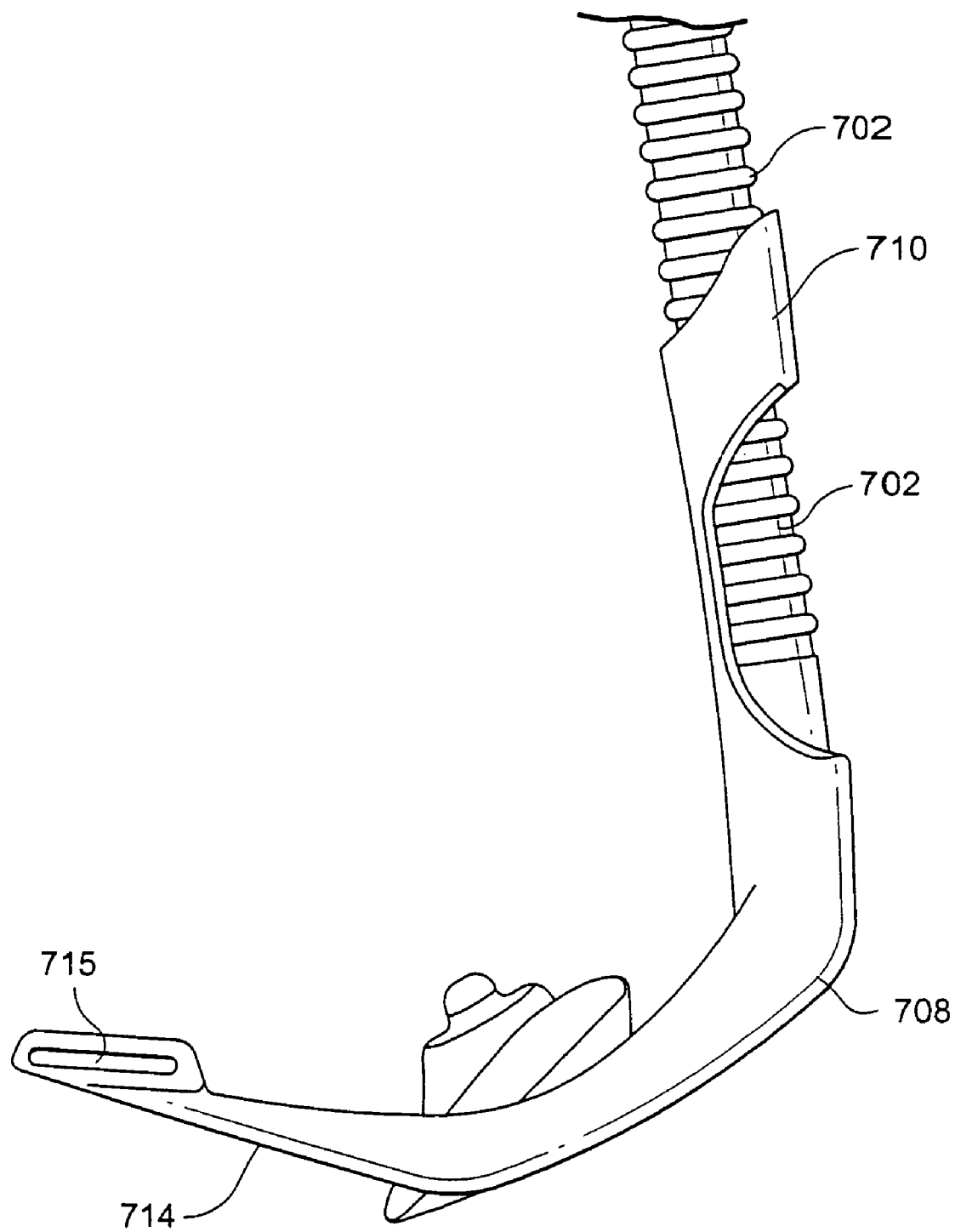
Figure 107F:
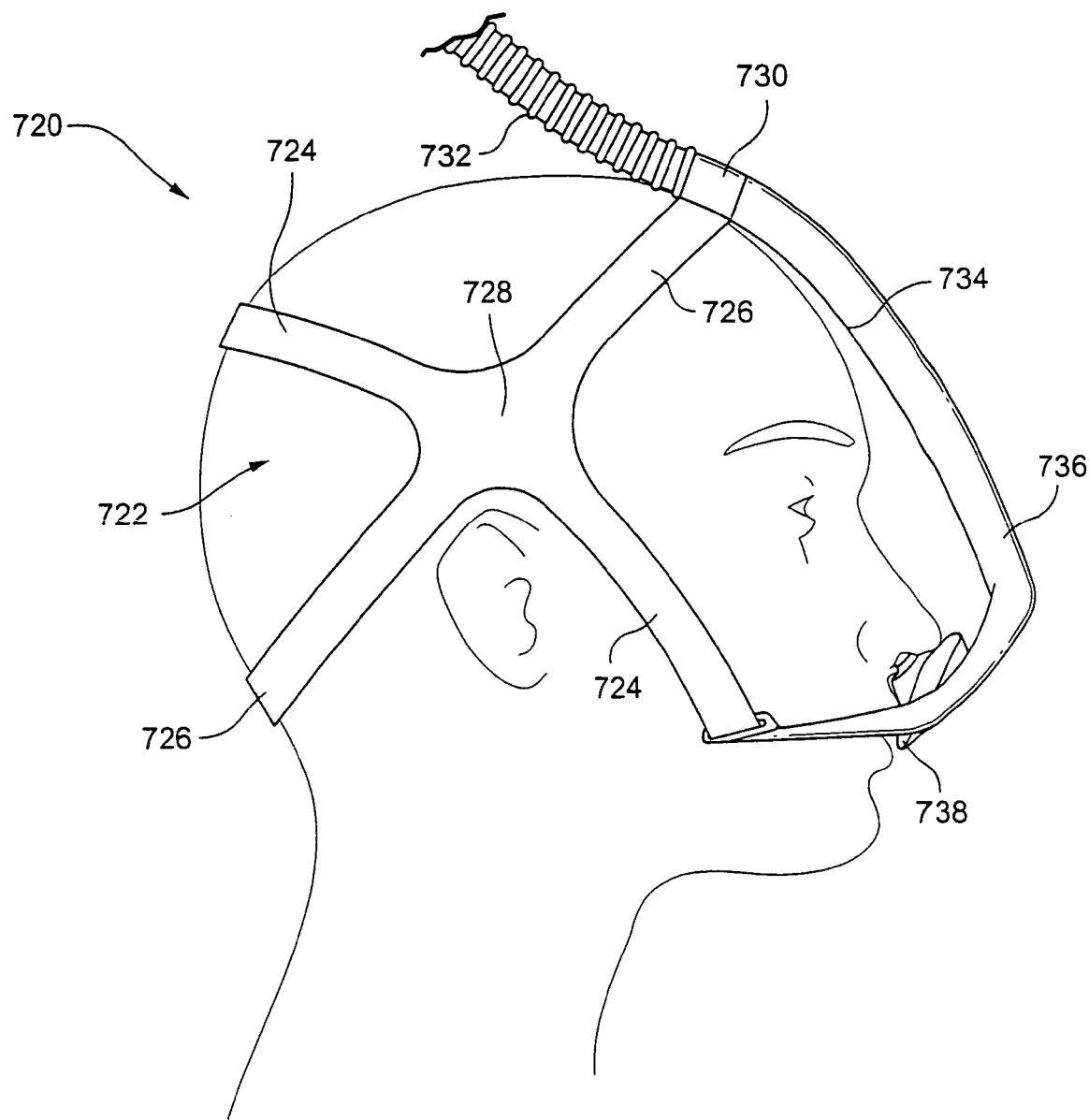
Figure 107G:
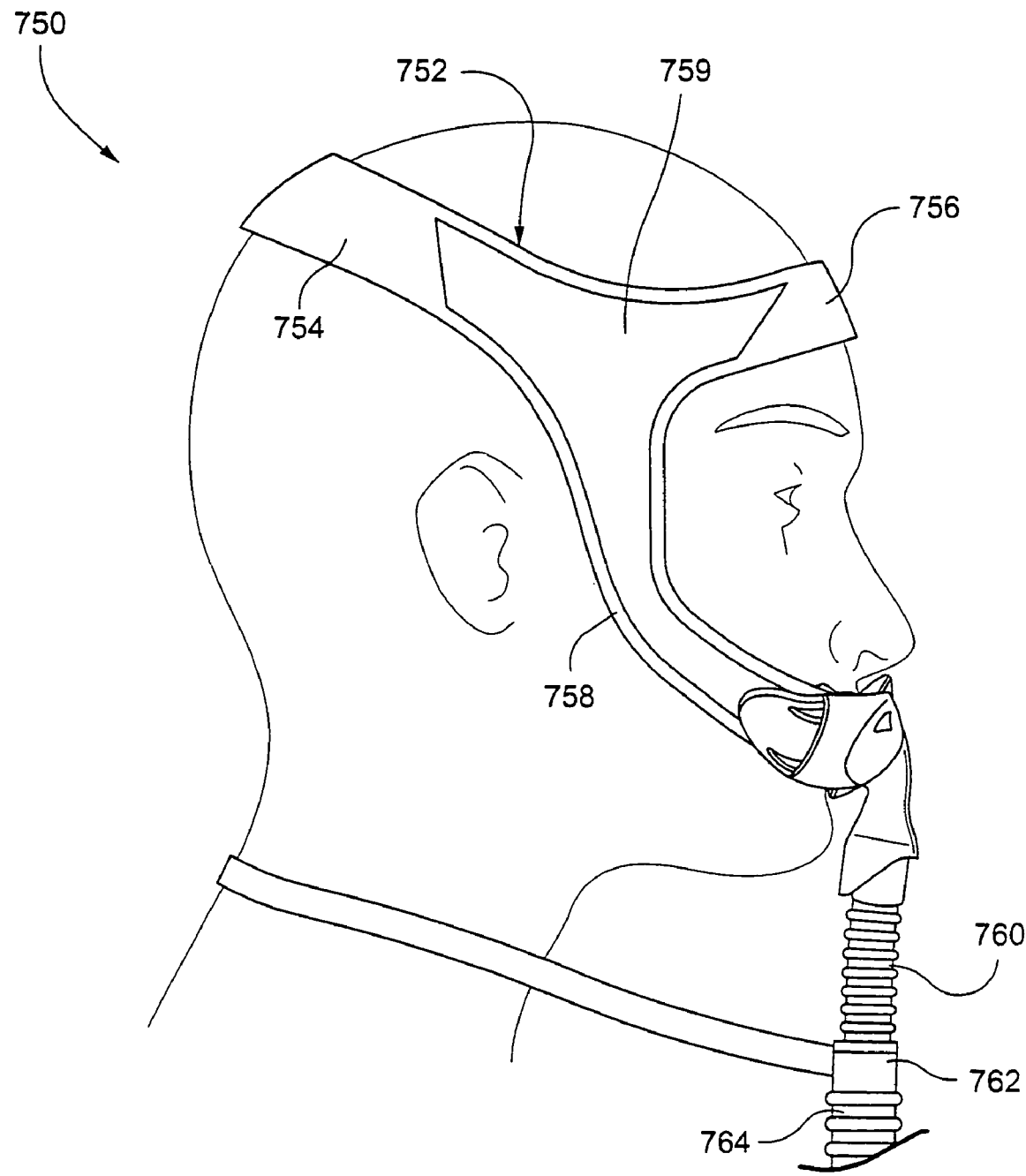
Figure 107H:
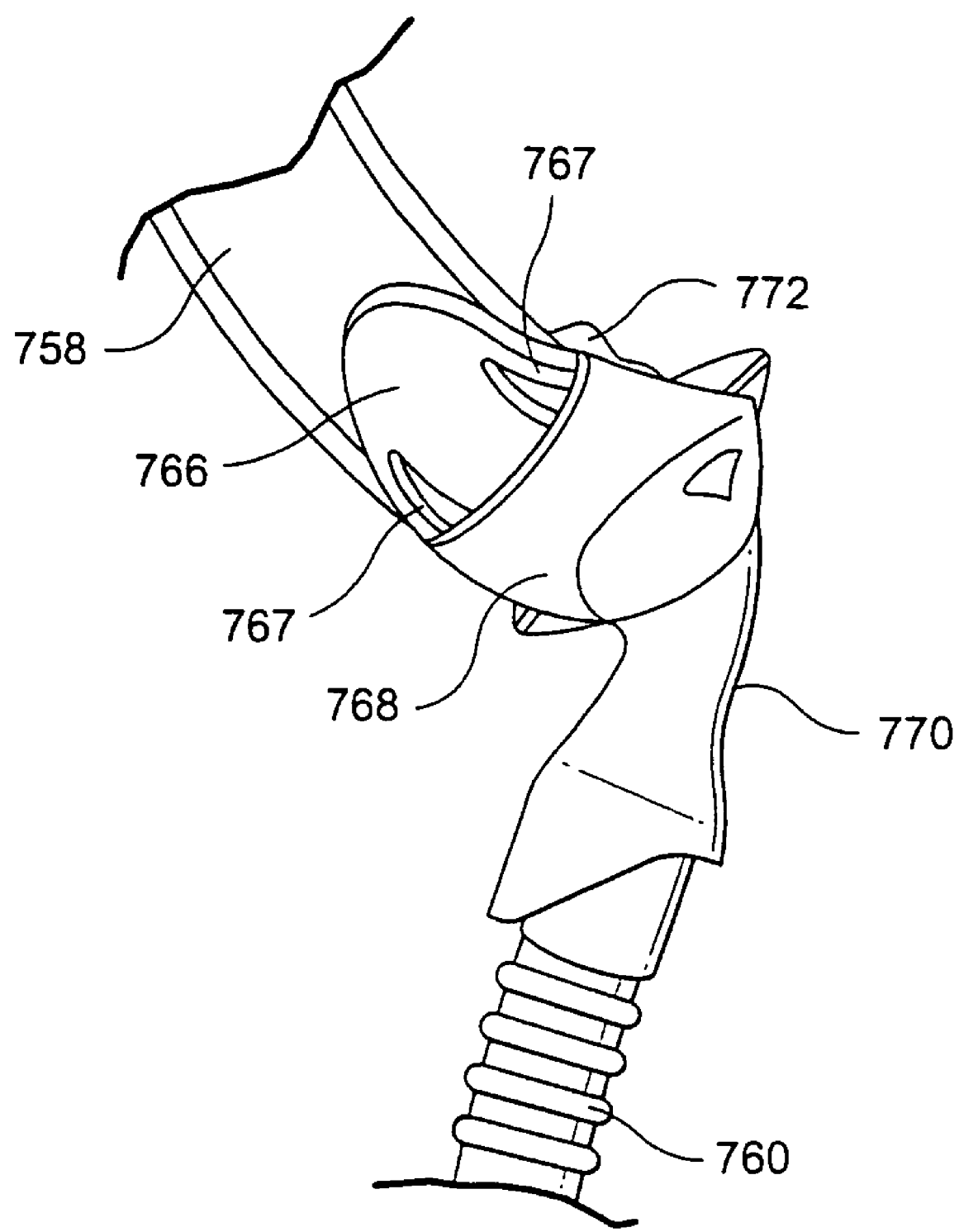
Figure 107I:
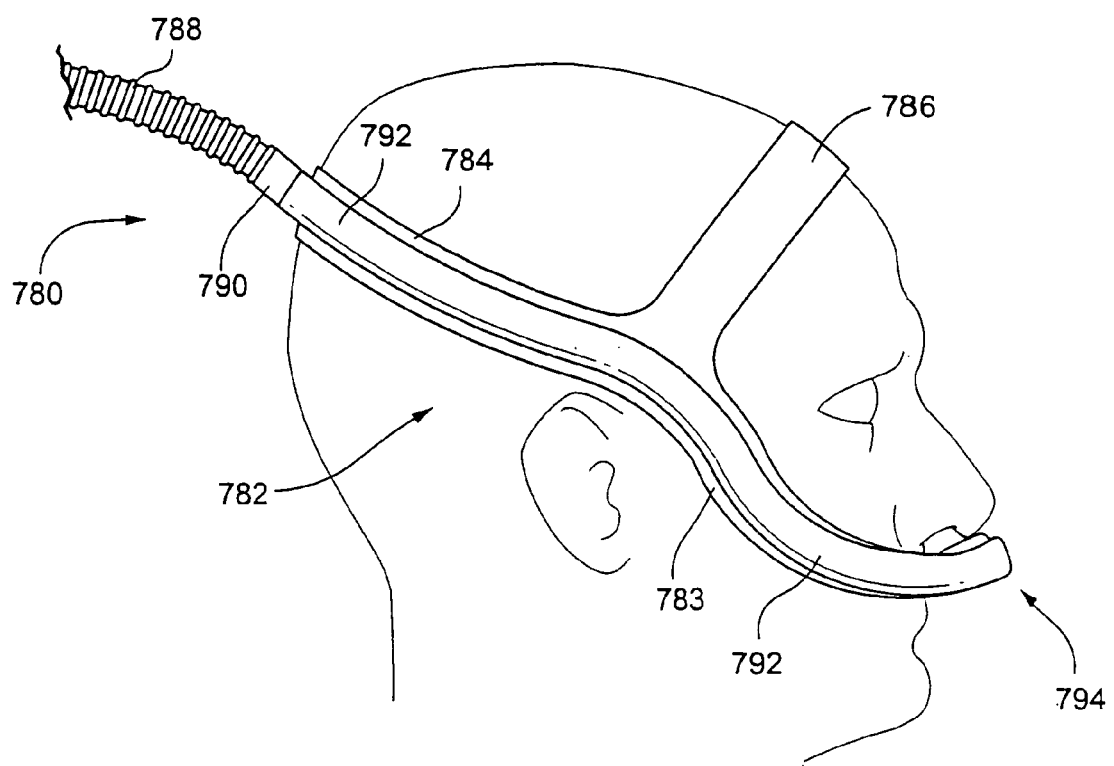
Figure 107J:
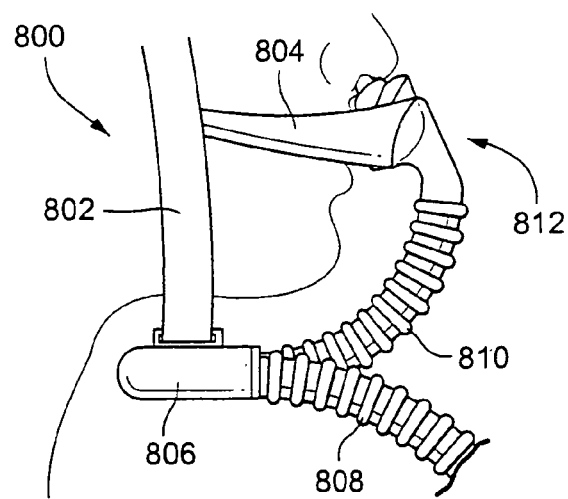
Figure 107K:
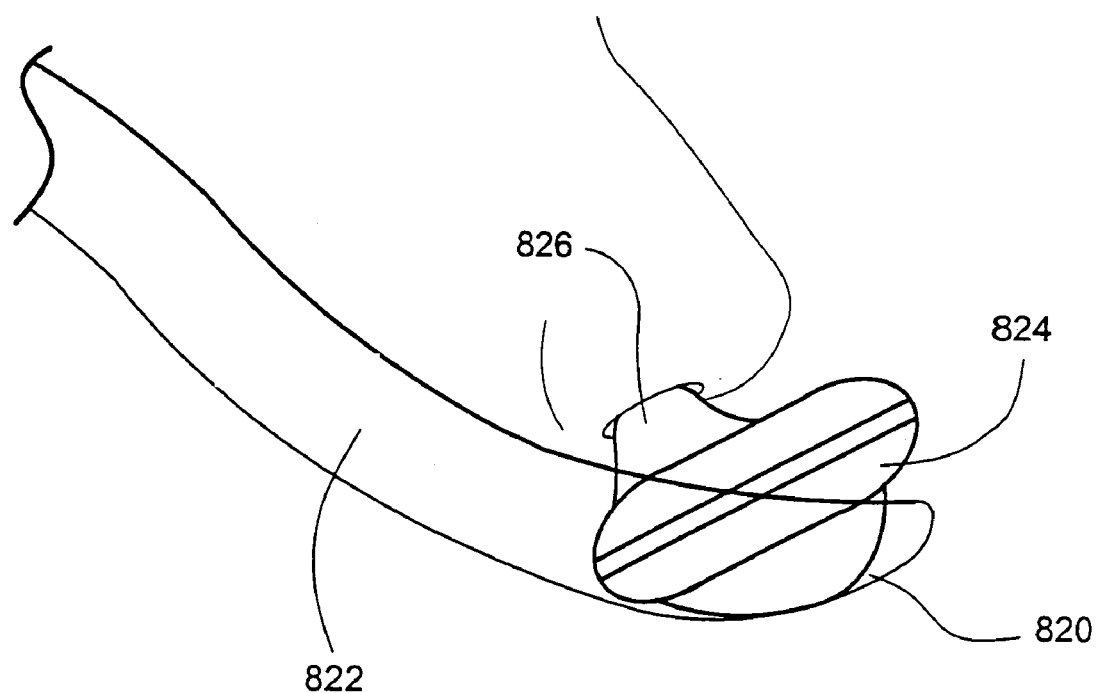
Figure 107L:
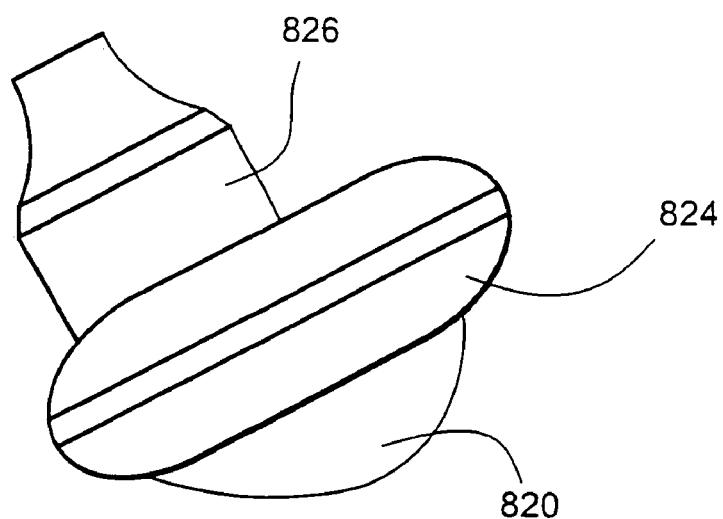
Figure 107M:
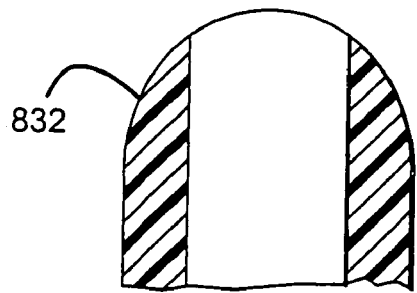
Figure 107N:
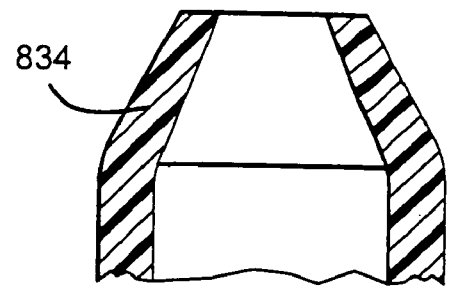
Figure 107O:
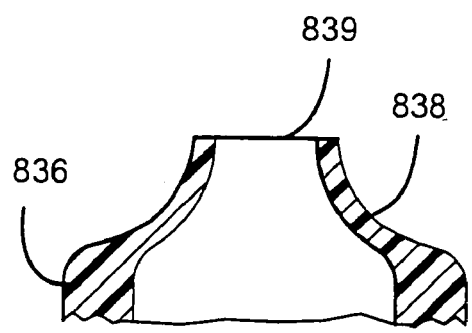
Figure 107P:
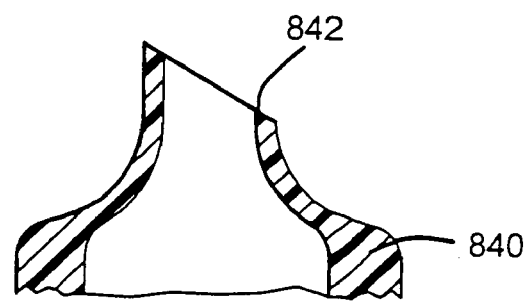
Figure 107R:
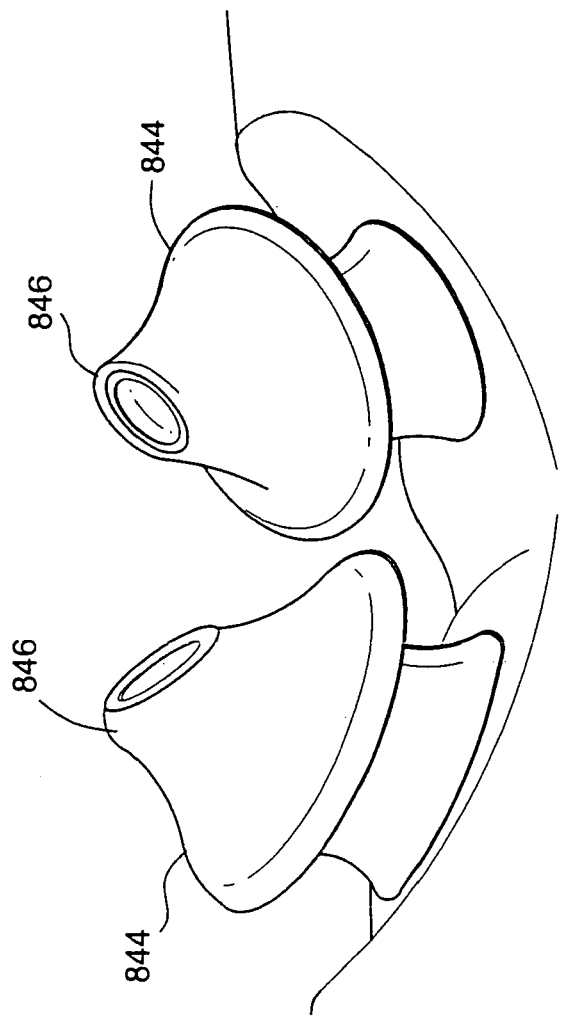
Figure 107Q:
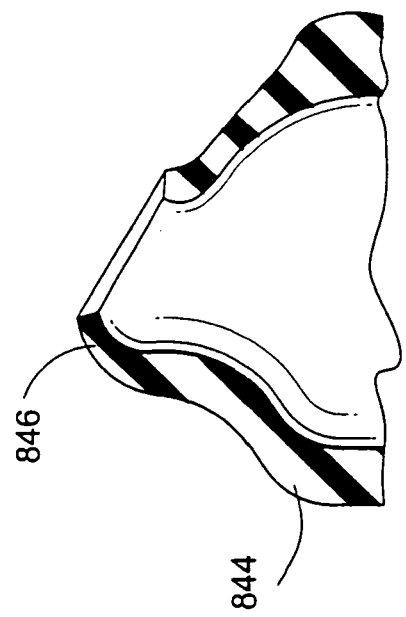
Figure 108:
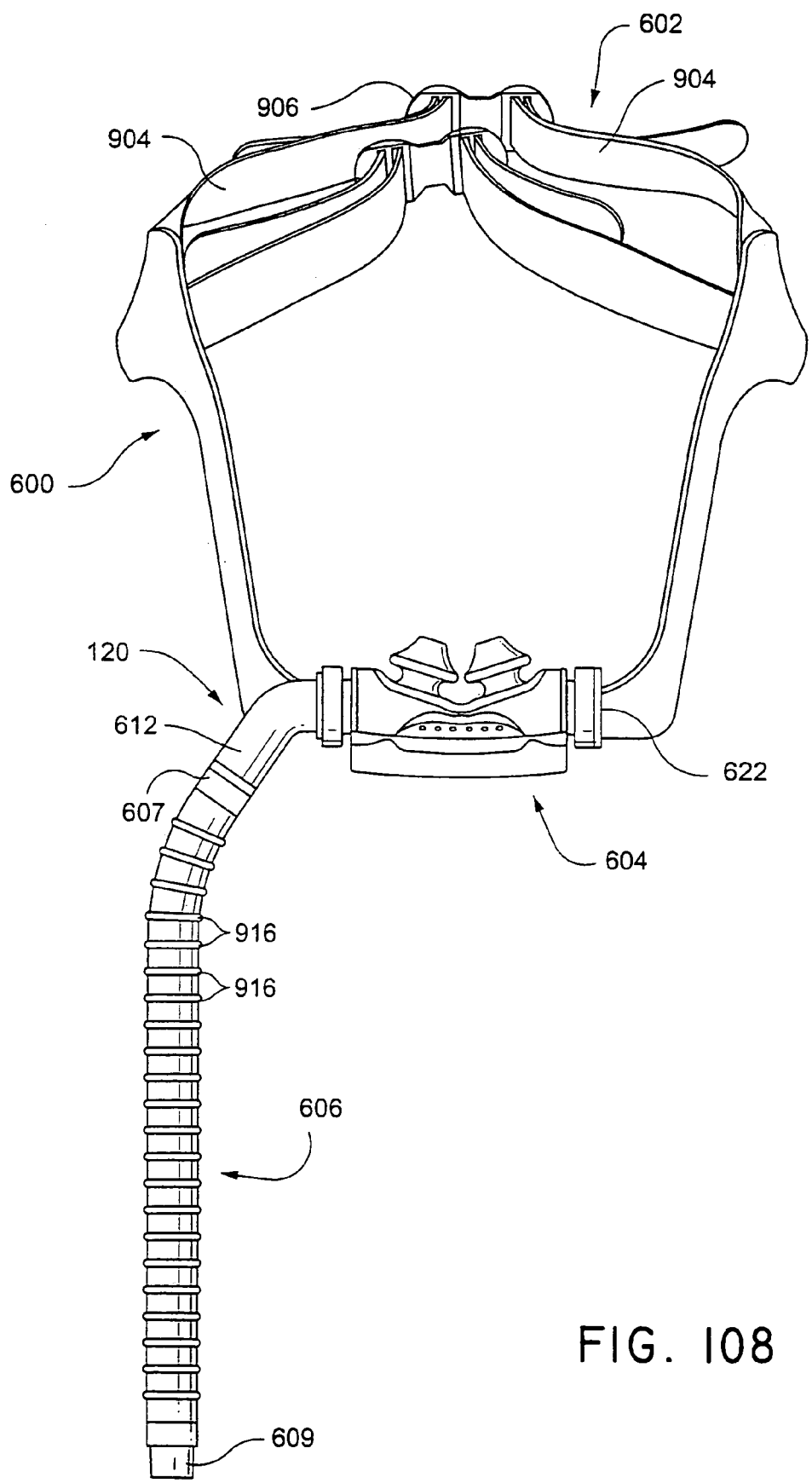
Figure 108A:
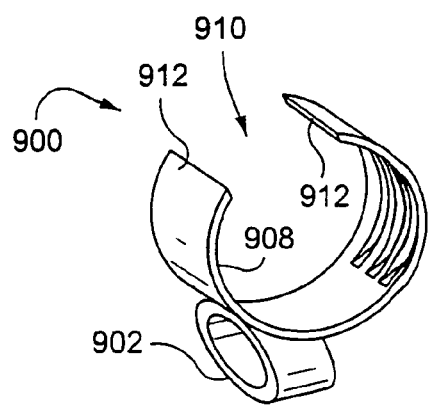
Figure 108B:
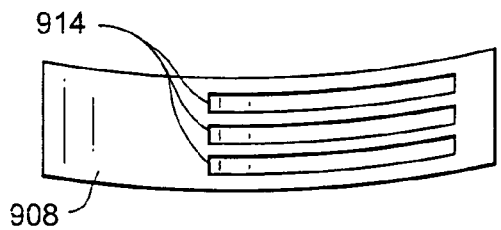
Figure 108C:
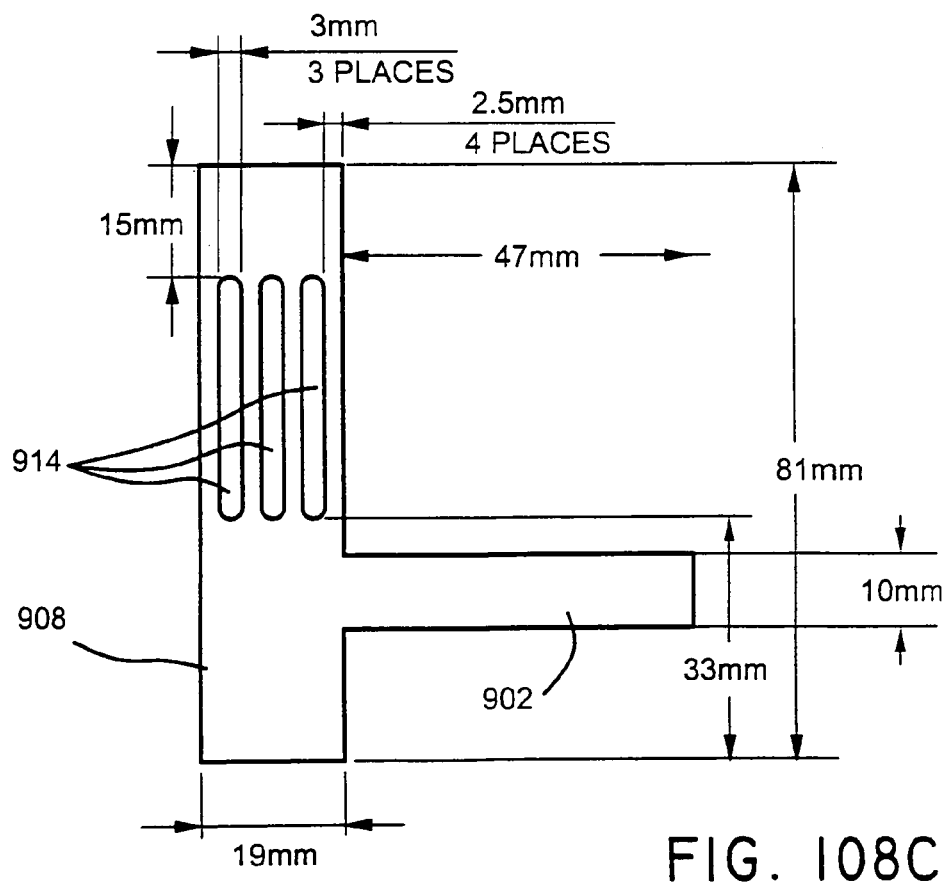
Figure 109:
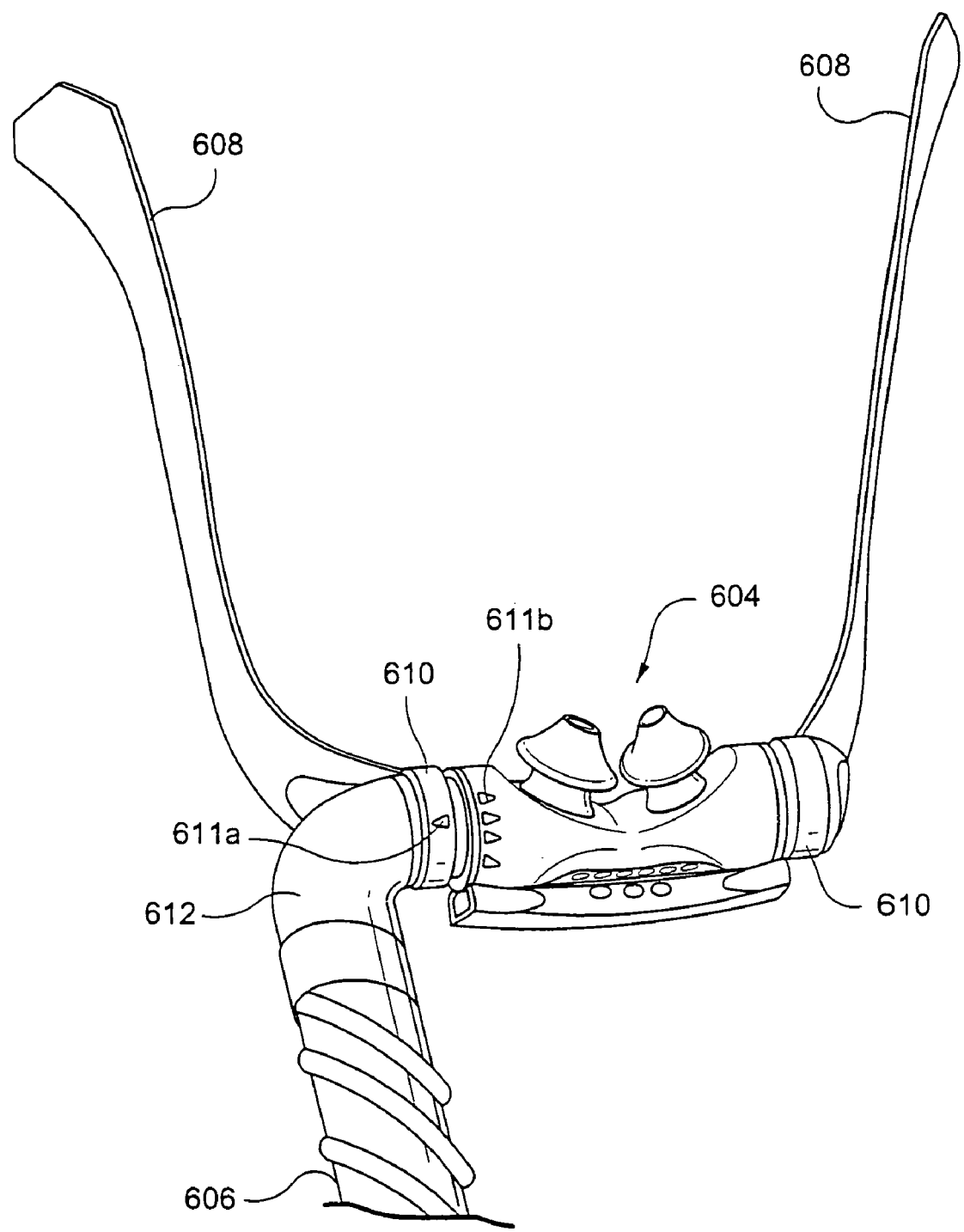
Figure 110:
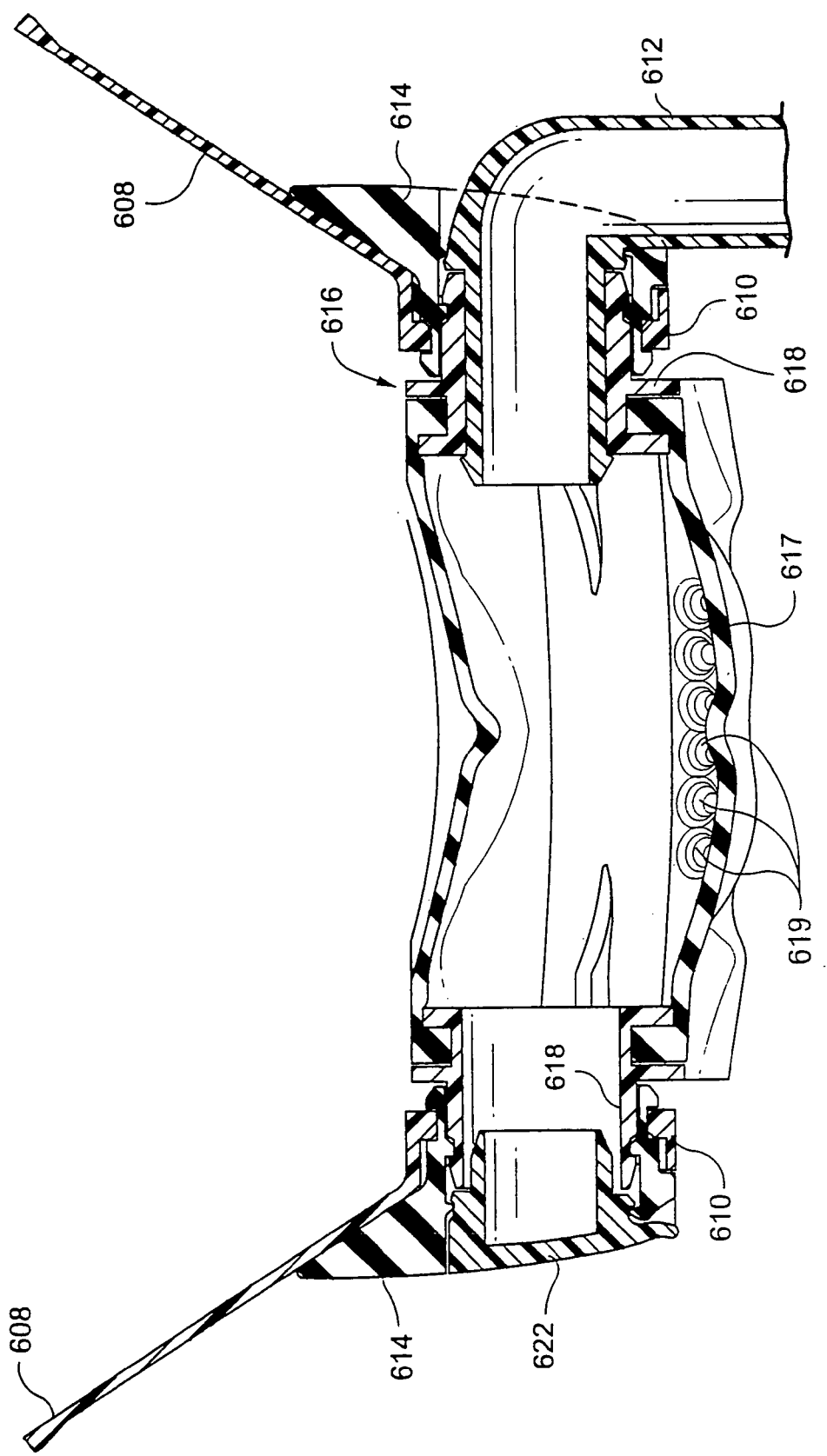
Figure 110A:
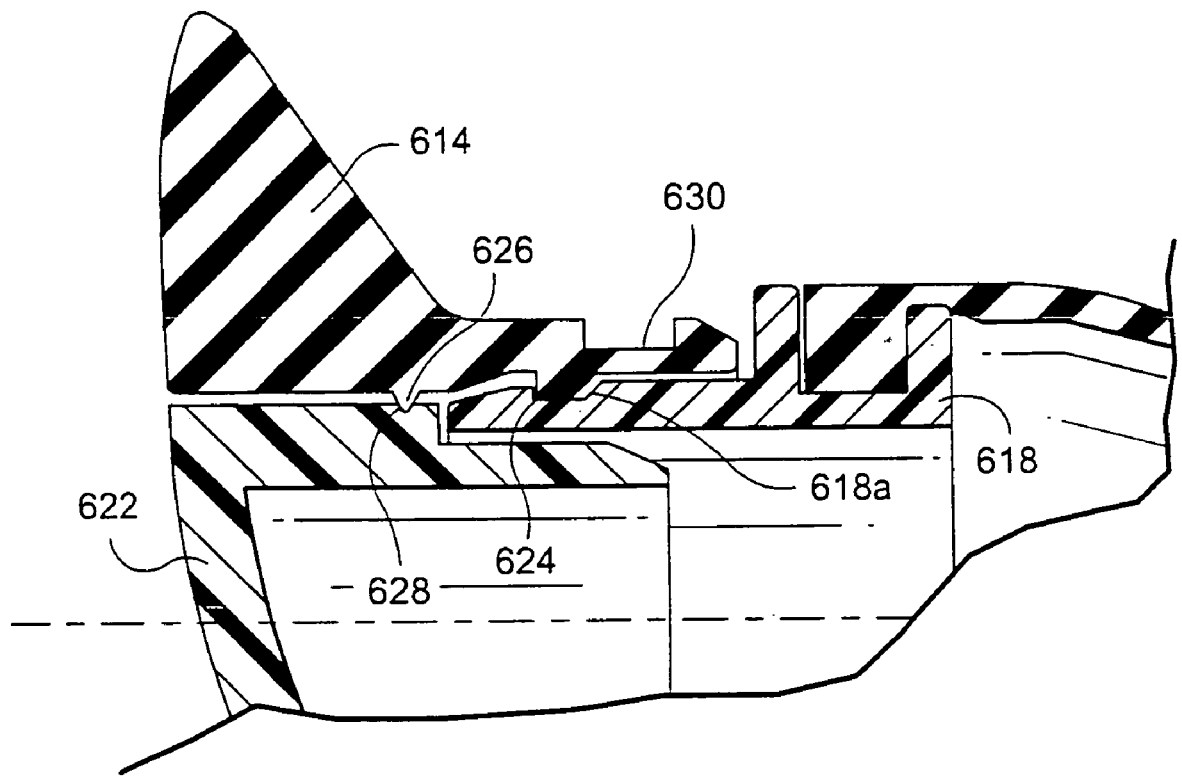
Figure 110B:
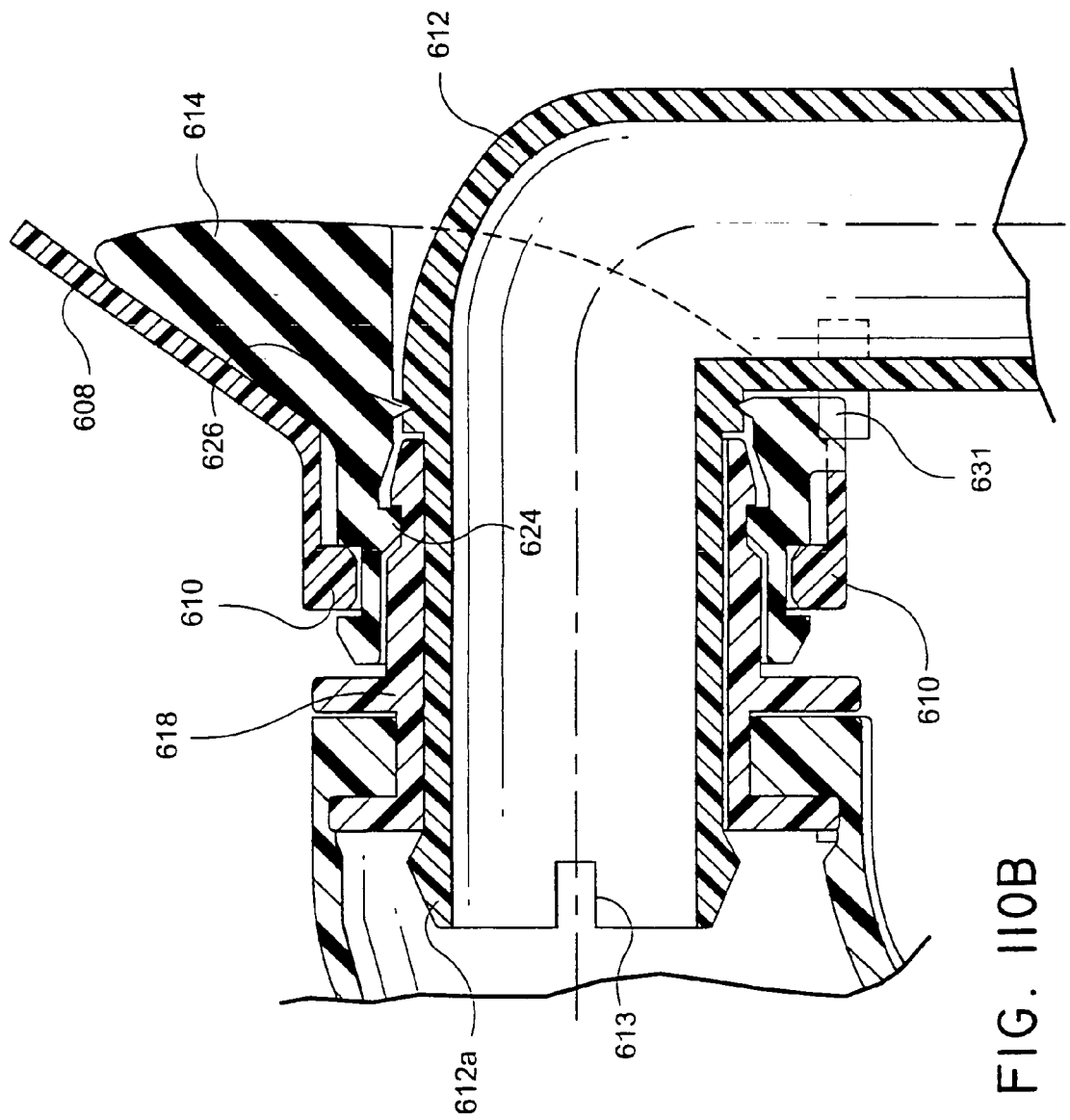
Figure 112:
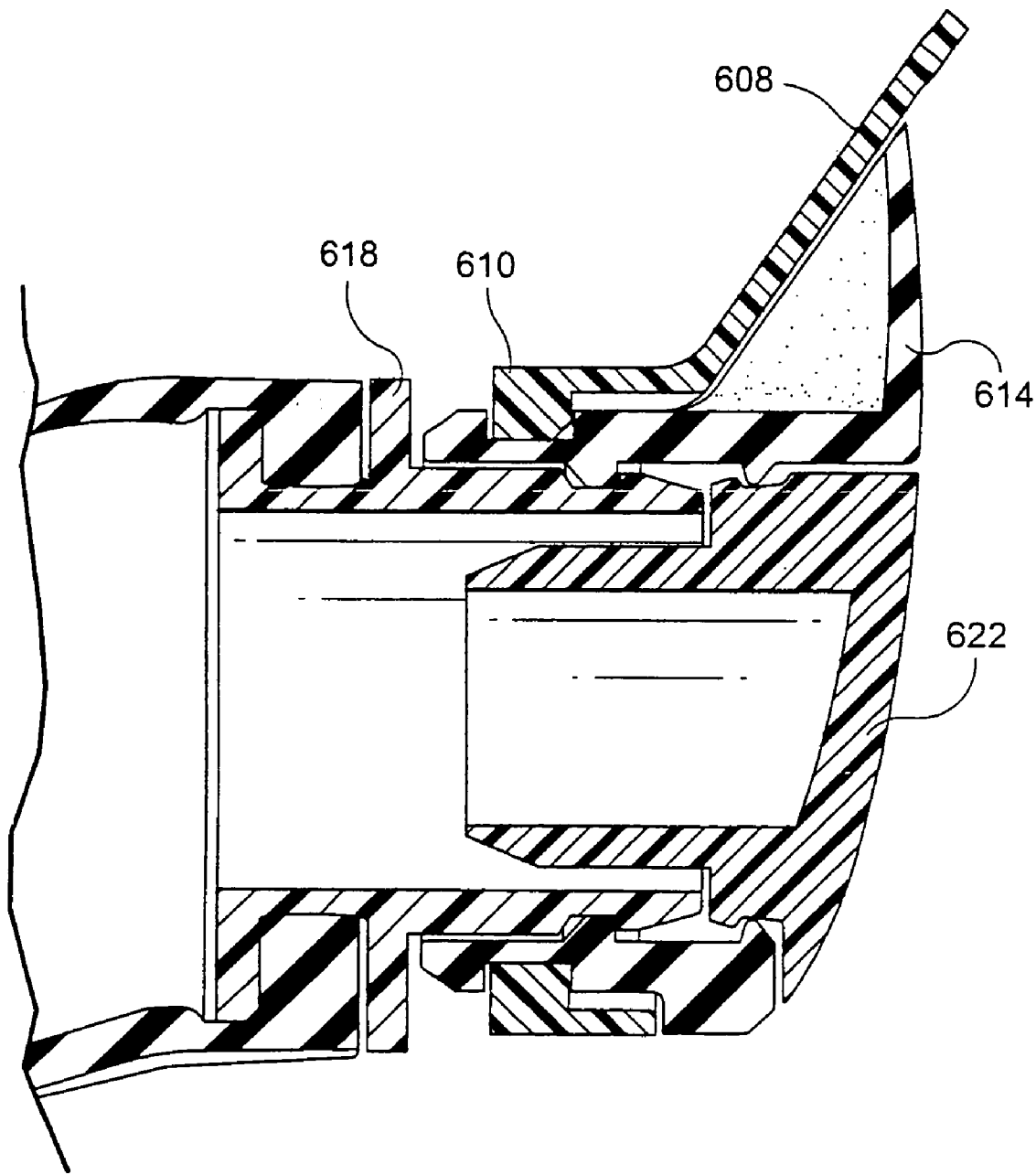
Figure 113:
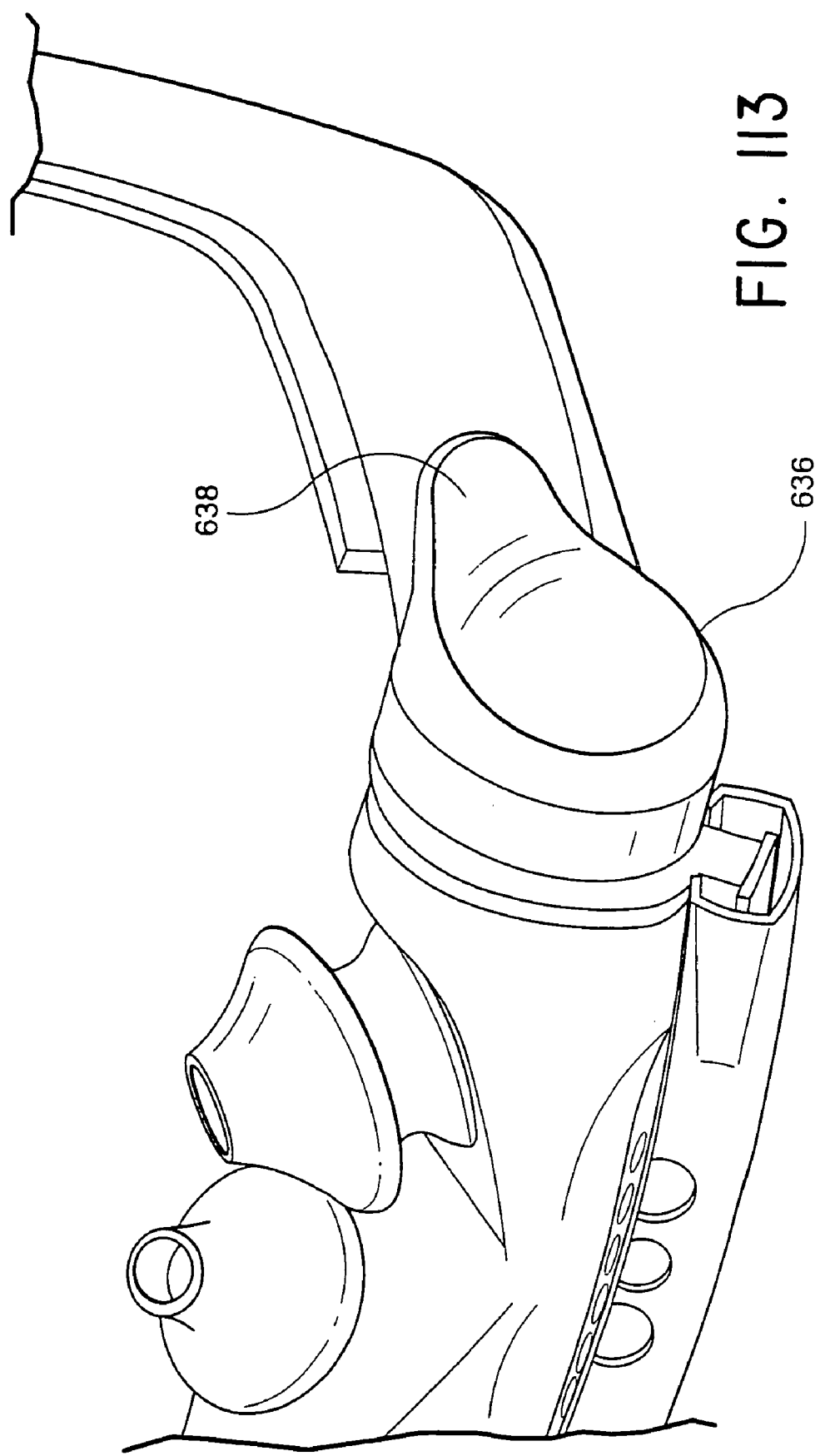
Figure 131:
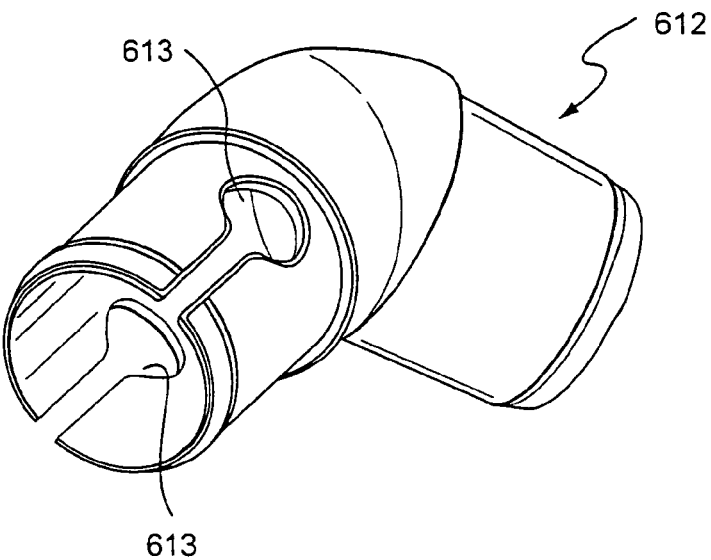
Figure 132:
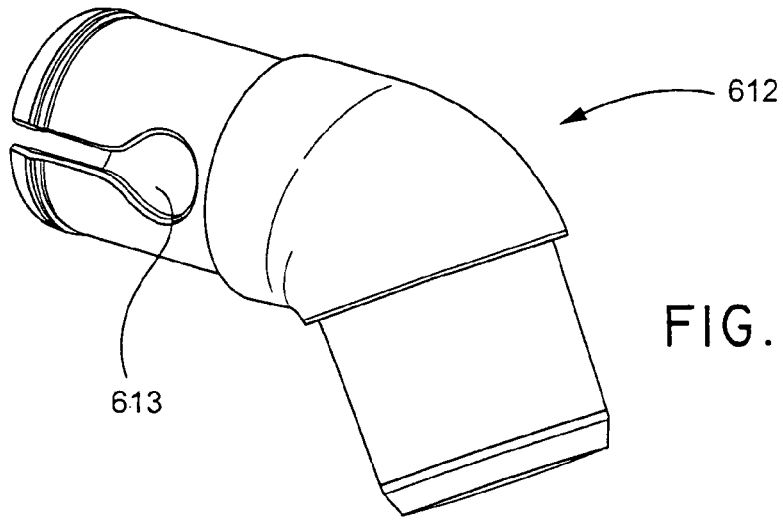
Figure 133:
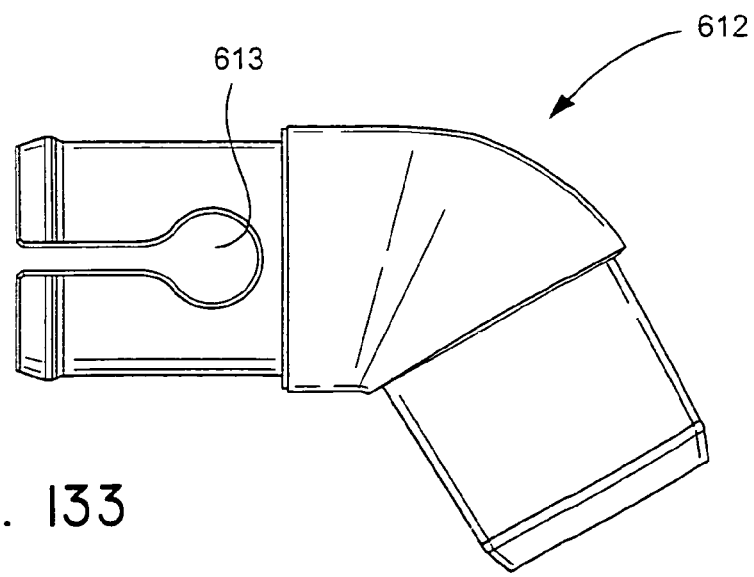
Figure 134:
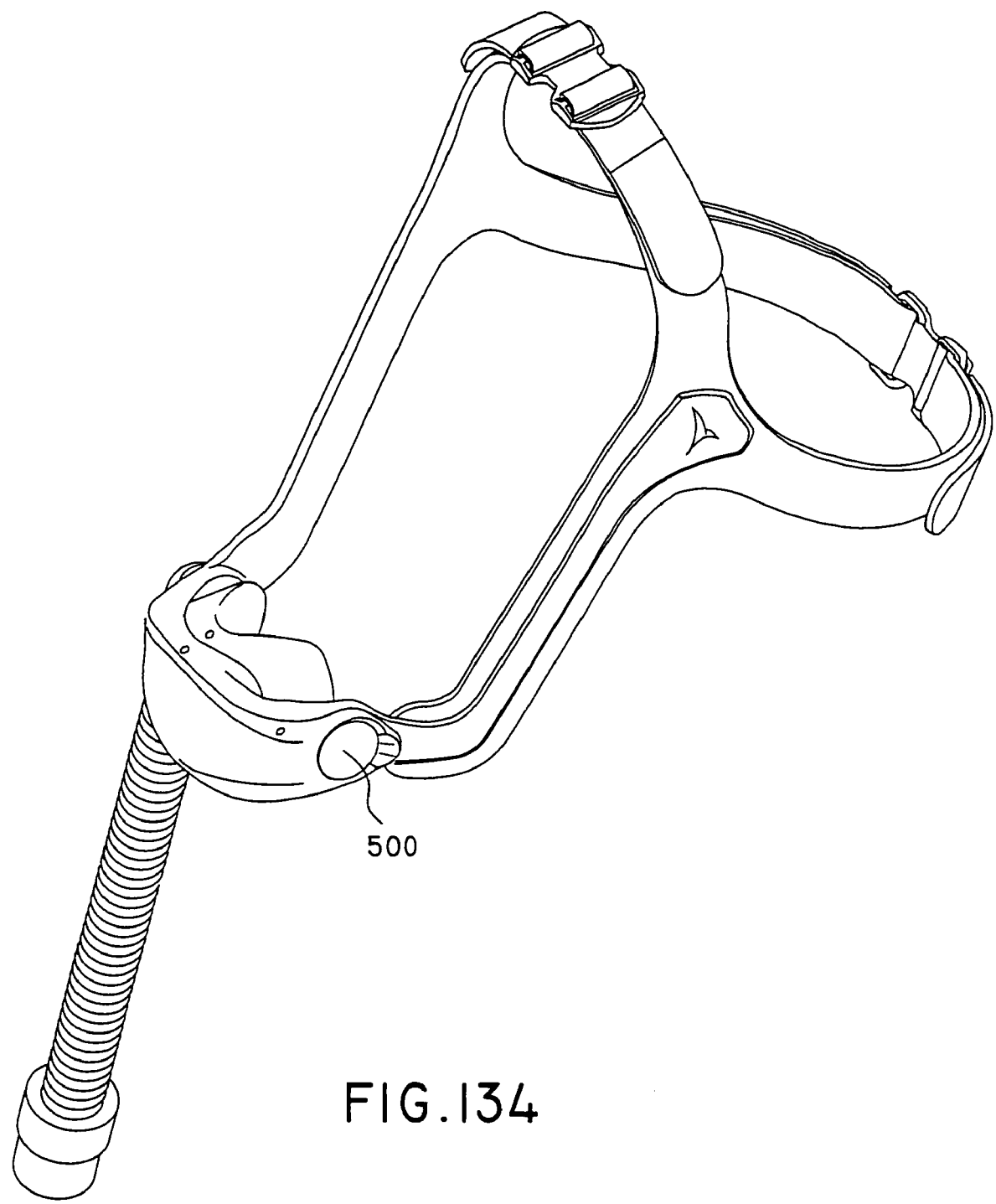
Figure 135:
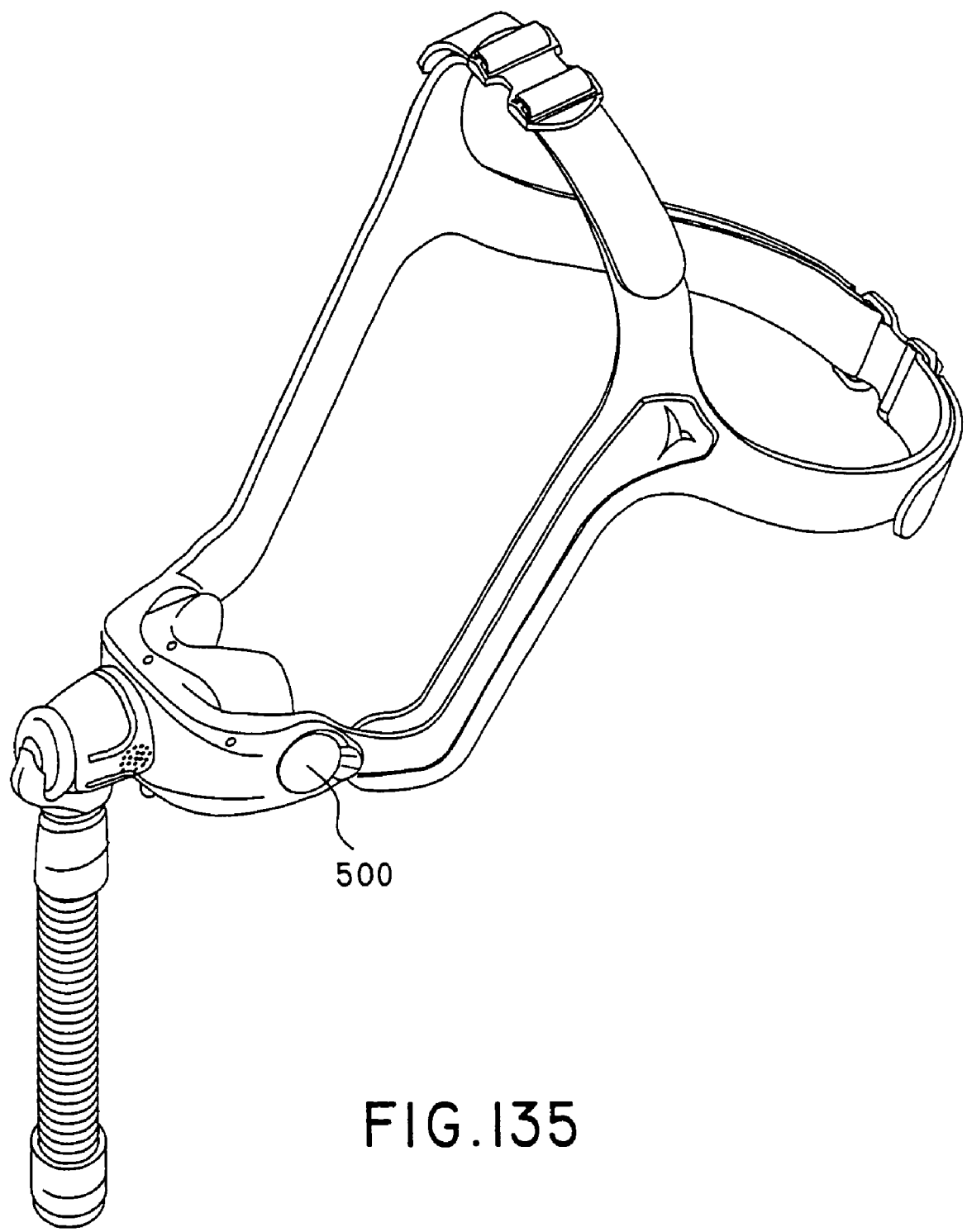

FIG. 107R illustrates a perspective view of two nozzles like the nozzle shown in FIG. 107Q;

FIG. 108 is a perspective view of yet another embodiment of a nasal assembly;

FIGS. 108A and 108B illustrate a tube retainer according to an embodiment of the present invention;

FIG. 108C illustrates another tube retainer according to an embodiment of the present invention;

FIG. 109 is an isometric view illustrating a portion of the nasal assembly shown in FIG. 108;

FIG. 110 is a cross-sectional view of a portion of a nasal assembly according to the present invention;

FIGS. 110-1 and 110-2 illustrate cross-sectional views of a vent aperture according to the present invention;

FIG. 110A is a partial enlarged cross-sectional view of the left hand side of FIG. 110;

FIG. 110B is an partial enlarged cross-sectional view of the right hand side of FIG. 110;

FIG. 111 is an exploded perspective view showing the interface between seal ring and elbow swivel according to an embodiment of the present invention;

FIG. 112 is a partial cross-sectional view of a portion of the mask assembly shown in FIG. 108;

FIG. 113 illustrates still another embodiment of the present invention with an integral plug and seal assembly;

FIGS. 114-126 illustrate yet another embodiment of the present invention;

FIGS. 127-130 illustrate still another embodiment of the present invention;

FIGS. 131-133 illustrate yet another swivel elbow according to an embodiment of the present invention; and FIGS. 134-135 illustrate further alternative embodiments of the present invention.

DETAILED DESCRIPTION OF ILLUSTRATED EMBODIMENTS

The following includes descriptions of several main illustrated embodiments of the present invention. Each illustrated main embodiment includes features that may be used with and/or in the other embodiments, as would be apparent to those of ordinary skill in the art.

First Illustrated Embodiment

FIG. 1 shows an embodiment of a nasal assembly 10 structured to deliver breathable gas to nasal passages 12 of a patient's nose 14. The nasal assembly 10 includes a frame 16 and a nozzle assembly 18 that may be permanently or removably connected to the frame 16. A headgear assembly 20 (see FIG. 18) is preferably removably attached to connection assembly 22 to maintain the frame 16 and nozzle assembly 18 in a desired adjusted position on the patient's face. Inlet conduits (see FIG. 49 for example) are also removably attached to the frame 16 by a connection assembly 22 to deliver breathable gas into the frame 16 and nozzle assembly 18 for breathing by the patient. The headgear assembly 20 and inlet conduits are removably attached to the frame 16 by an inlet conduit and headgear connection assembly 22. The connection assembly 22 includes first connector portions 24 (see FIGS. 2 and 3) provided by the frame 16 and second connector portions 26 adapted to be removably coupled with the first connector portions 24. The second connector portions 26 are removably connected to the headgear assembly 20 and the inlet conduits, as will be further discussed.

Figure 3:
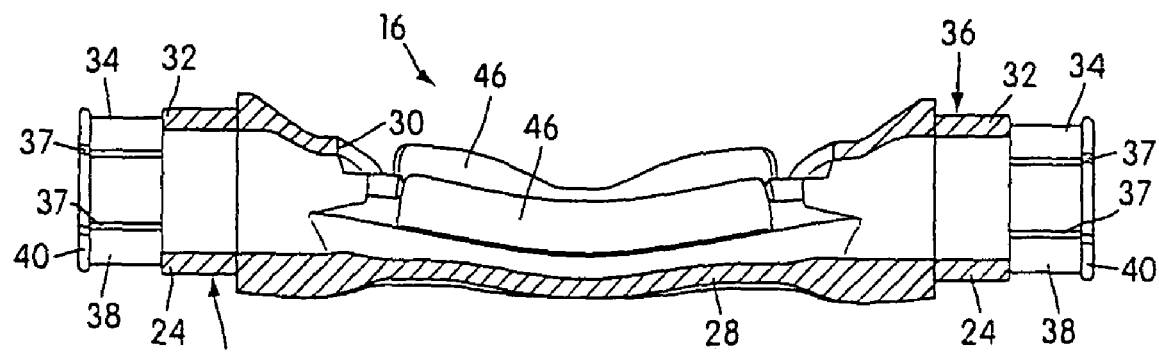
FIG. 3 is a cross-sectional view of the frame shown in FIG. 2.
Figure 4:
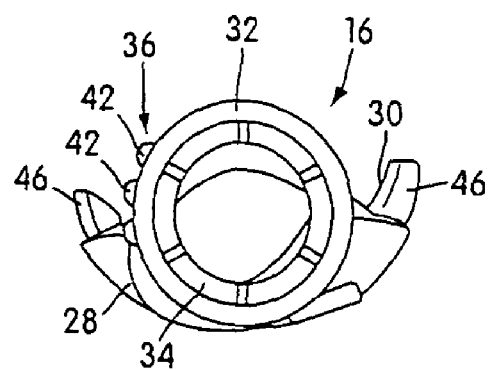
FIG. 4 is a side view of the frame shown in FIG. 2.

As shown in FIGS. 2-4, the frame 16 includes a main body 28 that provides a central opening 30 for accommodating the nozzle assembly 18. The frame 16 also includes side frame members 32 provided on each lateral side of the main body 28. The side frame members 32 are preferably formed in one piece with the main body 28 of the frame 16. In the illustrated embodiment, the frame 16 is a rigid or semi-rigid structure formed from a polymer material. However, the frame 16 may be semi-rigid to allow flexibility of the frame 16 with respect to the patient's face in use. The frame 16 may also be semi-rigid in certain regions for customized flex in certain regions of the frame 16.

Each side frame member 32 includes a first connector portion 24 that is integrally formed therewith. As best shown in FIGS. 2 and 3, the first connector portion 24 includes a connecting section 34 and an indexing section 36. The connecting section 34 is structured to interlock with the second connector portion 26 to prevent axial disengagement of the second connector portion 26 from the first connector portion 24. The indexing section 36 is structured to ratchet/detent with the second connector portion 26 to allow selective circumferential adjustment of the second connector portion 26 with respect to the first connector portion 24 about an axis during fit whilst remaining "locked" in adjusted position during usage.

Specifically, the connecting section 34 of each side frame member 32 includes a series of grooves or slots 37 that separates the connecting section 34 into a plurality of resiliently flexible arms 38 that are structured to flex radially inwardly and outwardly. Each arm 38 provides a rib portion 40 at the free end thereof. In use, the rib portions 40 of the plurality of arms 38 are adapted to engage with corresponding portions of the second connector portion 26 for coupling the first and second connector portions 24, 26 with one another. For example, the first and second connector portions 24, 26 interlock with one another to prevent accidental disengagement of the second connector portion 26 from the first connector portion 24 if a force is applied to the second connector portion 26 axially away from the first connector portion 24. Moreover, the first and second connector portions 24, 26 mate with one another to provide a good seal.

The indexing section 36 of each side frame member 32 includes a plurality of teeth 42. The teeth 42 are structured so as to selectively engage a tooth 44 provided on the second connector portion 26 (see FIGS. 9 and 10). As a result, the second connector portion 26 can be rotated to a desired position with respect to the frame 16. In use, the tooth 44 on the second connector portion 26 engages between selective teeth 42 provided on the indexing section 36 in the desired position and rotationally locks the second connector portion 26 with respect to the first connector portion 24 and hence the frame 16. For adjustment, the user can manually change the position of the tooth 66 and the teeth 42.

In accordance with one embodiment, the teeth 42 of the indexing section 36 can be configured so that when a predetermined torque is applied to the second connector portion 26, the teeth 42 will automatically force the tooth 44 of the second connector portion 26 outwardly to allow rotation of the second connector portion 26 until the torque is removed and the teeth 42 reengage with the tooth 44 of the second connector portion 26. The second connector portion 26 can thus be rotationally adjusted or indexed with respect to the frame 16 within a predetermined angle. The angle of available rotational adjustment can be altered as desired by altering the number and positioning of the teeth 42 on the indexing section 36. The adjustment angle range allows the patient to adjust the position of the nozzle assembly 18 relative to the nose of the patient. For optimal positioning, in one preferred embodiment, nozzle assembly 18 is formed from a one part molded silicone piece that attaches to frame 16.

In the illustrated embodiment, the adjusting or indexing operation is oriented perpendicular to the connecting operation in order to minimize potential disengagement of the second connector portion 26 from the first connector portion 24.

As best shown in FIG. 4, the main body 28 includes opposing side walls 46 that define the central opening 30 for accommodating the nozzle assembly 18. The side walls 46 are adapted to engage with corresponding portions of the nozzle assembly 18 for coupling the nozzle assembly 18 and the frame 16 with one another, as will be further discussed.

As shown in FIGS. 5-8, the nozzle assembly 18 includes a base portion 48 and a pair of nozzles 50 attached thereto. The base portion 48 has side walls 52 adapted to sealingly engage with the side walls 46 of the frame 16 and a central wall 54. The pair of nozzles 50 each have a first portion 56 and a second portion 58. The first portion 56 is attached to the central wall 54 of the base portion 48 in communication with respective outlet openings provided in the central wall 54. The second portion 58 is structured to sealingly engage with nasal passages 12 of the patient's nose 14 in use and to provide a seal between the nasal assembly 10 and the patient's nasal passages 12. When the nozzle assembly 18 is attached to the frame 16, the nozzle assembly 18 and the frame 16 together form a conduit for directing breathable gas to the patient's nose through the pair of nozzles 50.

In the illustrated embodiment, the nozzle assembly 18 is removably attached to the frame 16 with a snap, e.g., snap-fit, push-pin fit, or stretch over fit, which allows for simple assembly. For example, the side walls 52 of the base portion 48 may include a rib or groove/recess that is structured to interlock with a recess/rib provided on respective side walls 46 of the frame 16 with a snap-fit. However, the nozzle assembly 18 may be removably attached to the frame 16 in any other suitable manner, e.g., friction or interference fit and/or a tongue and groove arrangement, as is known in the art. Alternatively, the nozzle assembly 18 may be rigidly coupled to the frame 16 by an adhesive or fasteners, for example. Also, the nozzle assembly 18 may be formed in one piece with the frame 16, or over-molded. That is, the nozzle assembly and frame may be a one-piece structure with different thicknesses and hardnesses to add rigidity.

Preferably, the nozzle assembly 18 is flexible, to thereby allow relative movement between the nozzle assembly 18 and the frame 16, for increased comfort and accommodation of variations in patient facial features. Moreover, the base portion 48 is structured such that it can expand and contract to alter a distance between the frame 16 and the pair of nozzles 50, as will be further discussed below. That is, the central wall 54 is preferably made of a resilient and/or flexible material structured to deform, e.g., inflate upon introduction of pressurized gas, from a generally flat configuration to a generally curved configuration in use to thereby move the nozzles 50 towards the patient's nose. Other portions of the base portion 48, e.g., side walls 52, may be structured to deform/inflate as well.

In the illustrated embodiment, the base portion 48 has a generally dog-bone shape. However, the base portion 48 may have any suitable shape, including shapes to avoid contact with sensitive regions of the patient's face, e.g., notched base shape, to prevent contact with the patient's septum or otherwise minimize contact pressure in these sensitive regions.

Figure 5:
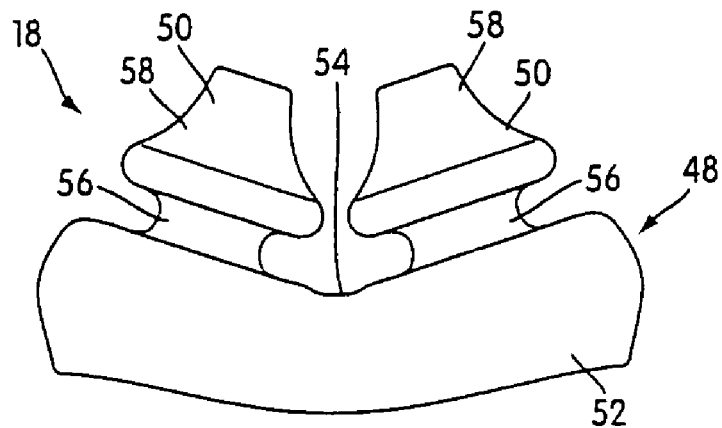
FIG. 5 is a front view of a nozzle assembly of the nasal assembly shown in FIG. 1.
Figure 6:
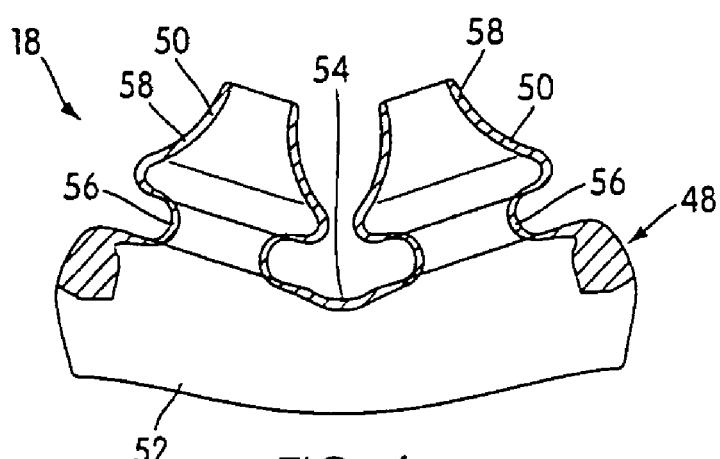
FIG. 6 is a front cross-sectional view of the nozzle assembly shown in FIG. 5.
Figure 7:
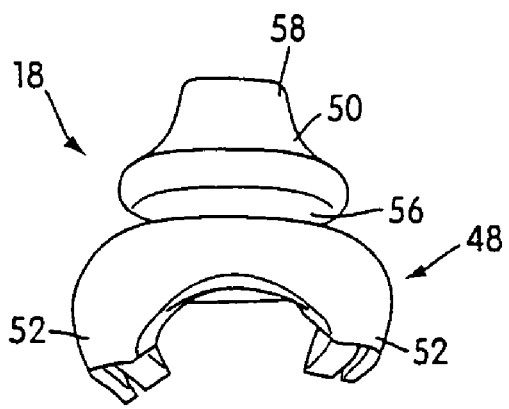
FIG. 7 is a side view of the nozzle assembly shown in FIG. 5.
Figure 8:
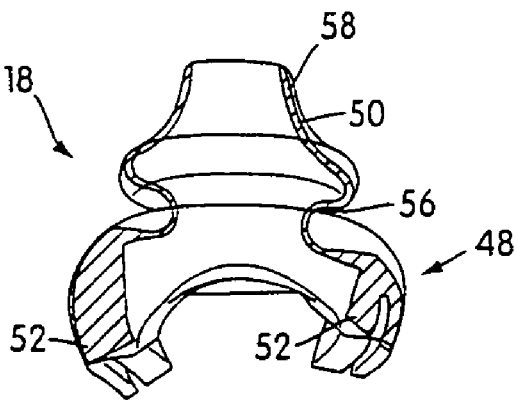
FIG. 8 is a side cross-sectional view of the nozzle assembly shown in FIG. 5.

As best shown in FIGS. 1, 5, and 6, the second portion 58 of the nasal assembly is contoured (e.g., tapered, cone-shaped, truncated hollow cone, etc.) with a portion that seals on the underside of the nostrils (e.g., an area about the rim of the nostril openings) and another portion that enters into the nasal passage of the patient's nose in use. However, the nozzles 50 may be in the form of nasal prongs, cannula, or nasal puffs, for example, and may sealingly engage with the nasal passages 12 in any suitable manner. For example, the nozzles 50 may seal within the nasal passages 12, against the nasal passages 12, around the nasal passages 12, or combinations thereof. The nozzles 50 may be contoured to match the interior anatomical profile of the patient's nose. Moreover, different size and/or shape nozzles, e.g., small, medium, and large, may be provided to accommodate a range of patient's noses.

In the illustrated embodiment, the first portion 56 of the nozzles 50 have a reduced cross-section with respect to the second portion 58 to allow the nozzles 50 to move relative to the base portion 48, and hence the frame 16, for increased comfort and accommodation of variations in patient facial features.

In one embodiment, the nasal assembly 10 uses patient-customized nozzles which may be removably mounted to the base portion 48 or the frame 16. In a preferred form, the nozzles are constructed from a substantially flexible polymer material, such as a silicone elastomer. A unique nozzle can be made match each patient's nose by first scanning their nose, either in situ or remotely, and then using the data for manufacture of the interface, for example, a mold maker. Scanning can be done using either non-contact or contact methods. Non-contact, for example photographically, or by physical contact with a probe or by collecting an impression of the inside of the nares of the desired contact interface. Once a pair of suitable nozzles are made, they are sent to the customer to be fitted to a patient. Advantage of the pre-formed or customized shape is that cross-sectional area may be maximized to reduce flow impedance. Also, the use of pre-formed shapes improves comfort and increased stiffness materials such as semi-rigid plastics may be used that have greater resistance to distorting, thus minimizing nozzle distortion of the patient's nares. Further, rigid plastics may be used that allows thin wall sections and allows flexibility of the nozzle due to its connection to the base portion 48, e.g., the base portion 48 is soft and compliant.

In the illustrated embodiment, the nozzles 50 are molded in one piece with the base portion 48 from deformable and inflatable materials. The nozzles 50 and base portion 48 may be constructed from a soft, flexible, skin-compatible material such as silicone. The nozzles 50 and base portion 48 may be formed, for example, in an injection, compression, and/or transfer molding process as is known in the art.

However, the nozzles 50 and base portion 48 may be formed with any suitable material and may be formed by any suitable process. For example, the base portion 48 and nozzles 50 may be formed separately and permanently attached to one another with an adhesive and/or mechanical fasteners, for example. Alternatively, the base portion 48 and nozzles 50 may be formed separately and removably attached to one another.

Figure 9:
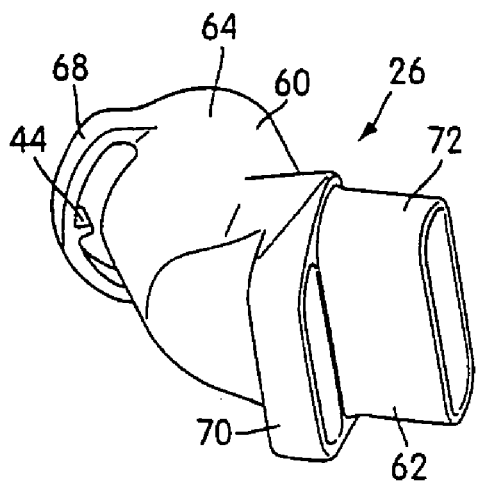
FIG. 9 is a perspective view of an embodiment of an inlet conduit and headgear connector assembly of the nasal assembly shown in FIG. 1.
Figure 10:
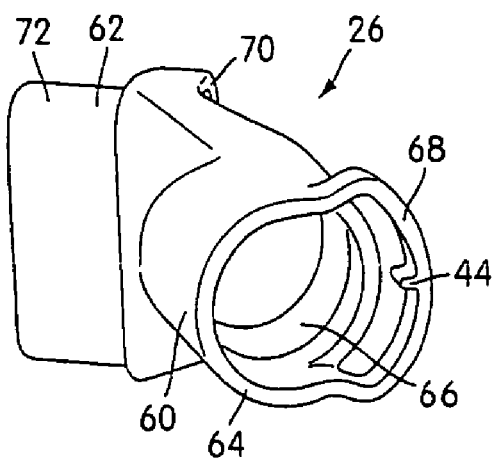
FIG. 10 is a rear perspective view of the inlet conduit and headgear connector assembly shown in FIG. 9.

As aforesaid, second connector portions 26 are provided to removably connect the headgear assembly 20 and the inlet conduits with the frame 16. As shown in FIGS. 9 and 10, each second connector portion 26 is a unitary polymeric piece (e.g., silicone) formed by injection molding, compression molding, or blow-molding, for example. Each second connector portion 26 includes a main body having a front portion 60 and a rear portion 62. The front portion 60 is interlocked with the first connector portion 24 provided on the frame 16 and the rear portion 62 is removably connected to the headgear assembly 20 and the inlet conduits. The front and rear portions 60, 62 are angled with respect to one another such that the second connector portions 26 follow the contour of the patient's face in use, as shown in FIG. 1.

Specifically, the front portion 60 provides a generally cylindrical conduit 64 having a recess 66 on an inner surface thereof. The recess 66 is adapted to receive the rib portions 40 of the plurality of arms 38 on the first connector portion 24. That is, the plurality of arms 38 are forced towards one another as the first connector portion 24 is inserted into the conduit 64 of the second connector portion 26. Once the rib portions 40 of the arms 38 reach the recess 66, the arms 38 can spring outwardly into the recess 66 to provide an interlocking engagement between the first and second connector portions 24, 26. To disengage the second connector portion 26 from the frame 16, the patient simply pulls the second connector portion 26 axially outwardly from the frame 16 with sufficient force to release the rib portions 40 from the recess 66.

The front portion 60 also provides a cross-bar 68 that provides the tooth 44 of the second connector portion 26. As discussed above, the tooth 44 engages the plurality of teeth 42 provided by the first connector portion 24 to allow selective rotational adjustment of the second connector portion 26 with respect to the first connector portion 24 and hence the frame 16. The cross bar 68 acts as a leaf spring to resiliently bias the tooth 44 into engagement with the teeth 42 of the first connector portion 24.

Figure 11:
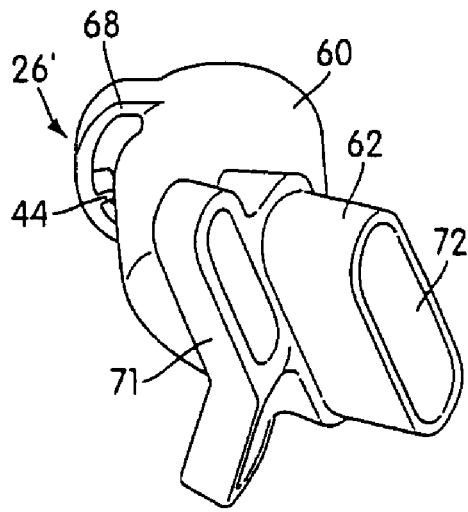
FIG. 11 is a perspective view of another embodiment of an inlet conduit and headgear connector assembly adapted to be used with the nasal assembly shown in FIG. 1.
Figure 12:
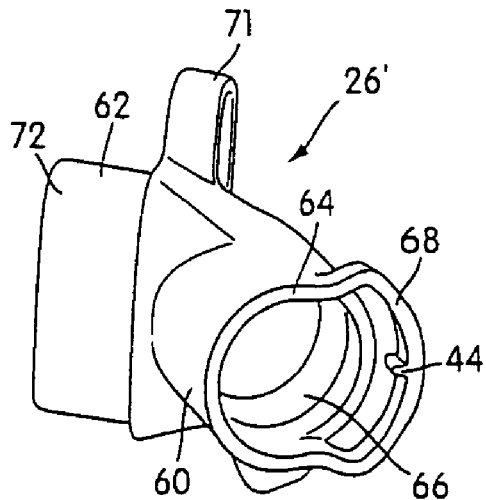
FIG. 12 is a rear perspective view of the inlet conduit and headgear connector assembly shown in FIG. 11.

As shown in FIGS. 9 and 10, the rear portion 62 of the second connector portion 26 includes a cross-bar 70 that forms an opening through which a strap of the headgear assembly 20 may pass and be removably connected. However, the cross-bar 70 may be configured to provide more than one opening for connection to the headgear assembly 20. For example, as shown in FIGS. 11 and 12, the second connector portion 26' includes a cross-bar 71 that provides a pair of openings through which a pair of straps of the headgear assembly 20 may pass and be removably connected.

The rear portion 62 also provides an elongated conduit 72 adapted to be connected to an inlet conduit that delivers breathable gas to the frame 16 and nozzle assembly 18. In the illustrated embodiment, the conduit 72 of the rear portion 62 has a different cross-sectional shape than the conduit 64 of the front portion 60 to facilitate connection to the inlet conduit. However, the conduits 72, 64 of the rear and front portions 62, 60, respectively, may have similar cross-sectional areas.

Figure 13:
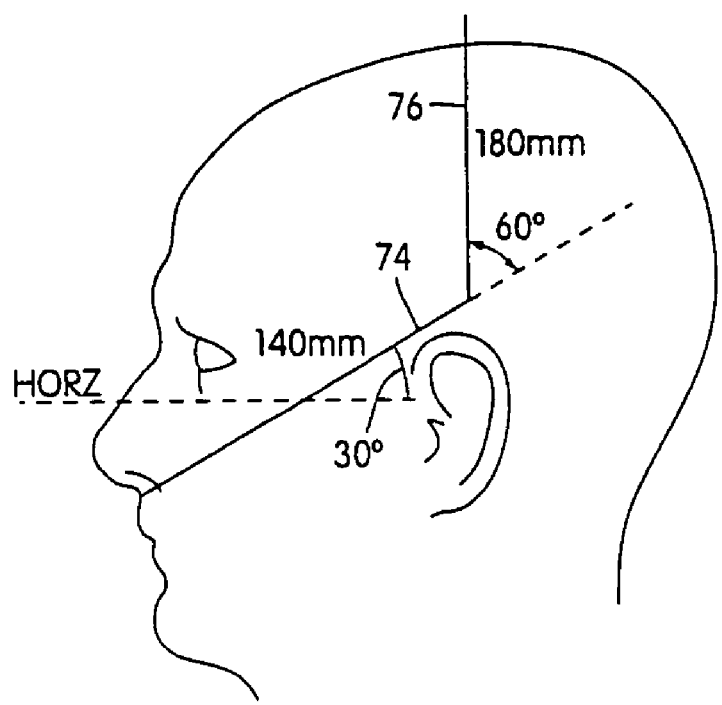
FIG. 13 is a side view illustrating an over-the-head inlet conduit routing for the nasal assembly shown in FIG. 1.
Figure 14:
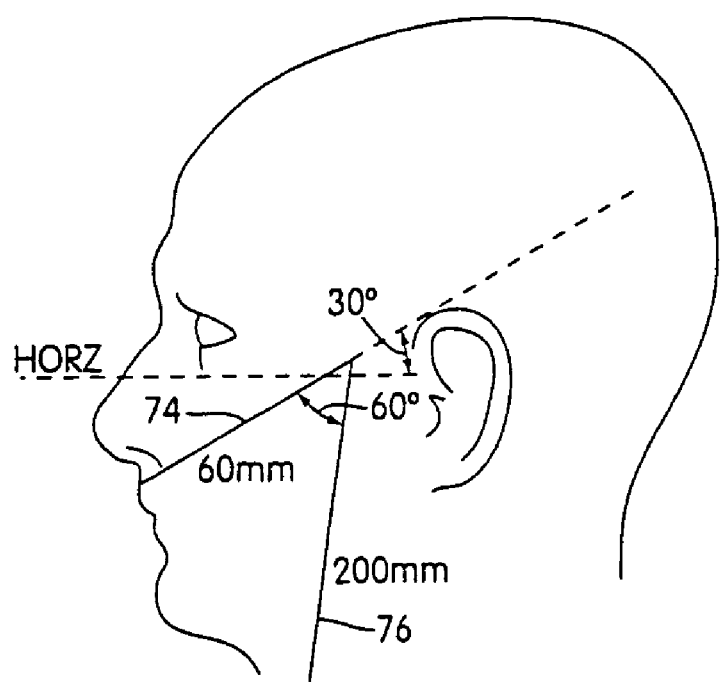
FIG. 14 is a side view illustrating an under-the-chin inlet conduit routing for the nasal assembly shown in FIG. 1.

FIGS. 13 and 14 schematically illustrate the routing of on of the first pair of inlet conduits 74 and one of the second pair of inlet conduits 76 of the nasal assembly 10. First ends of the first pair of conduits 74 are connected to respective conduits 72 of the second connector portions 26. Second ends of the first pair of conduits 74 are connected to respective first ends of the second pair of inlet conduits 76. Second ends of the second pair of inlet conduits are connected to a pressurized supply that supplies pressurized breathable gas. As a result, pressurized gas can pass through the first and second pairs of inlet conduits 74, 76 into the frame 16 and base portion 48, and through the nozzles 50 for breathing by the patient. As shown in FIG. 1, the frame 16 includes an exhaust vent 78 that protrudes slightly outwardly from the frame 16 and includes a series of openings for $CO_2$ washout.

As schematically shown in FIG. 13, the first and second pairs of inlet conduits 74, 76 may be routed to extend upwardly over the head of the patient. For example, in FIG. 13, the first pair of inlet conduits 74 may have a length of about 120-160 mm, preferably about 140 mm and the second pair of inlet conduits 76 may have a length of about 160-200 mm, preferably about 180 mm. However, other length dimensions may be used as well. In the illustrated embodiment, the first pair of inlet conduits 74 are angled about 30° from horizontal and the second pair of inlet conduits 76 are angled about 90° from horizontal, or about 60° from the first pair of inlet conduits 74. However, the first and second pairs of inlet conduits 74, 76 may have any suitable length and may be routed in any suitable manner to extend upwardly over the head of the patient.

Alternatively, as schematically shown in FIG. 14, the first and second pairs of inlet conduits 74, 76 may be routed to extend downwardly under the chin of the patient. For example, in FIG. 14, the first pair of inlet conduits 74 may have a length of about 40-80 mm, preferably about 60 mm and the second pair of inlet conduits 76 may have a length of about 180-220 mm, preferably about 200 mm. In the illustrated embodiment, the first pair of inlet conduits are angled about −20° to 40° from horizontal, preferably about 30° from horizontal and the second pair of inlet conduits 76 are angled about −90° from horizontal, or about −120° from the first pair of inlet conduits 74. However, the first and second pairs of inlet conduits may have any suitable length and may be routed in any suitable manner to extend upwardly over the head of the patient.

Figure 15:
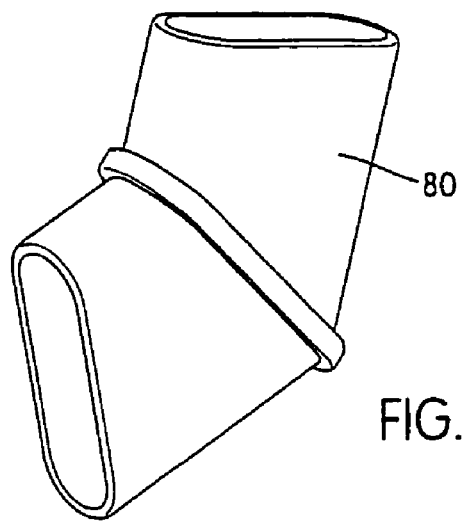
FIG. 15 is a perspective view illustrating a connector for use in routing the inlet conduits over the head of the patient.
Figure 16:
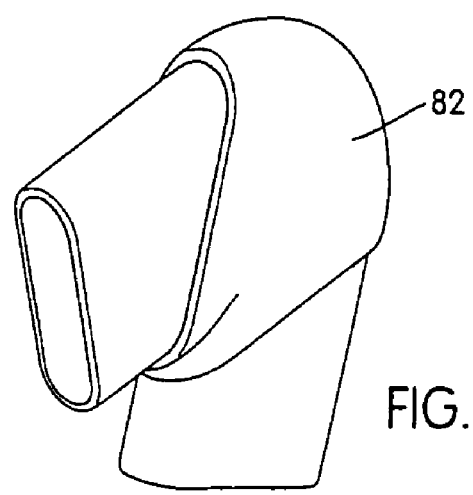
FIG. 16 is a perspective view illustrating a connector for use in routing the inlet conduits under the chin of the patient.

FIGS. 15 and 16 illustrate embodiments of connectors structured to interconnect the second ends of the first pair of conduits 74 with respective first ends of the second pair of inlet conduits 76. The connector 80 shown in FIG. 15 is suitably angled to route the conduits 74, 76 upwardly over the head of the patient. The connector 82 shown in FIG. 16 is suitably angled to route the conduits 74, 76 downwardly under the chin of the patient.

Figure 17:
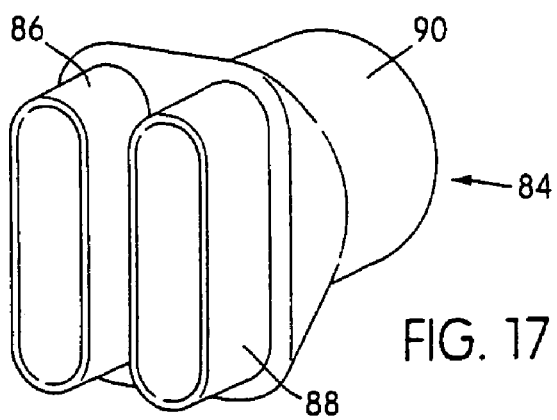
FIG. 17 is a perspective view illustrating a flow generator connector for use in connecting the nasal assembly shown in FIG. 1 to a pressurized supply.

FIG. 17 illustrates a flow generator connector 84 structured to interconnect the second ends of the second pair of inlet conduits 76 with a pressurized supply. Specifically, the flow generator connector 84 includes a first conduit 86 structured to connect to one of the second pair of inlet conduits 76 and a second conduit 88 structured to connect to the other of the second pair of inlet conduits 76. The flow generator connector 84 includes a third conduit 90 structured to connect to a conduit that is connected to the pressurized supply. The third connector 90 may include a swivel mechanism or flexible joint to allow relative movement between the flow generator connector 84 and the conduit associated with the pressurized supply.

In the illustrated embodiment, the inlet conduits 74, 76 provide a single air flow channel. However, the conduits 74, 76, connector portions 24, 26, and connectors 80, 82, 84 may be structured to provide more than one air flow channel.

The inlet conduits 74, 76 may be manufactured in any suitable manner. For example, the conduits 74, 76 may be extruded or the conduits may be injection molded. Also, the inlet conduits 74, 76 may be structured from any suitable polymeric material such as silicone or a thermoplastic elastomer, such as Krayton®, for example.

Also, the inlet conduits 74, 76 may be formed of crush-resistant, anti-crush or anti-kinking tubing such as that disclosed in U.S. Pat. No. 6,044,844, the entirety of which is incorporated herein by reference.

The inlet conduits 74, 76 and respective connector portions 24, 26 and/or connectors 80, 82, 84 may be retained with a friction-type fit, mechanical fasteners, adhesive, co-molded, insert molded, or any other suitable means.

In use, pressurized gas enters through connector 90 of the flow generator connector 84 and proceeds through the second set of inlet conduits 76 into the first set of inlet conduits 74 and into both side frame members 32 of the frame 16. Air passes through the frame 16, into the base portion 48 and nozzles 50, and into the nasal passages 12 of the patient. Exhaust gasses from the patient's nose can exit through the exhaust vent 78 provided in the frame 16.

Figure 18:
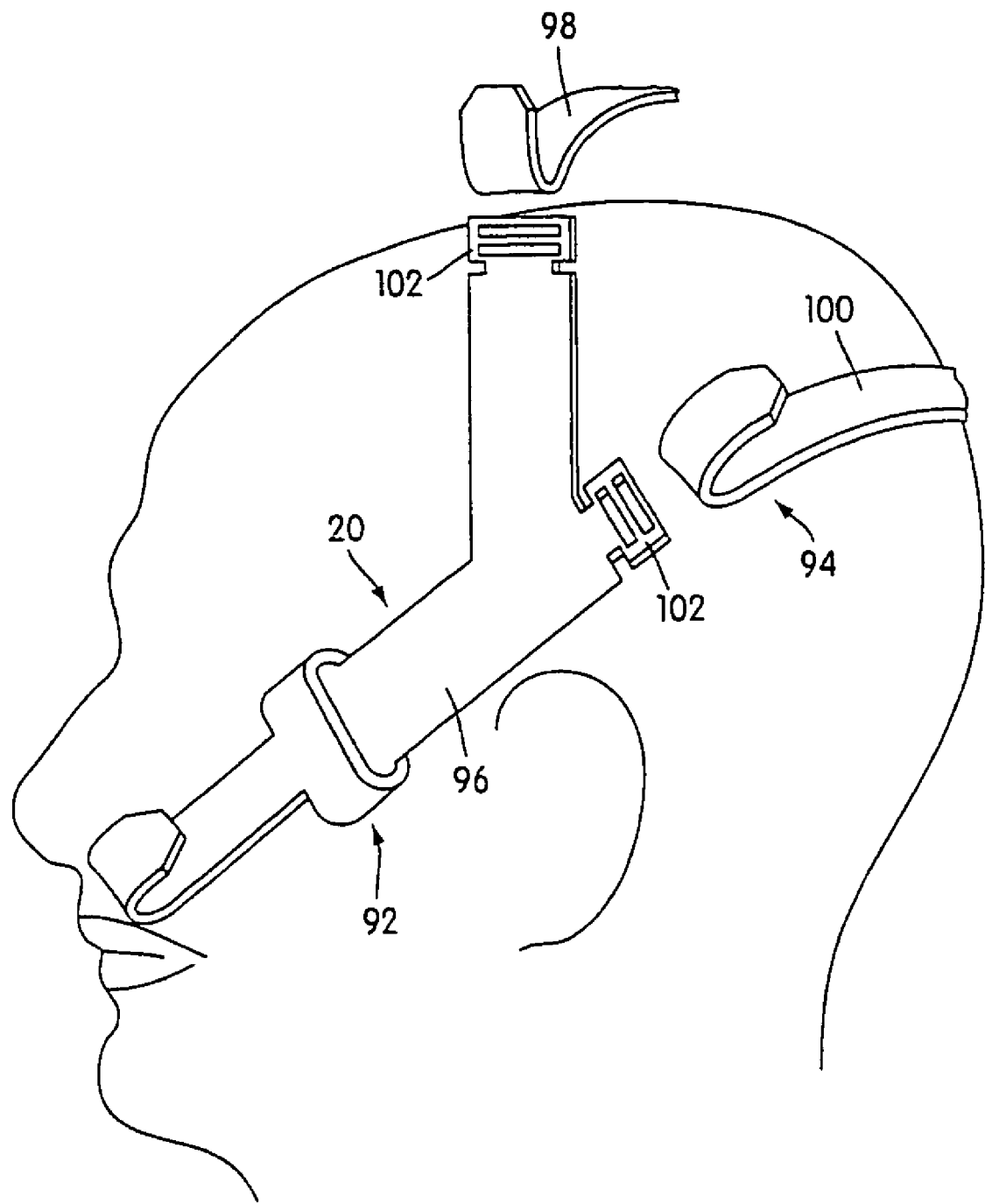
FIG. 18 is a side view illustrating an embodiment of headgear components for use with the nasal assembly shown in FIG. 1.

The headgear assembly 20 is removably attached to second connector portion 26 attached to the frame 16 to maintain the frame 16 and nozzle assembly 18 in a desired adjusted position on the patient's face. As shown in FIG. 18, the headgear assembly 20 includes two side portions 92 with a rear portion 94 connecting the side portions 92. Each side portion 92 comprises a side strap 96. The rear portion 94, which interconnects the two side portions 92, includes an upper strap 98 that passes over the top of the patient's head and a rear strap 100 that passes around the rear portion of the patient's head. However, the headgear assembly may be permanently attached to the frame.

Each side strap 96 is removably connected to the second connector portion 26. Specifically, the end portion of each side strap 96 has a reduced width that enables the side strap 96 to be wrapped around the cross-bar 70 provided on the second connector portion 26. Fastening of the side straps 96 to respective cross-bars 70 may be assisted by use of a hook and loop material, such as Velcro®. Thus, the side straps 96 may be adjusted with respect to the second connector portion 26 for proper fit.

The upper strap 98 and rear strap 100 are removably connected to the side straps 96 by buckles 102 provided on the side straps 96. The buckles 102 can be attached to the side straps 96 with adhesives, stitching and/or other known manners. In the illustrated embodiment, the buckles 102 includes a single cross-bar to enable the upper and rear straps 98, 100 to be coupled therewith. However, any other suitable buckle arrangement may be provided to interconnect the side straps 96 with the upper and rear straps 98, 100.

The straps 96, 98, 100 of the headgear assembly 20 may be constructed from a soft, flexible composite material. For example, the straps 96, 98, 100 may include two layers of material with one of the layers made of a fabric material and the other of the layers made of a polymeric material. Also, the headgear assembly 20 may include one or more stiffeners attached thereto in order to add to the rigidity of the headgear assembly 20 in certain planes and directions, which would assist in stabilizing the nasal assembly 10 on the head of the patient during use.

Further, the headgear assembly 20 may include any number of straps to support the nasal assembly 10 on the patient's head. For example, each of the side straps 96 may include a pair of straps to be used with the second connector portion 26' shown in FIGS. 11 and 12. Alternatively, the headgear assembly 20 may be constructed as a one piece structure.

As best shown in FIG. 1, the base portion 48 extends outwardly from the frame 16 to provide additional surface area or footprint area. As air under pressure enters the frame 16, the base portion 48 inflates, which moves the nozzles 50 into sealing engagement with the nasal passages 12 of the patient. For example, expansion of the base portion in the direction of the nostrils causes the nozzles to move into sealing engagement with the nasal passages.

Also, a portion of the sealing force may be provided by the first portion 56, which may be pre-loaded, like a spring, against the patient's nostril.

That is, the base portion 48 is structured such that it can expand and contract to alter a distance between the frame 16 and the nozzles 50. The base portion 48 moves the nozzles 50 between a first position in which the nozzles 50 are adjacent to the nasal passages 12 of the patient and a second position in which the nozzles 50 are moved into sealing engagement with the nasal passages 12 of the patient. Specifically, in an uninflated condition, the nozzles 50 are spaced from the nasal passages 12 of the patient or in light contact therewith. When the nasal assembly 10 is pressurized by a gas, the base portion 48 is inflated and moves the nozzles 50 into sealing engagement with the nasal passages 12 of the patient to form a seal between the nasal assembly 10 and the patient's nasal passages 12. As the gas pressure is increased, the force applied to the underside of the nasal passages is increased through the base portion 48.

The base portion 48 provides additional surface area or footprint area to the frame 16, which in turn provides an additional force on the nozzles 50 which increases the sealing efficiency of the nozzles 50. That is, the base portion 48 is configured and positioned to force the nozzles 50 into contact with the patient's nose. The force or pressure on the patient's nose is proportional to: (a) the pressure in the frame 16 and nozzle assembly 18; (b) additional surface area of the base portion 48; and/or (c) the preload from materials and geometry of nozzles 50 or base portion 48, including central wall 54 and first portion 56 of the base portion 48. Thus, the surface area of the base portion 48 may be varied, e.g., to vary the force or pressure applied to the patient's nose.

The side walls 52 of the base portion 48 may act as a spring structure to provide a component of force on the patient's face through the nozzles 50. The force may be tailored by adjusting the thickness of the side walls 52. Moreover, the thickness of the side walls 52 may be varied in conjunction with the additional surface area provided by the base portion 48. Thus, the force provided by the base portion 48 along with the air pressure provides an effective sealing force against the nasal passages 12 of the patient.

The base portion 48 reduces the headgear assembly tension required to achieve a suitable seal. That is, the sealing force applied to the patient's nose may be provided by the base portion 48, preload and/or air pressure, and not by the tension from the headgear assembly 20. This improves patient comfort as well as sealing properties.

Accordingly, it is desirable when adjusting the headgear assembly 20 to bring the nozzles 50 only near or in very light contact with the patient's nose. In this way, the base portion 48 is not compressed substantially. In use, contact will need to be sufficient for seal.

The base portion 48 also provides a decoupling joint between the frame 16 and the nozzles 50, thus allowing some relative movement between the nasal assembly 10 and the user's face. As a result, the nozzles 50 can accommodate small variations in the shape of the patient's nasal features without undue force, and can account for small movement of the nasal assembly 10 relative to the patient's nose during use, while maintaining an effective seal.

Moreover, the connection assembly 22 including the first and second connector portions 24, 26 enables the position of the nozzles 50 to be easily adjusted with respect to the patient's nose. Specifically, the patient can rotate the frame 16 with respect to the headgear assembly 20 to adjust the positioning of the nozzles 50.

Also, the base portion 48 need not be a single base form discussed above, but can have alternative configurations. For example, the base portion 48 may be in the form of two or more base portions provided in series.

Figure 19:
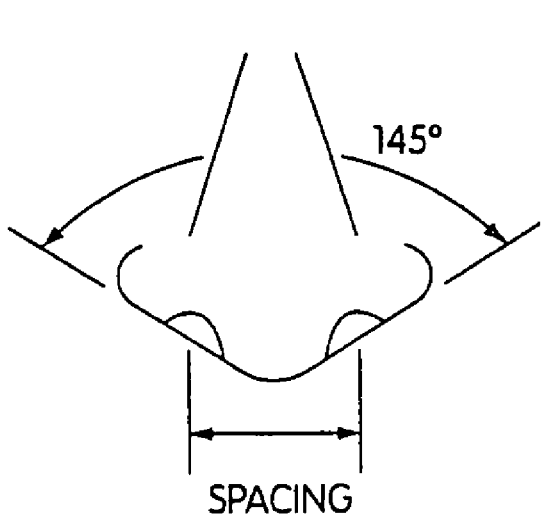
FIG. 19 is a schematic view illustrating a patient's nose having a substantially flat alar angle.
Figure 20:
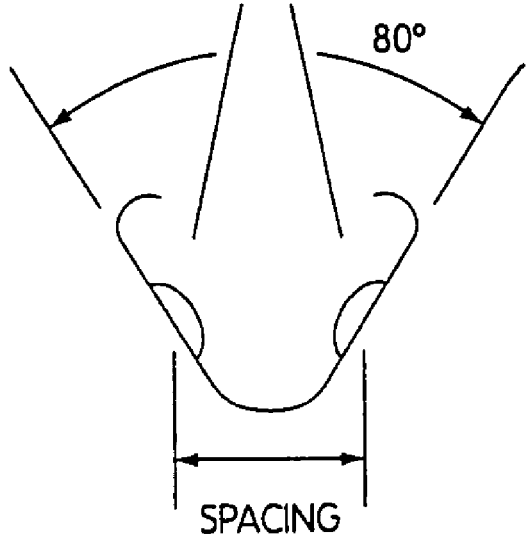
FIG. 20 is a schematic view illustrating a patient's nose having a substantially steep alar angle.

As shown in FIGS. 5 and 6, end portions of the base portion 48 are angled with respect to one another so as to angle the nozzles 50 attached thereto with respect to one another. This angle, also referred to as an alar angle, can be adjusted to accommodate different shaped noses of patients. For example, the nozzle assembly 10 shown in FIGS. 5 and 6 has an alar angle in the range of 135-155°, preferably about 145°, to accommodate a substantially flat nose (see FIG. 19). Alternatively, the alar angle may be in the range of 70-90°, preferably about 80°, to accommodate a substantially pointed or steep nose (see FIG. 20). However, the alar angle may have any suitable size to accommodate any shape nose. Movement of the nozzles helps accommodate steeper noses.

Figure 21:
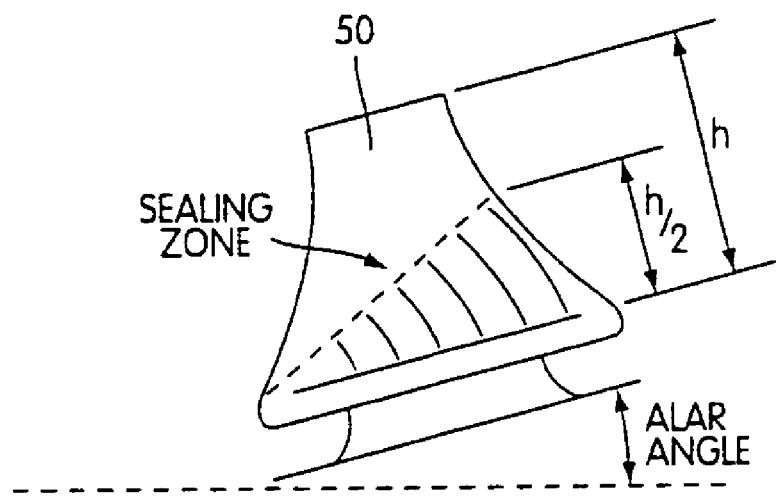
FIG. 21 is a schematic view illustrating an embodiment of a sealing zone of a nozzle.

As shown in FIG. 21, the sealing zone of the nozzle 50 may extend at an angle from about half the height of the nozzle 50. In the illustrated embodiment, the nozzle 50 has a height of about 9 mm. However, the nozzle 50 may have any suitable height and may provide any suitable sealing zone.

The nozzles 50 are appropriately spaced with respect to one another on the base portion 48. The spacing is based on the size of the nozzles 50 and the available space on the base portion 48.

Figure 22:
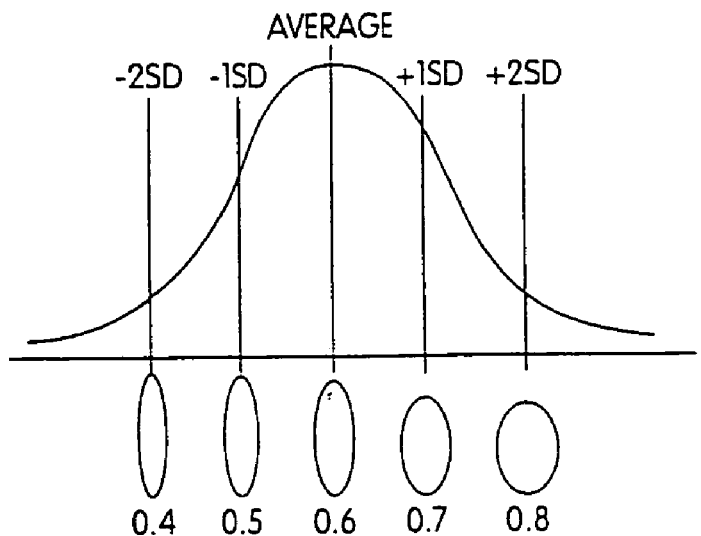
FIG. 22 is a graph illustrating average nostril ratios opening/entrance.
Figure 23:
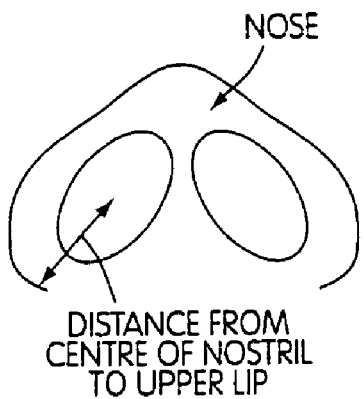
FIG. 23 is a schematic view illustrating an embodiment for calculating a base major axis of a nozzle.
Figure 24:
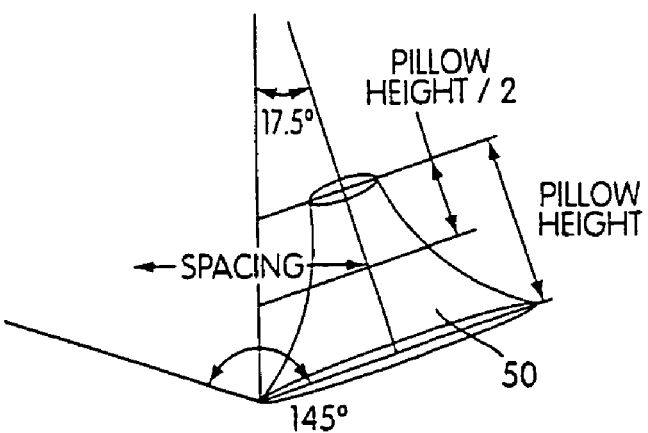
FIG. 24 is a schematic view illustrating an embodiment for calculating a base minor axis of a nozzle.

The size of the nozzles 50 is based on the patient's nostril circumference. In one embodiment, ellipse ratios may be used to determine nozzle geometry (see FIG. 22). For example, an ellipse ratio of 0.7 (Average+1 Standard Deviation) may be used to determine nozzle geometry. As shown in FIG. 23, the base major axis of the nozzle may be defined by measurement from the center of a nostril to the upper lip. As shown in FIG. 24, the base minor axis of the nozzle may be defined by the maximum space available between nozzles. However, any other suitable method may be used to determine the size of the nozzles.

The above-noted alar angle, sealing zone, spacing between nozzles, and size of the nozzles may be determined so that a wide range of patients can be accommodated. Also, different size nasal assemblies, e.g., small, medium, and large, may be provided to accommodate different size patients. However, any other suitable measurements and methods may be used to provide a nasal assembly that fits the widest range of patients.

One aspect of the invention relates to a nasal assembly that provides separate sealing and stability forces. That is, the nasal assemblies are structured such that the stability forces that act to maintain the nasal assembly on the patient's face are separated or at least better distinguished from the sealing forces that act to maintain a seal between the nasal assembly and the patient's face. In use, the sealing forces act on more sensitive regions of the patient's face, e.g., nose, and the stability forces act on less sensitive regions of the patient's face, e.g., upper lip, cheeks and back of the patient's head. Moreover, the stability forces tend to be higher than the sealing forces. Thus, the nasal assembly is structured such that the higher stability forces are substantially separated from the lower sealing forces to improve patient comfort.

Specifically, the nasal assembly is structured such that stability forces applied by the headgear assembly are distributed to the back of the patient's head, the patient's cheeks, and the patient's upper lip to maintain the nasal assembly on the patient's face in use. The nasal assembly includes the nozzle assembly structured to apply sealing forces to nasal passages of the patient's nose in use. Features of the headgear have been designed to achieve substantially independent adjustment of sealing and stability forces. Thus, the higher stability forces do not effect the more sensitive regions of the patient's face, e.g., nose, as much.

Another aspect of the invention relates to the association between the nozzles and the base portion to apply a force to the patient's face. Specifically, the base portion is structured to apply a component of force to the patient's face and the nozzles are structured to apply a component of force to the patient's face.

As shown in FIG. 1, for example, the base portion may have a substantially rigid structure such that it applies a relatively small component of force on the patient's face. That is, the base portion may not be substantially inflatable or expandable when pressurized by a gas. In contrast, the nozzles may have a flexible structure such that they provide a relatively larger component of force on the patient's face. That is, the first portion 56 of the nozzles 50 may act as a spring structure, e.g., spring-loaded or resilient, to provide a component of force on the patient's face through the nozzles 50. By spring-loaded, it is meant that the nozzles apply a predetermined force against the user's nasal sealing area, for sealing purposes. Preferably, nozzles are preloaded before introducing pressurized gas to provide a sealing force with the user. As a result, the base portion and nozzles together provide a force to provide a seal between the nasal assembly and the patient's nasal passages.

Alternatively, the base portion may have a flexible structure such that it applies a relatively large component of force on the patient's face when inflated. In contrast, the nozzles may have a more rigid structure such that they apply a relatively smaller component of force on the patient's face. As a result, the base portion and nozzles together provide a force to provide a seal between the nasal assembly and the patient's nasal passages.

Thus, the nozzle assembly may be structured such that the nozzles are spring-loaded or resilient to apply a sufficient component of force for sealing. Thus, the base portion can be structured more rigidly to apply a smaller component of force for sealing. Alternatively, the nozzle assembly may be structured such that the base portion is sufficiently expandable to apply a sufficient component of force for sealing and the nozzles can be structured more rigidly to apply a smaller component of force for sealing. Alternatively, the nozzles may be substantially rigid, e.g., where the nozzles are tailored for a particular user. This alternative can be combined with the earlier embodiment (relating rigid base portions and spring-loaded (e.g. preloaded) nozzles). In this event, the base of the nozzle may be structured to provide a variable amount of preload, and the sealing portion of the nozzle, preferably tailored to the user, may be relatively more rigid. Also, the nozzle assembly may be structured such that the base portion and nozzles provide substantially similar components of force for sealing.

Second Illustrated Embodiment

Figure 25:
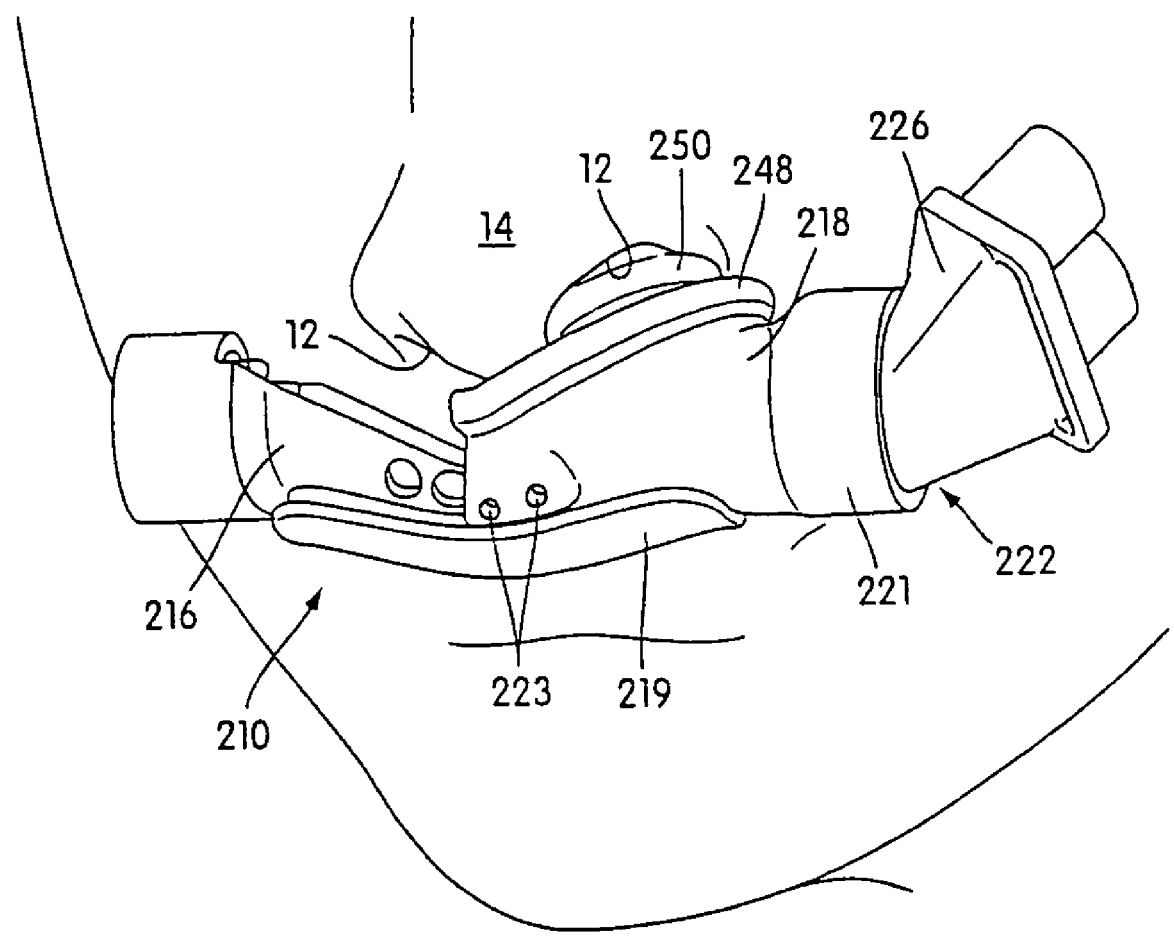
FIG. 25 is a partial perspective view illustrating another embodiment of a nasal assembly mounted to a patient's head and engaged with nasal passages of the patient.
Figure 26:
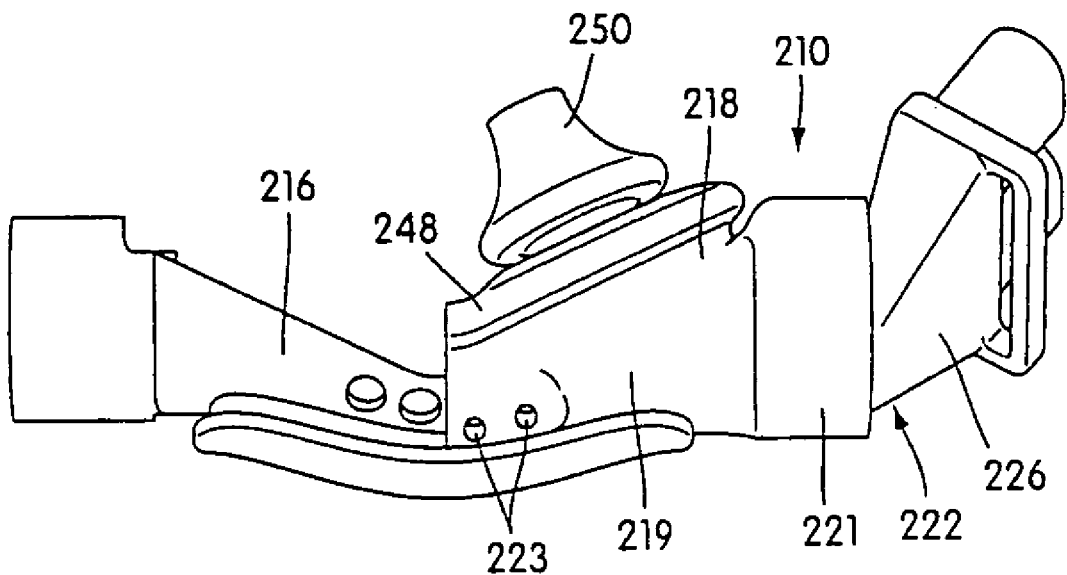
FIG. 26 is a partial front perspective view of the nasal assembly shown in FIG. 25.
Figure 27:
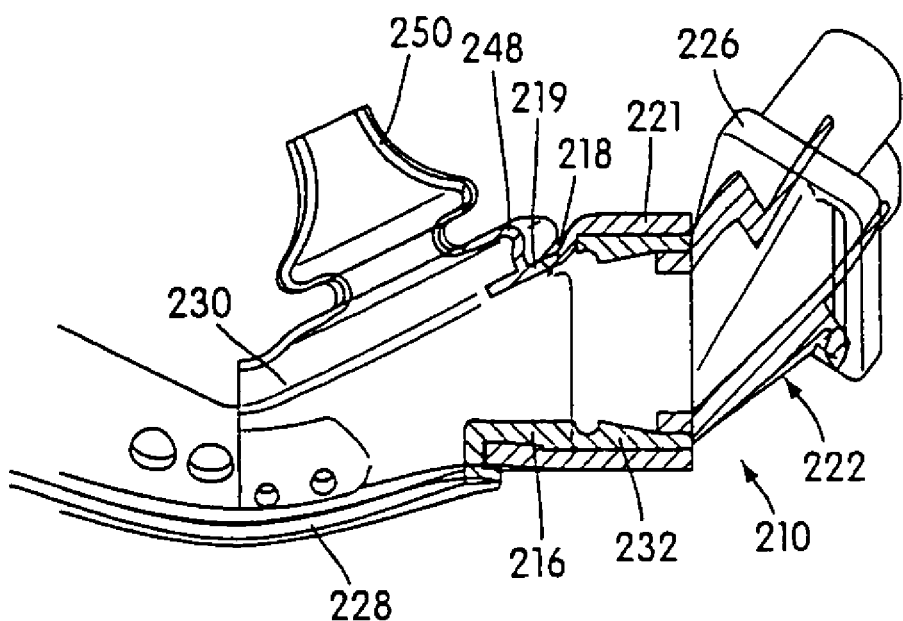
FIG. 27 is a cross-sectional view of the nasal assembly shown in FIG. 25.

FIGS. 25-37 illustrate another embodiment of a nasal assembly, indicated as 210. As best shown in FIGS. 25-27, the nasal assembly 210 includes a frame 216 and a nozzle assembly 218 that is removably connected to the frame 216. A headgear assembly 220 (see FIG. 37) is removably attached to the frame 216 to maintain the frame 216 and nozzle assembly 218 in a desired adjusted position on the patient's face. Inlet conduits 274 (see FIGS. 36 and 37) are also removably attached to the frame 216 to deliver breathable gas into the frame 216 and nozzle assembly 218 for breathing by the patient. The headgear assembly 220 and inlet conduits 274 are removably attached to the frame 216 by an inlet conduit and headgear connection assembly 222. The connection assembly 222 includes first connector portions 224 (see FIGS. 28 and 29) provided by the frame 216 and second connector portions 226 adapted to be removably coupled with the first connector portions 224. The second connector portions 226 are removably connected to the headgear assembly 220 and the inlet conduits 274, as will be further discussed.

Figure 28:
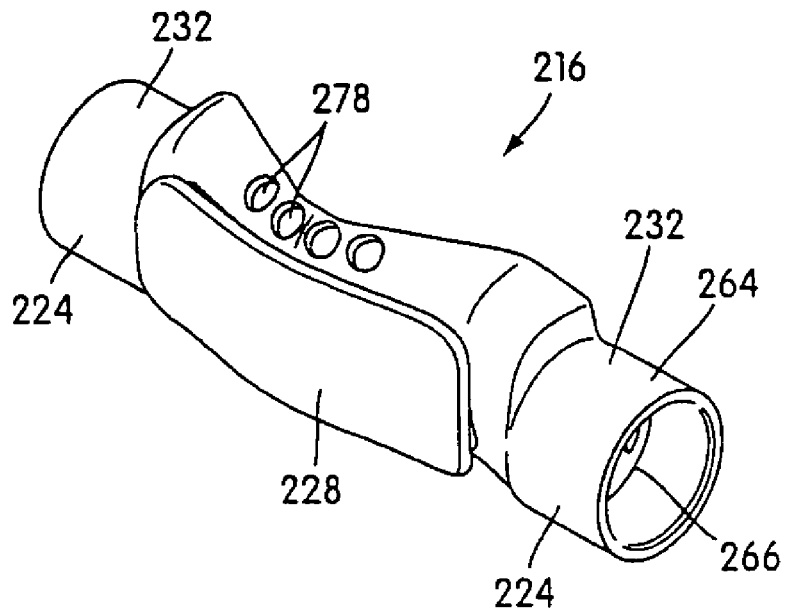
FIG. 28 is a front perspective view of a frame of the nasal assembly shown in FIG. 25.
Figure 29:
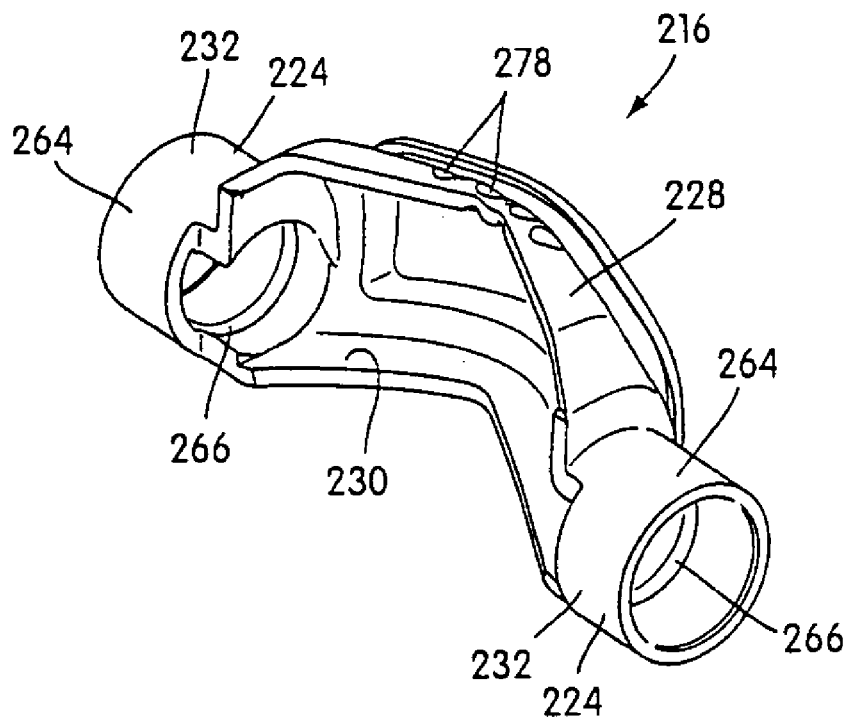
FIG. 29 is a rear perspective view of the frame shown in FIG. 28.
Figure 30:
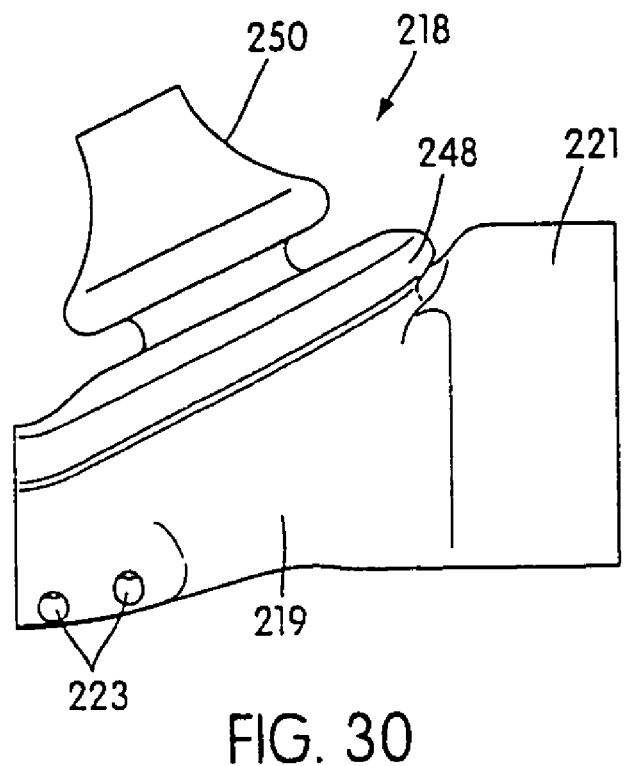
FIG. 30 is a partial front perspective view of a half of the nozzle assembly of the nasal assembly shown in FIG. 25.
Figure 31:
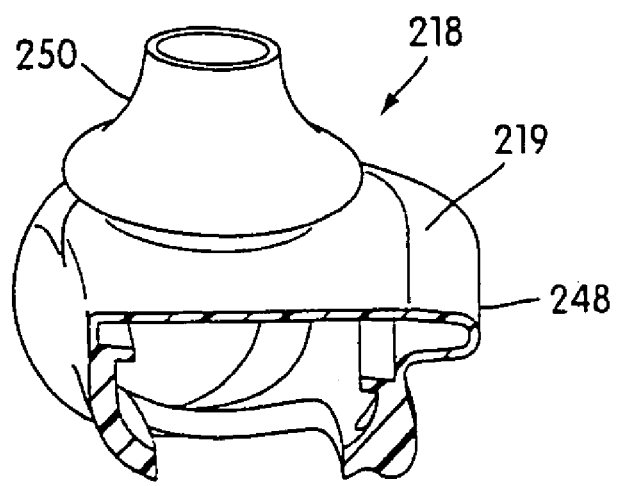
FIG. 31 is a side cross-sectional view of the nozzle assembly shown in FIG. 30.

As shown in FIGS. 28 and 29, the frame 216 includes a main body 228 that provides a central opening 230 for accommodating the nozzle assembly 218. The frame 216 also includes side frame members 232 provided on each lateral side of the main body 228. Each side frame member 232 includes a first connector portion 224 that is integrally formed therewith. The first connector portion 224 is in the form of a conduit 264 having a recess 266 on an inner surface thereof. The frame 216 also includes a series of openings 278 for $CO_2$ washout.

As shown in FIGS. 25-27 and 30-31, the nozzle assembly 218 forms a conduit that includes a main body 219 and opposing end portions 221 (only half of the nozzle assembly 218 is shown in the figures). As best shown in FIG. 27, the end portions 221 are stretched over the side frame members 232 of the frame 216 with the main body 219 in covering relation to the main body 228 and central opening 230 of the frame 216. When the nozzle assembly 218 is attached to the frame 216, the frame 216 adds rigidity to the relatively flexible nozzle assembly 218.

The main body 219 of the nozzle assembly 218 includes a gusset portion 248 and a pair of nozzles 250 attached thereto. The nozzles 250 may be designed and structured in a similar manner to the nozzles 50 described above. The main body 219 of the nozzle assembly also includes a series openings 223 that align with the series of openings 278 provided on the frame 216 for $CO_2$ washout.

Figure 32:
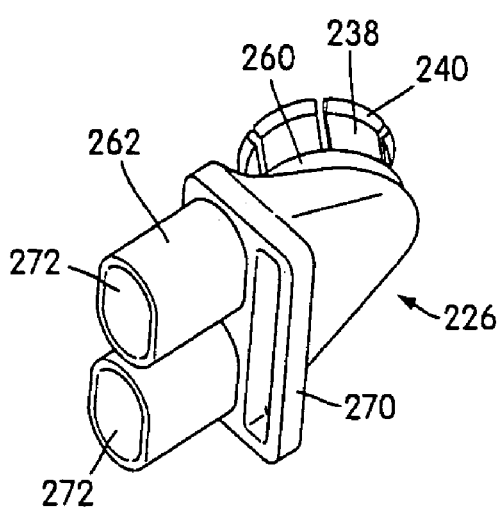
FIG. 32 is a perspective view illustrating an embodiment of an inlet conduit and headgear connector assembly of the nasal assembly shown in FIG. 25.
Figure 33:
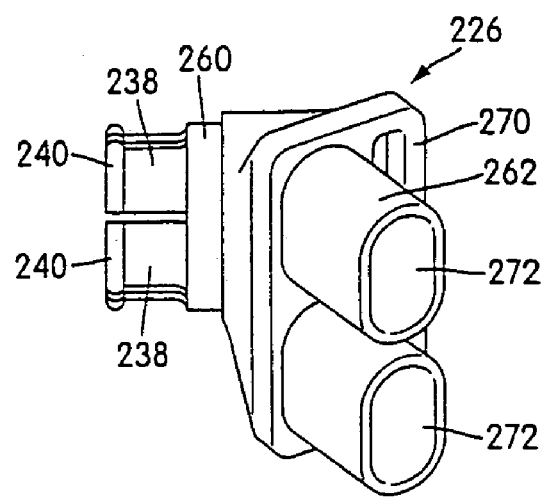
FIG. 33 is a rear perspective view of the inlet conduit and headgear connector assembly shown in FIG. 32.
Figure 34:
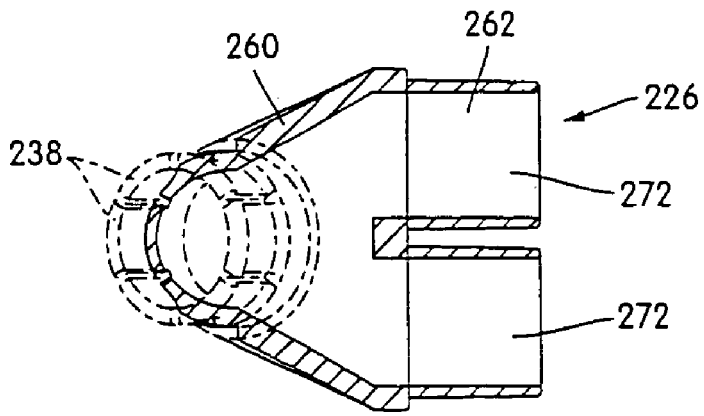
FIG. 34 is a cross-sectional view of the inlet conduit and headgear connector assembly shown in FIG. 32 with the flexible arms in phantom.

As shown in FIGS. 32-34, the second connector portion 226 includes a main body having a front portion 260 and a rear portion 262. The front portion 260 includes a plurality of resiliently flexible arms 238 that are structured to flex radially inwardly and outwardly. Each arm 238 provides a rib portion 240 at the free end thereof. In use, the rib portions 240 of the plurality of arms 238 are adapted to engage within the recess 266 of the first connector portion 224 for coupling the first and second connector portions 224, 226 with one another. In contrast to the connection assembly 22 described above, the connection assembly 222 does not provide an indexing section. Thus, the second connector portion 226 may rotate with respect to the first connector portion 224 for an infinite amount of settings for alignment of the nozzles 250 with respect to the nasal passages of the patient. The settings may be locked by way of friction, for example.

The rear portion 262 of the second connector portion 226 includes a cross-bar 270 that forms an opening through which a strap of the headgear assembly 220 may pass and be removably connected. The rear portion 262 also provides a pair of conduits 272 adapted to be connected to an inlet conduit that delivers breathable gas to the frame 216 and nozzle assembly 218.

Figure 36:
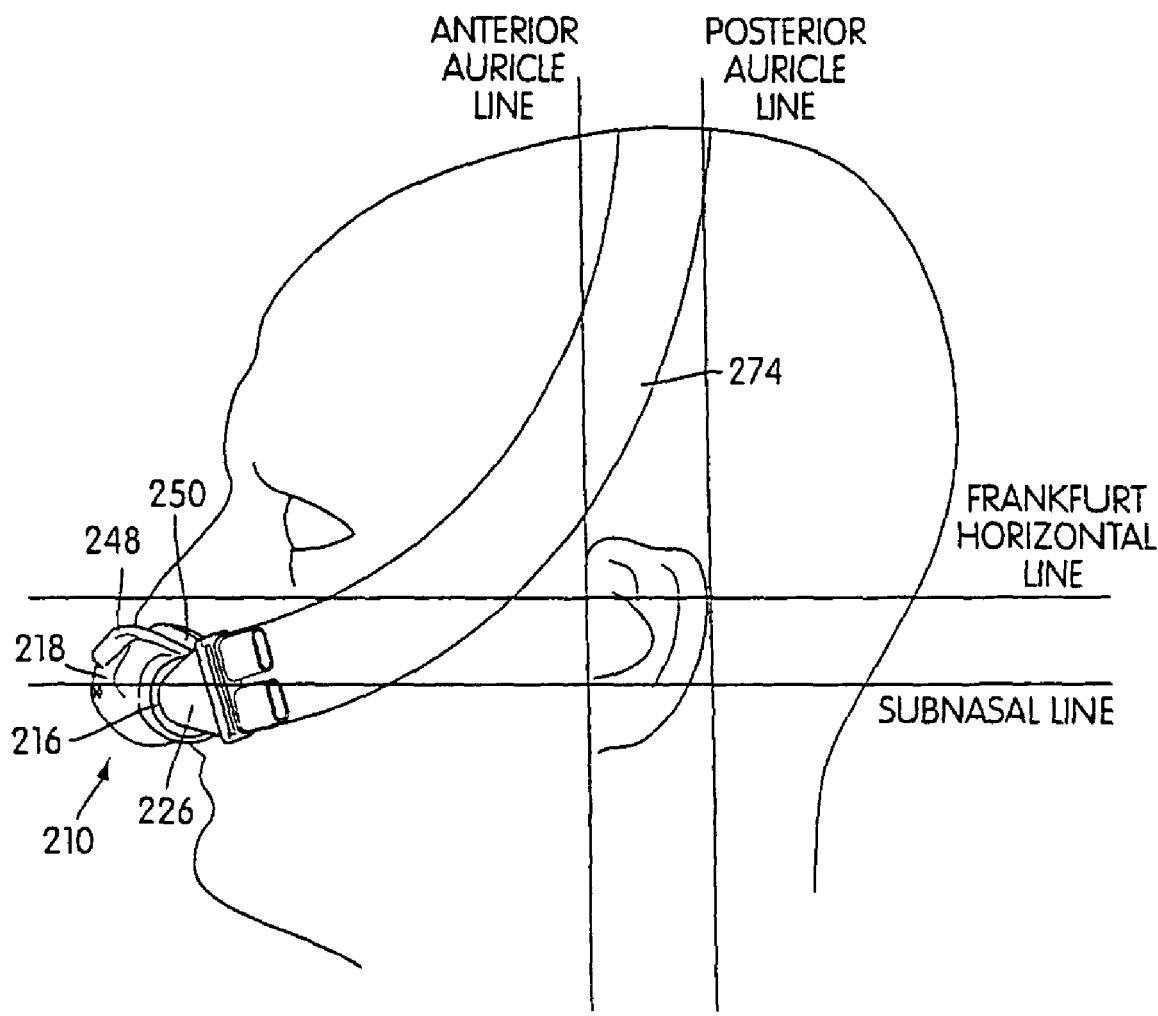
FIG. 36 is a side view illustrating the routing of the inlet conduits of the nasal assembly shown in FIG. 25.
Figure 37:
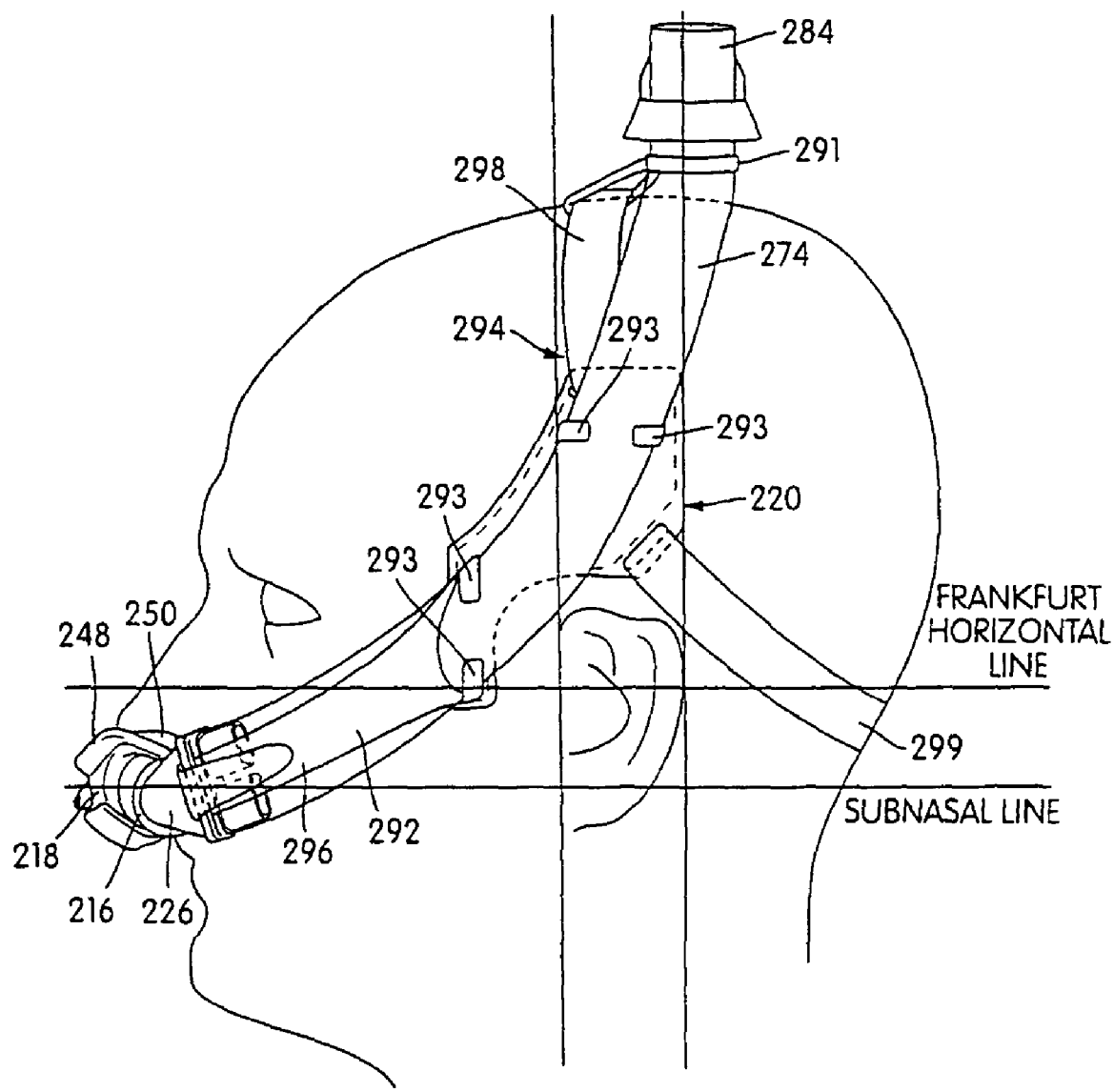
FIG. 37 is a side view illustrating the nasal assembly shown in FIG. 25 mounted to a patient's head.

As shown in FIG. 36, the nasal assembly 210 includes a pair of inlet conduits 274 (only one of the inlet conduits 274 being visible in FIG. 36). First ends of the pair of conduits 274 are connected to respective second connector portions 226 connected to the frame 216. Second ends of the pair of conduits 274 are connected to a pressurized supply that supplies pressurized breathable gas. As shown in FIGS. 36 and 37, the pair of inlet conduits 274 are routed to extend upwardly over the head of the patient. However, the pair of inlet conduits 274 may be routed in any suitable manner, e.g., routed to extend downwardly under the chin of the patient.

As a result, pressurized gas can pass through the pair of inlet conduits 274 into the frame 216 and nozzle assembly 218, and through the nozzles 250 for breathing by the patient.

Figure 35:
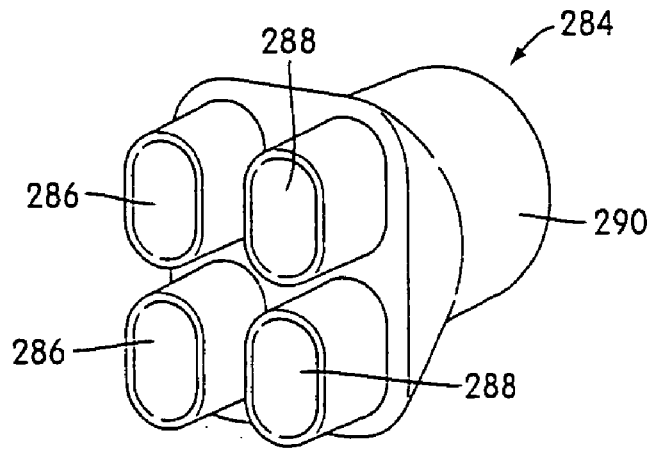
FIG. 35 is a perspective view of a flow generator connector for use in connecting tubes for use with the nasal assembly shown in FIG. 25 to a pressurized supply.

FIG. 35 illustrates a flow generator connector 284 structured to interconnect the second ends of the pair of inlet conduits 274 with a pressurized supply. Specifically, the flow generator connector 284 includes a pair of first conduits 286 structured to connect to one of the pair of inlet conduits 274 and a pair of second conduits 288 structured to connect to the other of the pair of inlet conduits 274. The flow generator connector 284 includes a third conduit 290 structured to connect to a conduit that is connected to the pressurized gas, air, or fluid supply. The third connector 290 may include a swivel or flexible joint mechanism to allow relative movement between the flow generator connector 284 and the conduit associated with the pressurized supply. Also, the third connector 290 may include a ball and socket joint so that when the third connector 290 is on top of the patient's head in an over the head configuration, the tube pull is minimized.

In the illustrated embodiment, the inlet conduits 274 provide a dual air flow channel with a central support wall to prevent kinking and occlusion. However, the conduits 274, connector portions 224, 226, and connector 284 may be structured to provide one air flow channel or more than two air flow channels.

The headgear assembly 220 is removably or fixedly attached to second connector portion 226 attached to the frame 216 to maintain the frame 216 and nozzle assembly 218 in a desired adjusted position on the patient's face. As shown in FIG. 37, the headgear assembly 220 includes two side portions 292 (only one of the side portions 292 being visible in FIG. 37) with a rear portion 294 connecting the side portions 292. Each side portion 292 comprises a side strap 296. The rear portion 294, which interconnects the two side portions 292, includes an upper strap 298 that passes over the top of the patient's head and a rear strap 299 that passes around the rear portion of the patient's head. Upper and rear strap 298, 299 can be adjusted for fit and can be a single strap or loop. Also, the headgear assembly may be permanently attached to the frame.

Each side strap 296 has a reduced width that enables the side strap 296 to be wrapped around the cross-bar 270 provided on the second connector portion 226. Fastening of the side straps 296 to respective cross-bars 270 may be assisted by use of a hook and loop material, such as Velcro®. Thus, the side straps 296 may be adjusted with respect to the second connector portion 226 for proper fit.

Openings or buckles are provided on the side straps 296 to enable the upper and rear straps 298, 299 to be coupled therewith. However, the headgear assembly 220 may include any number of straps to support the nasal assembly 210 on the patient's head. Alternatively, the headgear assembly 220 may be constructed as a one piece structure.

As shown in FIG. 37, the headgear assembly 220 includes a retaining strap 291 to hold the flow generator connector 284 and the inlet conduits 274 in a position over the head of the patient. The headgear assembly 220 also includes retaining prongs 293 to hold the inlet conduits 274 adjacent to the headgear assembly 220 as they extend upwardly over the head of the patient.

Similar to the nasal assembly 10 described above, the force provided by the gusset portion 248 along with the air pressure provides an effective sealing force against the nasal passages 12 of the patient. Thus, the gusset portion 248 reduces the headgear assembly tension required to achieve a suitable seal. Also, the position of the nozzles 250 may be adjusted with respect to the user's nose to improve patient comfort.

As shown in FIG. 25, for example, the gusset portion 248 has a flexible structure such that it applies a relatively large component of force on the patient's face when inflated. In contrast, the nozzles have a more rigid structure such that they apply a relatively smaller component of force on the patient's face. That is, the first portion of the nozzles may have less of a spring-load to provide a relatively small component of force on the patient's face through the nozzles. As a result, the gusset portion and nozzles together provide a force to provide a seal between the nasal assembly and the patient's nasal passages.

Third Illustrated Embodiment

Figure 38:
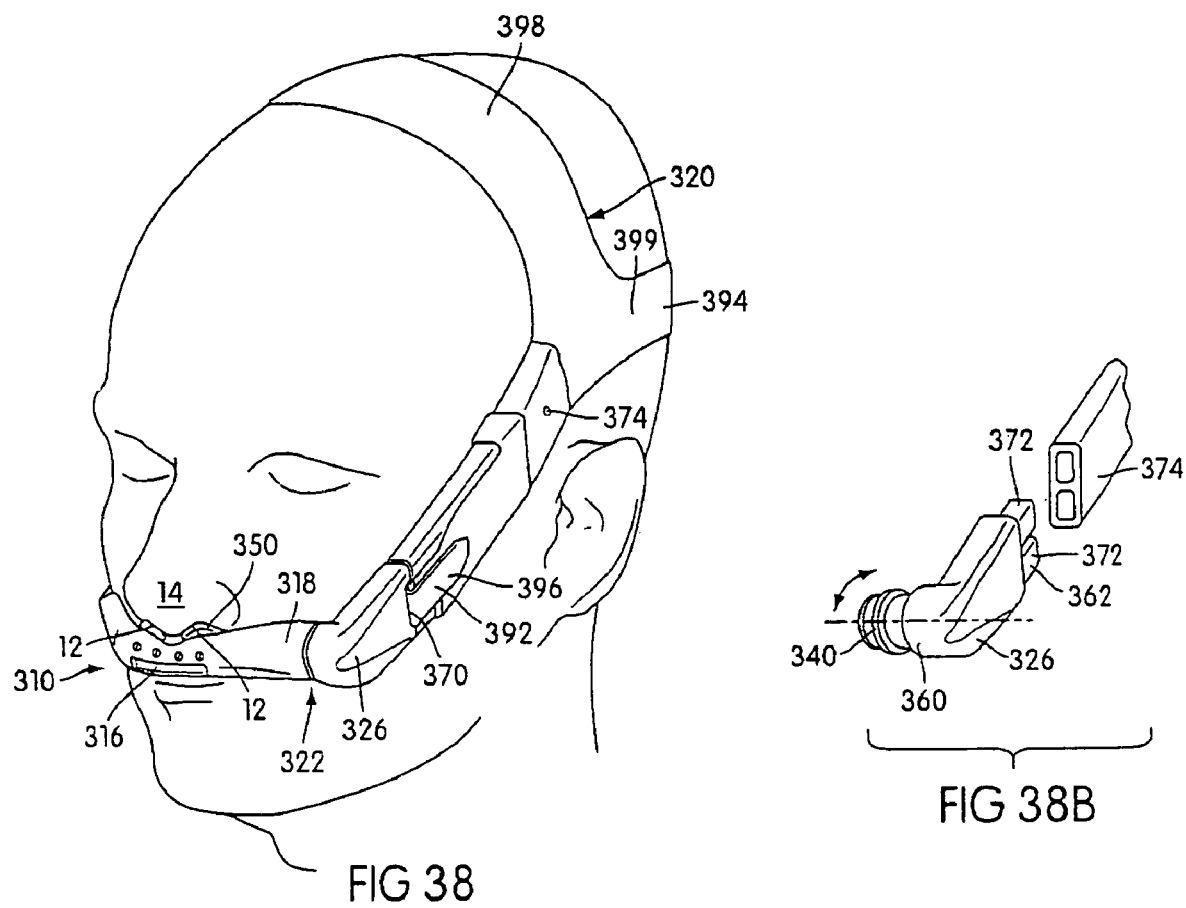
FIG. 38 is a perspective view illustrating another embodiment of a nasal assembly mounted to a patient's head and engaged with nasal passages of the patient.
Figure 39:
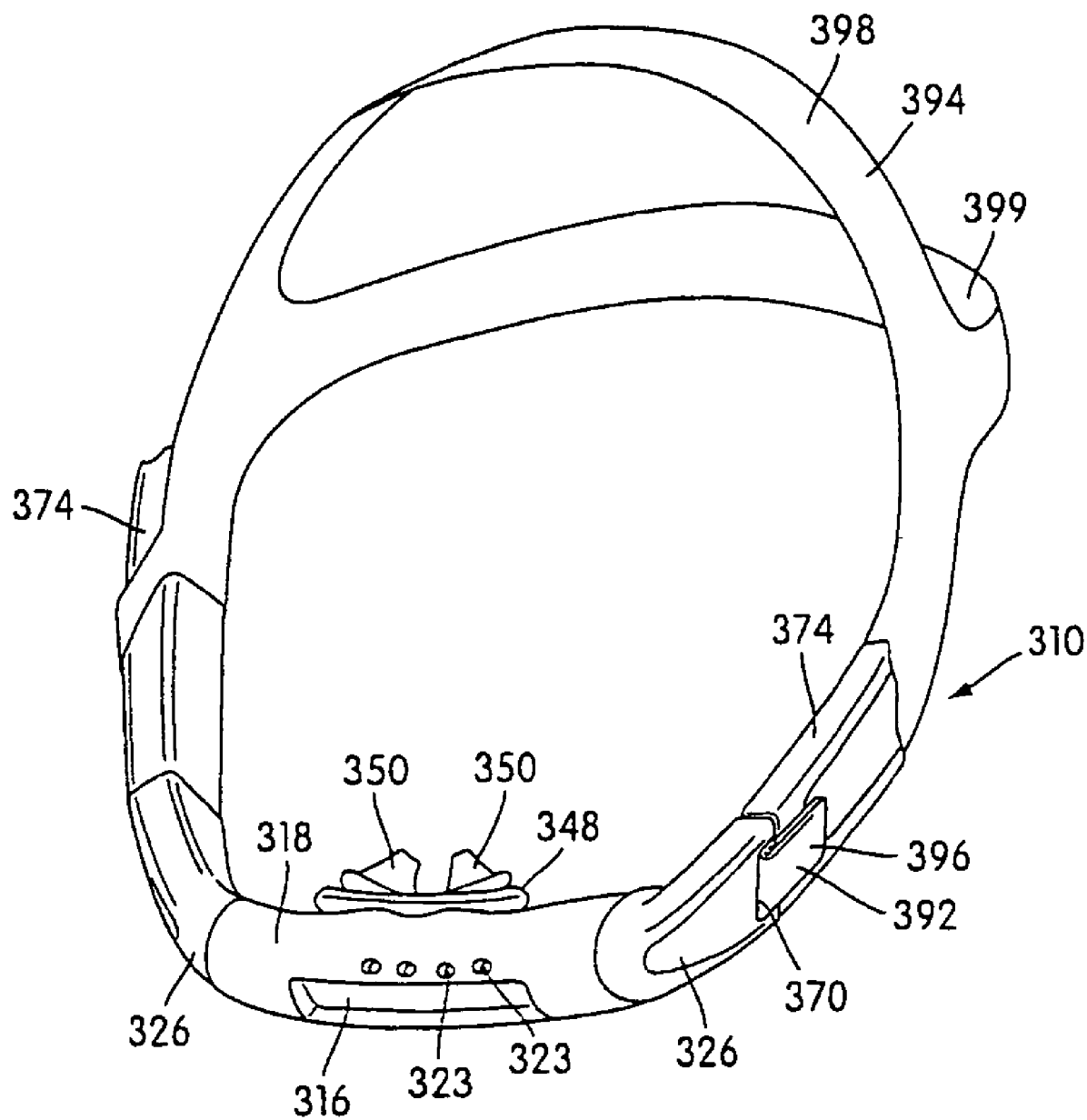
FIG. 39 is a perspective view of the nasal assembly shown in FIG. 38.
Figure 42:
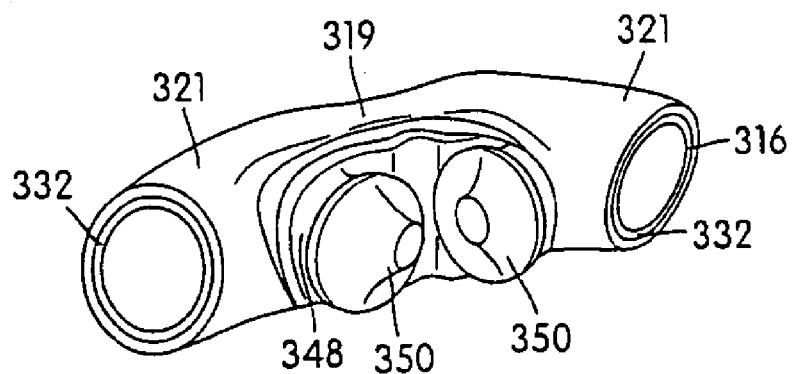
FIG. 42 is a perspective view illustrating the nozzle assembly shown in FIG. 41 mounted to the frame to shown in FIG. 40.
Figure 43:
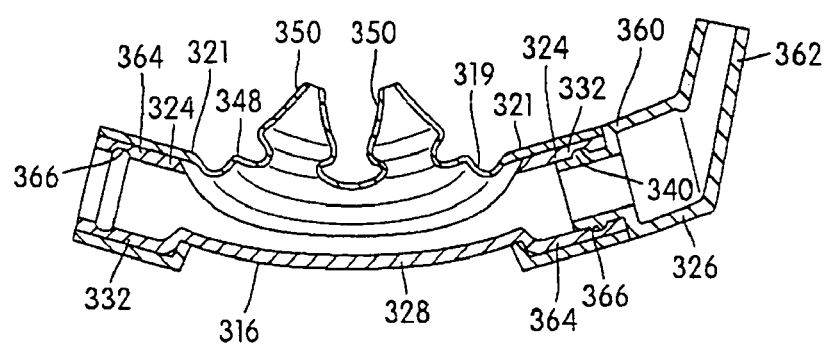
FIG. 43 is a cross-sectional view of the nasal assembly shown in FIG. 38.

FIGS. 38-51 illustrate another embodiment of a nasal assembly, indicated as 310. As best shown in FIGS. 38, 39, and 43, the nasal assembly 310 includes a frame 316 and a nozzle assembly 318 that is removably connected to the frame 316. A headgear assembly 320 is removably attached to the frame 316 to maintain the frame 316 and nozzle assembly 318 in a desired adjusted position relative to the patient's face. Inlet conduits 374 are also removably attached to the frame 316 to deliver breathable gas into the frame 316 and nozzle assembly 318 for breathing by the patient. The headgear assembly 320 and inlet conduits 374 are removably attached to the frame 316 by an inlet conduit and headgear connection assembly 322. The connection assembly 322 includes first connector portions 324 (see FIGS. 40 and 43) provided by the frame 316 and second connector portions 326 adapted to be removably coupled with the first connector portions 324. The second connector portions 326 are removably connected to the headgear assembly 320 and the inlet conduits 374, as will be further discussed.

Figure 40:
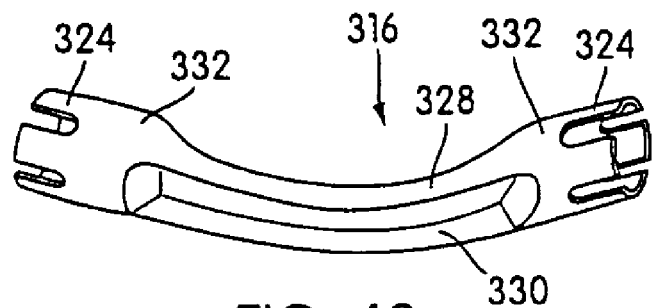
FIG. 40 is a perspective view of a frame of the nasal assembly shown in FIG. 38.

As shown in FIG. 40, the frame 316 includes a main body 328 that provides a central opening 330 for accommodating the nozzle assembly 318. The frame 316 also includes side frame members 332 provided on each lateral side of the main body 328. Each side frame member 332 includes a first connector portion 324 that is integrally formed therewith. The first connector portion 324 is in the form of a conduit 364 having a recess 366 (see FIG. 43) on an inner surface thereof.

Figure 41:
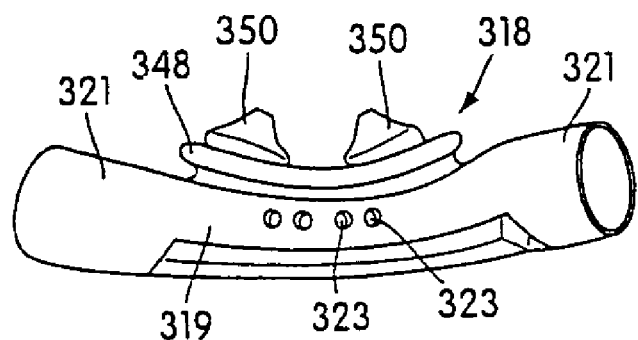
FIG. 41 is a perspective view of a nozzle assembly of the nasal assembly shown in FIG. 38.
Figure 44:
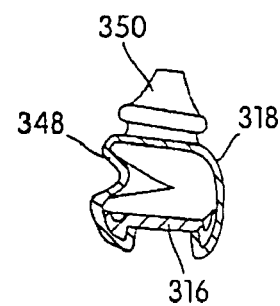
FIG. 44 is a side cross-sectional view of the nasal assembly shown in FIG. 38.

As shown in FIG. 41, the nozzle assembly 318 forms a conduit that includes a main body 319 and opposing end portions 321. As best shown in FIGS. 42, 43, and 44, the end portions 321 are stretched over the side frame members 332 of the frame 316 with the main body 319 in covering relation to the main body 328 and central opening 330 of the frame 316. When the nozzle assembly 318 is attached to the frame 316, the frame 316 and nozzle assembly 318 form a conduit for delivering breathable gas to the patient's nose. Also, the frame 316 adds rigidity or structural integrity to the relatively flexible nozzle assembly 318.

As shown in FIGS. 43 and 44, the main body 319 of the nozzle assembly 318 includes a base portion 348 and a pair of nozzles 350 attached thereto. The nozzles 350 may be designed and structured in a similar manner to the nozzles 50 described above. The main body 319 of the nozzle assembly 318 also includes one or more openings 323 (e.g., see FIGS. 39 and 41) for $CO_2$ washout.

As shown in FIGS. 38B and 43, the second connector portion 326 includes a main body having a front portion 360 and a rear portion 362. The front portion 360 includes a rib portion 340. In use, the rib portion 340 is adapted to engage within the recess 366 of the first connector portion 324 for coupling the first and second connector portions 324, 326 with one another. Similar to the connection assembly 222 described above, the second connector portion 326 may rotate with respect to the first connector portion 324 for an infinite amount of settings for alignment of the nozzles 350 with respect to the nasal passages of the patient. The setting may be optionally locked by friction, for example.

As shown in FIGS. 38 and 38B, the rear portion 362 of the second connector portion 326 includes an opening 370 through which a strap of the headgear assembly 320 may pass and be removably connected. As shown in FIG. 38B, the rear portion 362 also provides a pair of conduits 372 adapted to be connected to an inlet conduit that delivers breathable gas to the frame 316 and nozzle assembly 318.

Figure 45:
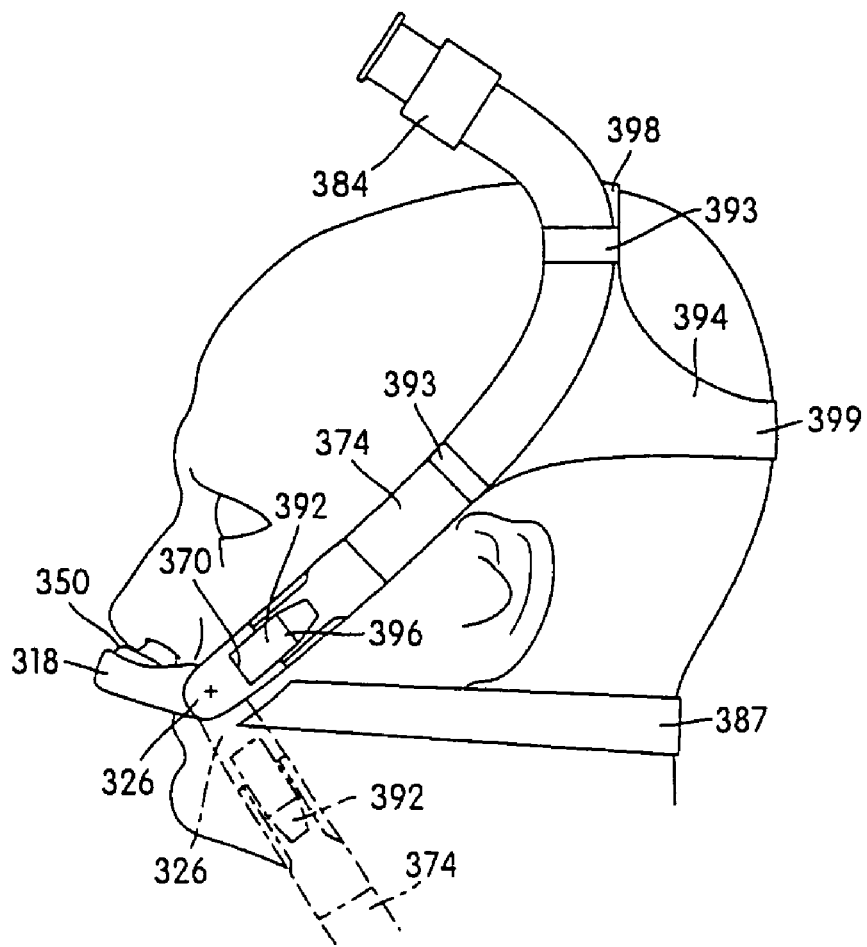
FIG. 45 is a side view illustrating the nasal assembly shown in FIG. 38 mounted to a patient's head showing two inlet configurations.

As shown in FIGS. 38, 39, and 45, the nasal assembly 310 includes a pair of inlet conduits 374. First ends of the pair of conduits 374 are connected to respective second connector portions 326 connected to the frame 316. Second ends of the pair of conduits 374 are connected to a pressurized supply that supplies pressurized breathable gas. As shown in FIG. 45, the second connector portions 326 may be rotated with respect to the first connector portions 324 to route the pair of inlet conduits 374 upwardly over the head of the patient or downwardly under the chin of the patient, for example.

As a result, pressurized gas can pass through the pair of inlet conduits 374 into the frame 316 and nozzle assembly 318, and through the nozzles 350 for breathing by the patient.

Figure 47:
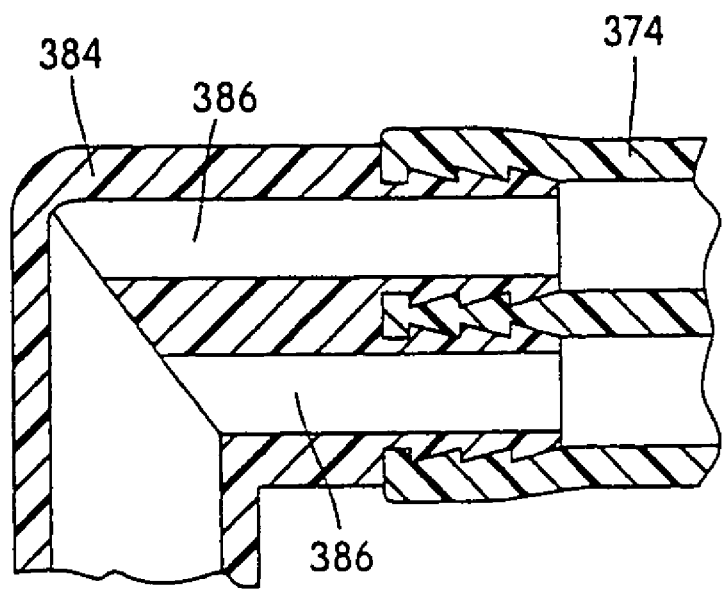
FIG. 47 is a cross-sectional view of an embodiment of an inlet conduit engaged with an embodiment of an angle connector for delivering breathable gas.
Figure 48:
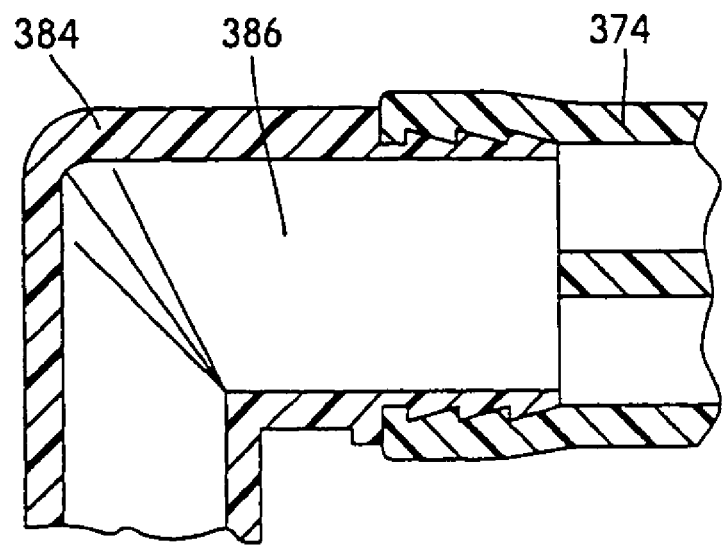
FIG. 48 is a cross-sectional view illustrating another embodiment of an inlet conduit engaged with another embodiment of a flow generator connector for delivering breathable gas.

FIGS. 45, 47, and 48 illustrate an angle connector 384 structured to interconnect the second ends of the pair of inlet conduits 374 with a pressurized supply. As shown in FIG. 47, the connector 384 may include a pair of double-conduits 386 to connect to respective inlet conduits 374. Alternatively, as shown in FIG. 48, the flow generator connector 384 may include a pair of single-conduits 386 to connect to respective inlet conduits 374. The end of the dual air flow channel inlet conduit 374 may be amended, as shown in FIG. 48, to facilitate connection with the connector 384 having a pair of single-conduits 386. Also, the ends of the inlet conduit 374 may include a series of ridges that interlock with a series of ridges provided on the connector 384 to reliably connect the inlet conduits 374 with the connector 384, as shown in FIGS. 47 and 48.

Figure 47B:
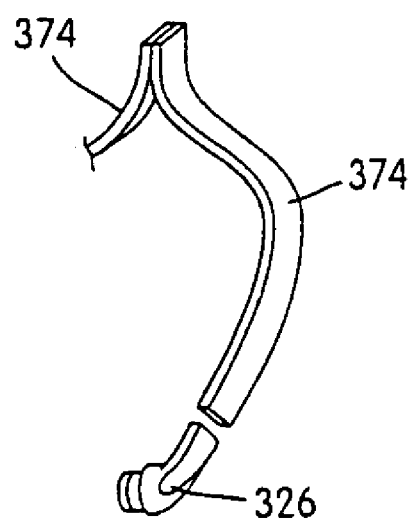
FIG. 47B is a perspective view illustrating another embodiment of an inlet conduit.
Figure 48B:
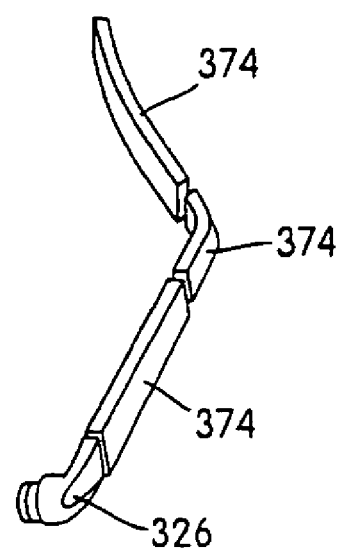
FIG. 48B is perspective view illustrating another embodiment of an inlet conduit.
Figure 49:
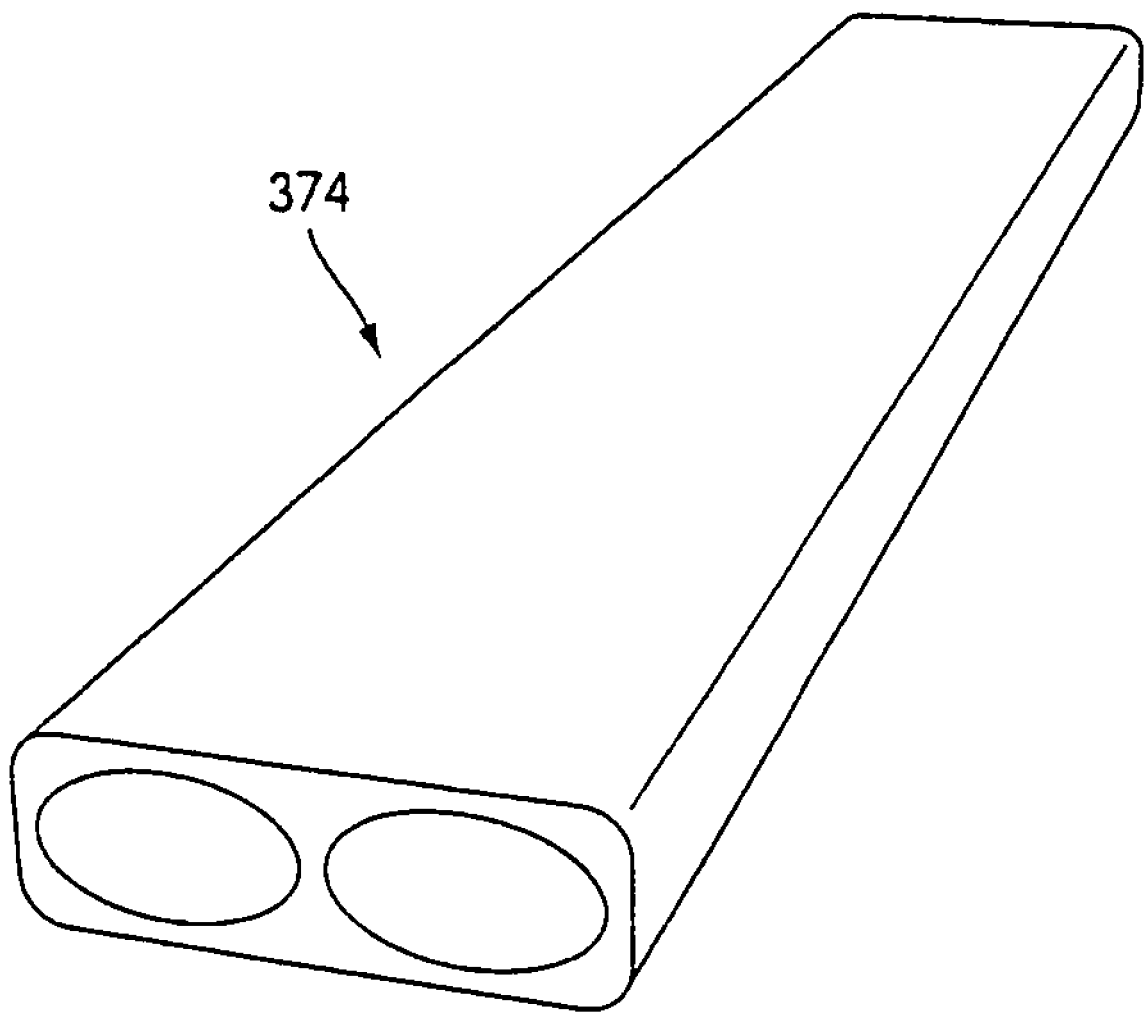
FIG. 49 is a perspective view illustrating an embodiment of an inlet conduit of the nasal assembly shown in FIG. 38.

As shown in FIG. 49, the inlet conduits 374 provide a dual air flow channel with a central support wall to prevent kinking or occlusion, e.g., anti-crush, and facilitate connection. Also, the inlet conduits may be constructed from a harder material, e.g., harder durometer silicone, to prevent kinking or occlusion. However, the conduits 374, connector portions 324, 326, and connector 384 may be structured to provide one air flow channel or more than two air flow channels. As shown in FIG. 47B, the inlet conduits 374 may be extruded or otherwise manufactured in one piece. Alternatively, as shown in FIG. 48B, the inlet conduits 374 may include a plurality of conduits formed by injection molding, co-molding, or insert molding, and connected to one another in any suitable manner, e.g., by connectors and/or other fasteners such as adhesive, or the entire assembly could be molded in one piece, thereby reducing components and complexity.

The headgear assembly 320 is removably attached to second connector portion 326 attached to the frame 316 to maintain the frame 316 and nozzle assembly 318 in a desired adjusted position on the patient's face. As shown in FIGS. 38, 39, and 45, the headgear assembly 320 includes two side portions 392 with a rear portion 394 connecting the side portions 392. Each side portion 392 comprises a side strap 396. The rear portion 394, which interconnects the two side portions 392, includes an upper strap 398 that passes over the top of the patient's head and a rear strap 399 that passes around the rear portion of the patient's head. As shown in FIG. 45, the rear portion 394 may include a second rear strap 387 to add additional stability.

Each side strap 396 has a reduced width that enables the side strap 396 to be wrapped around the opening 370 provided on the second connector portion 326. Fastening of the side straps 396 to respective openings 370 may be assisted by use of a hook and loop material, such as Velcro®. Thus, the side straps 396 may be adjusted with respect to the second connector portion 326 for proper fit.

In the illustrated embodiment, the headgear assembly 320 is constructed as a one piece structure. However, the headgear assembly 320 may include a plurality of straps suitably arranged to support the nasal assembly 310 on the patient's head. As shown in FIG. 45, the headgear assembly 320 may include retaining straps 393 to hold the inlet conduits 374 upwardly over the head of the patient.

Figure 50:
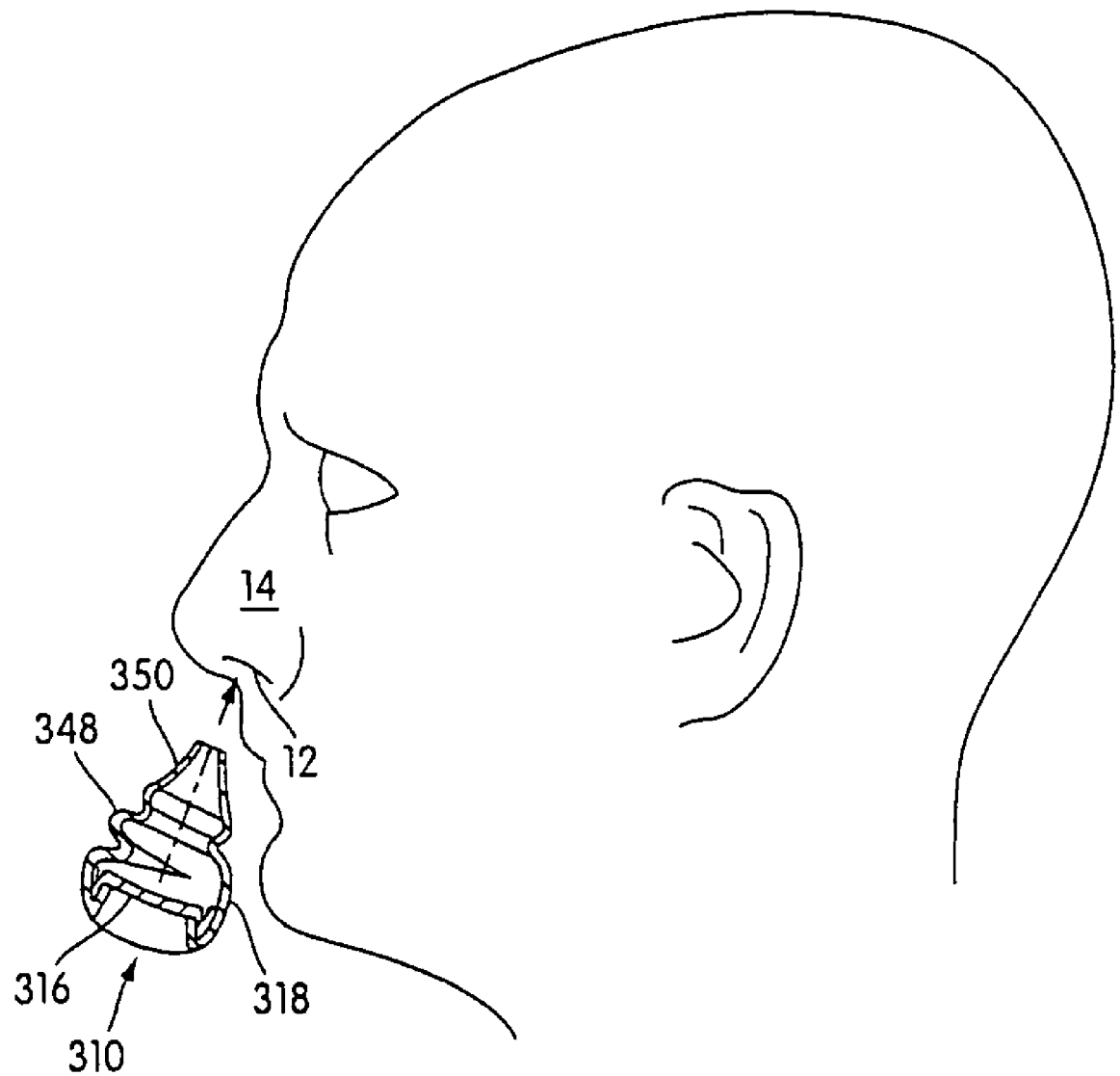
FIG. 50 is a side view illustrating the nasal assembly shown in FIG. 38 prior to engagement with nasal passages of the patient.
Figure 51:
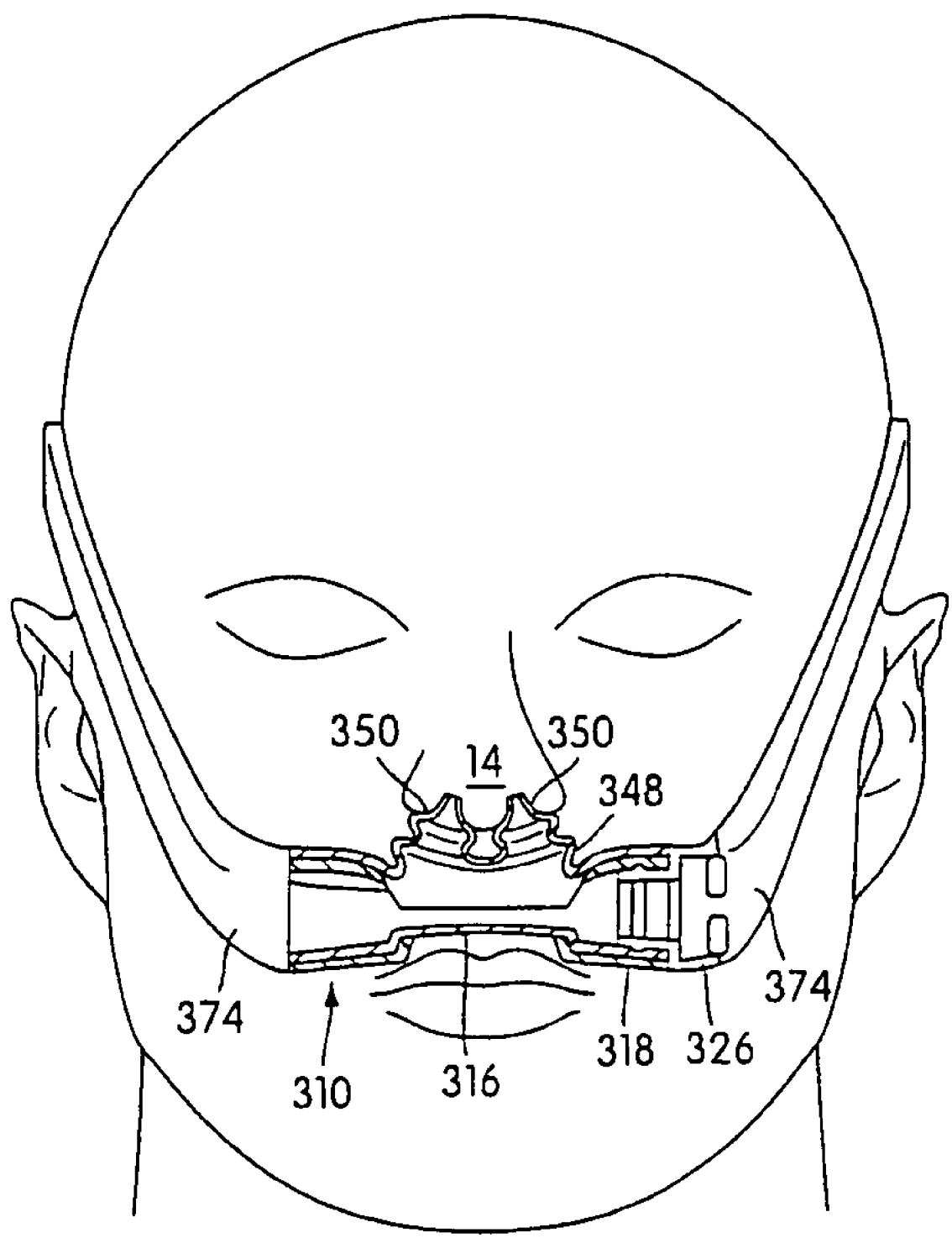
FIG. 51 is a front view illustrating the nasal assembly shown in FIG. 38 (in cross-section) engaged with nasal passages of the patient.

FIG. 50 illustrates the nasal assembly 310 about to be engaged with nasal passages 12 of a patient's nose 14. FIG. 51 illustrates the nasal assembly 310 engaged with nasal passages 12 of a patient's nose. The patient's upper lip contacts the silicone outer surface of the nozzle assembly 318 to help maintain the nasal assembly 310 in position on the patient's face.

Similar to the nasal assembly 10 described above, the force provided by the base portion 348 along with the air pressure provides an effective sealing force against the nasal passages 12 of the patient. Thus, the base portion 348 reduces the headgear assembly tension required to achieve a suitable seal. Also, the position of the nozzles 350 may be adjusted with respect to the user's nose to improve patient comfort.

As shown in FIG. 43, for example, the base portion 348 has a flexible structure such that it applies a relatively large component of force on the patient's face when inflated. In contrast, the nozzles have a more rigid structure such that they apply a relatively smaller component of force on the patient's face. That is, the first portion of the nozzles may have less of a spring-load to provide a relatively small component of force on the patient's face through the nozzles. As a result, the base portion and nozzles together provide a force to provide a seal between the nasal assembly and the patient's nasal passages.

Further, the base portion 348 may be structured to provide customized forces in desired directions, e.g., inwardly directed force to assist with sealing. The base portion 348 may offer greater displacement in some areas that would provide additional forces.

Figure 46:
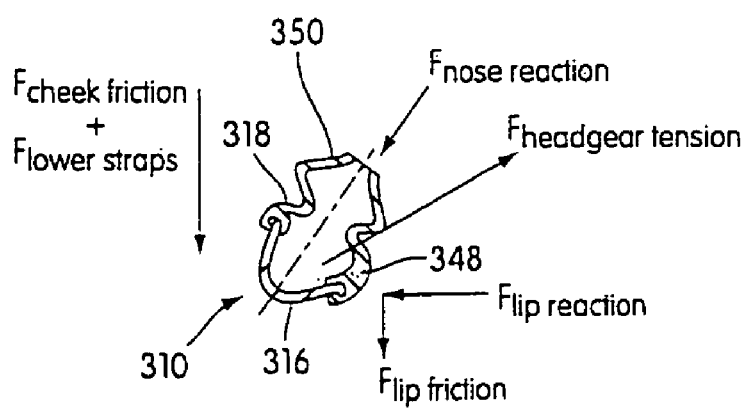
FIG. 46 is a schematic force diagram illustrating some of the forces that are developed when the nasal assembly shown in FIG. 38 is mounted to the patient's head.

FIG. 46 is a force diagram that illustrates some of the forces that are developed when the nasal assembly 310 is attached to the patient's head. For example, the headgear tension provides a force on the patient's face and the patient's nose and lip provide forces on the nasal assembly 310.

Fourth Illustrated Embodiment

Figure 52:
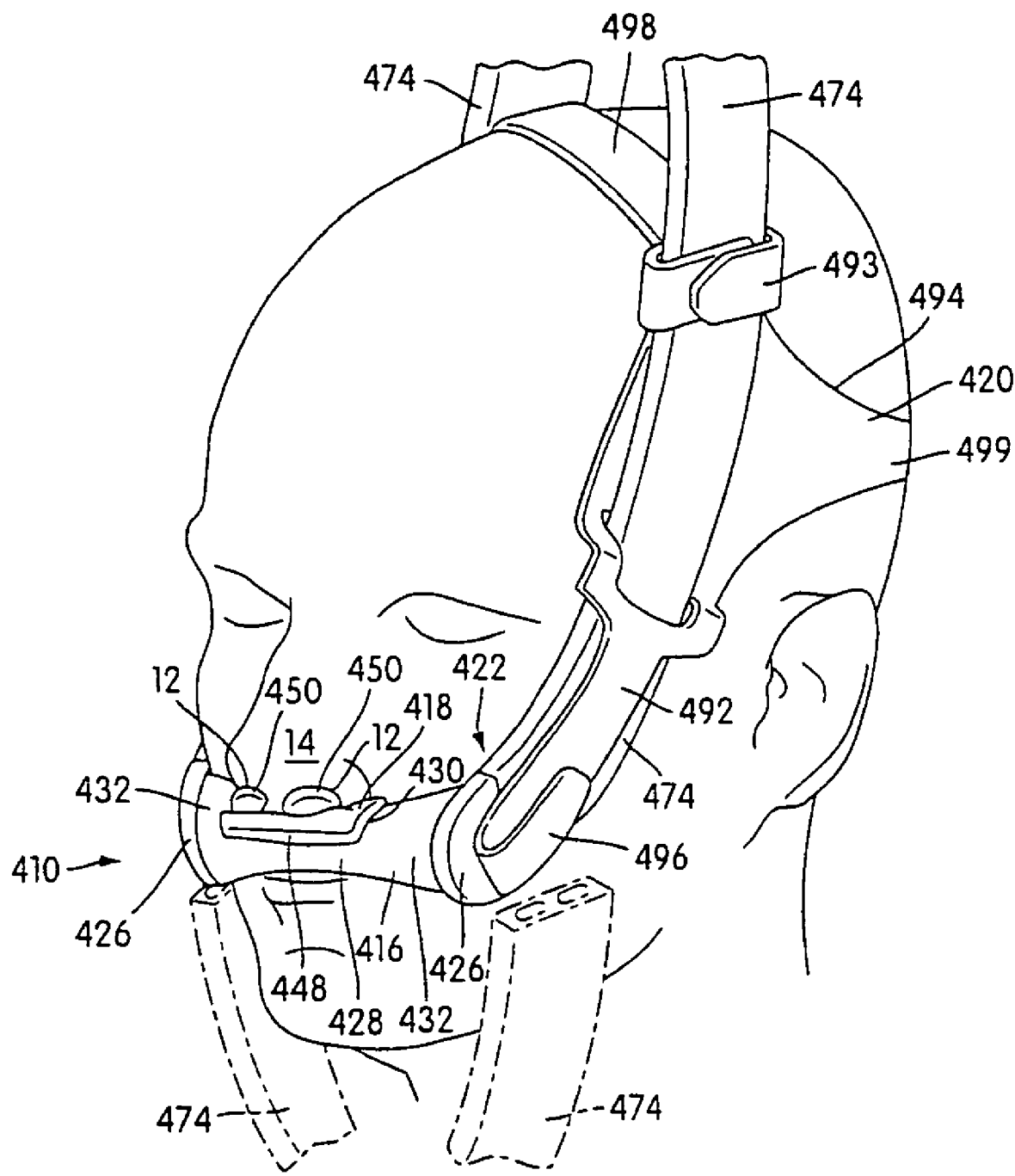
FIG. 52 is a perspective view illustrating another embodiment of a nasal assembly mounted to a patient's head and engaged with nasal passages of the patient with two inlet configurations shown.
Figure 53:
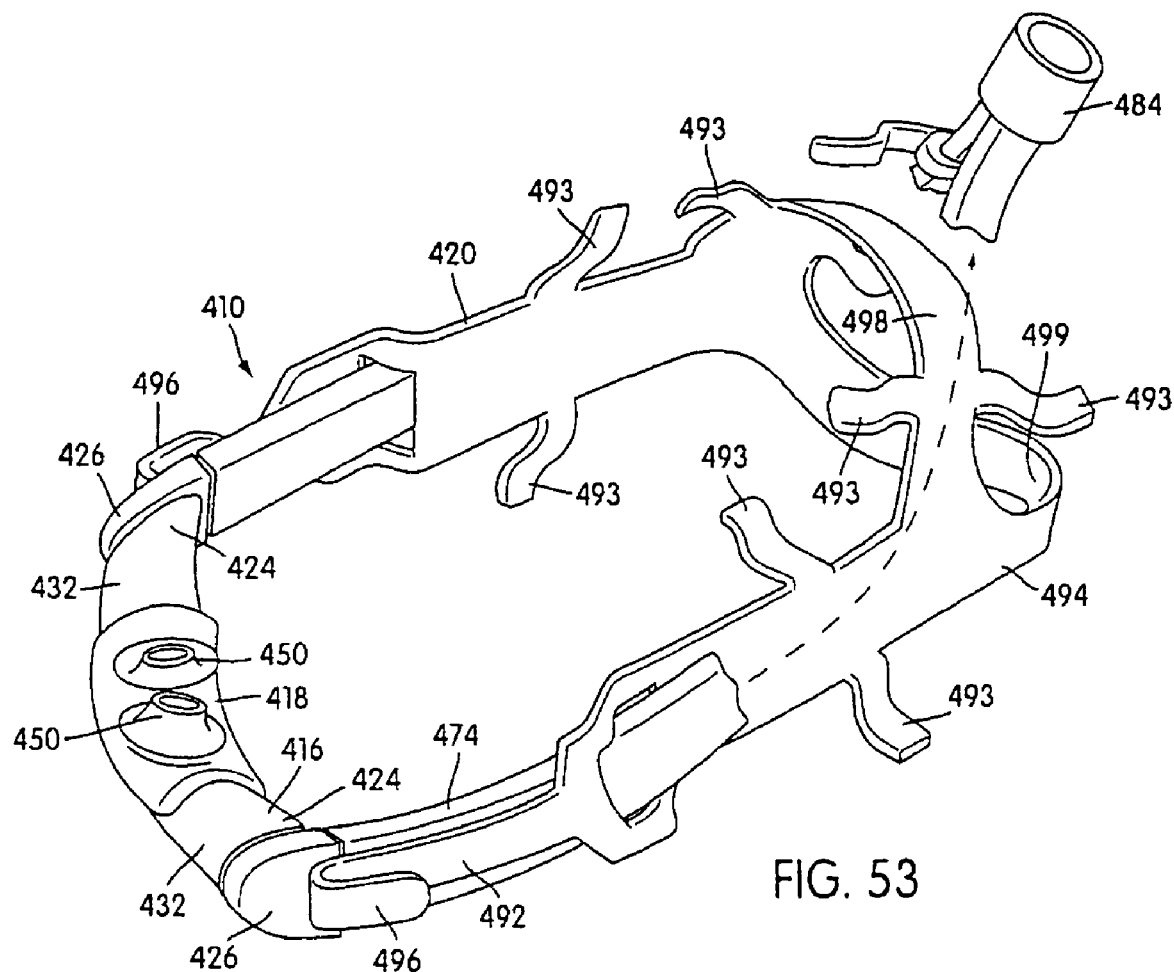
FIG. 53 is a perspective view illustrating the nasal assembly shown in FIG. 52.

FIGS. 52-58 illustrate another embodiment of a nasal assembly, indicated as 410. As best shown in FIGS. 52 and 53, the nasal assembly 410 includes a frame 416 and a nozzle assembly 418 that is removably connected to the frame 416. A headgear assembly 420 is removably attached to the frame 416 to maintain the frame 416 and nozzle assembly 418 in a desired adjusted position on the patient's face. Inlet conduits 474 are also removably attached to the frame 416 to deliver breathable gas into the frame 416 and nozzle assembly 418 for breathing by the patient. The headgear assembly 420 and inlet conduits 474 are removably attached to the frame 416 by an inlet conduit and headgear connection assembly 422. The connection assembly 422 includes first connector portions 424 (see FIGS. 55 and 56) provided by the frame 416 and second connector portions 426 adapted to be removably coupled with the first connector portions 424. The second connector portions 426 are removably or fixedly connected to the headgear assembly 420 and the inlet conduits 474, as will be further discussed.

Figure 54:
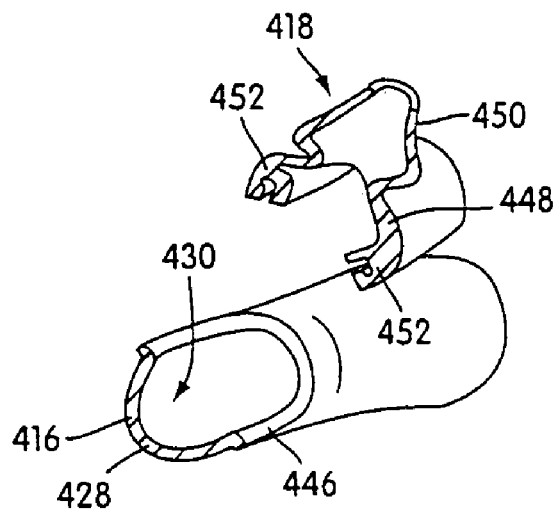
FIG. 54 is a cross-sectional view illustrating a nozzle assembly being engaged with a frame of the nasal assembly shown in FIG. 52.

As shown in FIGS. 52 and 54, the frame 416 includes a main body 428 that provides a central opening 430 for accommodating the nozzle assembly 418. The frame 416 also includes side frame members 432 provided on each lateral side of the main body 428. Each side frame member 432 includes a first connector portion 424 that is integrally formed therewith. The first connector portion 424 is in the form of cross-bar 466 (see FIGS. 55 and 56). As best shown in FIG. 54, the main body 428 includes rim 446 that define the central opening 430.

As shown in FIG. 54, the nozzle assembly 418 includes a gusset portion 448 and a pair of nozzles 450 attached thereto. The gusset portion 448 has side walls 452 adapted to sealingly engage with the rim 446 surrounding opening 430 of the frame 416. For example, the side walls 452 of the gusset portion 448 may include a recess that is structured to interlock with a respective tab provided on the rim 446 of the frame 416 with a snap-fit. However, the nozzle assembly 418 may be removably attached to the frame 416 in any other suitable manner, such as a friction fit, for example. When the nozzle assembly 418 is attached to the frame 416, the nozzle assembly 418 and the frame 416 together form a conduit for directing breathable gas to the patient's nose through the pair of nozzles 450.

The nozzles 450 may be designed and structured in a similar manner to the nozzles 50 described above. The frame 416 may include one or more openings (not shown) for exhaled $CO_2$ washout.

Figure 55:
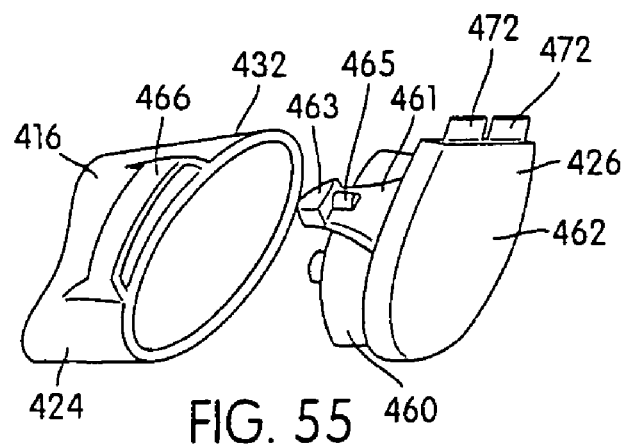
FIG. 55 is a perspective view illustrating an inlet conduit and headgear connector assembly of the nasal assembly shown in FIG. 52.
Figure 56:
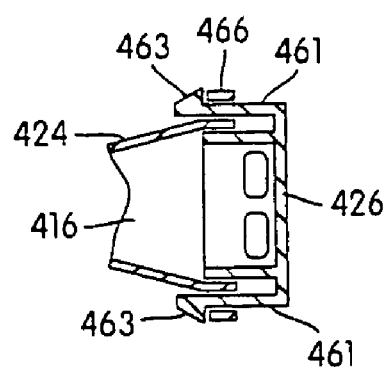
FIG. 56 is a cross-sectional view illustrating the inlet conduit and headgear connector assembly of the nasal assembly shown in FIG. 52.

As shown in FIG. 55, the second connector portion 426 includes a main body having a front portion 460 and a rear portion 462. The front portion 460 includes a pair of arm members 461 having an integral lug 463 at a distal end thereof. In use, the arm members 461 are flexed inwardly by the cross-bar 466 of the first connector portion 424 until the arm members 461 reach an operative position in which the arm members 461 flex back outwardly such that the shoulder of the lug 463 is positioned to interlock the second connector portion 426 with the first connector portion 424 (see FIG. 56).

The arm members 461 of the second connector portion 426 may rotate with respect to the cross-bar 466 of the first connector portion 424. As shown in FIG. 55, a protrusion 465 may be provided on the arm members 461 that selectively engages within a series of recesses provided on an inner surface of the cross-bar 466 so as to provide a predetermined number of settings for alignment of the nozzles 450 with respect to the nasal passages of the patient.

As shown in FIG. 55, the rear portion 462 provides a pair of conduits 472 adapted to be connected to an inlet conduit that delivers breathable gas to the frame 416 and nozzle assembly 418. The rear portion 462 of the second connector portion 426 also includes a cross-bar or opening (not shown) through which a strap of the headgear assembly 420 may pass and be removably connected.

As shown in FIGS. 52 and 53, the nasal assembly 410 includes a pair of inlet conduits 474. First ends of the pair of conduits 474 are connected to respective second connector portions 426 connected to the frame 416. Second ends of the pair of conduits 474 are connected to a pressurized supply that supplies pressurized breathable gas. As shown in FIG. 52, the second connector portions 426 may be rotated with respect to the first connector portions 424 to route the pair of inlet conduits 474 upwardly over the head of the patient or downwardly under the chin of the patient, for example.

As a result, pressurized gas can pass through the pair of inlet conduits 474 into the frame 416 and nozzle assembly 418, and through the nozzles 450 for breathing by the patient.

FIG. 53 illustrates a flow generator connector 484 structured to interconnect the second ends of the pair of inlet conduits 474 with a pressurized supply.

As shown in FIG. 52, the inlet conduits 474 provide a dual air flow channel to prevent kinking and facilitate connection. However, the conduits 474, connector portions 424, 426, and connector 484 may be structured to provide one air flow channel or more than two air flow channels.

The headgear assembly 420 is removably attached to second connector portion 426 attached to the frame 416 to maintain the frame 416 and nozzle assembly 418 in a desired adjusted position on the patient's face. As shown in FIGS. 52 and 53, the headgear assembly 420 includes two side portions 492 with a rear portion 494 connecting the side portions 492. Each side portion 492 comprises a side strap 496. The rear portion 494, which interconnects the two side portions 492, includes an upper strap 498 that passes over the top of the patient's head and a rear strap 499 that passes around the rear portion of the patient's head. However, the headgear assembly may be permanently attached to the frame.

Each side strap 496 has a reduced width that enables the side strap 496 to be wrapped around the cross-bar or opening provided on the second connector portion 426. Fastening of the side straps 496 to respective cross-bars or openings may be assisted by use of a hook and loop material, such as Velcro®. Thus, the side straps 496 may be adjusted with respect to the second connector portion 426 for proper fit.

In the illustrated embodiment, the headgear assembly 420 is constructed as a one piece structure. However, the headgear assembly 420 may include a plurality of straps suitably arranged to support the nasal assembly 410 on the patient's head. As shown in FIGS. 52 and 53, the headgear assembly 420 may include retaining straps 493 to hold the inlet conduits 474 upwardly over the head of the patient.

Figure 57:
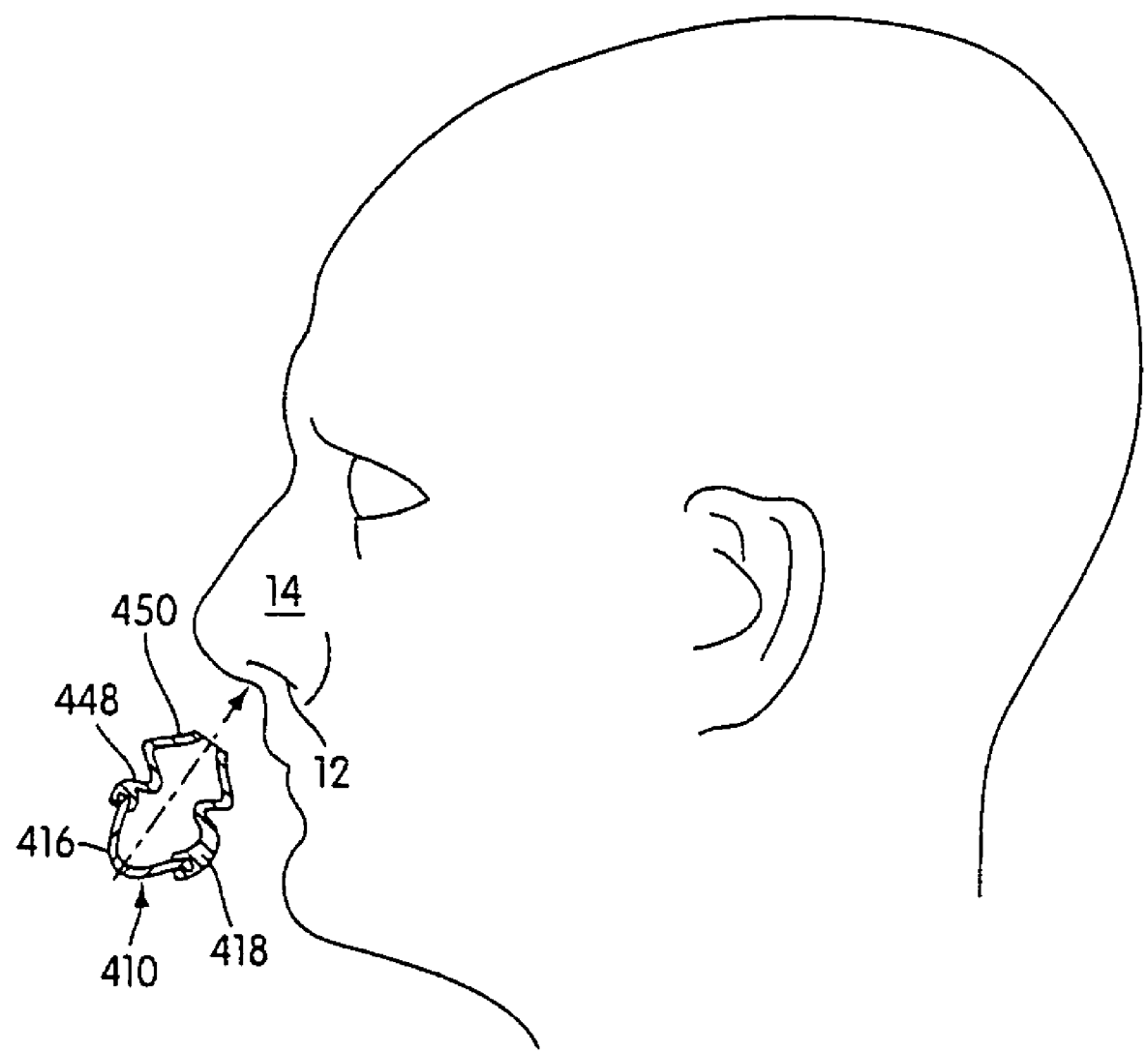
FIG. 57 is a cross-sectional side view illustrating the nasal assembly shown in FIG. 52 about to be engaged with nasal passages of the patient.
Figure 58:
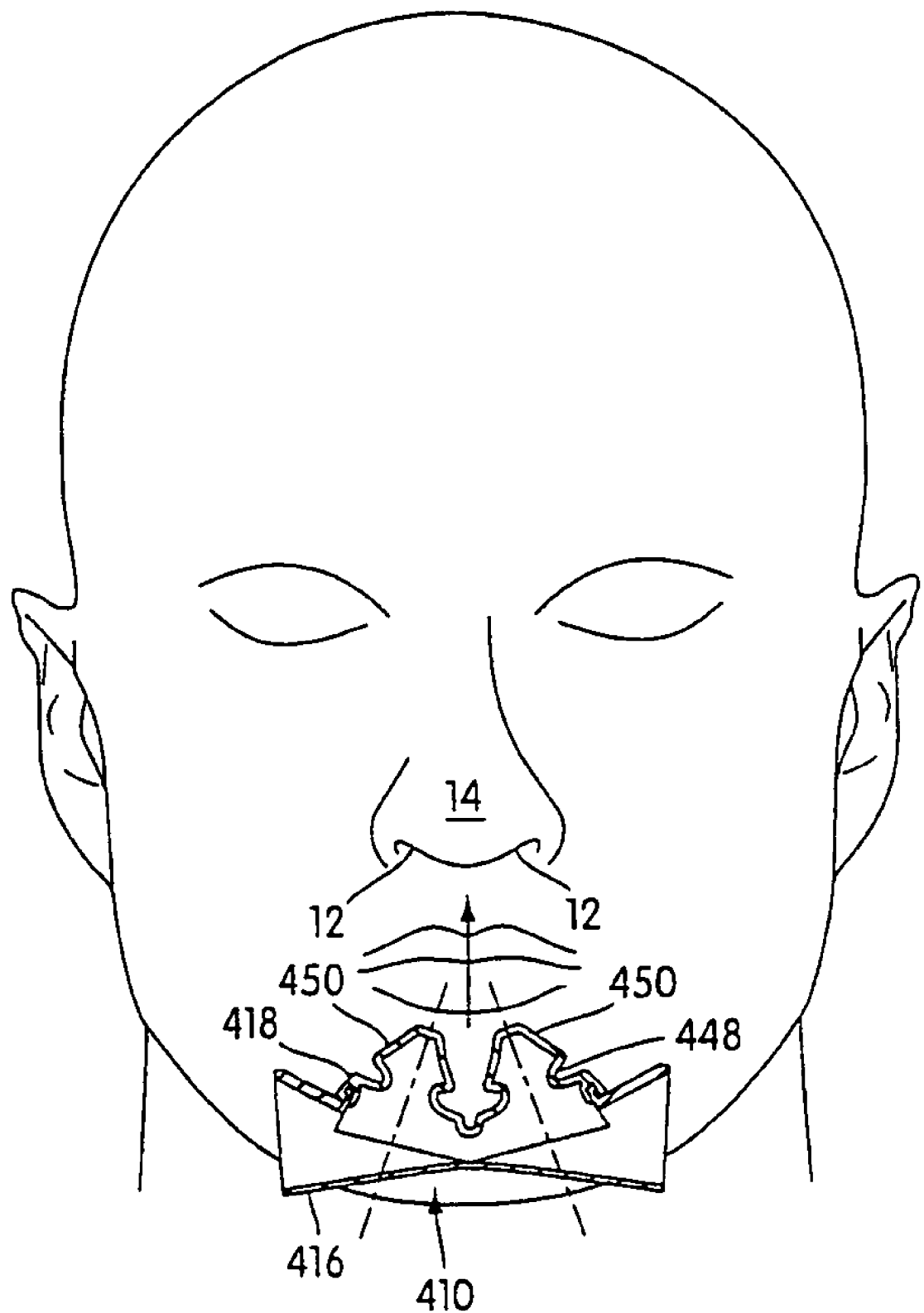
FIG. 58 is a front view illustrating the nasal assembly shown in FIG. 52 (in cross-section) being engaged with nasal passages of the patient.

FIGS. 57 and 58 illustrate the nasal assembly 410 being engaged with nasal passages 12 of a patient's nose. Similar to the nasal assembly 10 described above, the force provided by the gusset portion 448 along with the air pressure provides an effective sealing force against the nasal passages 12 of the patient. Thus, the gusset portion 448 reduces the headgear assembly tension required to achieve a suitable seal. Also, the position of the nozzles 450 may be adjusted with respect to the user's nose to improve patient comfort.

As shown in FIG. 58, for example, the gusset portion has a substantially rigid structure such that it applies a relatively small component of force on the patient's face when inflated. In contrast, the nozzles have a flexible structure such that they provide a relatively larger component of force on the patient's face. That is, the first portion of the nozzles may have a relatively large spring-load to provide a component of force on the patient's face through the nozzles. As a result, the gusset portion and nozzles together provide a force to provide a seal between the nasal assembly and the patient's nasal passages.

Fifth Illustrated Embodiment

FIGS. 59-85 illustrate another embodiment of a nasal assembly, indicated as 510. The nasal assembly 510 includes a frame 516 and a nozzle assembly 518 that is removably coupled to the frame 516. As best seen in FIG. 61, the frame 516 includes a pair of first connector portions 524. Referring back to FIG. 59, a pair of inlet conduits 574 are structured to deliver breathable gas into the frame 516 and nozzle assembly 518 for breathing by the patient. The breathable gas is transported from the inlet conduits 574 to the frame 516 and nozzle assembly 518, e.g., via a pair of second connector portions 526 and a pair of angle connectors 542. The second connector portions 526 are removably and rotatably connected to respective first connector portions 524 (FIG. 61) of the frame 516. The angle connectors 542 are connected or positioned between the second connector portions 526 and respective inlet conduits 574. A headgear assembly 520 is removably connected to (a) the pair of second connector portions 526 and/or (b) the angle connectors 542, so as to maintain the frame 516 and the nozzle assembly 518 in a desired adjusted position on the patient's face, as will be further discussed.

As shown in FIG. 61, the frame 516 includes a main body 528 and a side frame member 532 provided on each lateral side of the main body 528. Each side frame member 532 includes an integrally formed first connector portion 524. The first connector portion 524 is in the form of a conduit 564 having an annular recess 566 on an outer surface thereof. Also, the main body 528 includes an elongated channel 565 on opposing sides thereof and each side frame member 532 includes an annular channel 567. The channels 565, 567 are structured to receive the ends of the nozzle assembly 518, as will be further discussed.

As shown in FIGS. 61-65, the nozzle assembly 518 includes a gusset or base portion 548 and a pair of nozzles 550 attached thereto. The nozzle assembly 518 is coupled with the frame 516 with the pair of nozzles 550 structured to sealingly engage with nasal passages of a patient's nose in use and provide a seal between the nasal assembly 510 and the patient's nasal passages. The nozzles 550 may be designed and structured in a similar manner to the nozzles 50 described above. Also, the nozzle assembly 518 includes one or more openings 549 for exhaled $CO_2$ washout.

Figure 65:
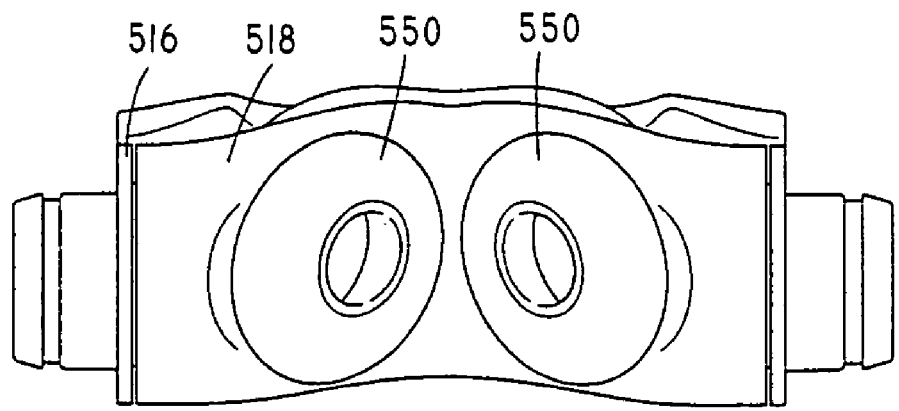
FIG. 65 is a top perspective view of a portion of the nasal assembly shown in FIG. 59.
Figure 65A:
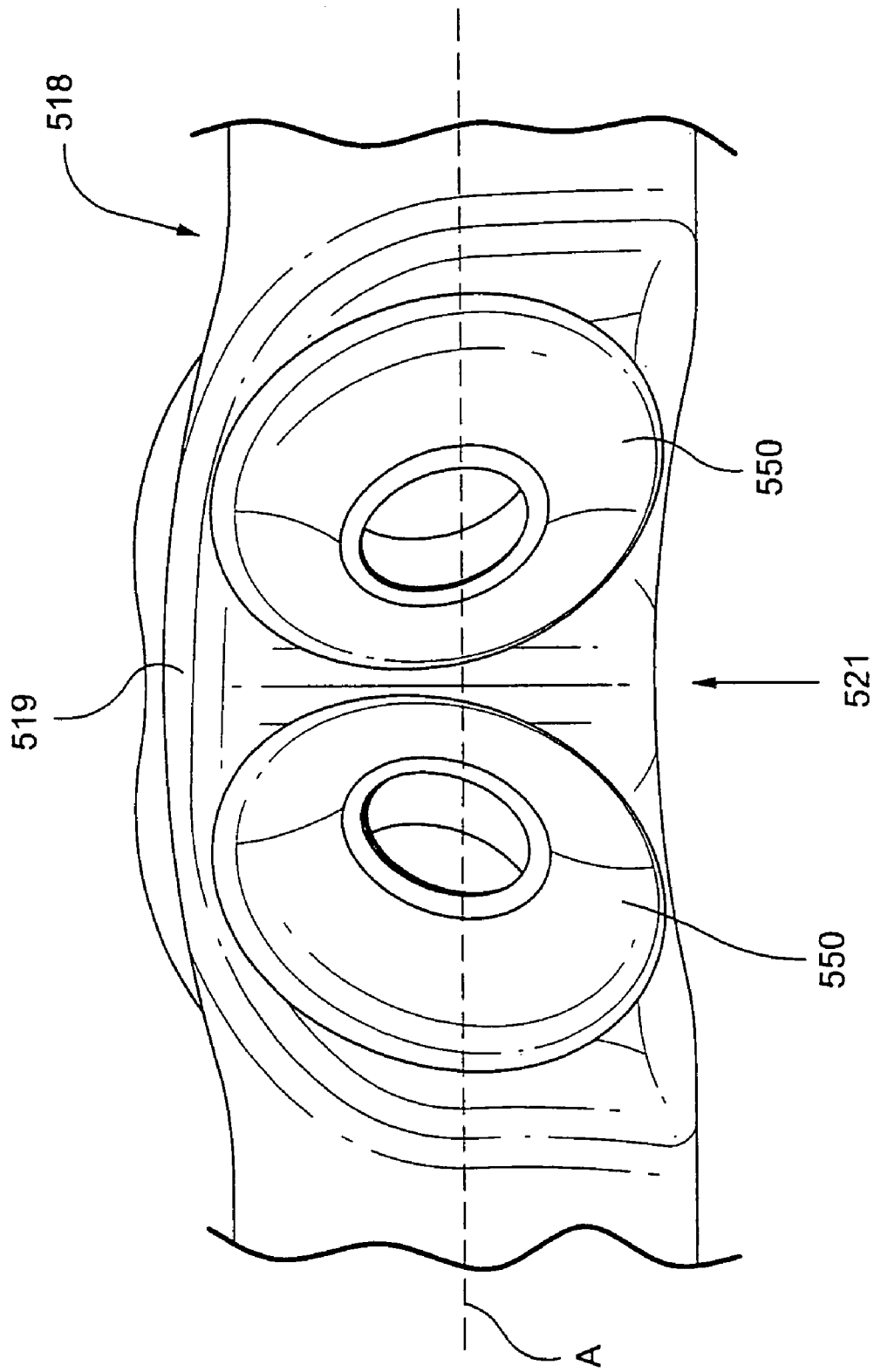
FIG. 65A is a partial enlarged view of the cushion shown in FIG. 65.
Figure 119:
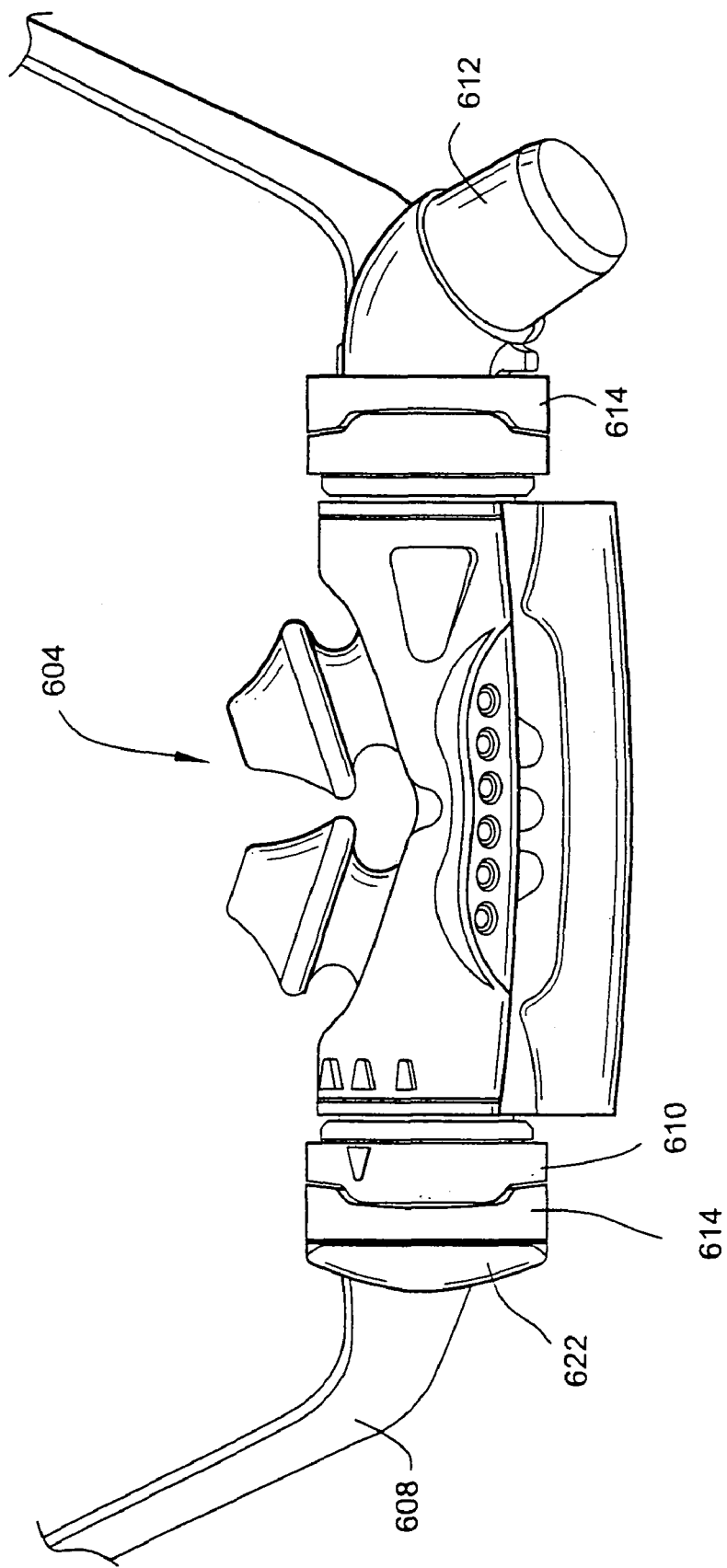
Figure 120:
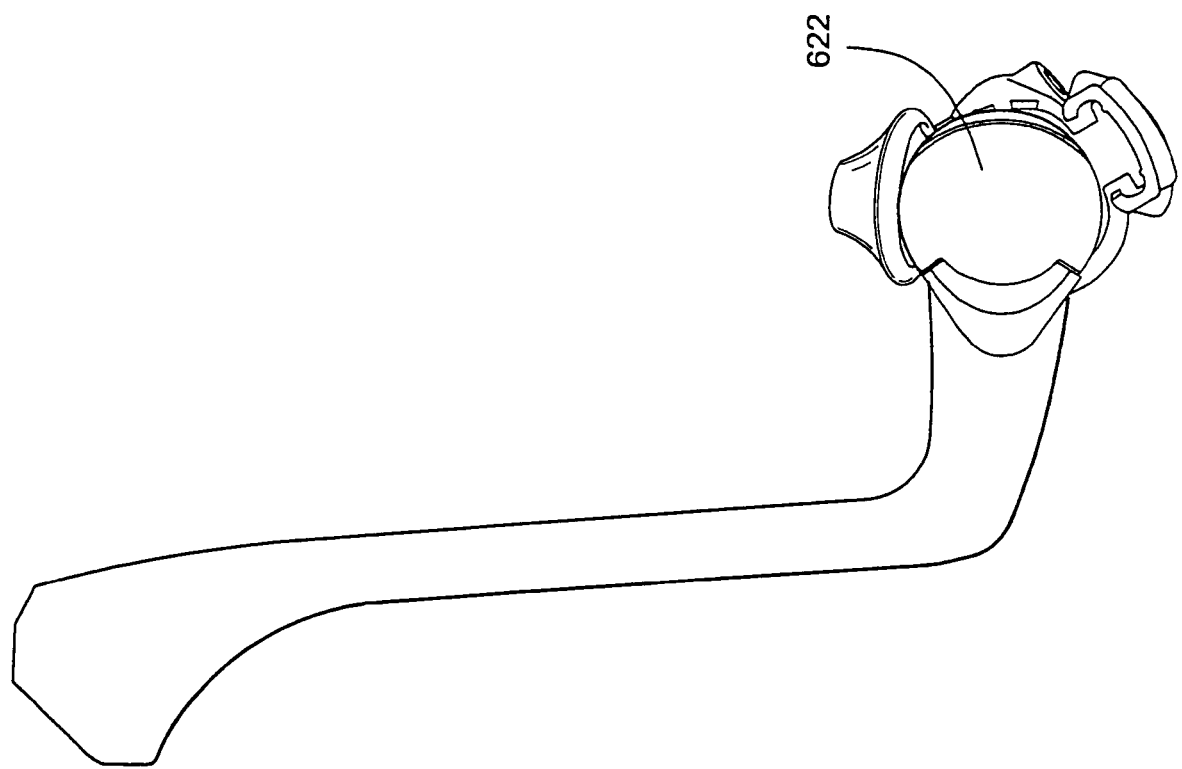
Figure 121:
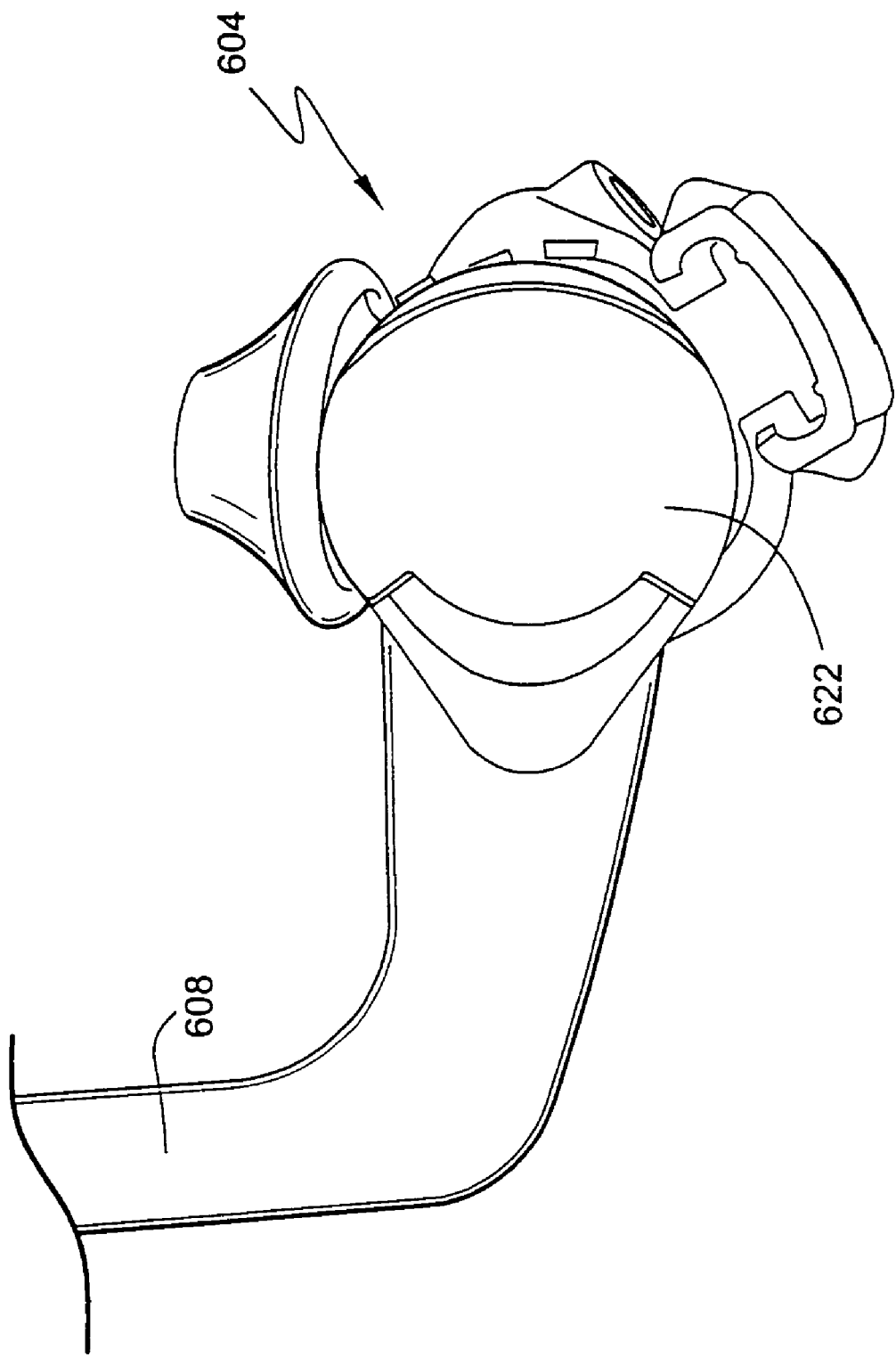
Figure 122:
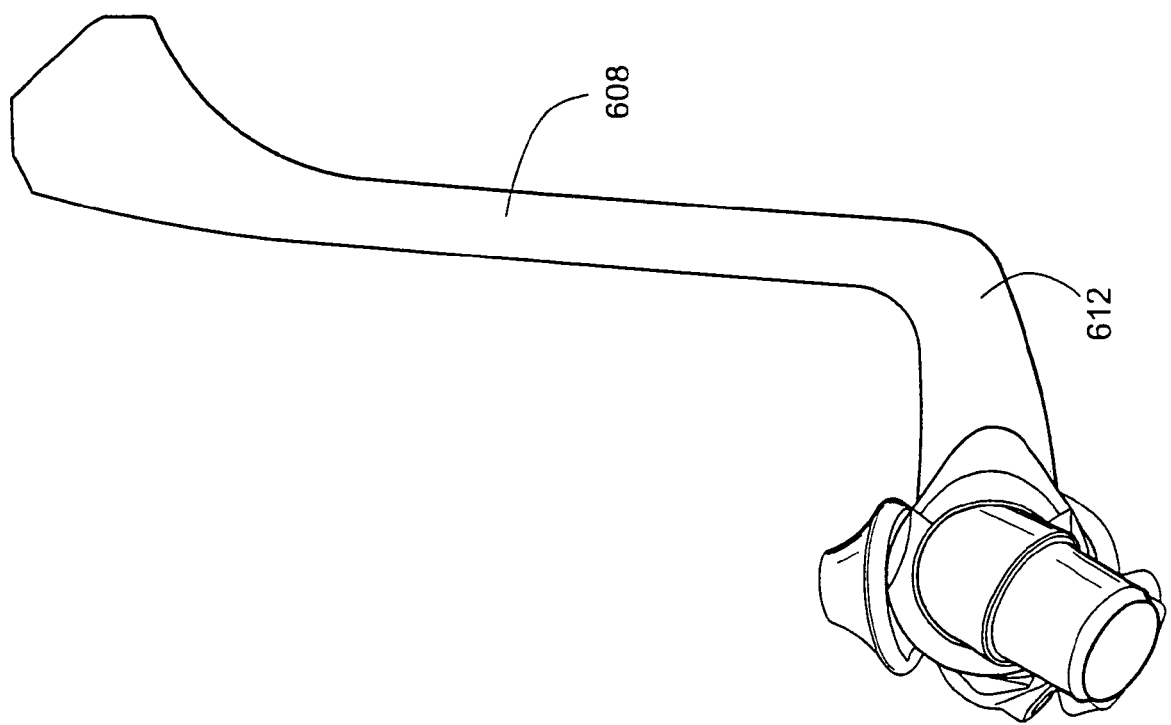
Figure 123:
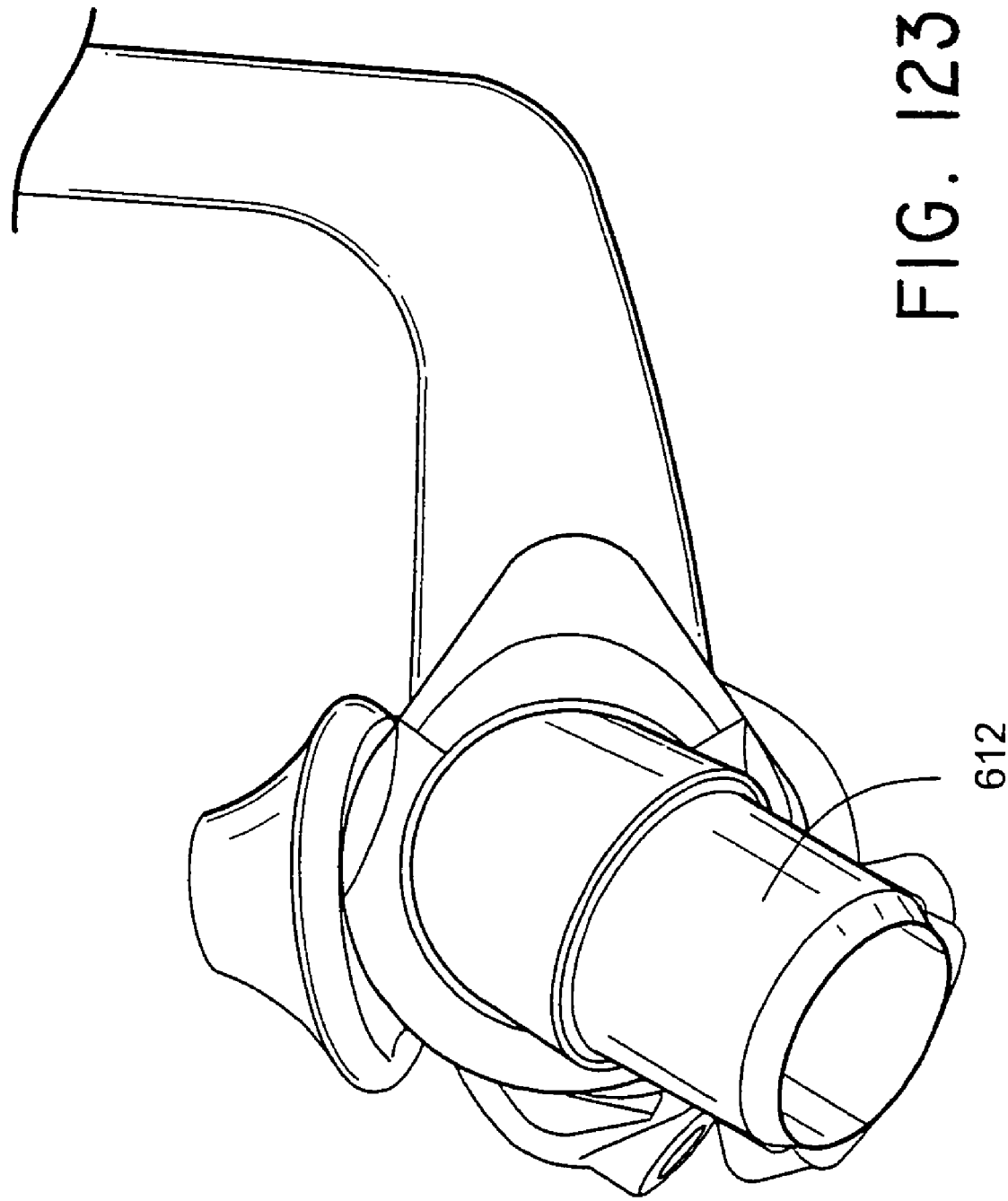
Figure 124:
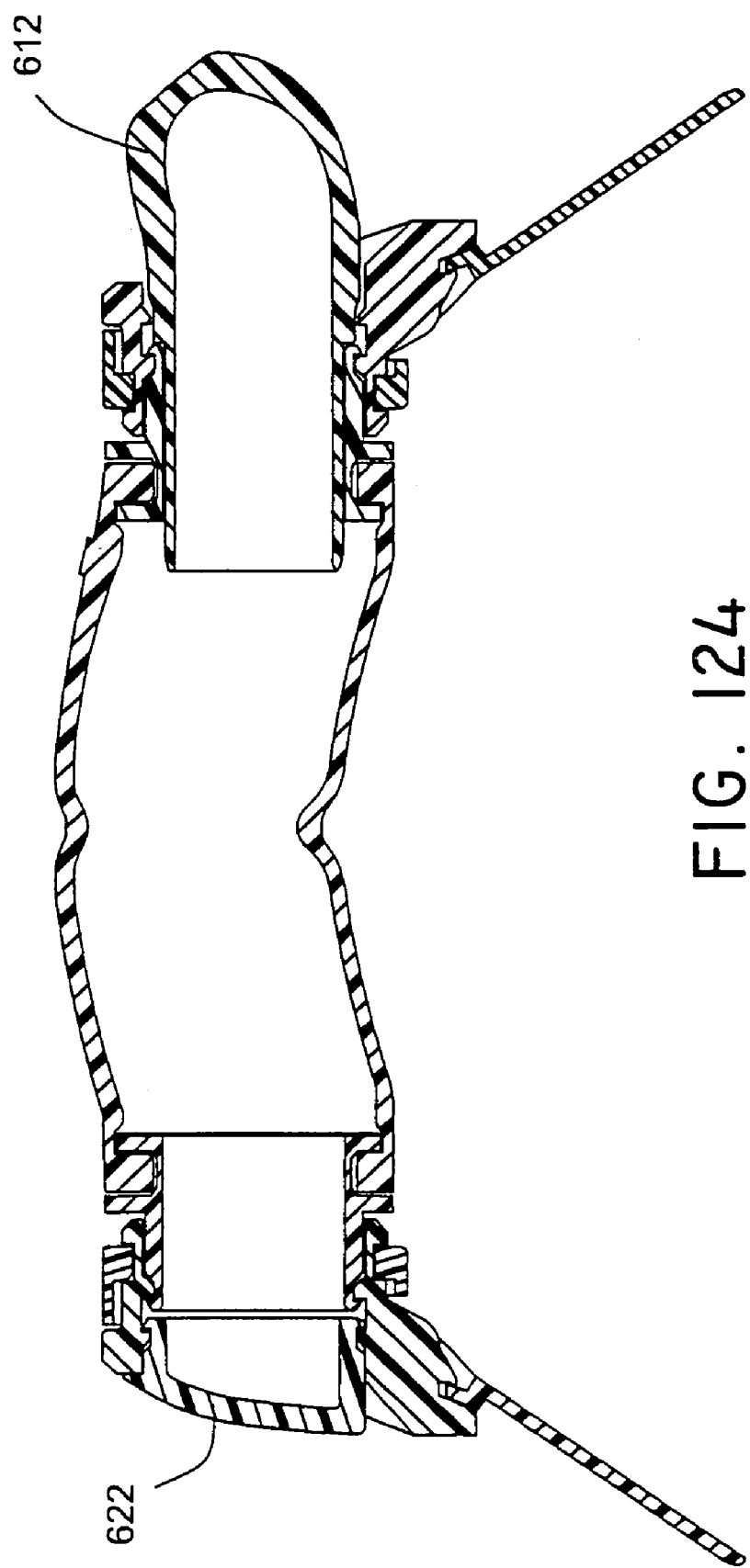
Figure 125:
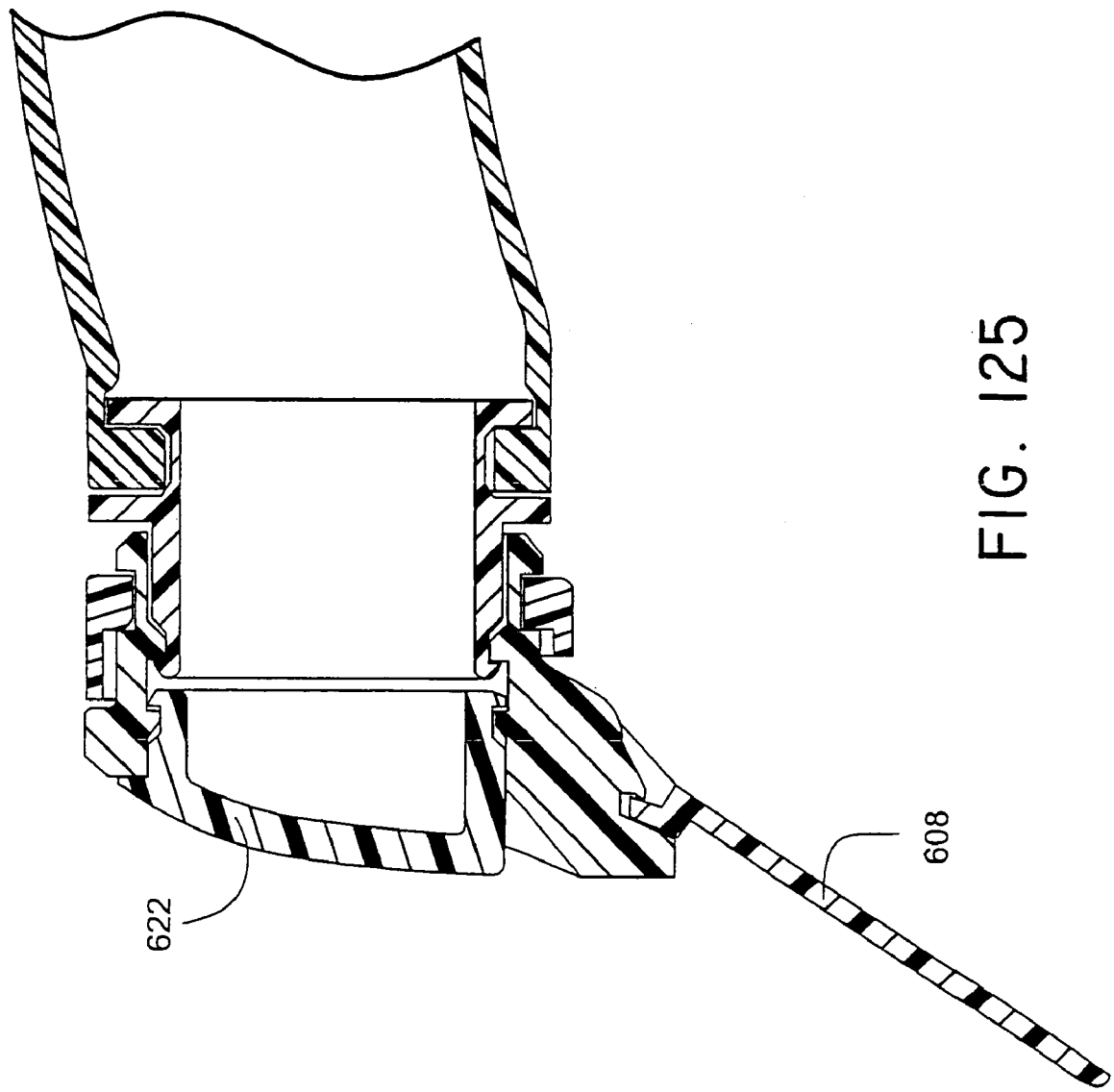
Figure 126:
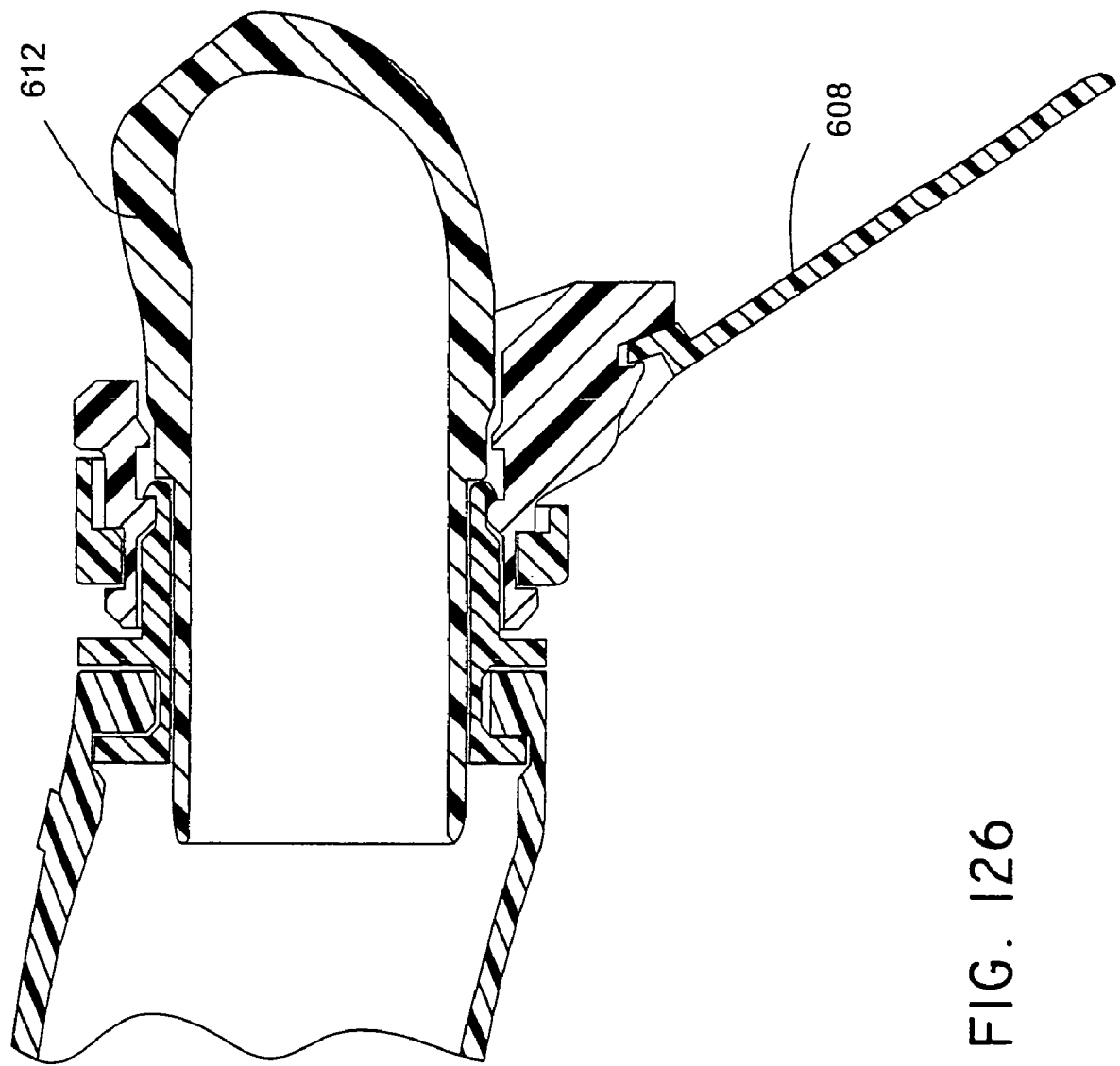
Figure 127:
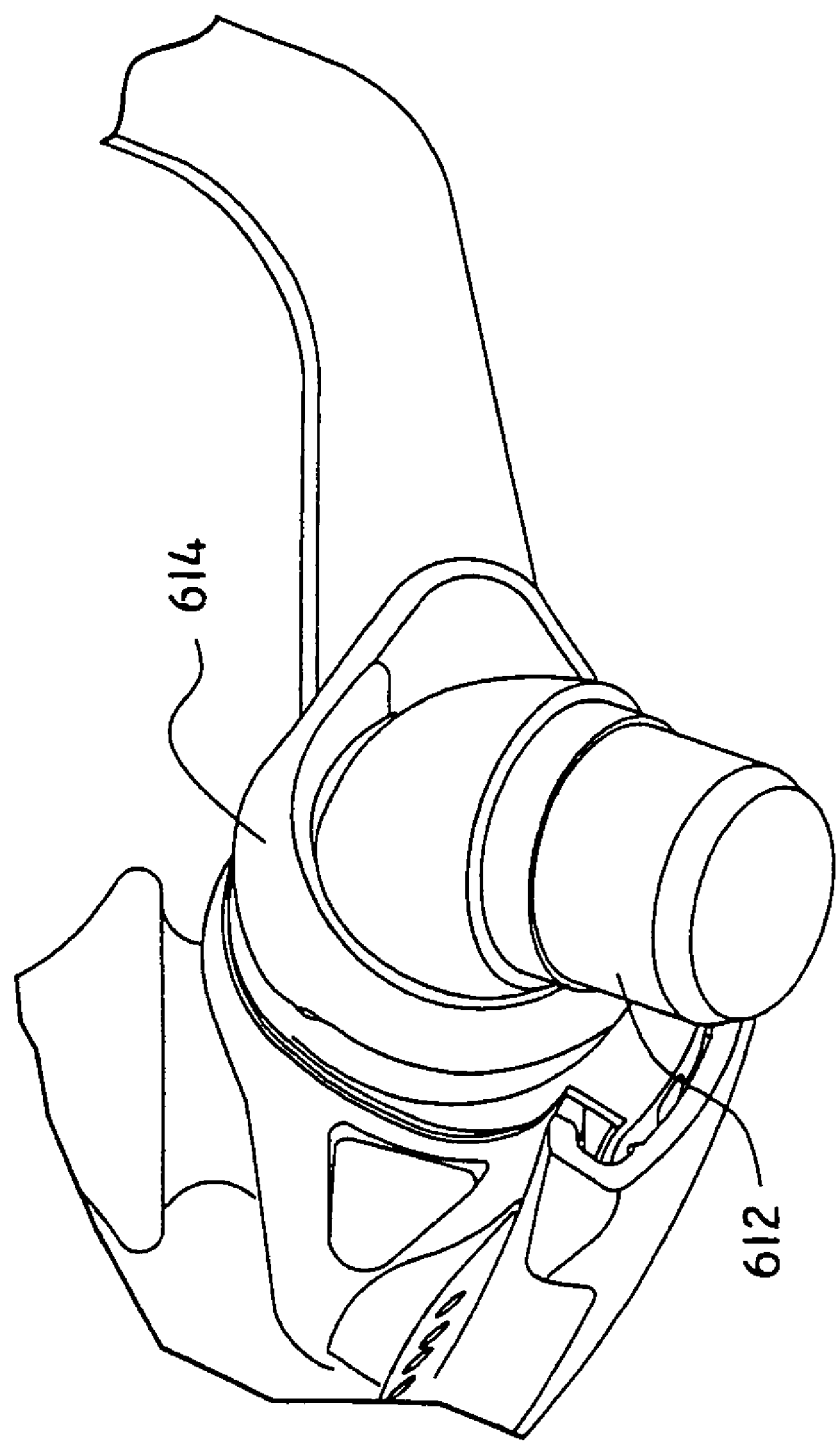
Figure 128:
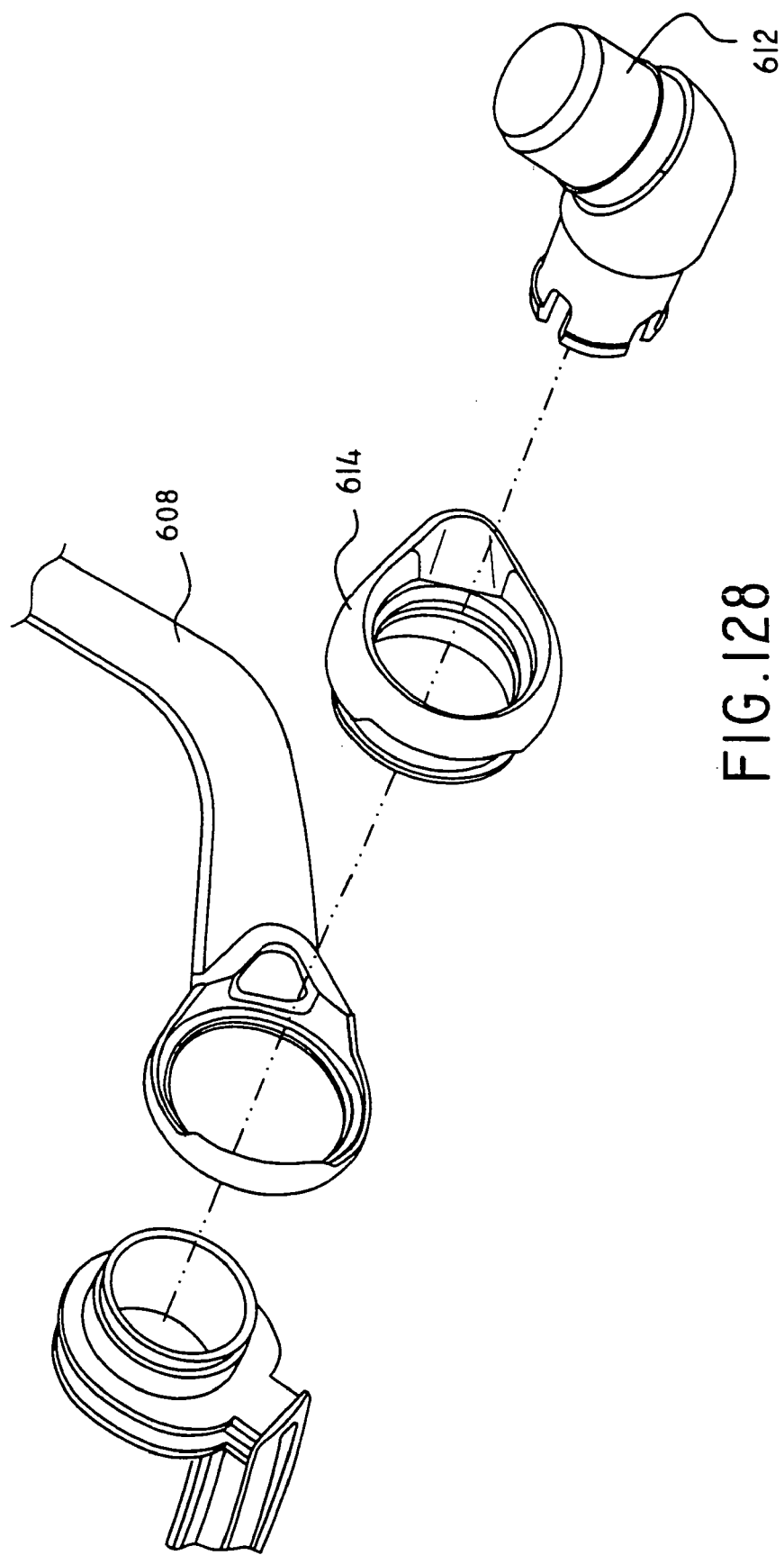

FIG. 65A is an enlarged view of the nozzle assembly 518 shown in FIG. 65. The nozzle assembly preferably includes an upper contour portion 519 that maintains generally the same cross-sectional area through the assembly. Therefore, the assembly generally follows the line of the face so as not to protrude from the face thereby keeping a low profile. Similarly, FIG. 119 shows a nozzle or cushion assembly 604 that generally follows the contour of the face, from the top view.

The nozzle assembly 518 in FIG. 65A also includes a lower contour portion 521 that generally matches the contour of the face. Further, the nozzle assembly 518 is asymmetric about an axis A to provide a better fit in comparison with symmetric prior art masks, which may be subject to creasing or buckling upon distribution to fit the face. The lower contour 521 is also useful for patients with moustaches.

Forces from the patient interface retainer, e.g., headgear, are transferred to the face via nozzles 550 as well as lower contour portion 521. The increased overall area reduces the force per unit area, to spread the load. The increased overall area also helps to better anchor the patient interface. The shape of lower contour portion 521 is customizable. The lower contour portion 521 may be rigid, semi-rigid, elastic or some combination thereof. The maxilla region of the face can withstand more pressure without being uncomfortable.

Figure 65B:
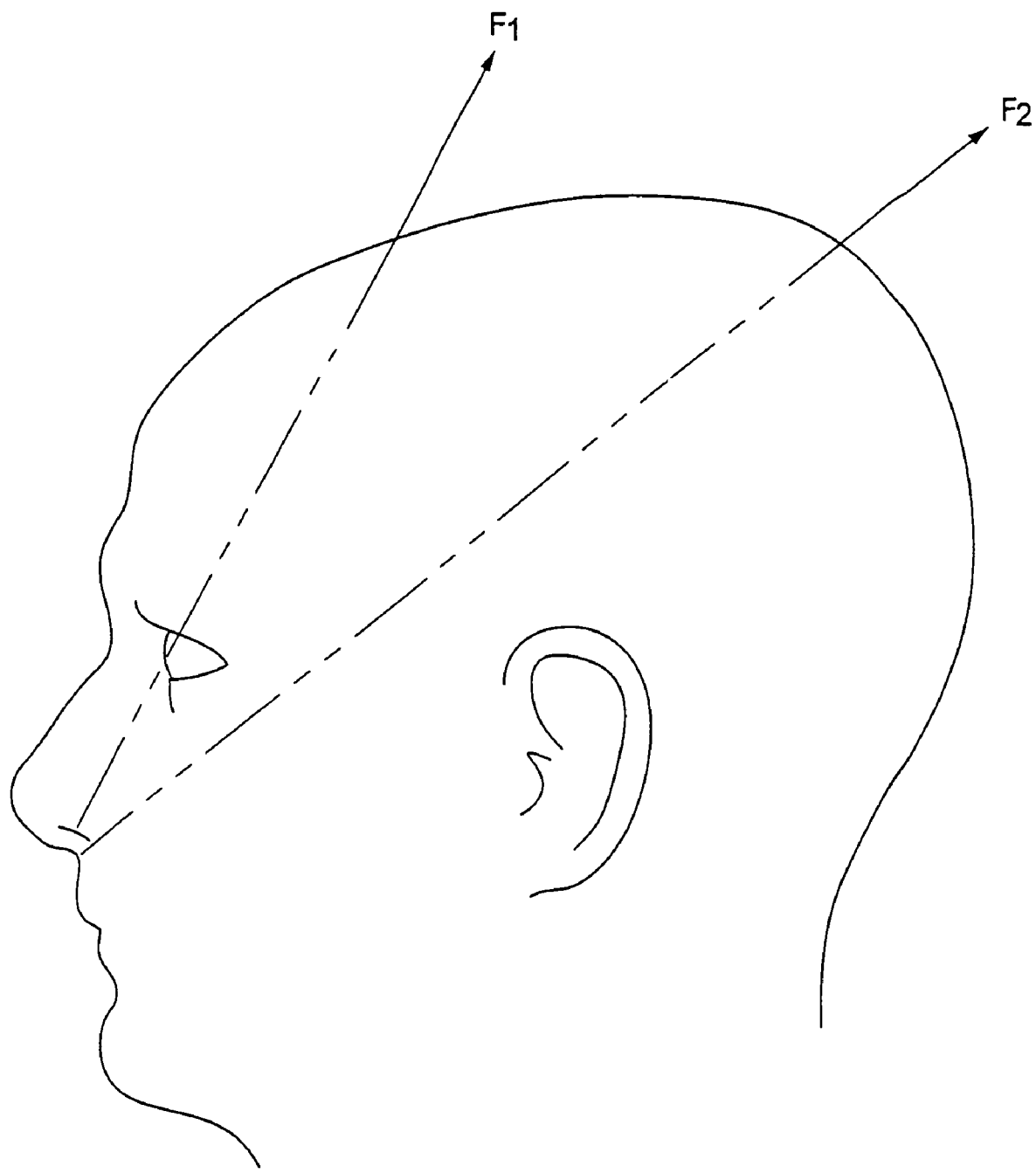
FIG. 65B is a schematic diagram illustrating force distribution according to one aspect of the present invention.
Figure 66:
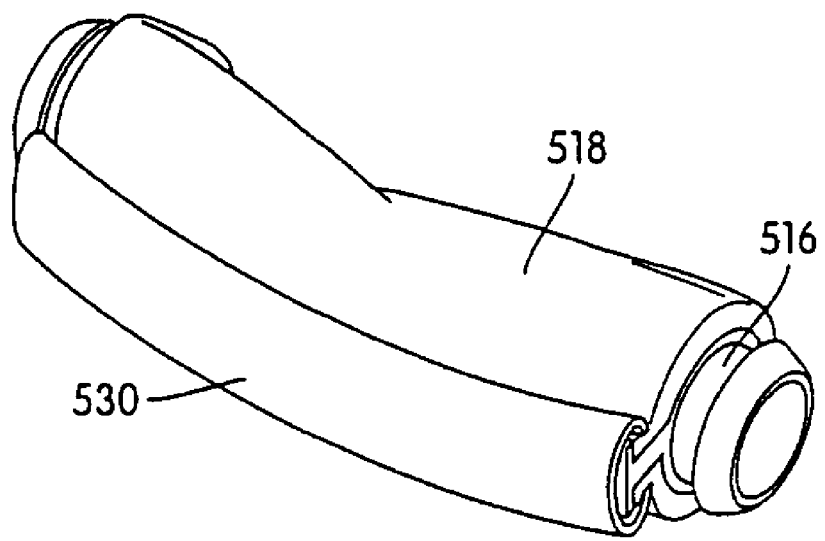
FIG. 66 is a rear perspective view of a portion of an alternative embodiment of a nasal assembly illustrating the engagement between the frame, nozzle assembly, and clip.

FIG. 65B schematically illustrates the force distribution due to the increased area. In particular, the region immediately under the nose is only soft tissue and cartilage.

If the only contact region is the immediate underside of the nose (i.e., not including maxilla) then to hold a nozzle in place with the least amount of force would require a resultant force in direction F1. This might distort the nose and cause discomfort. If such a strap is tightened, it might slip off the front of the head. However, when some of the load is taken by the maxilla (i.e., some force under the nose and some on the maxilla), the direction of the resultant force can be changed to F2, the load is spread. Since the maxilla does not move, F2 could be higher without causing discomfort. Such an arrangement may be more tolerant of overtightening. There is also greater ability to cup the occiput.

Figure 64:
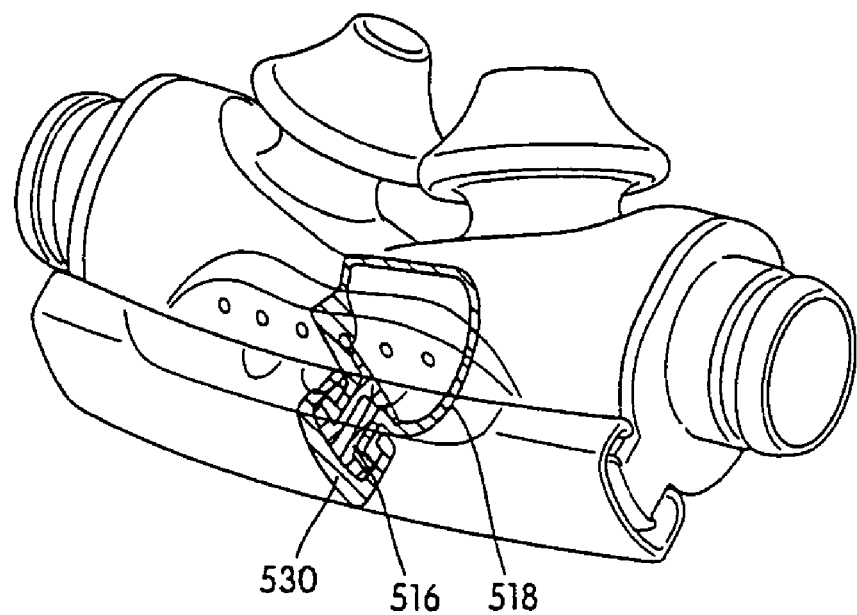
FIG. 64 is a partial cross-sectional view of a portion of the nasal assembly shown in FIG. 59 illustrating the engagement between the frame, nozzle assembly, and clip.
Figure 68:
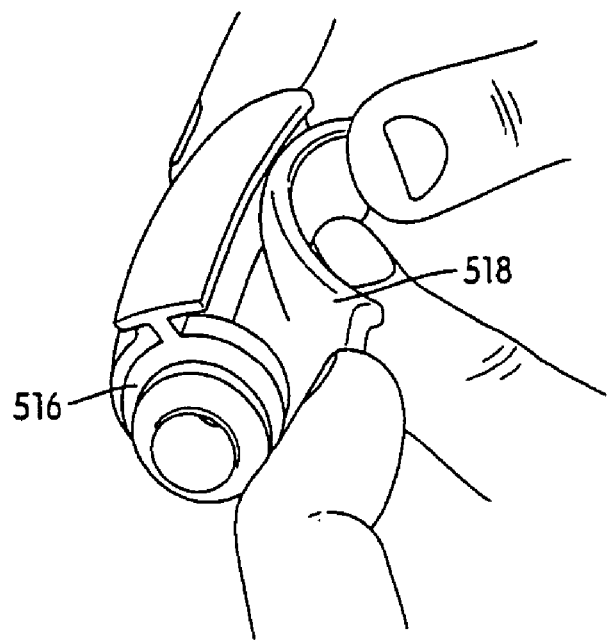
FIG. 68 is a perspective view illustrating the nozzle assembly shown in FIG. 66 being engaged with the frame shown in FIG. 66.

In the illustrated embodiment, the nozzle assembly 518 wraps around the main body 528 and each side frame member 532 of the frame 516 and is secured to the frame 516 with a clip 530. In another embodiment, the cushion can be pulled over the frame like a sock. An annular channel 567 is formed in each side frame member 532 and side portions 536 of nozzle assembly 518 wrap into channels 567. Specifically, as shown in FIG. 61, the nozzle assembly 518 has a generally open-ended tubular configuration with a longitudinal opening. This configuration provides the nozzle assembly 518 with a pair of opposing spaced apart end portions 534 and side portions 536. When the nozzle assembly 518 is coupled to the frame 516, the side portions 536 engage within respective annular channels 567 and the end portions 534 engage within respective elongated channels 565 on opposing sides of the main body 528, as best shown in FIGS. 64 and 68.

As best shown in FIGS. 62-64 and 66, the end portions 534 are secured between the frame 516 and the clip 530. That is, the end portions 534 are secured between respective flanges of opposing channels 565 and flanges of the clip 530. When the nozzle assembly 518 is attached to the frame 516, the nozzle assembly 518 and the frame 516 together form a conduit for directing breathable gas to the patient's nose through the pair of nozzles 550.

Figure 62:
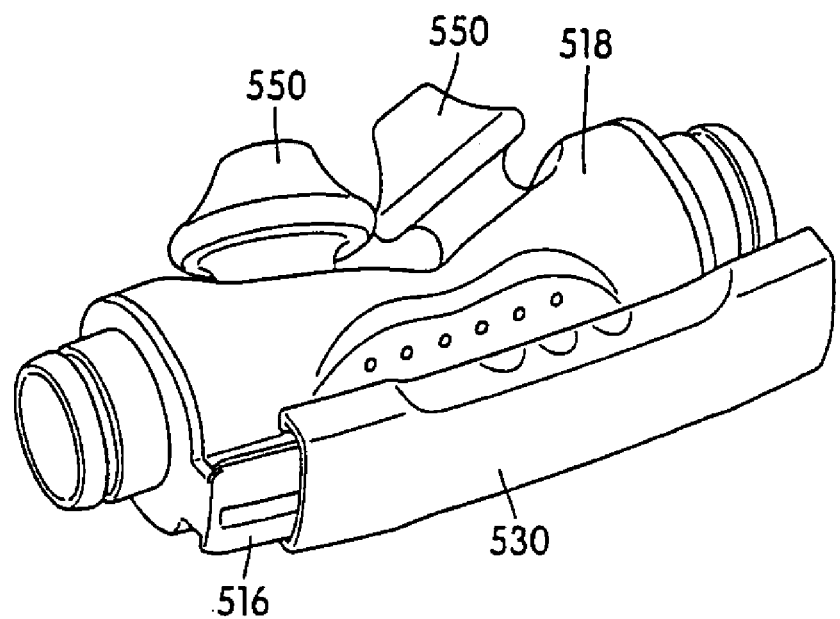
FIG. 62 is a perspective view of a portion of the nasal assembly shown in FIG. 59 illustrating the clip being engaged with the frame and nozzle assembly.
Figure 63:
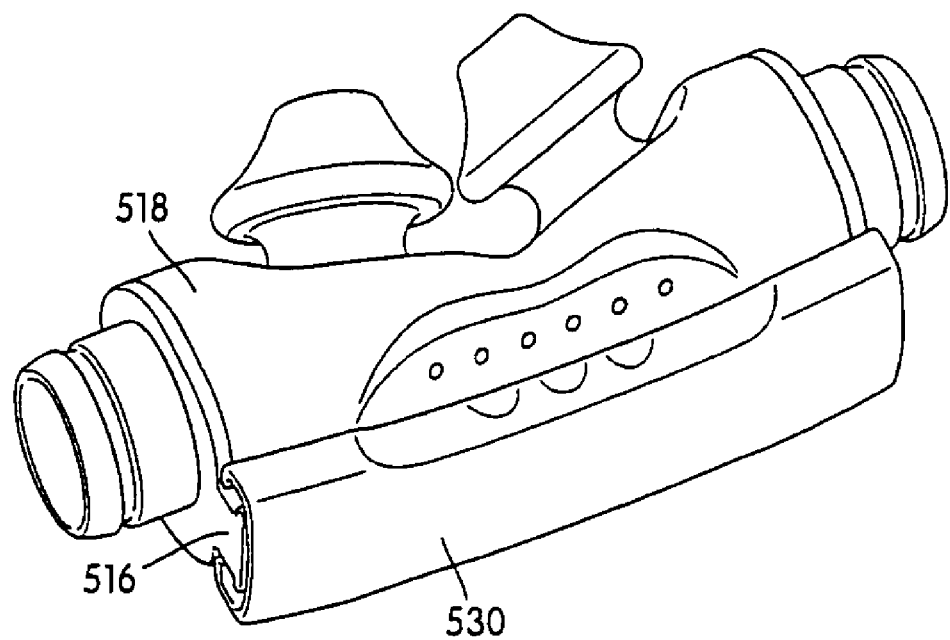
FIG. 63 is a perspective view of a portion of the nasal assembly shown in FIG. 59 illustrating the engagement between the frame, nozzle assembly, and clip.
Figure 70:
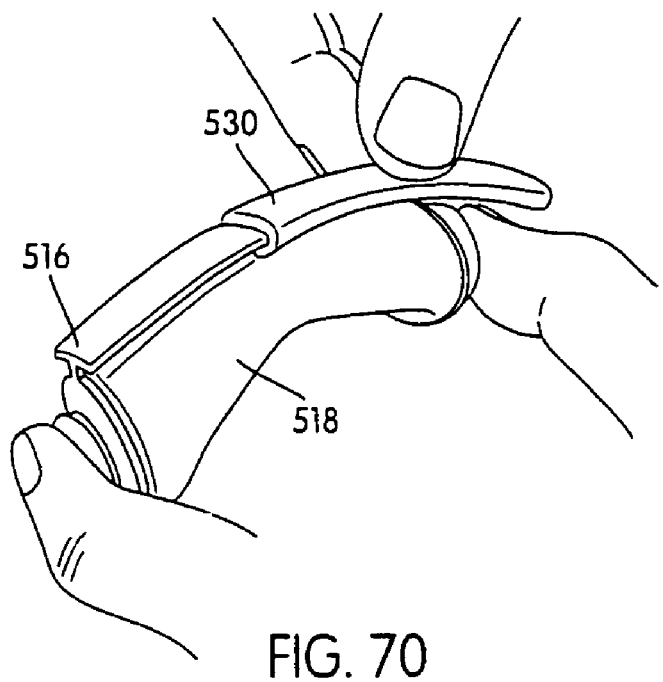
FIG. 70 is a perspective view illustrating the clip shown in FIG. 66 being engaged with the frame and nozzle assembly shown in FIG. 66.

The clip 530 may be engaged with the frame 516 and nozzle assembly 518 in any suitable manner. For example, as shown in FIGS. 62 and 70, the clip 530 may be slid onto the frame 516. Alternatively, the clip 530 may be engaged with the frame 516 with a snap-fit.

Figure 59:
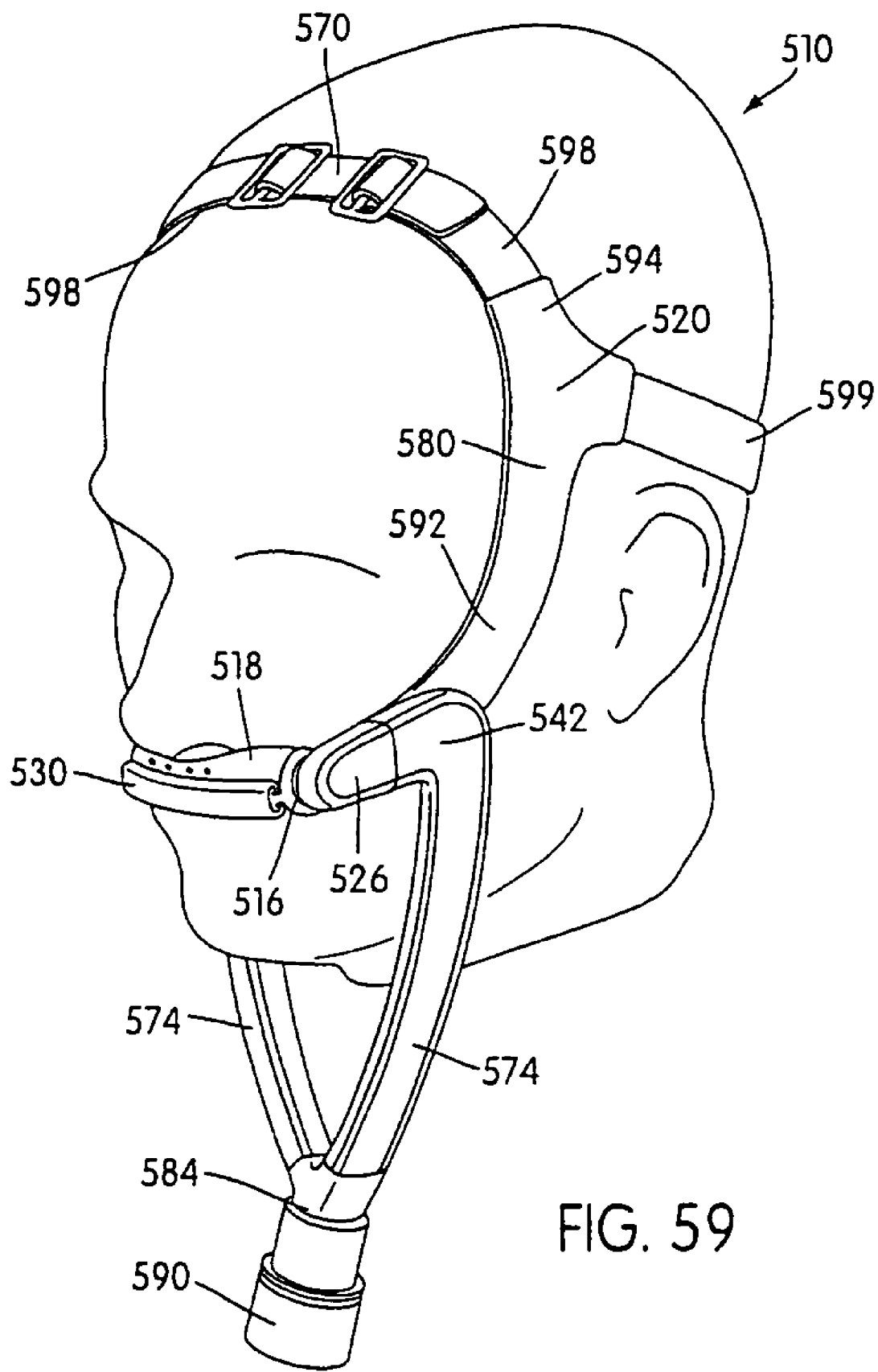
FIG. 59 is a perspective view illustrating another embodiment of a nasal assembly mounted to a patient's head and engaged with nasal passages of the patient.

As shown in FIG. 59, the frame 516 is secured to the nozzle assembly 518 such that the frame 516 is angled away from an upper lip of the patient in use. This positions the clip 530 away from the patient such that it does not irritate the patient's face. Also, the nozzle assembly 518 may be contoured to accommodate a patient's septum in use.

The above-described coupling of the frame 516 and nozzle assembly 518 allows the nozzle assembly 518 to be easily removable from the frame 516 to facilitate cleaning of the nozzle assembly 518. Moreover, the configuration of the nozzle assembly 518 allows interior portions of the nozzle assembly 518 to be accessible for cleaning. The nozzle assembly's configuration also facilitates manufacturing.

Figure 67:
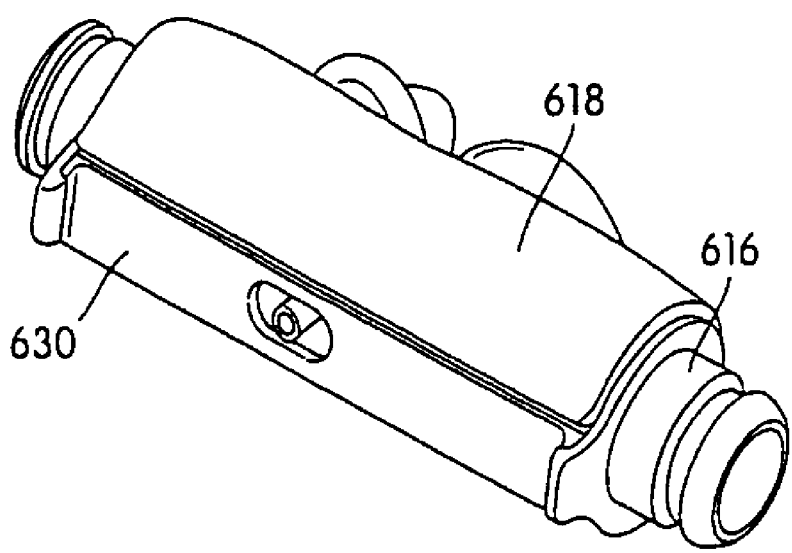
FIG. 67 is a rear perspective illustrating the engagement between another embodiment of the frame, nozzle assembly, and clip.
Figure 69:
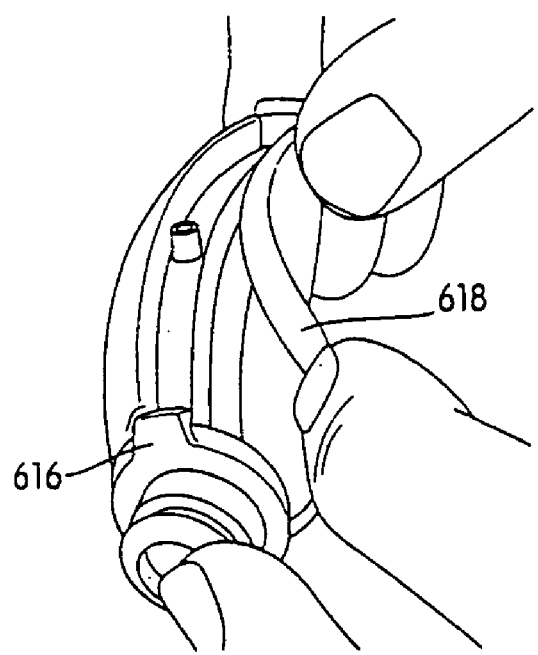
FIG. 69 is a perspective view illustrating the nozzle assembly shown in FIG. 67 being engaged with the frame shown in FIG. 67.
Figure 71:
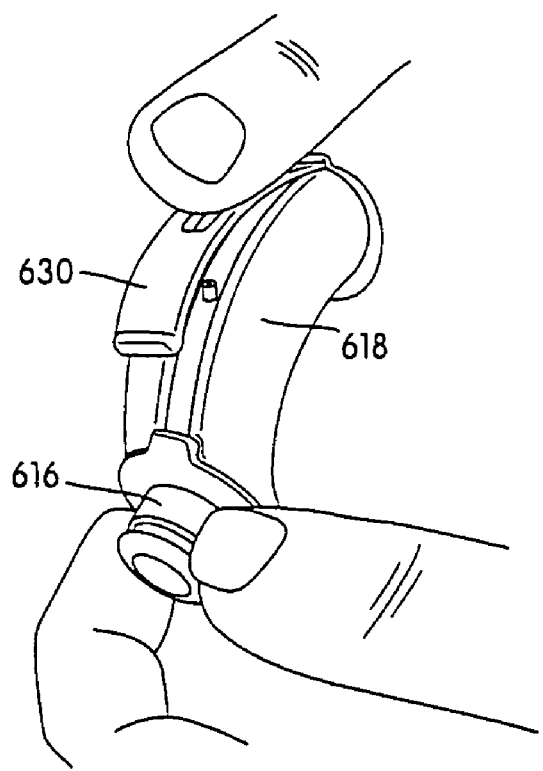
FIG. 71 is a perspective view illustrating the clip shown in FIG. 67 being engaged with the frame and nozzle assembly shown in FIG. 67.

However, the nozzle assembly 518 may be removably attached to the frame 516 in any other suitable manner. For example, FIGS. 67, 69, and 71 illustrate another method of attaching the nozzle assembly to the frame. As illustrated, the frame 616 is structured without channels in the main body such that the nozzle assembly 618 wraps around the main body and the clip 630 is secured between the side frame members of the frame 616 to hold the end portions of the nozzle assembly 618.

Figure 72:
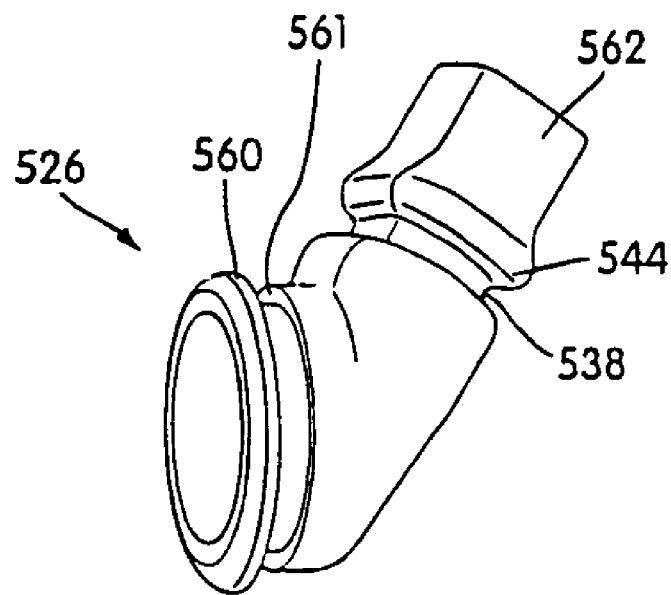
FIG. 72 is a perspective view of a second connector portion of the nasal assembly shown in FIG. 59.
Figure 73:
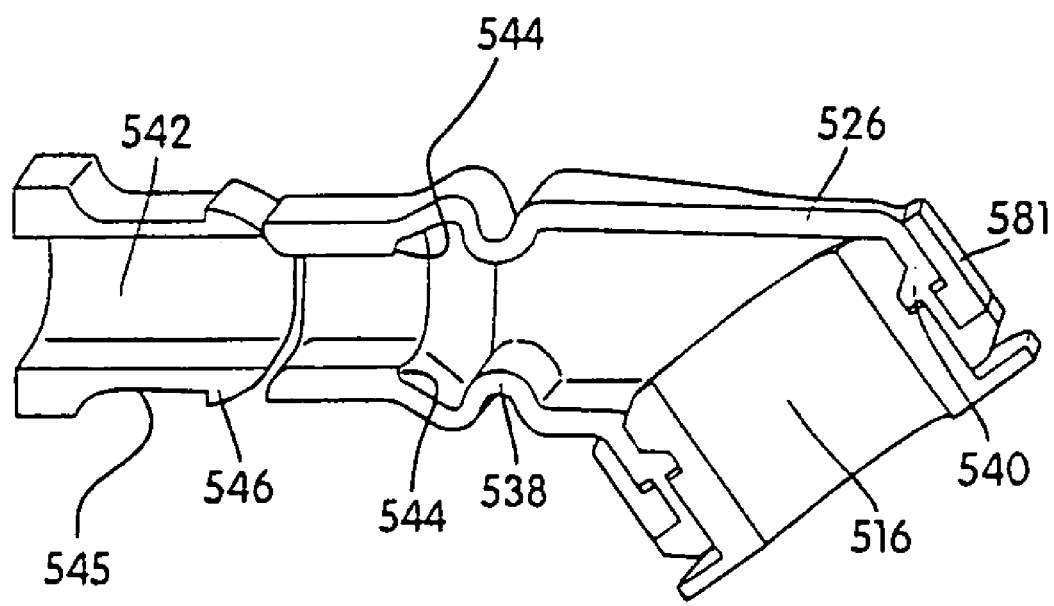
FIG. 73 is a cross-sectional view of a portion of the nasal assembly shown in FIG. 59 illustrating the engagement between the frame, second connector portion, and angle connector.

As shown in FIG. 72, the second connector portion 526 includes a main body having a front portion 560 and a rear portion 562. A groove 561 is provided adjacent the front portion 560. The front portion 560 includes an annular rib portion 540 (FIG. 73). The front portion 560 of the second connector portions 526 are stretched over the respective first connector portion 524 to provide an interference fit. Also, the rib portion 540 is adapted to engage within the recess 566 of the first connector portion 524 for coupling the first and second connector portions 524, 526 with one another, as shown in FIG. 73. The second connector portion 526 may rotate with respect to the first connector portion 524 for an infinite amount of settings for alignment of the nozzles 550 with respect to the nasal passages of the patient. The setting may be optionally locked by friction, for example. That is, the rotatable coupling allows the frame 516 to be rotated with respect to the second connector portions 526 so as to adjust the position of the nozzles 550 with respect to the patient's nose in use.

The second connector portions 526 may be formed of silicone with a hardness of about 50-60 Shore A hardness. This hardness facilitates assembly, swiveling movement, and seal with the frame 516. However, the second connector portions 526 may be formed of any other suitable material and may have any suitable hardness.

Each second connector portion 526 is also formed with a feature that allows relative movement between the angle connector 542 and the frame 516 for different facial widths. In the illustrated embodiment, the feature is a corrugation 538 in the second angle connector 542. This feature isolates the connection between the second connector portion 526 and the frame 516 to prevent detachment. This feature also allows the second connector portions 526 to be flexible so as to dampen tube drag forces. Moreover, the second connector portions 526 are flexible without obstructing airflow. However, the feature may have any other suitable structure to provide flexibility.

In the illustrated embodiment, each of the second connector portions 526 is provided with or connected to the angle connector 542 (see FIGS. 74-76) that connects with the respective inlet conduit 574. The second connector portions 526 and the angle connectors 542 may be formed in an integral one piece unit. The rear portion 562 of each second connector portion 526 includes an interlock in the form of an undercut 544 (FIG. 73) for engagement with the angle connector 542. The angle connector 542 includes a conduit 545 with a shoulder portion 546 that engages the undercut 544 to secure the angle connector 542 to the second connector portion 526, as can be determined from FIG. 73, an exploded view prior to connection.

Figure 76:
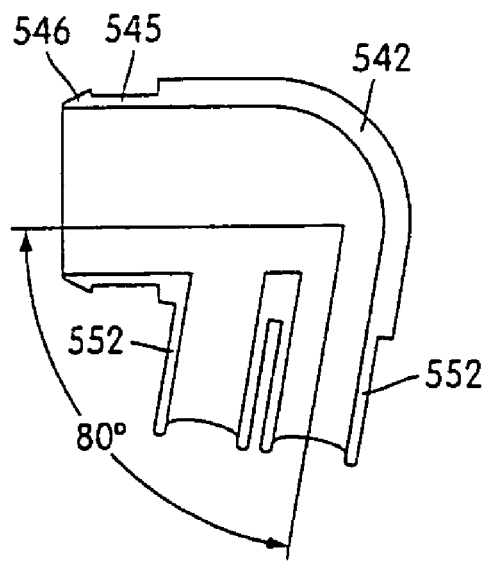
FIG. 76 is a cross-sectional view of the angle connector shown in FIG. 74.

The angle connector 542 includes elongated connectors 552 structured to engage the respective inlet conduit 574. In the illustrated embodiment, the elongated connectors 552 have a tapered configuration to facilitate connection. Also, the connectors 552 are arranged to wedge the inlet conduit 574 therebetween to secure the inlet conduit 574 thereto. As shown in FIG. 76, the conduit 545 and elongated connectors 552 of the angle connector 542 are angled about 80° from one another. However, the angle between the conduit 545 and elongated connectors 552 may have any other suitable dimension.

Figure 60:
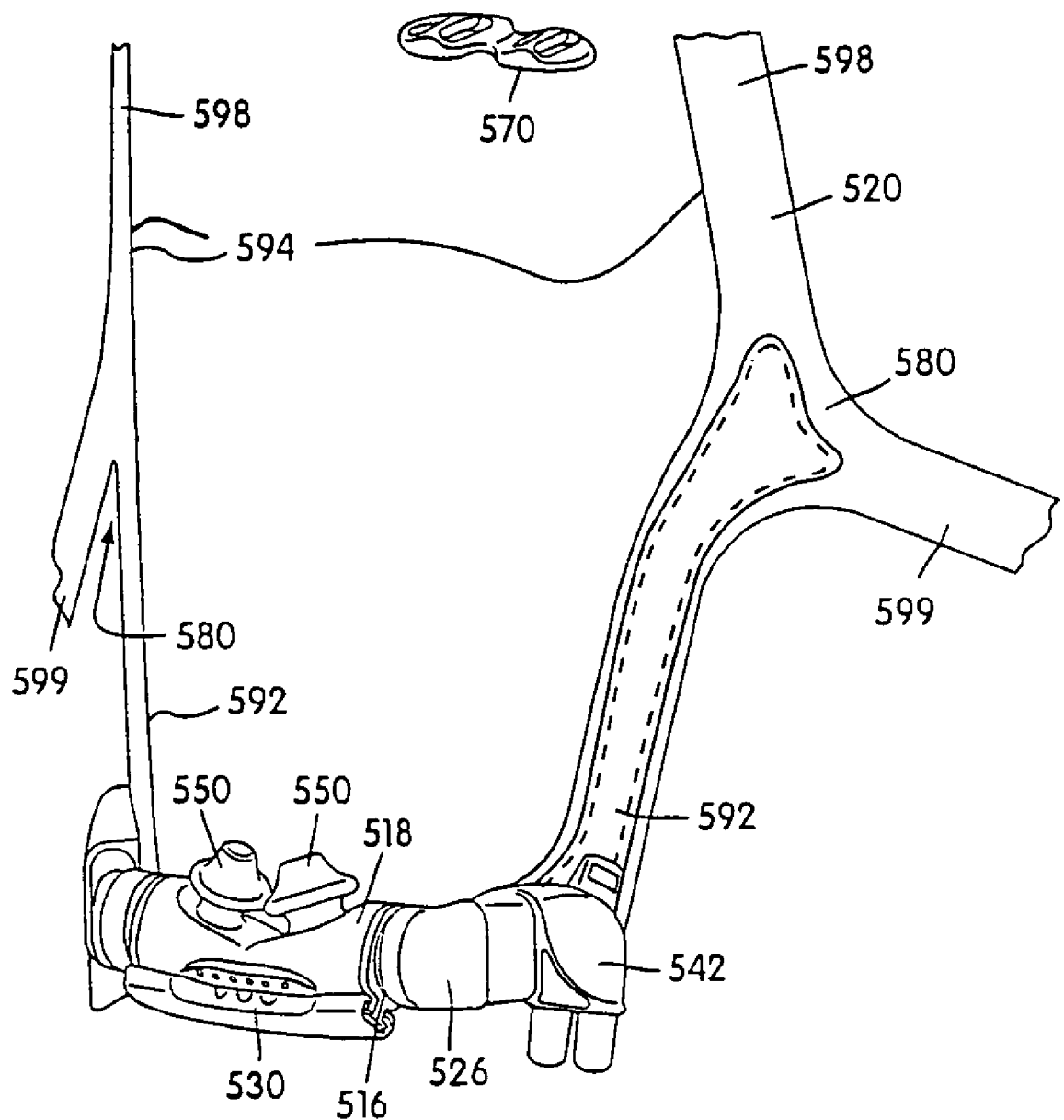
FIG. 60 is a perspective view of the nasal assembly shown in FIG. 59 removed from a patient's head.
Figure 61:
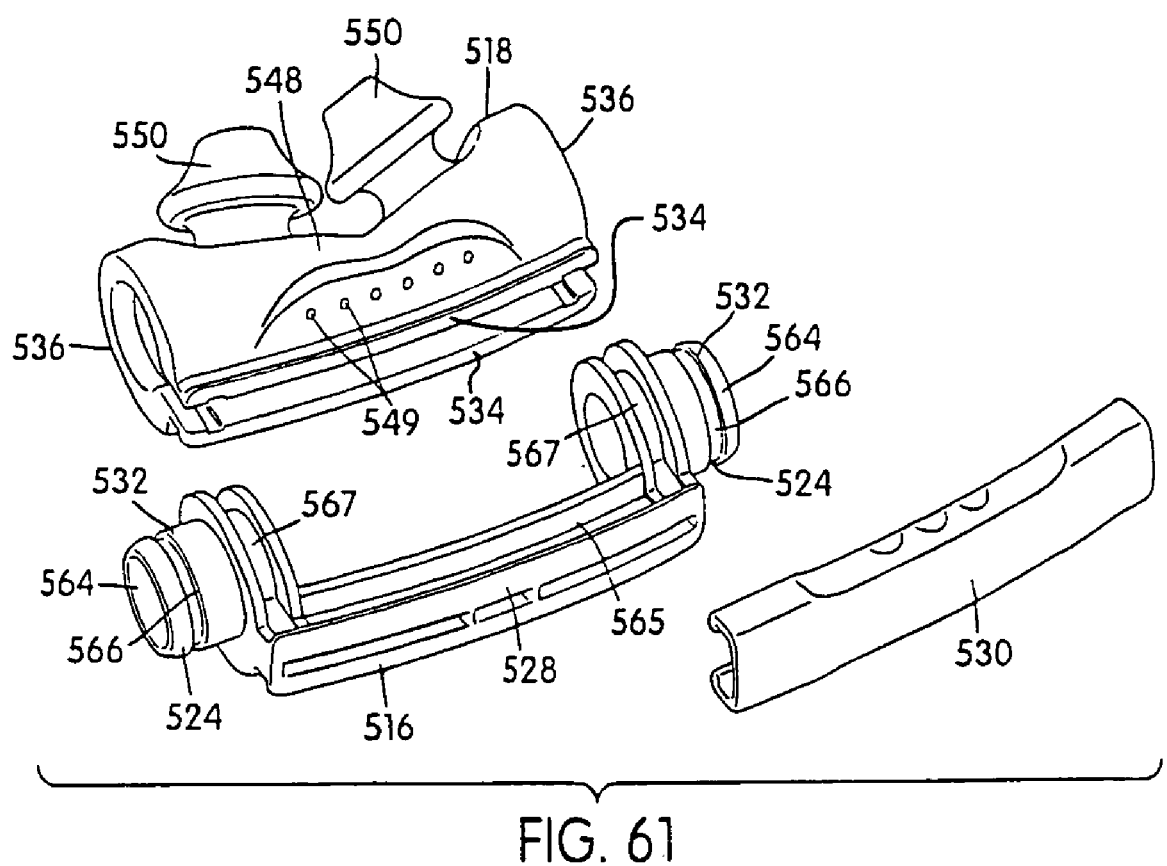
FIG. 61 is an exploded view of a portion of the nasal assembly shown in FIG. 59 illustrating the frame, nozzle assembly, and clip thereof.
Figure 76A:
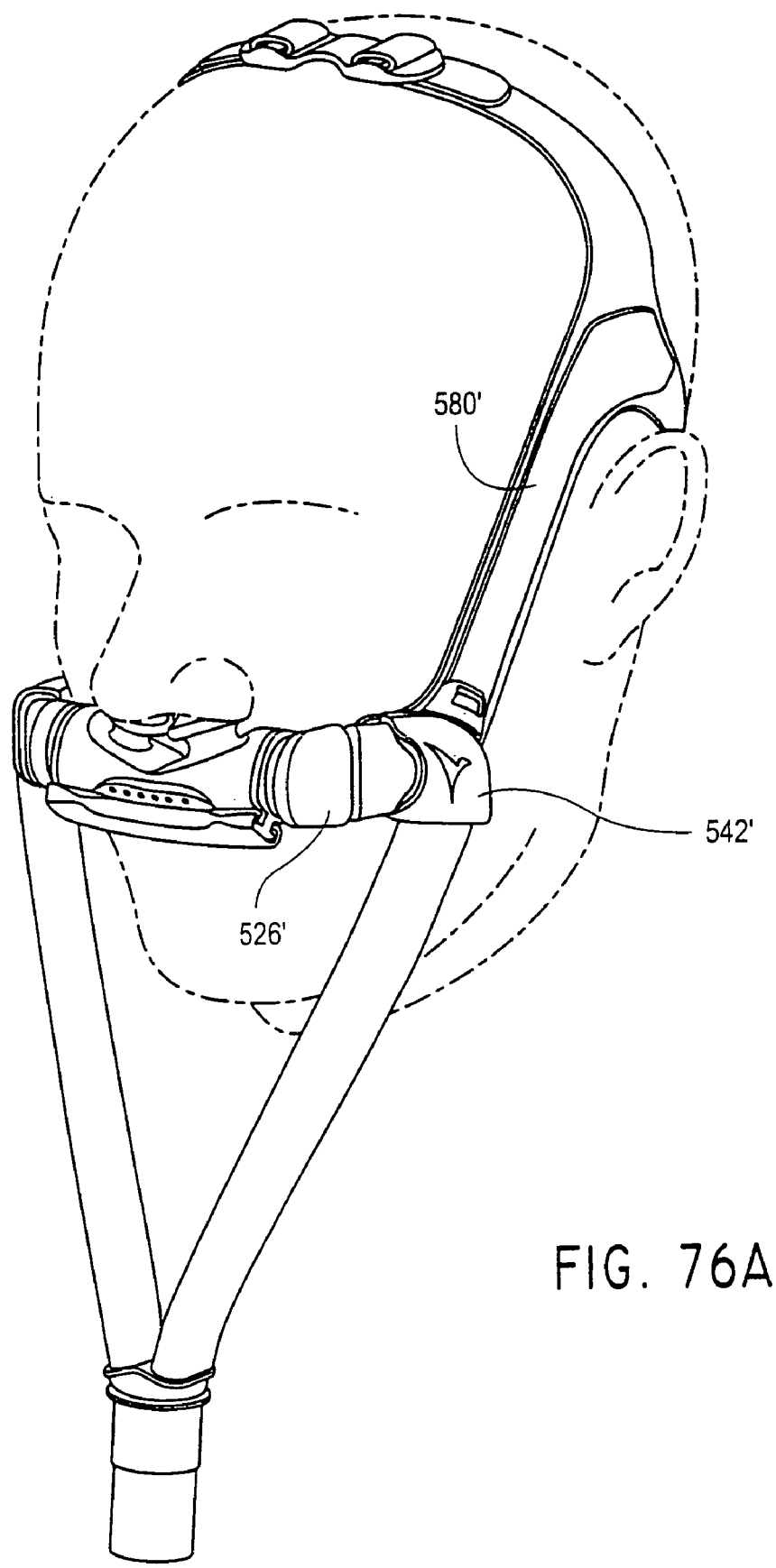
FIG. 76A illustrates another embodiment of the present invention.
Figure 76C:
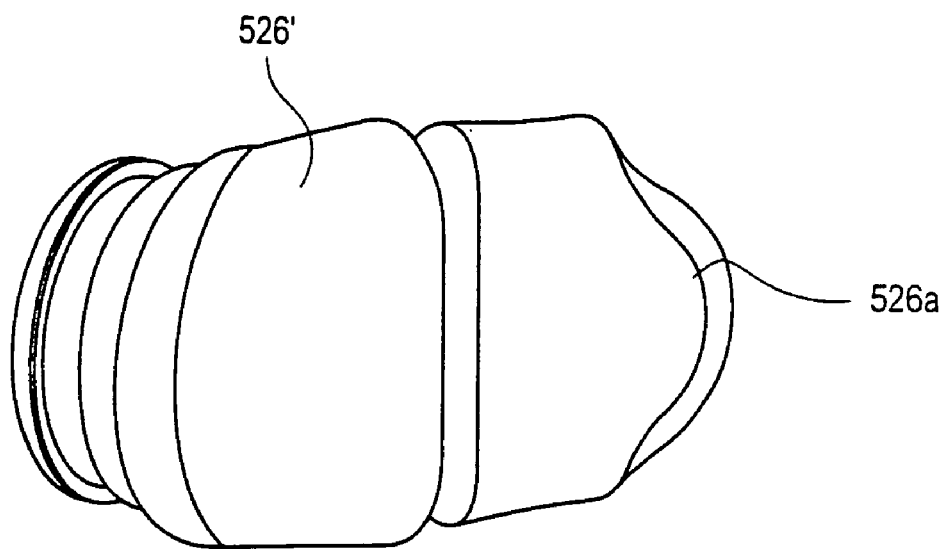
FIG. 76C illustrates a second connector portion of the assembly of FIG. 76A.
Figure 76D:
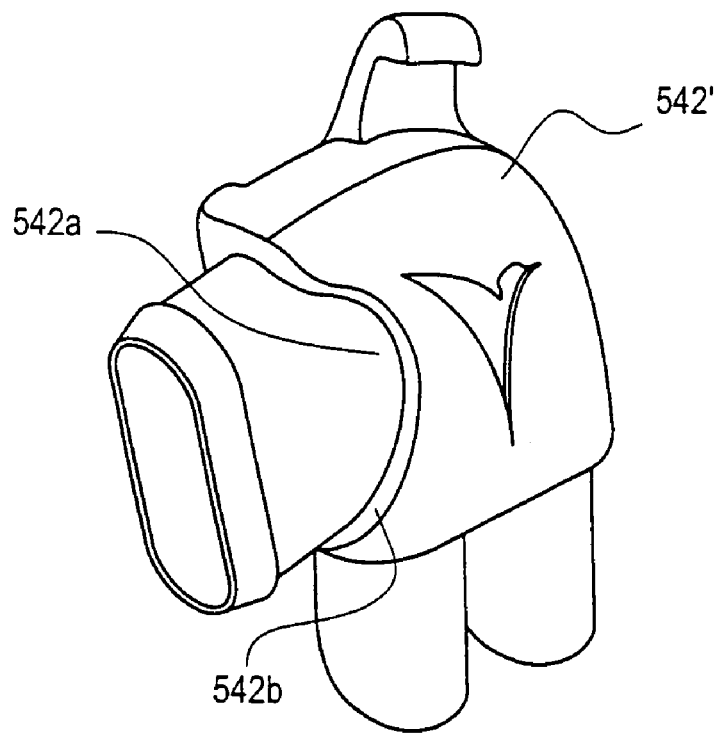
FIG. 76D illustrates an angle connector used in the assembly of FIG. 76A.

FIG. 76A illustrates another embodiment of a mask assembly similar to that shown in FIG. 60. FIG. 76B is an exploded view of the mask assembly in FIG. 76A. A yoke 580' in FIGS. 76A and 76B is somewhat different from the yoke 580 shown in FIG. 60 in that the yoke 580' in FIGS. 76A and 76B has dimensions that are more streamlined, styled and/or optimized for use with the headgear straps. In addition, a second connector portion 526' and elbow connector 542' in FIG. 76A are structured to facilitate alignment (or prevent misalignment) therebetween. In particular, as best shown in FIG. 76C, the second connector portion 526' includes a tab 526a which is intended to be received within a key way or recess 542a of elbow connector 542'. The elbow connector 542' also includes a ridge 542b which receives a tip portion of the tab 526A.

Returning to FIG. 59, first ends of the pair of conduits 574 are connected to respective angle connectors 542. Second ends of the pair of conduits 574 are connected to a flow generator connector 584 coupled or provided to a swivel 590, which in turn is in communication with a pressurized supply that supplies pressurized breathable gas. As illustrated, the angle connectors 542 route the pair of inlet conduits 574 downwardly under the chin of the patient.

As a result, pressurized gas can pass through the pair of inlet conduits 574, angle connectors 542, second connector portions 526, frame 516 and nozzle assembly 518, and through the nozzles 550 for breathing by the patient.

Figure 77:
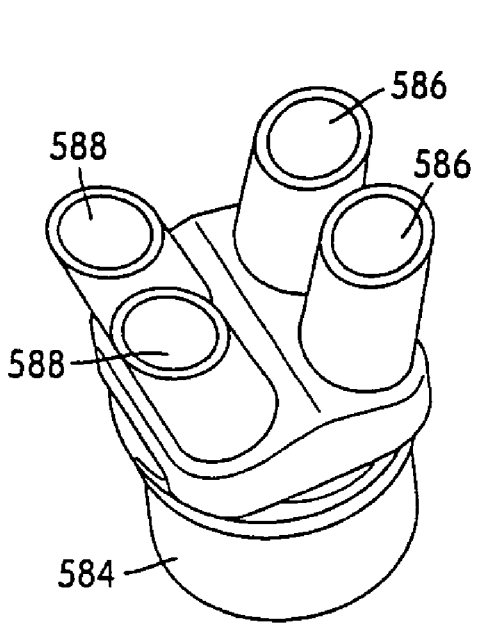
FIG. 77 is a perspective view of a flow generator connector of the nasal assembly shown in FIG. 59.
Figure 78:
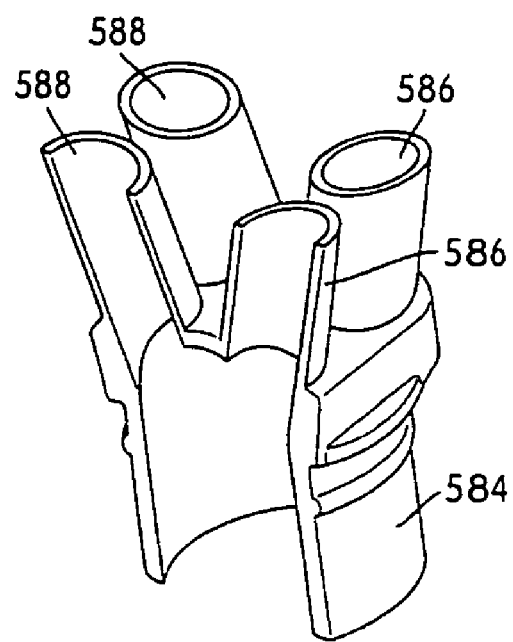
FIG. 78 is a cross-sectional view of the flow generator connector shown in FIG. 77.

FIGS. 77 and 78 illustrate the flow generator connector 584 structured to interconnect the second ends of the pair of inlet conduits 574 with the swivel 590 which is in communication with a pressurized supply. The flow generator connector 584 includes first elongated connectors 586 structured to engage one of the inlet conduits 574 and second elongated connectors 588 structured to engage the other of the inlet conduits 574. In the illustrated embodiment, the first and second elongated connectors 586, 588 have a tapered configuration, e.g., the tops are formed at an angle, to facilitate connection. Also, the first and second elongated connectors 586, 588 are arranged to wedge the respective inlet conduit 574 therebetween to secure the respective inlet conduit 574 thereto, e.g., by friction. Moreover, the flow generator connector 584 has a general Y-shape with the first elongated connectors 586 angled with respect to the second elongated connectors 588. The Y-shape of the flow generator connector 584 prevents incorrect assembly with the inlet conduits 574 and assists in merging the air paths. As shown in FIG. 59, a swivel 590 may be attached to the flow generator connector 584 to allow relative movement with respect to the pressurized supply.

Figure 79:
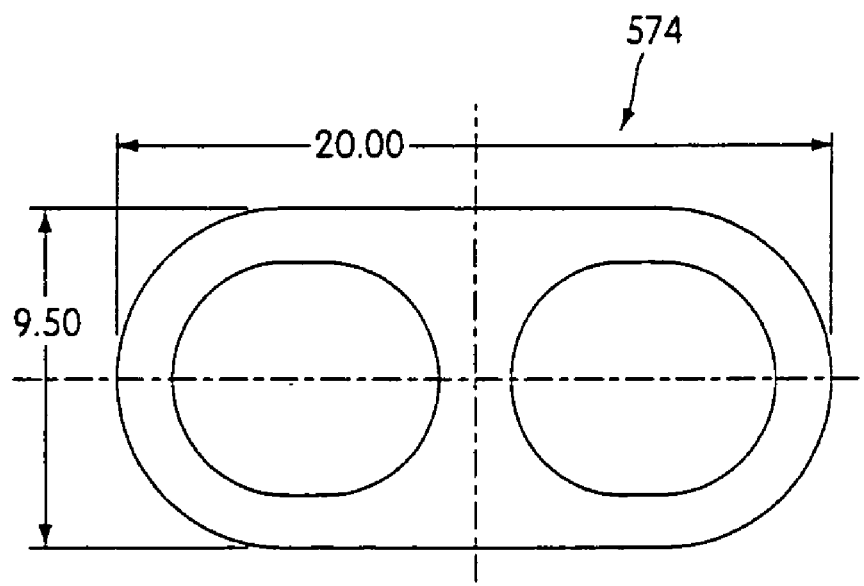
FIG. 79 is a cross-sectional view of an embodiment of an inlet conduit of the nasal assembly shown in FIG. 59.

As shown in FIG. 79, each inlet conduit 574 includes a plurality of channels. In the illustrated embodiment, each inlet conduit 574 is constructed with tubing that provides a dual air flow channel to prevent or at least reduce kinking and crushing and facilitate connection. However, the conduits 574, angle connectors 542, and connector 584 may be structured to provide one air flow channel or more than two air flow channels. The inlet conduits 574 may be formed with silicone and have a hardness of about 50 shore A hardness. However, the inlet conduits 574 may be formed of any other suitable material and have any suitable hardness.

The inlet conduits 574 are structured to provide low impedance. In one embodiment, the inlet conduits 574 provide impedance less than about 3 cmH$_2$O, for a given flow rate. Also, the inlet conduits 574 have a low profile. As shown in FIG. 79, each inlet conduit 574 has a width of about 20 mm and a height of about 9.5 mm. However, the inlet conduits 574 may have any other suitable shape, size and structure. For example, the inlet conduits 574 may have a substantially D-shaped cross section. The width dimension of 20 mm can be adjusted to change the impedance. For example, if the width is decreased while the height and pressure remain constant, the impedance will be increased, as the cross-sectional area decreases. Conversely, if the width is increased, keeping the height and pressure constant, the impedance can be lowered. The result is that impedance can be lowered without increasing the height, thereby maintaining a low profile of the inlet conduits 574, such that they are less obtrusive to the patient and/or do not uncomfortably dig into the patient's face or skin. Other components of the air delivery path, e.g., the angle connectors 542, have been designed with a view towards decreasing impedance. By contrast, impedance of an inlet conduit or angle connector with a round cross section can be similarly lowered by increasing the diameter of the conduit, but the profile also increases with commensurate discomfort to the patient since the conduit may assume a position further outward from the patient's face, and/or the conduit may be pressed against the patient's face, which decreases comfort and compliance.

The headgear assembly 520 is removably attached to second connector portions 526 and angle connectors 542 to retain the second connector portions 526 on the frame 516.

Also, the headgear assembly 520 is structured to transfer a tube pulling force to the headgear assembly 520 or the frame 516, to thereby avoid or reduce the chances that the tube pulling force is applied to the nozzle assembly, which may compromise the seal between the nozzles and the patient's airways.

Figure 80:
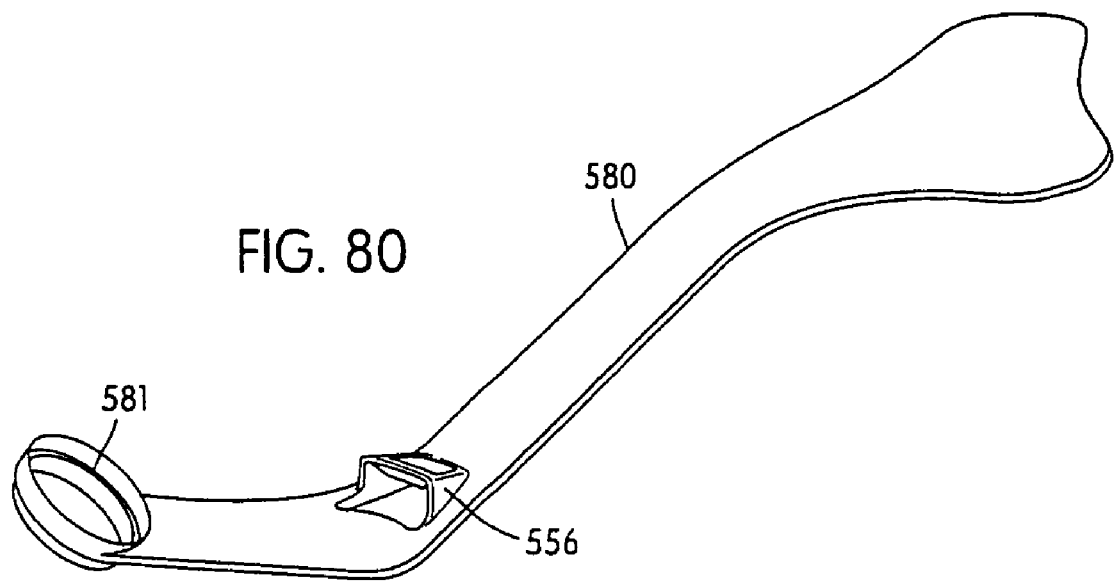
FIG. 80 is a perspective view of headgear yoke of the headgear assembly of the nasal assembly shown in FIG. 59.
Figure 81:
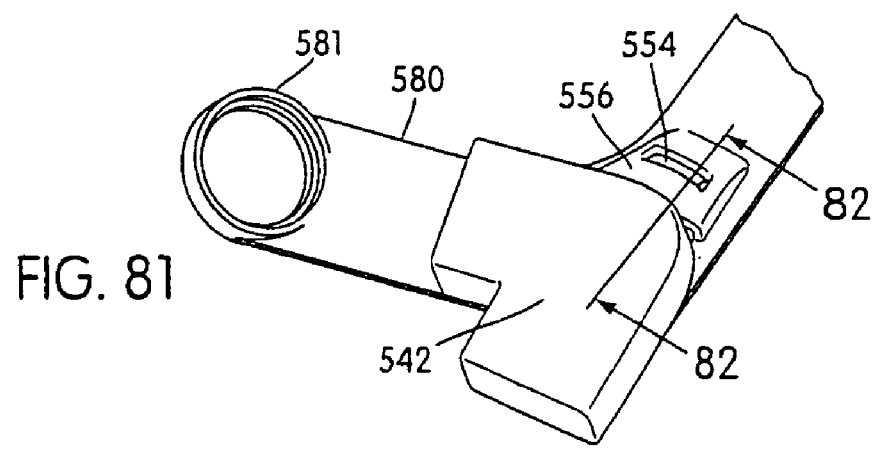
FIG. 81 is a perspective view illustrating engagement between the headgear yoke (FIG. 80) and angle connector (FIG. 74)
Figure 82:
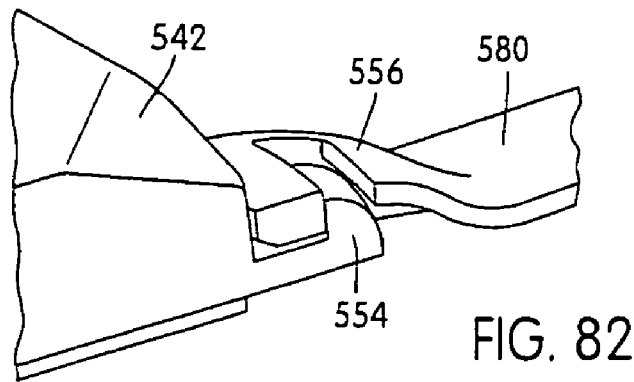
FIG. 82 is a cross-section through line 82-82 of FIG. 81.

As shown in FIGS. 59 and 60, the headgear assembly 520 includes two side portions 592 with a rear portion 594 connecting the side portions 592. The side portions include side straps and a headgear yoke 580 is attached to each side strap. The headgear yoke 580 acts as a stiffener to add rigidity to the headgear assembly 520. FIGS. 59 and 60 show slightly different yoke configurations. In FIG. 59, the yoke is shown as a member which covers at least a portion of flexible straps 598, 599, to add stiffness or rigidity thereto. In FIG. 60, the yoke 580 is a semi-rigid layer, such as plastic, which is provided to, e.g., sewn onto, the headgear straps 598 and/or 599. The yoke in FIG. 60 may be more or less co-extensive with the straps 598 and/or 599, depending on the desired stiffness. The yoke 580 in FIG. 60 is also shown in FIGS. 80-82. The rear portion 594 includes upper straps 598 that pass over the top of the patient's head and rear straps 599 that pass around the rear portion of the patient's head. The upper straps 598 are structured to adjust the sealing force because they pull the frame 516 up into the patient's nose. The rear straps 599 are structured to adjust the stability of the nasal assembly 510 because they pull the frame 516 back into the patient's face on the top lip of the patient.

Figure 83:
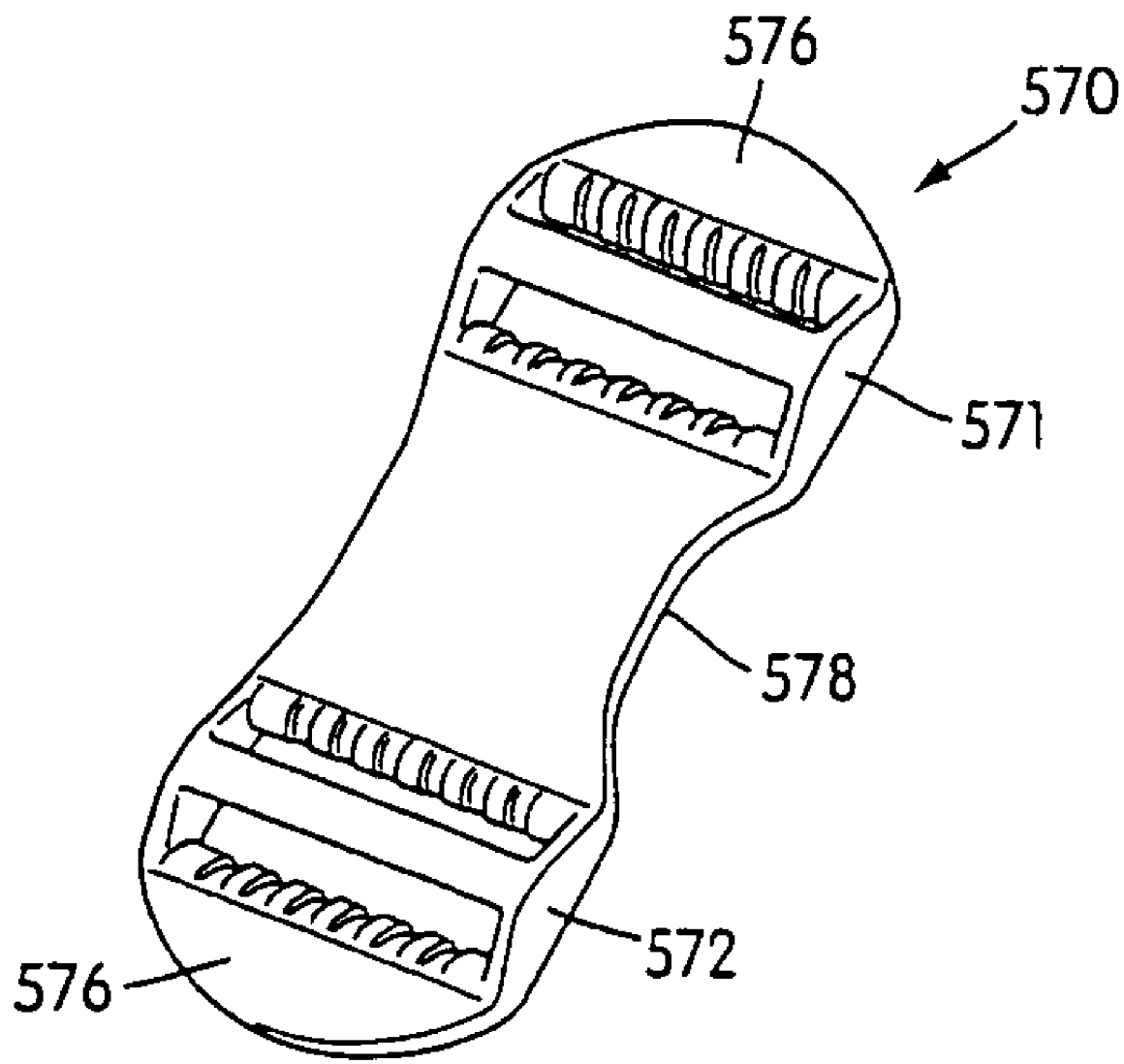
FIG. 83 is a perspective view of a headgear buckle of the nasal assembly shown in FIG. 59.

The upper straps 598 are coupled to one another by a headgear buckle 570. The headgear buckle 570 is structured to allow symmetrical adjustment of the headgear assembly 520. Specifically, as shown in FIG. 83, the headgear buckle 570 includes a first locking portion 571 and a second locking portion 572. The first locking portion 571 is adapted to be removably and adjustably coupled with one of the upper straps 598 extending from one of the headgear yokes 580 and the second locking portion 572 is adapted to be removably and adjustably coupled with the other of the upper straps 598 extending from the other of the headgear yokes 580. Each of the upper straps 598 may be wrapped around the cross-bar of the associated locking portion 571, 572 of the buckle 570, as best shown in FIG. 59. A tab 576 is provided on each locking portion 571, 572 to facilitate the patient in adjusting headgear tension. Also, the headgear buckle 570 includes a curved surface 578 that prevents contact of the buckle 570 with the patient's head. The rear straps 599 may be coupled to one another by a buckle (as upper straps 598 are) or in any other suitable manner.

The headgear yokes 580 of the headgear assembly 520 include retaining members 581 engaged with respective second connector portions 526 so as to retain the second connector portions 526 on the frame 516. In the illustrated embodiment, the retaining members 581 are ring-shaped and enclose the respective second connector portions 526. As shown in FIG. 73, the ring-shaped retaining members 581 have an annular protrusion that engages within the annular groove 561 in a respective second connector portion 526 so as to securely retain the second connector portions 526 on the frame 516.

Also, the pair of retaining members 581 are engaged with respective grooves 561 (FIG. 72) provided in second connector portions 526 so as to transfer the headgear force to the frame 516. This allows a more accurate adjustment of the force applied by the headgear assembly 520 to the frame 516. Moreover, the headgear buckle 570 is centrally located on the patient's head to allow symmetrical adjustment of the headgear assembly 520 and hence adjust the headgear force applied to the frame 516.

Figure 74:
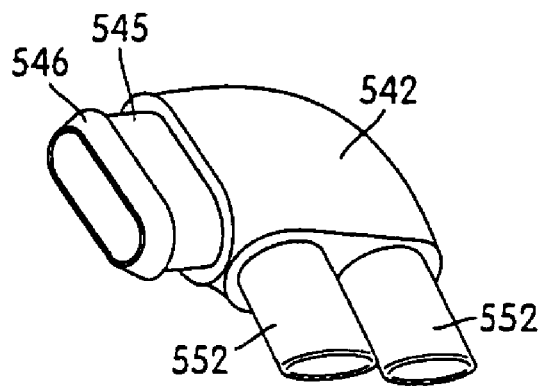
FIG. 74 is a perspective view of an angle connector of the nasal assembly shown in FIG. 59.
Figure 74B:
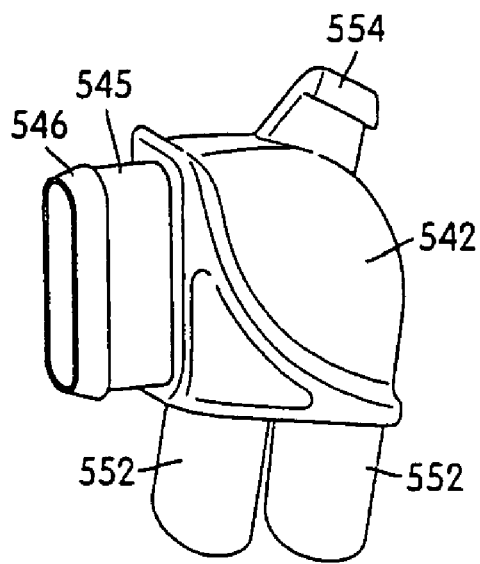
FIG. 74B is a perspective similar to FIG. 74 but at a different angle.
Figure 75:
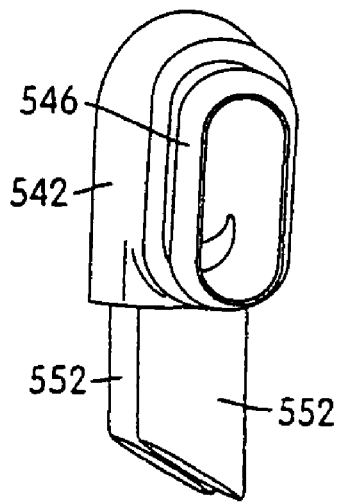
FIG. 75 is a side view of the angle connector shown in FIG. 74.

The angle connectors 542 of the second connector portions 526 are releasably interlockable with the headgear assembly 520. Specifically, the angle connectors 542 include first locking members 554 (see FIG. 74B) that are interlockable with second locking members 556 (see FIG. 80) provided on the headgear yoke 580 of the headgear assembly 520. In the illustrated embodiment, the first locking members 554 are hook-shaped members that interlock with a cross-bar provided by the second locking members 556, as shown in FIGS. 81 and 82. The locking members are tapered and designed to keep a low profile.

Figure 84:
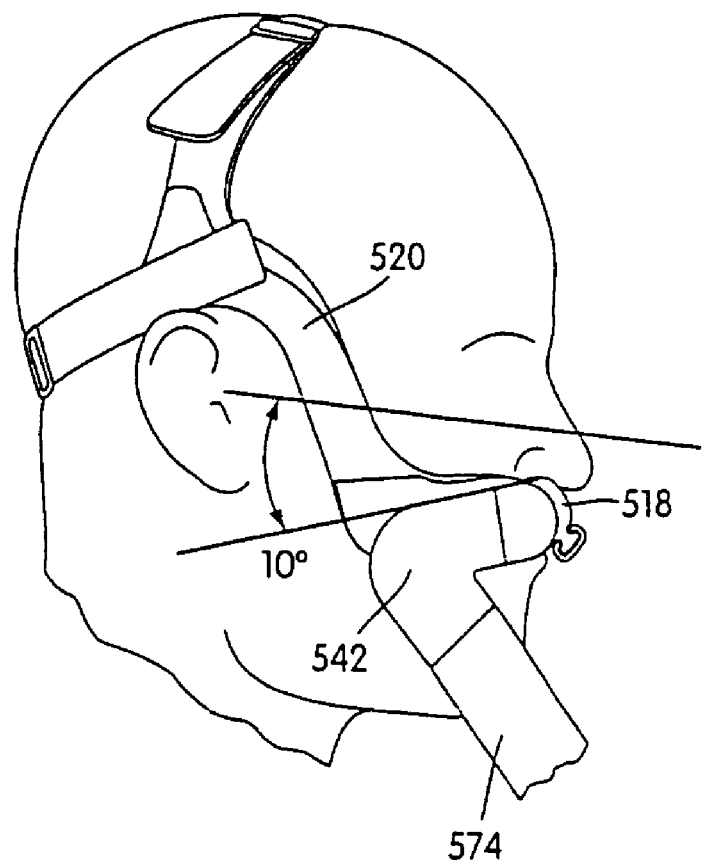
FIG. 84 is a perspective view of the nasal assembly shown in FIG. 59 illustrating the routing of the headgear assembly.
Figure 85:
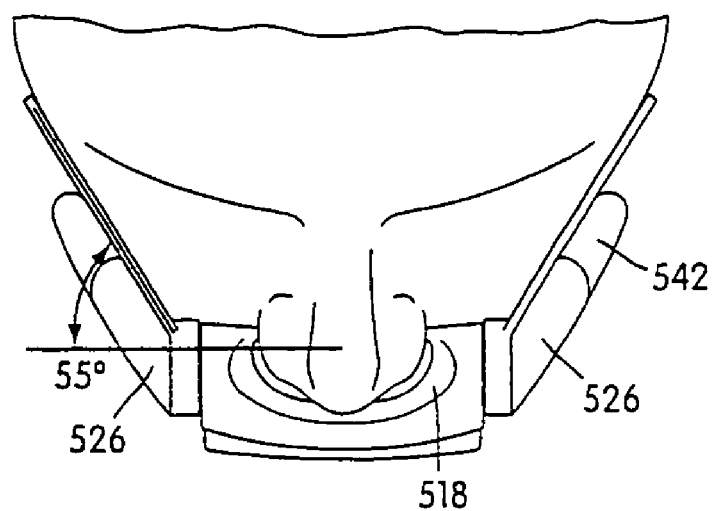
FIG. 85 is another perspective view of the nasal assembly shown in FIG. 59 illustrating the routing of the headgear assembly.

FIGS. 84 and 85 illustrate the nasal assembly 510 engaged with nasal passages of a wearer's nose. As shown in FIG. 84, the nasal assembly 510 is structured such that the angle connectors are angled about 10° below the horizontal so that the nasal assembly 510 avoids contact with the patient's cheekbone. Also, FIG. 84 shows that the clip 530 which holds the split ends of the nozzle assembly is angled upwardly and outwardly away from the lips of the patient, to prevent inadvertent contact with the patient. The angle may be in the range of 10-90 degrees, and preferably 20-60 degrees or about 30 degrees. As shown in FIG. 85, the second connector portions 526 are angled about 55° from the frame 516. The corrugation 538 (FIG. 73) may be provided to flex (inward and outward) so as to accommodate patients with faces varying in width. However, the angles noted above are only exemplary and the nasal assembly 510 may be structured to provide any suitable angle with the patient's face.

Similar to the nasal assemblies described above, the inflation of the gusset or base portion 548 along with the headgear tension provides an effective sealing force against the nasal passages of the patient. Also, the springiness of the nozzles 550 provides an additional sealing force.

Sixth Illustrated Embodiment

Figure 88:
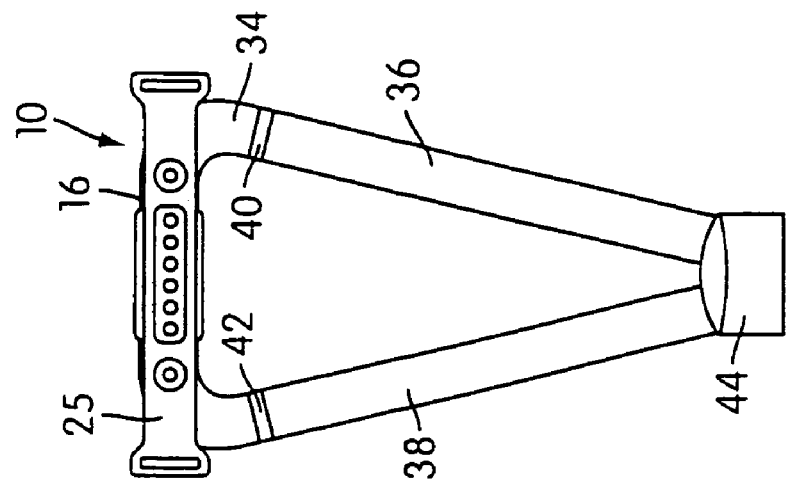
FIG. 88 is a bottom view of the nasal assembly shown in FIG. 86.
Figure 87:
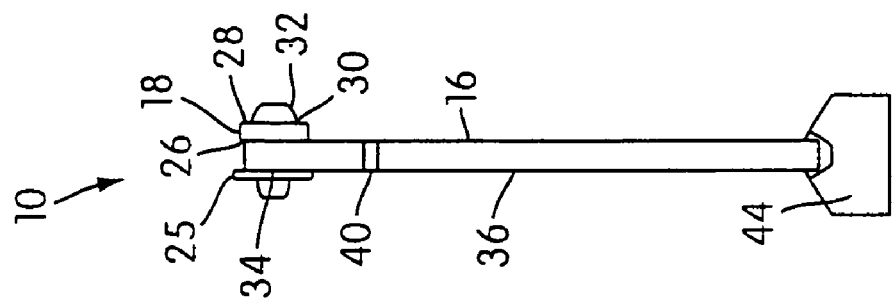
FIG. 87 is a side view of the nasal assembly shown in FIG. 86.
Figure 86:
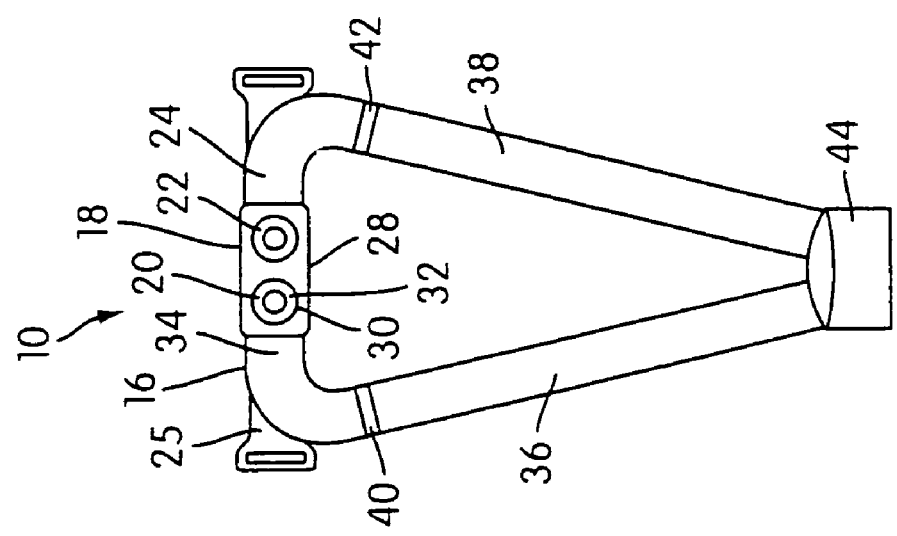
FIG. 86 is a top view illustrating a nasal assembly constructed in accordance with an embodiment of the invention.
Figure 97:
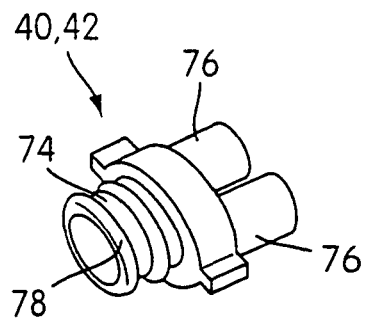
FIG. 97 is a perspective view of an inlet connector of the nasal assembly shown in FIG. 86.
Figure 97B:
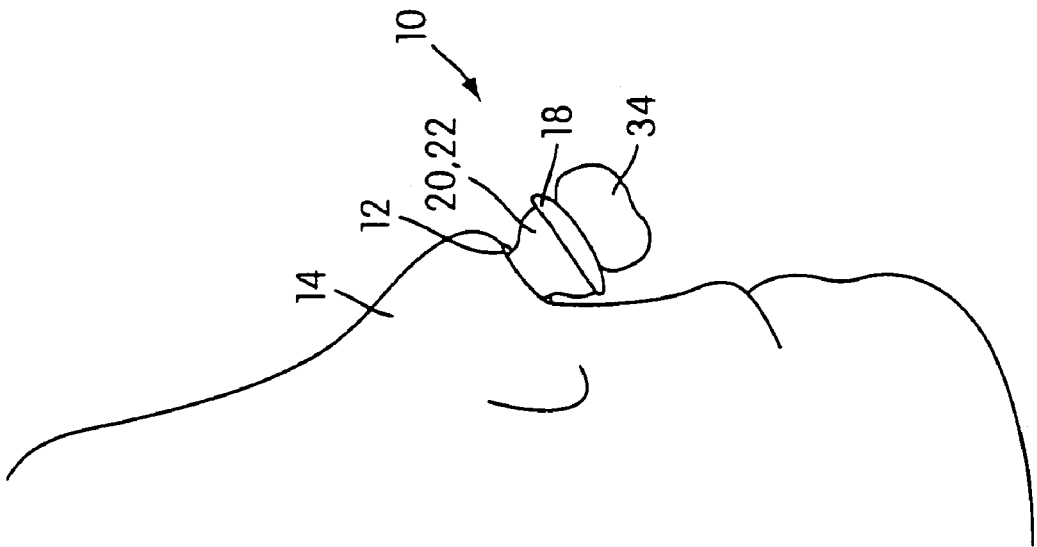
FIG. 97B is a schematic view of the nasal assembly shown in FIG. 86 with the nozzles in a second position in sealing engagement with the nasal passages of the patient.
Figure 97A:
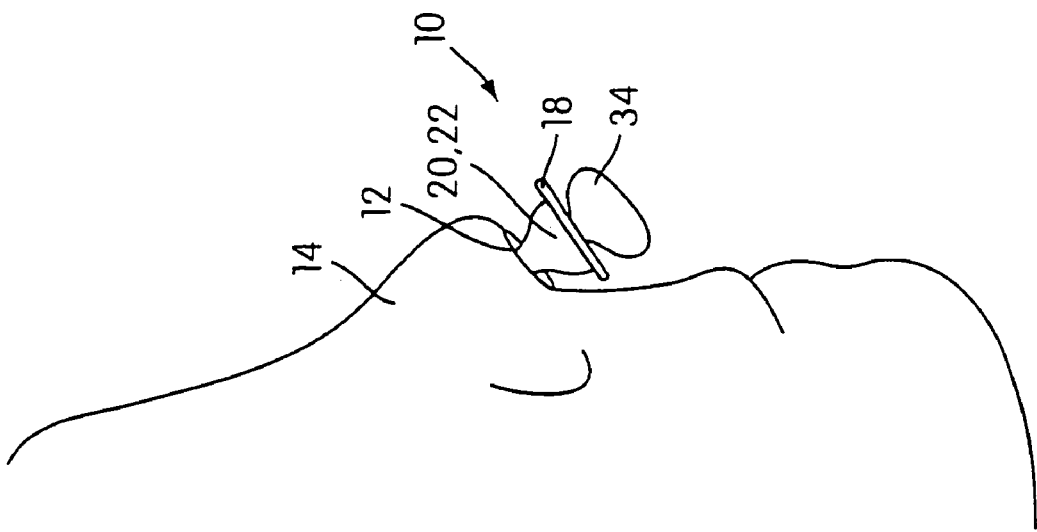
FIG. 97A is a schematic view of the nasal assembly shown in FIG. 86 with the nozzles in a first position adjacent to the nasal passages of the patient.

FIGS. 86-88 show another embodiment of a nasal assembly 10 structured to deliver breathable gas to the nasal passages 12 of the patient's nose 14 (see FIGS. 97A and 97B). The nasal assembly 10 includes a flexible conduit 16, a gusset portion 18, a pair of nozzles 20, 22, and a headgear connector 25. The flexible conduit 16 has a portion adapted to receive a supply of pressurized breathable gas and a patient side 24. The gusset portion 18 has a first side 26 (see FIG. 89) attached to the patient side 24 of the flexible conduit 16 and a second side 28. The pair of nozzles 20, 22 each have a first portion 30 attached to the second side 28 of the gusset portion 18 and a second portion 32 structured to sealingly engage with nasal passages 12 of the patient's nose 14 in use and provide a seal between the nasal assembly 10 and the patient's nasal passages 12 (see FIG. 90). The headgear connector 25 attaches the flexible conduit 16 to a headgear assembly positioned on the patient's head. The gusset portion 18 is structured such that it can expand and contract to alter a distance between the conduit 16 and the pair of nozzles 20, 22, as will be further discussed below.

Alternatively, the gusset portion can be eliminated in favor of a more rigid construction that does not allow significant, if any, expansion or contraction. Instead, as described above in relation to the other main illustrated embodiments, the nozzles may be structured to engage that patient's nares with some degree of pretension (before the mask is in use, e.g., pressurized), which pretension can be achieved by compressing the nozzles in an axial or longitudinal sense.

In the illustrated embodiment, the flexible conduit 16 includes a central conduit 34, a pair of inlet conduits 36, 38 connected to the central conduit 34 by respective inlet connectors 40, 42, and a Y-shaped inlet connector 44 that interconnects the inlet conduits 36, 38. The Y-shaped inlet connector 44 is structured to be connected to a conduit that is connected to a pressurized supply. The pressurized supply supplies pressurized breathable gas through the inlet conduits 36, 38 and central conduit 34, into the gusset portion 18, and into the nozzles 20, 22 for breathing by the patient.

Figure 89:
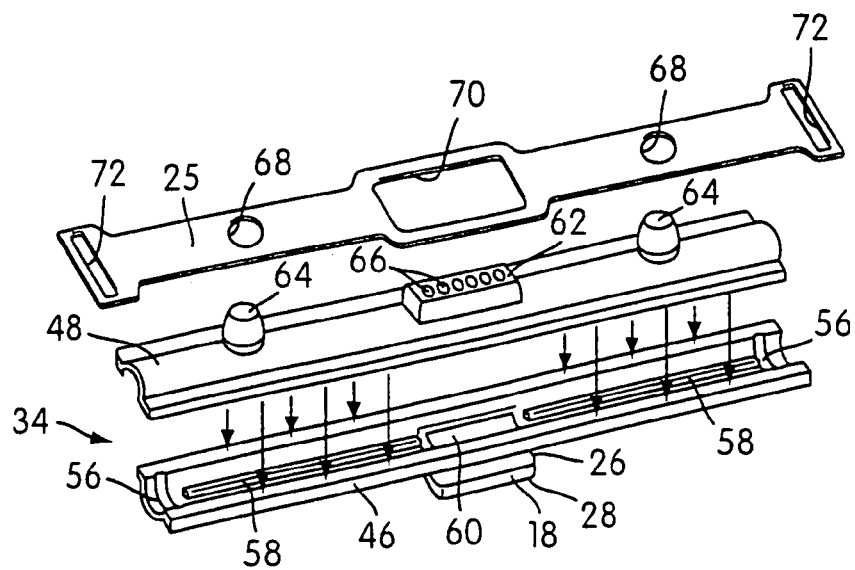
FIG. 89 is an exploded view of a portion of the nasal assembly shown in FIG. 86.
Figure 90:
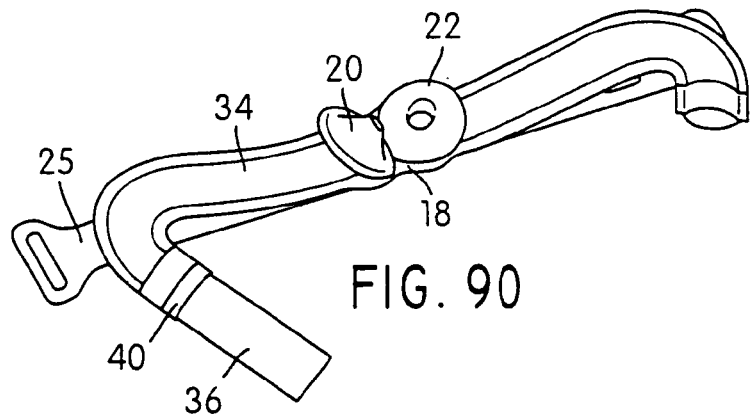
FIG. 90 is a perspective view of a portion of an embodiment of a nasal assembly.

As shown in FIG. 89, the central conduit 34 includes an upper portion 46 and a lower portion 48 that are coupled to one another. Each of the upper and lower portions 46, 48 includes an arcuate transverse cross-section such that the upper and lower portions 46, 48 form a conduit when coupled together at respective edges. In the illustrated embodiment, the upper and lower portions 46, 48 are rigidly coupled to one another by an adhesive, such as glue, for example. However, the upper and lower portions 46, 48 may be rigidly coupled to one another by any other suitable means, such as fasteners. Alternatively, the upper and lower portions 46, 48 may be removably coupled to one another, or they may be formed in a single unitary piece.

As shown in FIGS. 86, 88, 90 and 92-95, the upper and lower portions 46, 48 have a generally C-shape when viewed from above. Specifically, each of the upper and lower portions 46, 48 includes an elongated central section 50 and curved end sections 52, 54. However, the upper and lower portions 46, 48 may have any other suitable shape, such as an elongated shape, as shown in FIG. 89.

Figure 94:
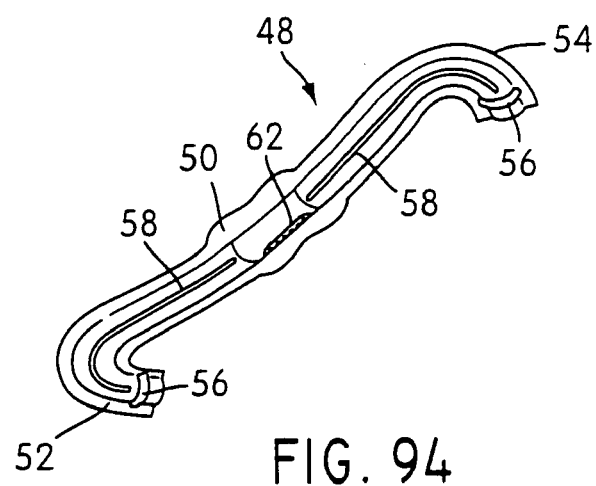
FIG. 94 is a perspective view of a lower portion of a central conduit of the nasal assembly shown in FIG. 90.
Figure 95:
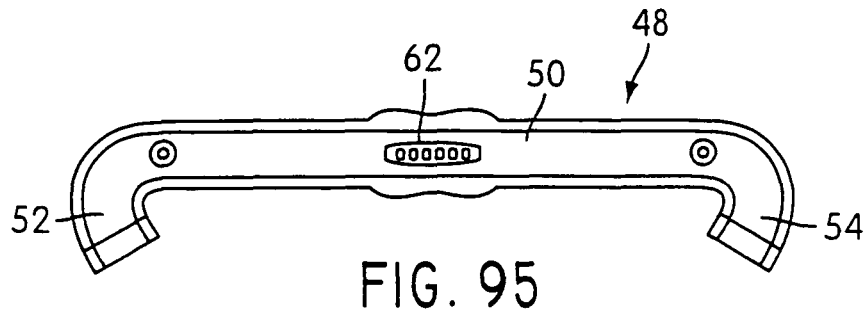
FIG. 95 is a bottom view of the lower portion of the central conduit shown in FIG. 94.

The curved end sections 52, 54 each include a groove 56, as shown in FIG. 94 for example. When the upper and lower portions 46, 48 are coupled to one another, the grooves 56 retain respective inlet connectors 40, 42, as will be further discussed. At least one of the upper and lower portions 46, 48 includes an anti-crush rib 58 that prevents the central conduit 34 from deformation that can prevent the flow of air therethrough. In FIG. 89, the groove 56 is provided on opposing ends thereof.

As shown in FIG. 89, the upper portion 46 of the central conduit 34 includes an opening 60. The gusset portion 18, which is in the form of an expandable and contractible pillow, includes a first side or sidewall 26 and a second side or sidewall 28 that define a space therebetween. The first sidewall 26 is attached to the upper portion 46. The first sidewall 26 includes an inlet opening that is communicated with the opening 60 in the upper portion 46. The second sidewall 28 has a pair of outlet openings. The connection between the gusset portion 18 and the upper portion 46 of the central conduit 34 is a flexible connection that allows relative movement between the gusset portion 18 and the central conduit 34, for increased comfort and accommodation of variations in patient facial features.

In the illustrated embodiment, the gusset portion 18 has a generally rectangular shape. However, the gusset portion 18 may have a generally circular or round cross-section, or any other suitable shape, including shapes to avoid sensitive regions of the patient's face, e.g. notched gusset shape to prevent contact with the patient's septum.

The pair of nozzles 20, 22 each has a first portion 30 attached the second sidewall 28 of the gusset portion 18 in communication with a respective outlet opening of the gusset portion 18. The second portion 32 of each of the nozzles 20, 22 is structured to sealingly engage with nasal passages 12 of the patient's nose 14 in use and provide a seal between the nasal assembly 10 and the patient's nasal passages 12. In the illustrated embodiment, the nozzles 20, 22 are in the form of nasal pillows wherein the second portion 32 is contoured (e.g., tapered, cone-shaped, truncated hollow cone, etc.) with a portion that seals on the underside of the nostrils and another portion that enters into the nasal passage of the patient's nose in use. However, the nozzles 20, 22 may be in the form of nasal prongs, cannula, or nasal puffs, for example, and may sealingly engage with the nasal passages in any suitable manner. For example, the nozzles 20, 22 may seal within the nasal passages, against the nasal passages, around the nasal passages, or combinations thereof. The nozzles 20, 22 may include a corrugated or flexible portion that allows the nozzles 20, 22 to move relative to the gusset portion 18 and the central conduit 34. The nozzles 20, 22 may be contoured to match the interior profile of the patient's nose 14.

In one embodiment, the nasal assembly uses patient-customized nozzles which may be removably mounted to the gusset portion. In a preferred form, the nozzles are constructed from a substantially flexible polymer material, such as a silicone elastomer. A unique nozzle can be made to match each patient's nose by first scanning their nose, either in situ or remotely, and then using the data for manufacture of the interface, for example, a mold maker. Scanning can be done using either non-contact or contact methods. Non-contact, for example photographically, or by physical contact with a probe or by collecting an impression of the inside of the nares or the desired contact interface. Once a pair of suitable nozzles are made, they are sent to the customer to be fitted to a patient. Advantages of the preformed or customized shape is that cross-sectional area may be maximized to reduce flow impedance.

Also, the use of preformed shapes improves comfort and increased stiffness materials such as semi-rigid plastics may be used that have greater resistance to distorting, thus minimizing nozzle distortion of the patient nares. Further, rigid plastics may be used that allows thin wall sections and allows flexibility of the nozzle due to its connection to the gusset portion, e.g., the gusset portion is soft and compliant.

In the illustrated embodiment, the upper portion 46 of the central conduit 34 is molded in one piece with the gusset portion 18 and nozzles or nasal pillows 20, 22 from deformable and inflatable materials. The central conduit 34, nasal pillows 20, 22, and gusset portion 18 may be constructed from a soft, flexible skin-compatible material such as silicone. The central conduit 34, nasal pillows 20, 22, and gusset portion 18 may be formed, for example, in an injection molding process as is known in the art.

However, the central conduit 34, nasal pillows 20, 22, and gusset portion 18 may be formed with any suitable material and may be formed by any suitable process. For example, the central conduit 34, gusset portion 18, and nasal pillows 20, 22 may be formed separately and permanently attached to one another with an adhesive, welding, and/or mechanical fasteners, for example. Alternatively, the central conduit 34, gusset portion 18, and nasal pillows 20, 22 may be formed separately and removably attached to one another.

The lower portion 48 of the central conduit 34 includes an exhaust vent 62 and a pair of tapered or barbed protrusions 64 structured to retain the headgear connector 25 to the central conduit 34. The exhaust vent 62 is aligned with the opening 60 in the upper portion 46. The exhaust vent 62 protrudes slightly outwardly from the central conduit 34 and includes a series of openings 66 for $CO_2$ washout.

As shown in FIG. 89, the headgear connector 25 is in the form of an elongated strap that includes a pair of openings 68 adapted to receive respective protrusions 64 of the lower portion 48 therethrough and a central opening 70 adapted to receive the exhaust vent 62 therethrough. Specifically, the openings 68 press over the tapered or barbed protrusions 64 to retain and locate the headgear connector 25 to the central conduit 34.

Further, the headgear connector 25 includes connection structures 72 on free ends thereof for connection to a headgear assembly (not shown). The headgear assembly can be removably connected to the connection structures 72 to maintain the nasal assembly 10 in a desired position on the patient's face. For example, the headgear assembly may include straps removably connected to respective connection structures 72.

Figure 91:
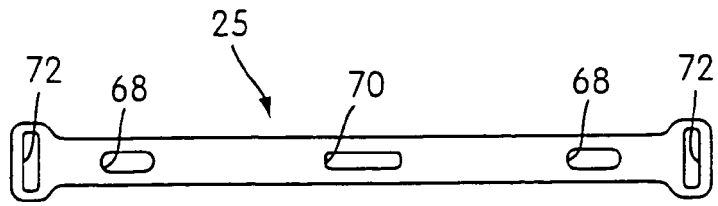
FIG. 91 is a top view of a headgear connector according to an alternative embodiment of the invention.
Figure 92:
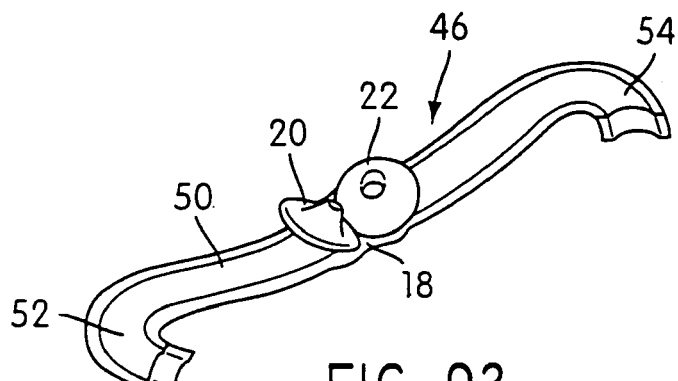
FIG. 92 is a perspective view of an upper portion of a central conduit of the nasal assembly shown in FIG. 90.
Figure 93:
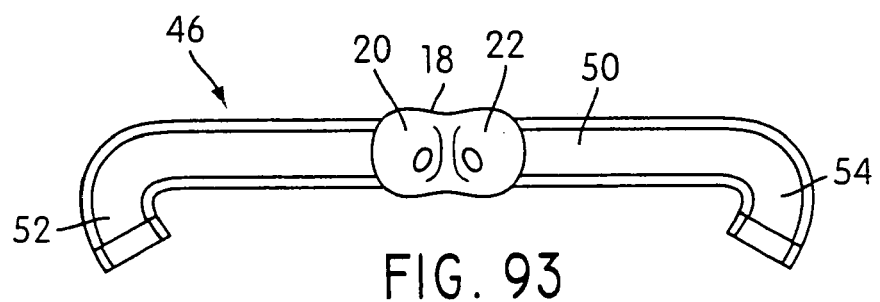
FIG. 93 is a top view of the upper portion of the central conduit shown in FIG. 92.

As shown in FIG. 91, the connection structures 72 may have rounded edges. Moreover, the openings 68, 70 may have any suitable shape (e.g. oval, circular, rectangular, etc.). For example, FIG. 91 illustrates openings 68, 70 with a generally oval shape and FIG. 89 illustrates openings 68 with a generally circular shape and opening 70 with a generally rectangular shape.

The headgear connector 25 is constructed of a deformable and resilient material so that it can deform in at least one bending plane, e.g., around the face of the patient in use. For example, the headgear connector 25 may be constructed of polypropylene or any other suitable polymer. Also, the headgear connector 25 may be constructed of a natural or synthetic fabric material, or a combination of materials such as a laminate combination. The headgear connector 25 is deformable such that it can conform to the contour of the patient's face when the nasal assembly 10 is mounted to the patient's head. Further, the headgear connector 25 bears the tension applied by the headgear assembly which prevents any tension from pulling on, and subsequently distorting, the flexible central conduit 16.

However, the headgear connector 25 may have any suitable structure for connection to a headgear assembly. For example, the headgear connector 25 may be the protrusions 64 provided on the central conduit 34 and the headgear assembly may attach directly to the protrusions 64. Alternatively, the headgear connector may be in the form of a locking clip receiver assembly structured to connect to a respective locking clip provided on the headgear assembly. Details of a locking clip receiver assembly and locking clips are provided in U.S. Provisional Applications of Moore et al., Ser. Nos. 60/377,254, 60/397,195, and 60/402,509, all of which are hereby incorporated into the present application by reference in their entireties.

The central conduit 34 is connected to the pair of inlet conduits 36, 38 by inlet connectors 40, 42. As shown in FIG. 97, each inlet connector 40, 42 includes a first conduit portion 74 that branches into a pair of second conduit portions 76. The first conduit portion 74 includes a radially expanded flange 78 that is received within a respective groove 56 provided by the central conduit 34 on opposing end sections 52, 54 thereof. Thus, a first inlet connector 40 is retained to one end section 52 of the central conduit 34 and a second inlet connector 42 is retained to the opposite end section 54 of the central conduit 34.

Figure 96:
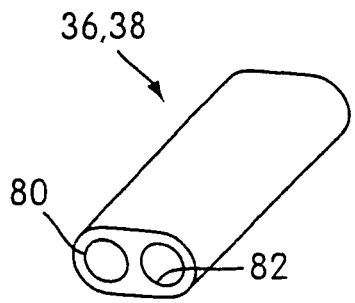
FIG. 96 is a perspective view of an inlet conduit of the nasal assembly shown in FIG. 86.

The inlet conduits 36, 38 each may have a first end connected to respective inlet connectors 40, 42 and a second end connected to the Y-shaped inlet connector 44. As shown in FIG. 96, each of the inlet conduits 36, 38 include first and second passageways 80, 82. The pair of second conduit portions 76 of the inlet connector 40, 42 are inserted through the first and second passageways 80, 82 of the first end of the inlet conduit 36, 38 to couple the inlet connectors 40, 42 with respective first ends of the inlet conduits 36, 38. The inlet connectors 40, 42 and inlet conduits 36, 38 may retained with a friction-type fit, mechanical fasteners, adhesive, co-molded, insert-molded, or any other suitable means.

Figure 96A:
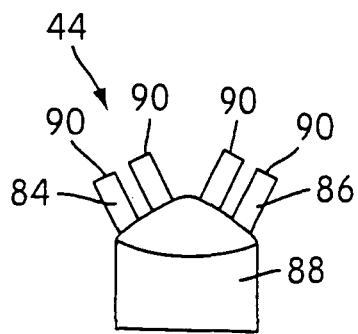
FIG. 96A is a schematic view of a Y-shaped inlet connector of the nasal assembly shown in FIG. 86.

As shown in FIG. 96A, the Y-shaped connector 44 includes a first connector 84 that is connected with the second end of one of the inlet conduits 36, a second connector 86 that is connected with the second end of other of the inlet conduits 38, and a third connector 88 that is connected to a pressurized supply for delivering pressurized gas to the nasal assembly 10. Each of the first and second connectors 84, 86 includes a pair of conduit portions 90 that are inserted through the first and second passageways 80, 82 of the inlet conduit 36, 38 to couple the Y-shaped connector 44 with respective inlet conduits 36, 38. The third connector 88 may include a swivel mechanism to allow relative movement between the Y-shaped connector 44 and the delivery conduit connected to the pressurized supply. The Y-shaped connector 44 and inlet conduits 36, 38 may retained with a friction-type fit, mechanical fasteners, adhesive, welding, insert molding or any other suitable means.

Figure 98:
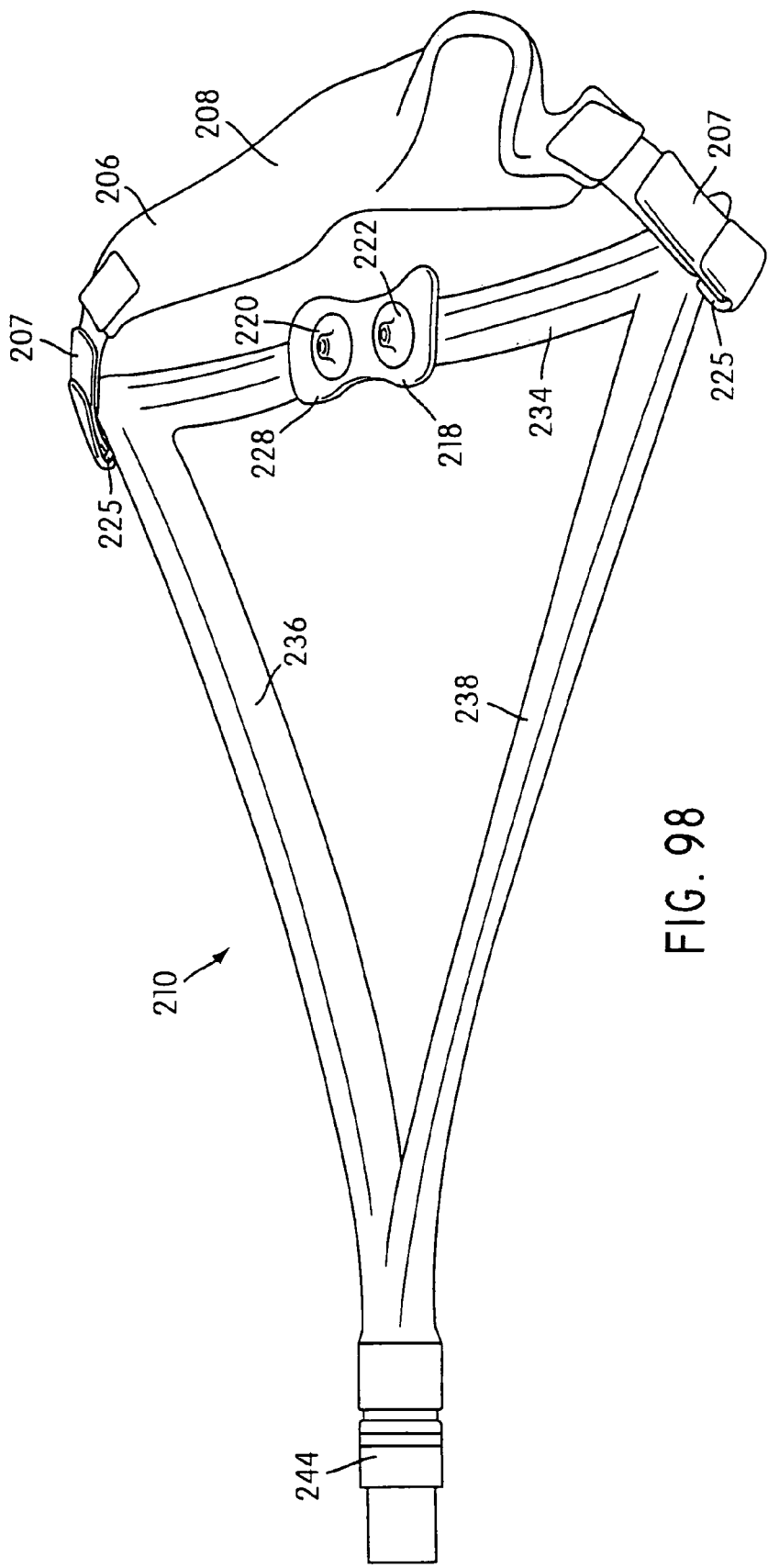
FIG. 98 is a perspective view of another embodiment of a nasal assembly.

As shown in FIG. 98, the central conduit 34 and inlet conduits 36, 38 may be formed of crush-resistant, anti-crush, or anti-kinking tubing such as that disclosed in U.S. Pat. No. 6,044,844, the entirety of which is incorporated herein by reference.

Pressurized gas enters through connector 88 of the Y-shaped connector 44 and proceeds through the first and second inlet conduits 36, 38 into both end sections of the central conduit 34. Air passes though the central conduit 34, into the gusset portion 18 and nasal pillows 20, 22, and into the nasal passages 12 of the patient. Exhaust gases from the patient's nose can exit through the exhaust vent 62 provided in the central conduit 34.

As best shown in FIGS. 86 and 89, the gusset portion 18 extends outwardly from the central conduit 34 to provide additional surface area or footprint area. As air under pressure enters the central conduit 34, both the central conduit 34 and gusset portion 18 inflate, which moves the nasal pillows 20, 22 into sealing engagement with the nasal passages 12 of the patient. However, the central conduit 34 may not be inflatable along with the gusset portion 18. That is, the gusset portion 18 is structured such that it can expand and contract to alter a distance between the central conduit 34 and the nasal pillows 20, 22. The gusset portion 18 moves the nasal pillows 20, 22 between a first position (as shown in FIG. 97A) in which the nasal pillows 20, 22 are adjacent to the nasal passages 12 of the patient and a second position (as shown in FIG. 97B) in which the nasal pillows 20, 22 are moved into sealing engagement with the nasal passages 12 of the patient. Specifically, the gusset portion 18 is uninflated or generally flat when not pressurized by a gas. However, the gusset portion 18 may not have a generally flat structure when uninflated. In the uninflated condition, the nasal pillows 20, 22 are spaced from the nasal passages 12 of the patient or in light contact therewith. When the nasal assembly 10 is pressurized by a gas, the gusset portion 18 is inflated and moves the nasal pillows 20, 22 into sealing engagement with the nasal passages 12 of the patient to form a seal between the nasal assembly 10 and the patient's nasal passages 12. As the gas pressure is increased, the force applied to the underside of the nasal passages 12 is increased through the gusset portion 18.

The gusset portion 18 provides additional surface area or footprint area to the central conduit 34, which in turn provides an additional force on the nasal pillows 20, 22 which increases the sealing efficiency of the nasal pillows 20, 22. That is, the gusset portion 18 is configured and positioned to force the nasal pillows 20, 22 into contact with the patient's nose. The force or pressure on the patient's nose is proportional to the pressure in the central conduit 34 and the additional surface area of the gusset portion 18. Thus, the surface area of the gusset portion 18 may be varied, e.g., to vary the force or pressure applied to the patient's nose.

The gusset portion 18 reduces the headgear assembly tension required to achieve a suitable seal. That is, the pressure applied to the patient's nose is provided by the gusset portion 18 and not relied on by the tension from the headgear assembly. This improves patient comfort as well as sealing properties.

Accordingly, it is desirable when adjusting the headgear assembly to bring the nasal pillows 20, 22 only near or in very light contact with the patient's nose. In this way, the gusset portion 18 is not compressed substantially.

The gusset portion 18 may include a connecting wall between the side walls 26, 28 thereof. The connecting wall may act as a spring structure to provide a component of force on the patient's face through the nasal pillows 20, 22. The force may be tailored by adjusting a thickness of the connecting wall. Moreover, the thickness of the connecting wall may be varied in conjunction with the surface area provided by the gusset portion 18.

The gusset portion 18 also provides a decoupling joint between the central conduit 34 and the nasal pillows 20, 22, thus allowing some relative movement between the nasal assembly 10 and the user's face. As a result, the nasal pillows 20, 22 can accommodate small variations in the shape of the patient's nasal features without undue force, and can account for small movement of the nasal assembly 10 relative to the patient's nose during use, while maintaining an effective seal.

Also, the gusset portion 18 need not be a single gusset form discussed above, but can have alternative configurations. For example, the gusset portion 18 may be in the form of a two or more gusset portions provided in series.

Figure 99:
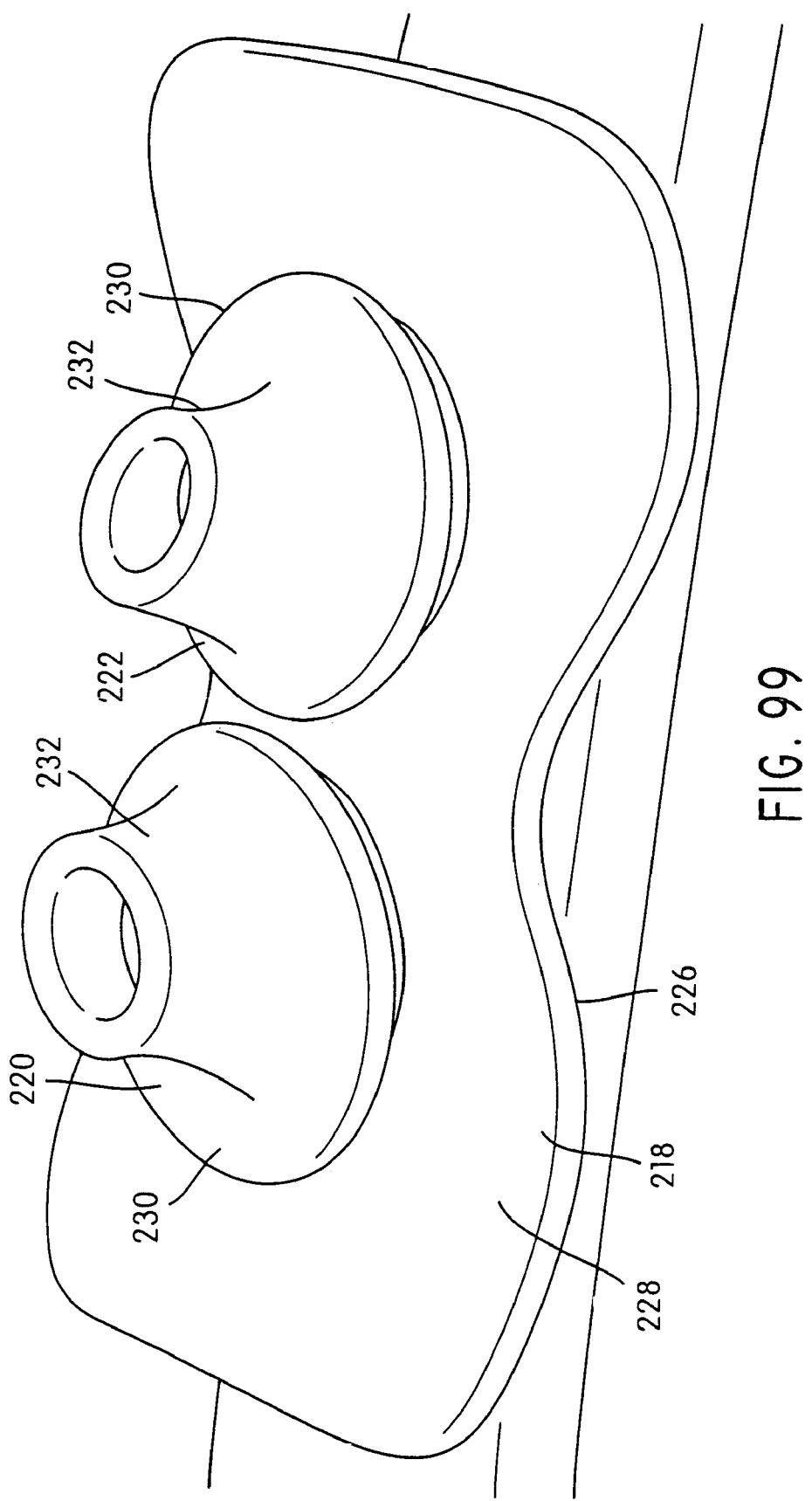
FIG. 99 is an enlarged perspective view of nozzles and a gusset portion of the nasal assembly shown in FIG. 98.
Figure 100:
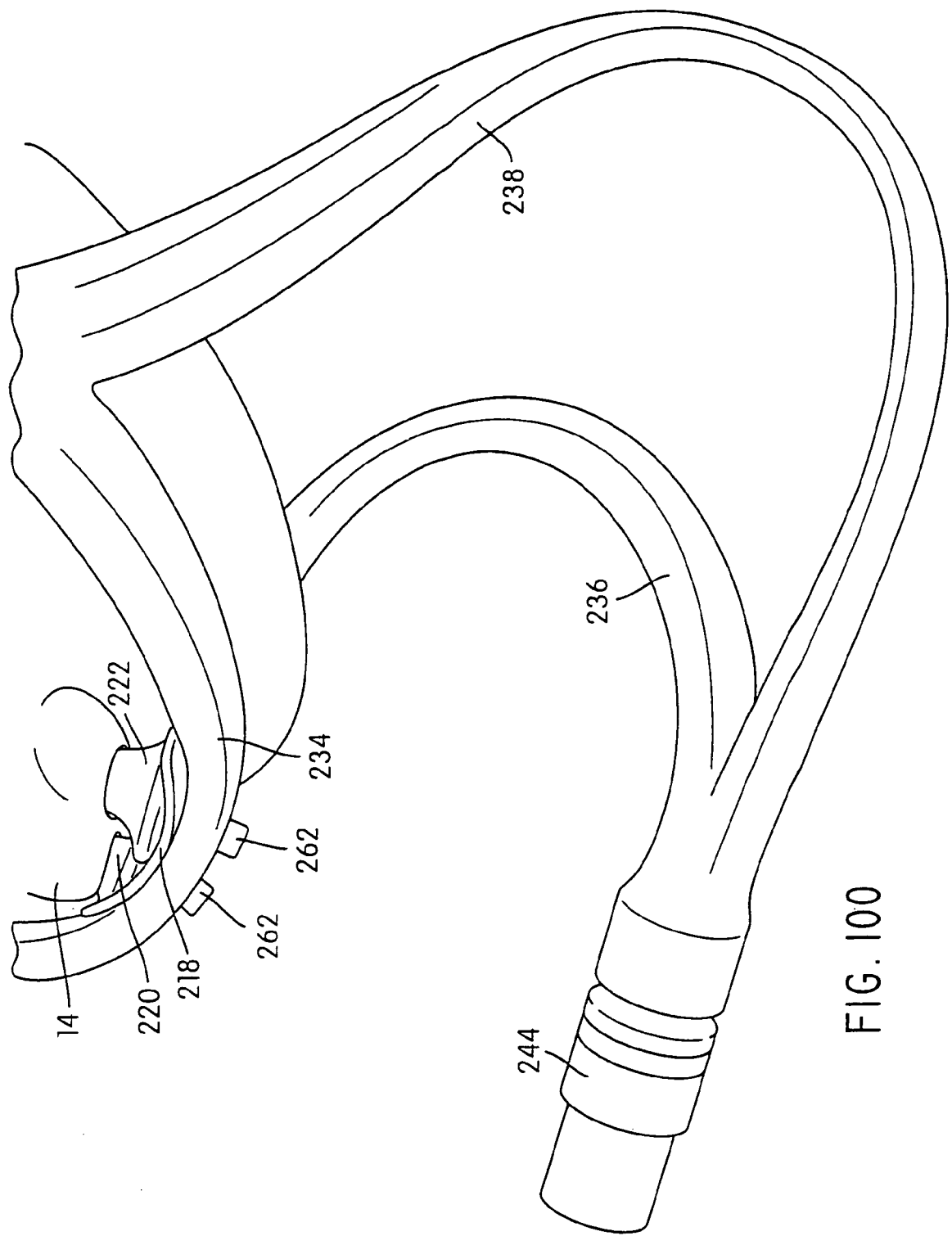
FIG. 100 is an enlarged perspective view of inlet conduits of the nasal assembly shown in FIG. 98.

FIGS. 98-106 illustrate another embodiment of a nasal assembly, indicated as 210. As best shown in FIGS. 98-100, the nasal assembly 210 includes a central conduit 234, a pair of inlet conduits 236, 238 connected to the central conduit 234 (e.g., by an adhesive), and an inlet connector 244 that interconnects the inlet conduits 236, 238. The inlet connector 244 is structured to be connected to a conduit that is connected to a pressurized supply. The inlet connector 244 may be axially swivelable to maximize stability by reducing kinking of the conduits.

A gusset portion 218 is provided that includes first and second side walls 226, 228 that define a space therebetween. The first side wall 226 includes an inlet opening that is communicated with an opening in the central conduit 234. The second side wall 228 has a pair of outlet openings. In the illustrated embodiment, the gusset portion 218 has a general bow-tie shape. However, the gusset portion 218 may have any other suitable shape.

A pair of nozzles 220, 222 in the form of nasal pillows are provided. Each nasal pillow 220, 222 has a first portion 230 attached the second side wall 228 of the gusset portion 218 in communication with a respective outlet opening of the gusset portion 218. The second portion 232 of each of the nasal pillows 220, 222 is structured to sealingly engage with the nasal passages 12 of the patient's nose 14 in use and provide a seal between the nasal assembly 210 and the patient's nasal passages 12.

In the illustrated embodiment, the central conduit 234, inlet conduits 236, 238, gusset portion 218, and nasal pillows 220, 222 are constructed from flexible materials, such as silicone, and attached to one another with an adhesive. However, the central conduit 234, inlet conduits 236, 238, gusset portion 218, and nasal pillows 220, 222 may be molded in one piece, or formed with any other suitable material in any suitable process.

Figure 101:
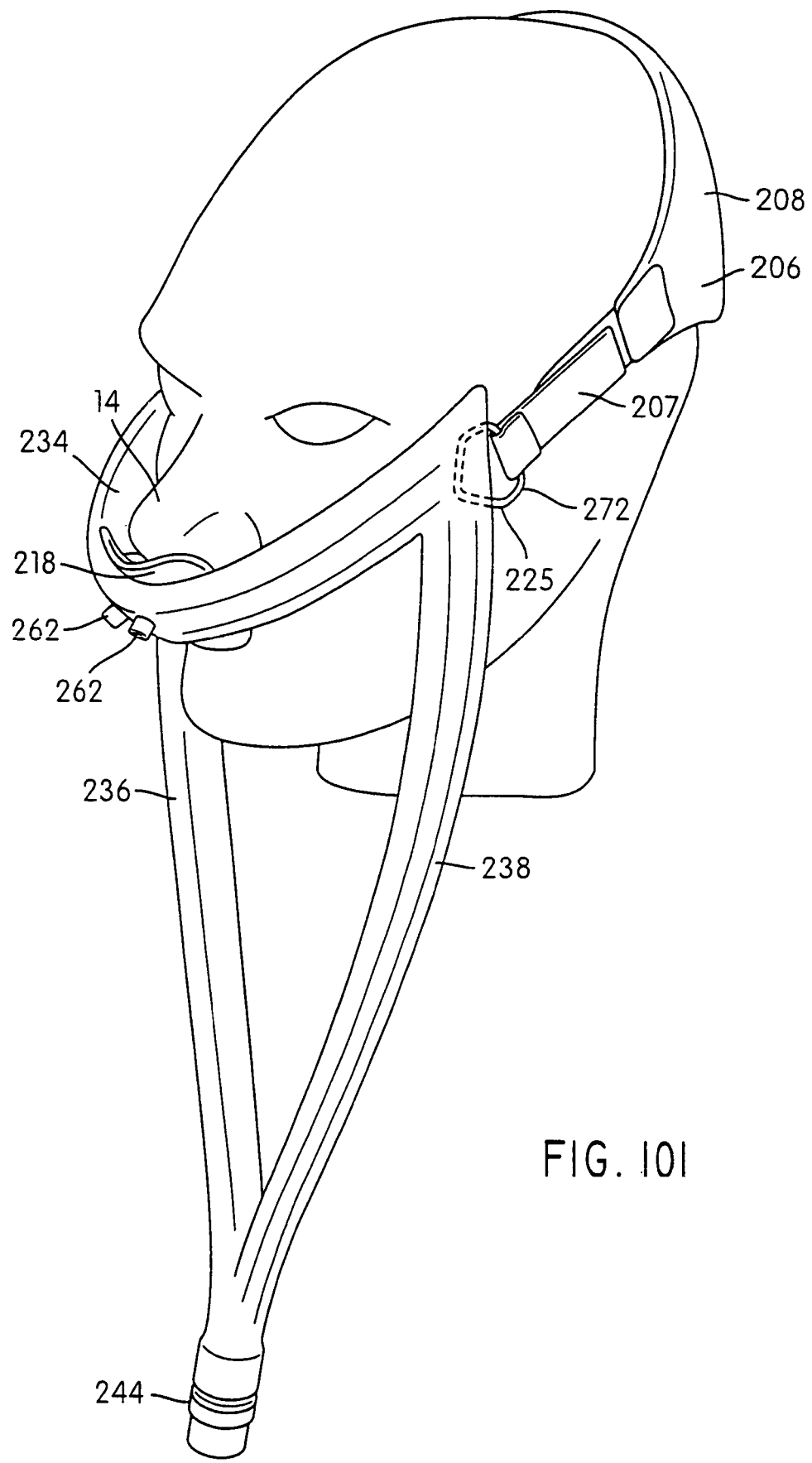
FIG. 101 is a front perspective view illustrating the nasal assembly shown in FIG. 98 mounted to a patient's head.
Figure 102:
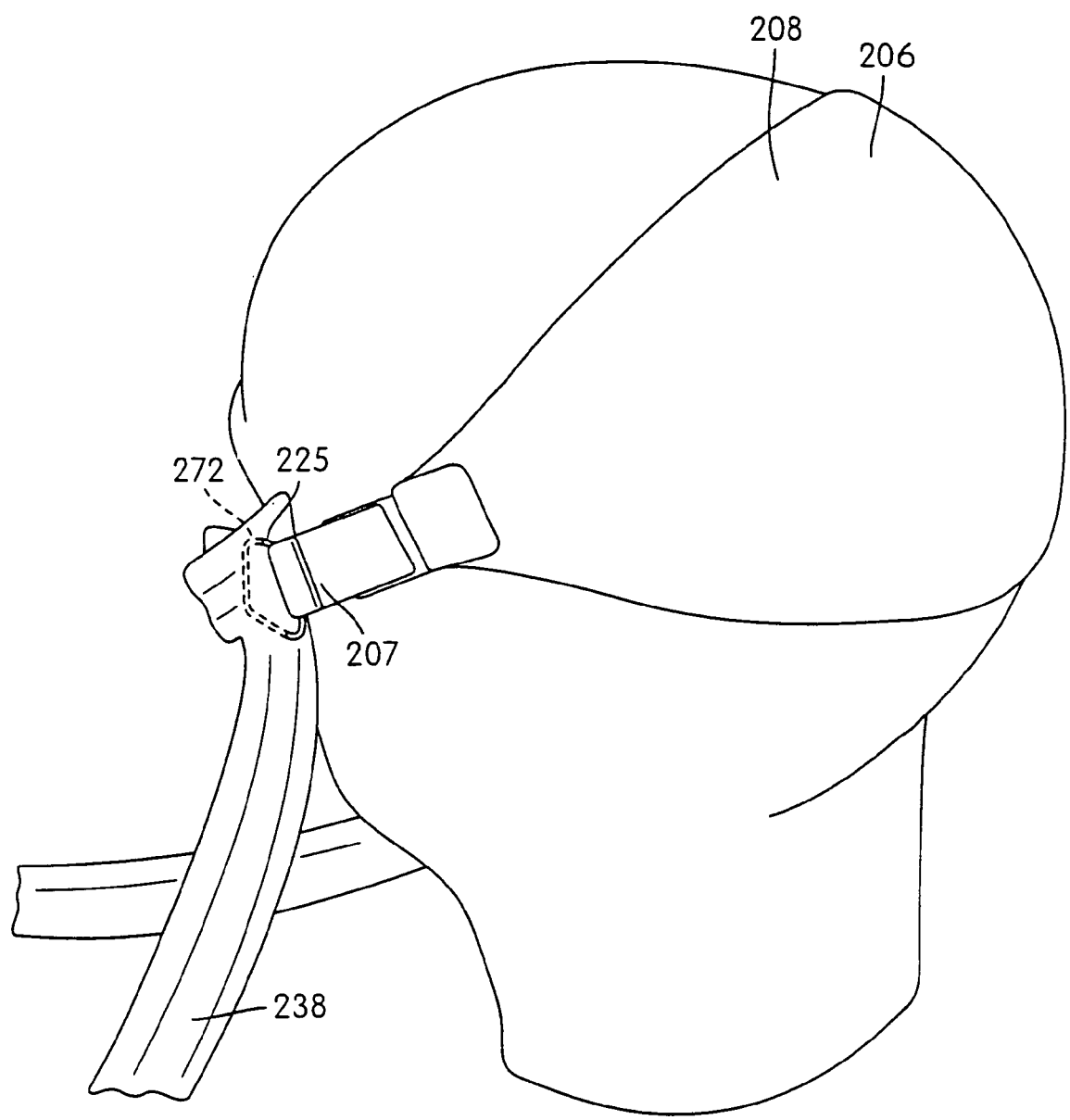
FIG. 102 is a rear perspective view illustrating the nasal assembly shown in FIG. 98 mounted to a patient's head.
Figure 103:
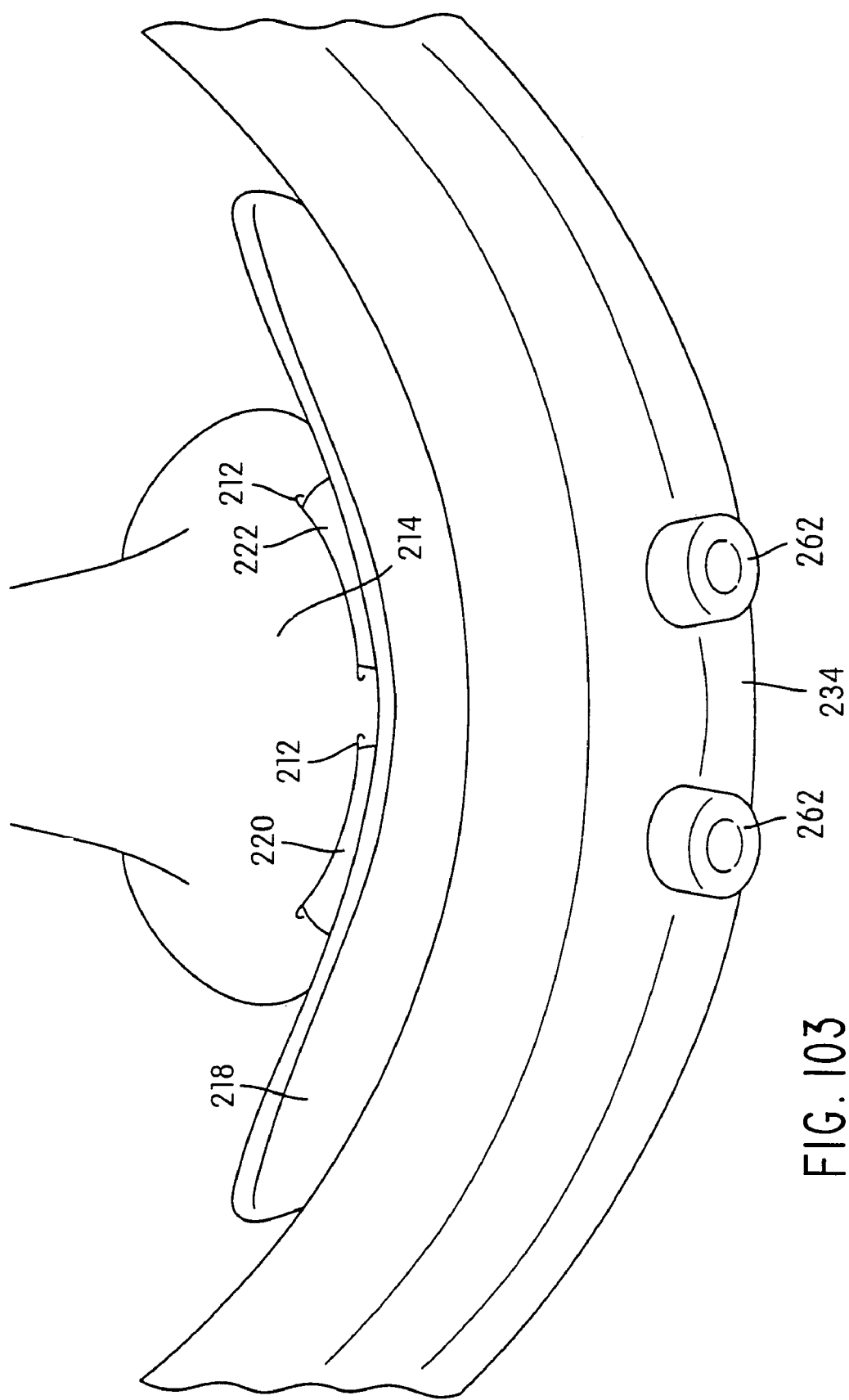
FIG. 103 is a front perspective view illustrating the nasal assembly shown in FIG. 98 engaged with nasal passages of the patient.
Figure 104:
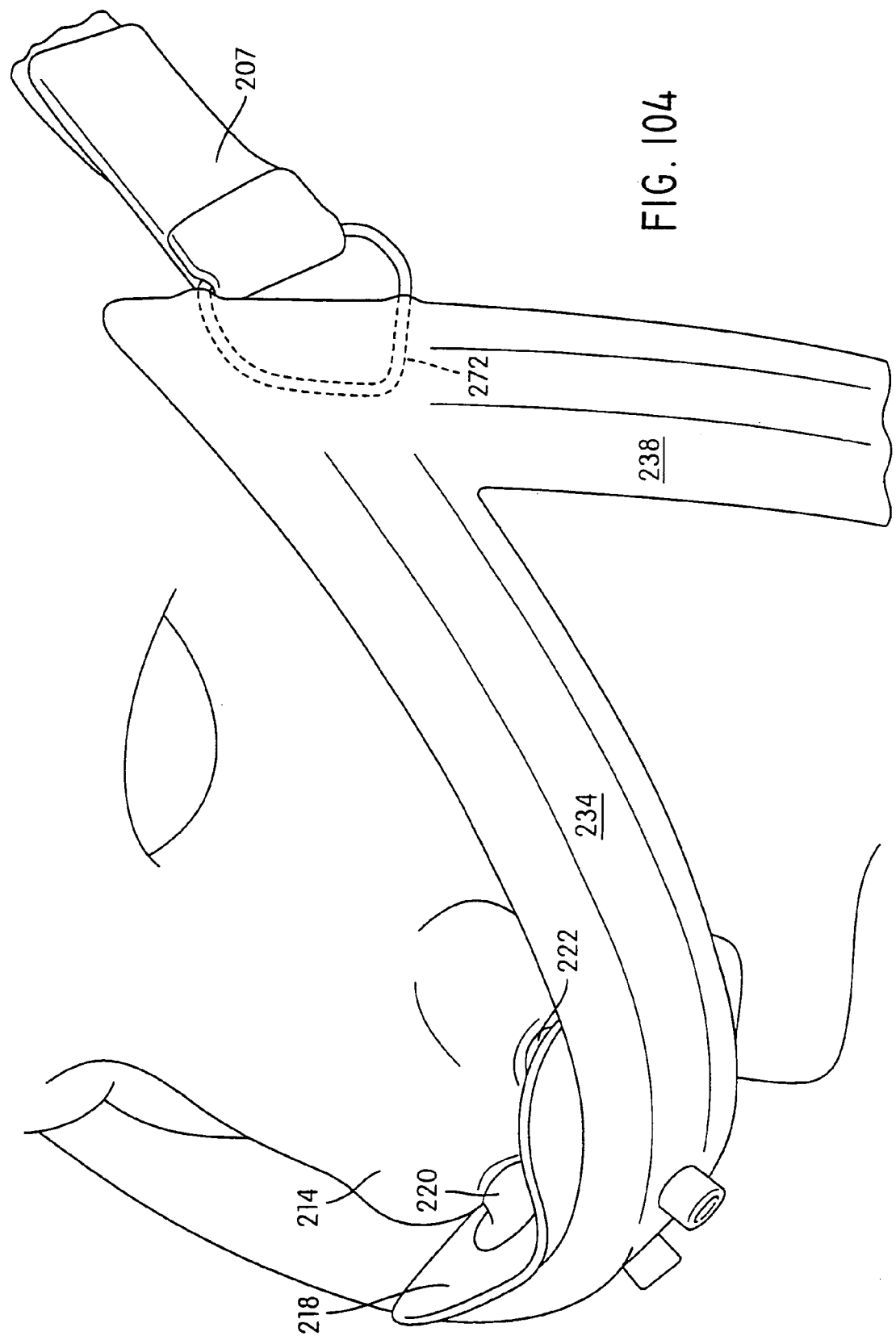
FIG. 104 is a side perspective view illustrating the nasal assembly shown in FIG. 98 engaged with the nasal passages of the patient.
Figure 105:
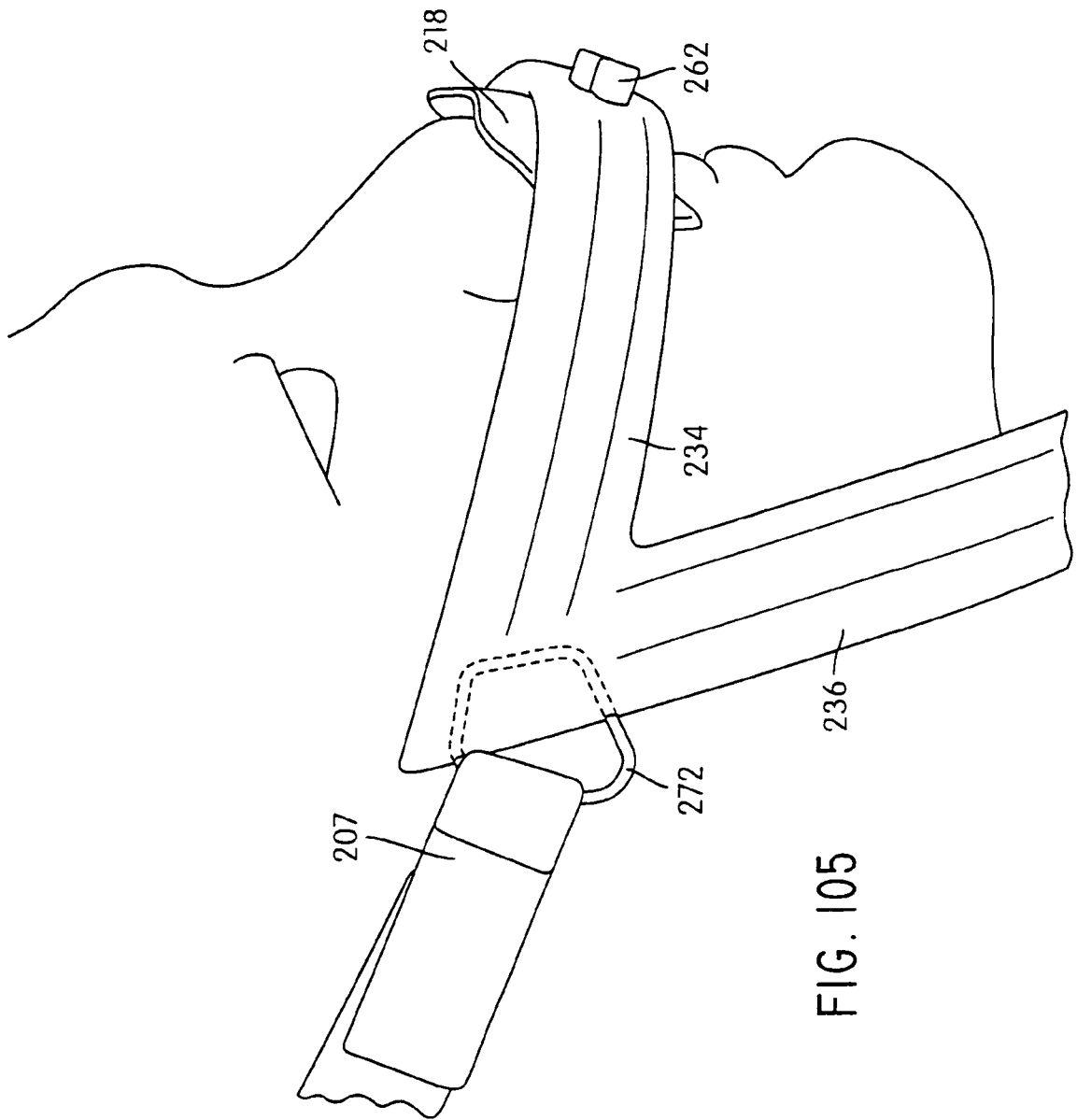
FIG. 105 is a side view illustrating the nasal assembly shown in FIG. 98 engaged with the nasal passages of the patient.
Figure 106:
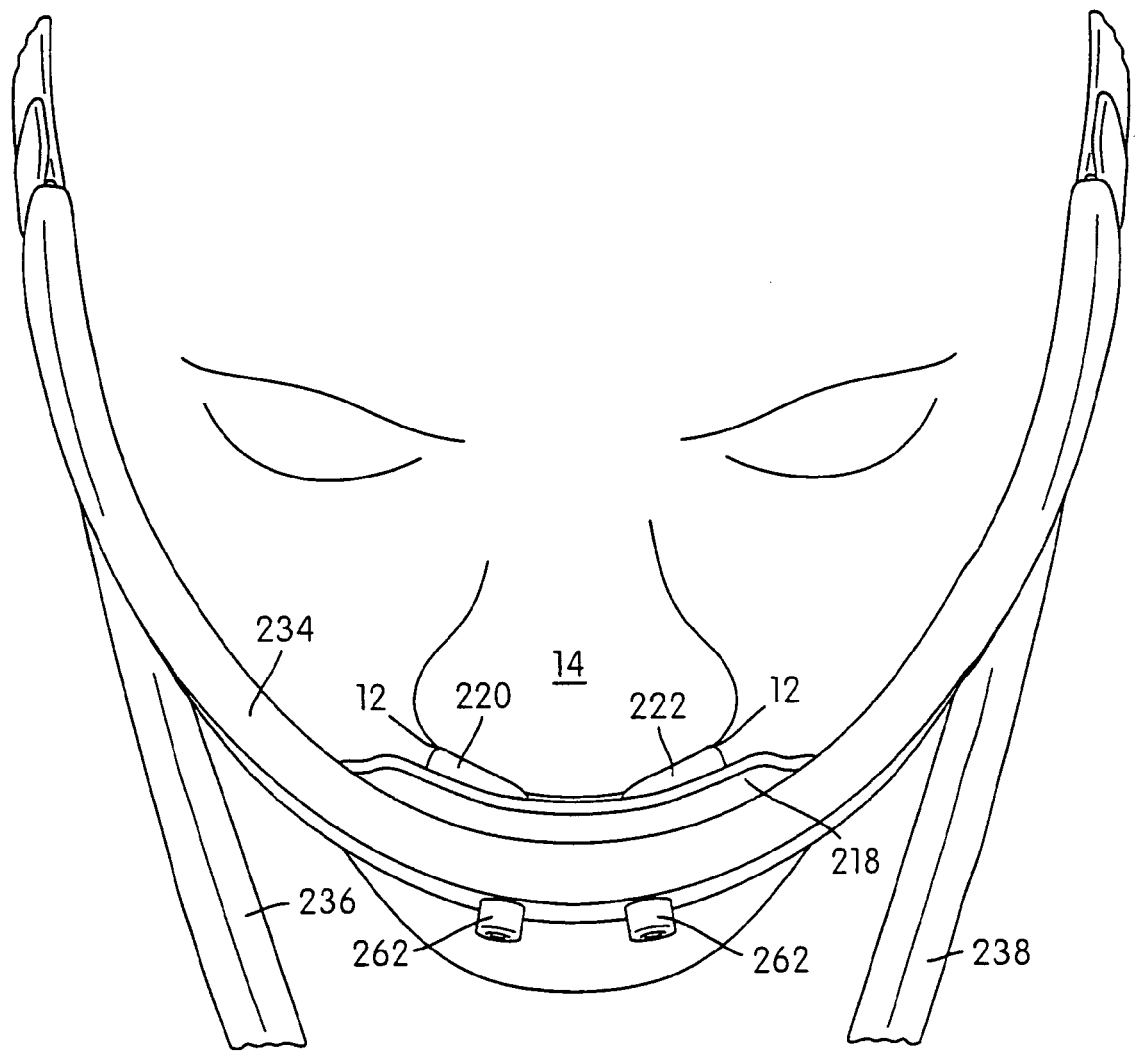

The central conduit 234 includes exhaust vents 262 (FIGS. 100 and 101) that protrude slightly outwardly therefrom for $CO_2$ washout. Also, a headgear connector 225 in the form of a pair of clips 272, are attached to the conduits 234, 236, 238 (e.g., by an adhesive) for connection to a headgear assembly 206. The headgear assembly 206 includes straps 207 removably connected to respective clips 272 by a hook and loop fastener, for example. As shown in FIGS. 101 and 102, the straps 207 pass over the ears of the patient and engage a head cloth 208 that sits on the upper portion of the patient's head to cup the occipital portion of the patient's head. However, the headgear assembly 206 may have any suitable structure for maintaining the nasal assembly 210 on the patient's head.

FIGS. 103-106 illustrate the nasal assembly 210 engaged with outer edges of the nasal passages 12 of the patient's nose 14. Similar to the nasal assembly 10 described above, as air enters the central conduit 234, both the central conduit 234 and gusset portion 218 inflate, which moves the nasal pillows 220, 222 into sealing engagement with the nasal passages 12 of the patient. However, the central conduit 234 may not be inflatable along with the gusset portion 218. That is, the gusset portion 218 moves the nasal pillows 220, 222 between a first position in which the nasal pillows 220, 222 are adjacent to the nasal passages 12 of the patient and a second position in which the nasal pillows 220, 222 are moved into sealing engagement with the nasal passages 12 of the patient.

In the embodiments of nasal assemblies 10, 210, the inlet conduits 36, 38, 236, 238 extend downwardly from the nasal pillows 20, 22, 220, 222 away from the patient's head. However, as shown in FIG. 107, the nasal assembly, indicated as 310, may be an over-the-head type assembly in which the inlet conduit(s) 336 extends upwardly from the nasal pillows 320, 322 over the head of the patient.

FIG. 107-1 illustrates an embodiment like that shown in FIG. 107, but which includes an adjustable forehead support 411. The forehead support 411 includes a first portion 413 provided to a tube support 415. Connection between the first portion 413 and the tube support 415 allows adjustment of a second portion 417 of the forehead support 411 relative to the patient's forehead, to achieve the best possible fit. The second portion 417 includes a bridge 419 to support one or more forehead cushions or pads 421, as described in U.S. Pat. No. 6,119,693 or in U.S. patent application Ser. No. 10/655,595 (each incorporated herein by reference in its entirety) and headgear connector portions 423 for releasable connector to headgear straps 425. The headgear connector portions may take the form of those shown in U.S. Pat. No. 6,374,826, incorporated herein by reference in its entirety, or in U.S. Provisional application No. 60/467,570, incorporated herein by reference in its entirety. The bridge 419 may include a central portion 427 structured to accommodate, guide and/or hold an upper portion of air delivery tube as it is guided over the head of the patient. Adjustment may be achieved via bending, flexing and/or pivoting of the first portion 413 relative to the support 415. For example, support 415 may include a pivot pin 429 which is introduced into an aperture on the first portion 413. Support 415 and first portion 413 may include a plurality of locking members 431 (e.g., protrusions and recesses), to allow locking of the forehead support 411 in a number (e.g., 3-5, preferably 4) of predetermined positions.

FIG. 107-2 illustrates another embodiment of an adjustable forehead support that operates like that disclosed in U.S. Pat. No. 6,532,961, incorporated herein by reference in its entirety.

FIGS. 107A-107C illustrate yet another alternative embodiment of the present invention. FIG. 107A is a perspective view of a mask assembly 650, while FIG. 107B is a side view of the mask assembly shown in FIG. 107A. The mask assembly 650 includes a headgear assembly 652 and a nasal cushion assembly 654. The headgear assembly includes a coronal strap 654 and an occipital strap 656.

A flexible tube 658 includes a first end 660 which may include a swivel connector. The tube 658 is provided with a suitable source of pressurized gas. The tube includes a second end 662 which is provided to the cushion assembly 654. The tube 658 is supported by a support frame 664. The support frame includes a lower portion 666 which supports a cushion 668 of the cushion assembly 654. The support frame also includes a central portion 670 and an upper portion 672. The upper portion 672 may include flexible arms separated by a gap. The arms may be resiliently deformed to allow insertion and removal of the tube between the two arms. The support frame 664 may include lateral support arms 674 which are configured to rest against the patient's forehead in use. Each lateral support arm 674 includes first and second connector slots 676 and 678 which provide a connection point for coronal strap 654 and occipital strap 656, respectively.

FIG. 107B is a side view of the mask assembly. FIG. 107C is an enlarged side view of a portion of the assembly 650 shown in FIGS. 107A and 107B. The lower portion 666 of the support frame 664 is adapted to support the cushion 668 as shown therein. The cushion 668 includes a pair of nozzles 680 (one shown) which are formed in an integral piece with a plenum chamber 682.

FIGS. 107D and 107E illustrate yet another embodiment of the present invention. A mask assembly 690 includes a headgear assembly 692 which includes an occipital strap 694, a coronal strap 696 and depending arm straps 698 each of which extends from a junction between the occipital and coronal straps 694 and 696 and forwardly of the ear along the user's face. The top portion of the coronal strap 696 may include a suitable connector 700 such as the flexible arms shown in FIG. 107A. Alternatively, the connector 700 may take the form of a VELCRO® loop which helps to fasten a tube 702. The tube 702 includes a first end 704 which may be provided with a swivel connector which in turn is connected to a suitable source of pressurized gas via an air delivery tube. The tube 702 is routed over the top of the forehead and is generally aligned with but spaced from the nose and bridge of the patient. A support frame 708 includes an upper portion 710 which helps to maintain the tube 702 in the desired position. The upper portion 710 may include flexible arms, like the upper portion 672 in FIG. 107A.

The support 708 may include a pair of lateral arms 714, best illustrated in the side view of FIG. 107E. Each lateral support arm 714 includes a connector slot 715 which is adapted to receive an end of the depending arm strap 698.

FIG. 107F illustrates an alternative embodiment of a mask assembly 720 including a headgear assembly 722 having the configuration generally corresponding to that of the letter "X", including a first cross strap 724 and a second cross strap 726. The first and second cross strap 724 and 726 meet at a junction or intersection 728. The forward end of second cross strap 726 is provided with a connector element 730, which may take the form of a VELCRO® loop. The connector element 730 may be adapted to support and/or hold a transitional tubing piece which includes a first end for connecting with relatively large bore tubing 732 and a second end for accommodating relatively small bore tubing 734. A support frame 736 is provided to support the tube 734 and a cushion 738 in the position shown in FIG. 107F.

FIG. 107G illustrates a mask assembly 750 according to yet another embodiment of the present invention. The mask assembly 750 includes a headgear assembly 752 including a rear strap 754 and a forehead strap 756. A depending arm strap 758 extends from a junction between the rear strap 754 and the forehead strap 756. One or more of the straps may include a yoke member 759 which helps to reinforce and maintain the position of the straps relative to one another. As shown in FIG. 107G, the mask assembly 750 includes a tube 760 including a first end 762 that may include a swivel connector, which can be connected to an air delivery tube 764, which is in turn provided to a source of pressurized air.

As shown in FIG. 107H, each strap 758 includes a first connector portion 766 having one or more arms 767 which can be resiliently flexed toward one another to insert and remove the connector portion 766 from a suitable recess in frame 768. The frame 768 is provided with a connector portion 770 which receives and/or connects to the tube 760. As shown in FIG. 107H, only a portion of one of the nozzles 772 is visible.

FIG. 107I illustrates another embodiment of the present invention. A mask assembly 780 includes a headgear assembly 782 including a rear strap 784 and a forward strap 786. A tube 788 is connected to a junction connector 790 which in turn is connected to one or more soft flexible tubes 792 that follow and/or are connected to rear strap 784 on each side of the user's head. The headgear assembly 782 may include depending arm straps 783 that are positioned forward of the ear and along the cheek of the user. Each tube 792 may be suitably attached to the depending arm strap 783. Each tube 792 is suitably connected to a cushion assembly 794.

FIG. 107J illustrates still another embodiment of the present invention. A mask assembly 800 may include a headgear assembly, only a portion of which is shown in the drawing. The headgear assembly may include depending arm straps 802 which support lateral support arms 804 which are connected or provided to a cushion assembly 812. Each depending arm strap 802 may also support an interchange 806, which may take the form of a U-shape coupling member having a first end connected to an air delivery tube 808 and a second end connected to tube 810 which is connected to the cushion assembly 812.

FIGS. 107K and 107L illustrate yet another embodiment of the present invention. As shown in FIG. 107K, a cushion assembly includes a frame 820, a plenum or bellows chamber 824 and a pair of nozzles 826 mounted on the plenum chamber 824. The cushion assembly may be supported by one or more lateral support arms 822, as shown in FIG. 107K. Alternatively, the cushion assembly can be supported by a support frame as shown, for example, in FIG. 107A. As shown in FIG. 107K, the nozzle 826 has a relatively low profile because it is engaged with a patient's nares. However, as shown in FIG. 107L, the nozzle 826 may extend from the low profile position shown in FIG. 107K to the higher profile position shown in FIG. 107L, by virtue of its resiliency.

FIGS. 107M-107Q illustrate cross-sections of various nozzles 832, 834, 836, 840 and 844 according to the present invention. As shown in FIG. 107I, the nozzle may include a ledge 838 which is intended to rest on the nostril edge while the middle portion 839 is received by the nare. As shown in FIG. 107P, the nozzle 840 includes a cut away 842 which may be advantageous to avoid or reduce the chances of rubbing on the center of the nose. As seen in FIG. 107Q, the nozzle 844 may include a protrusion 846 to deflect air away from nostril walls. FIG. 107R shows the position of the protrusions 846 on the nozzles in perspective view.

Seventh Illustrated Embodiment

FIGS. 108-113 illustrate yet another preferred embodiment of the present invention. As shown in FIG. 108, a mask assembly 600 includes headgear 602 and a cushion assembly 604, each of which is substantially similar to the headgear and cushion assembly shown, e.g., in FIGS. 60 and 61, respectively. Headgear 602 is designed to capture the crown of the patient's head. Adjustment of strap tension can be accomplished by pulling loose tabs on the top of the head in opposite directions. The pulling direction is not aligned with the force the nozzle assembly applies to the patient. Therefore, the patient is more isolated from the strap adjustment forces. Yokes provide stability to the sides. Yokes retain at least a partial portion of the basic shape of headgear, which facilitates donning of the headgear. Headgear need not include adjustability toward front of the face, as all adjustment of headgear can be effected at the back or top of the head.

In the embodiment of FIG. 108, one end of the cushion assembly 604 is provided with a plug 622 and the other end is provided with a swivel elbow 612. The positions of the swivel elbow 612 and the plug 622 may be interchanged, according to preference, e.g., the typical sleeping position of the patient. An air delivery tube 606 is joined to the swivel elbow 612. The air delivery tube 606 may include a swivel connector 607 and includes an end 609 which also may be provided with a swivel connector. The end 609 is provided with a source of pressurized gas.

As shown in FIG. 108, the elbow 612 is angled about 120' from the cushion assembly 604. This helps to keep the tube out of line of sight, to minimize pressure drop and to maintain the flexion point of tube as close to the face as possible. However, the elbow may have a typical 90° bend as shown, e.g., in FIGS. 109 and 110.

FIG. 109 is a schematic perspective view of the mask assembly 600 shown in FIG. 108, but only yokes 608 of headgear 602 are shown without straps. As with the fifth main illustrated embodiment, the yoke 608 may include a yoke ring 610. As shown in FIG. 109, the cushion assembly may be adjustably rotated with respect to headgear, to a position which best fits the patient. In FIG. 109, the ring 610 of the yoke 608 of the headgear includes an alignment marker 611*a* and the cushion includes a plurality of alignment markers 611*b* that can be selectively aligned with marker 611*a*.

FIG. 110 is a cross-sectional view of a portion of the cushion assembly 604. In particular, the cushion assembly 604 includes a frame 616 which supports a cushion 617. The frame 616 includes a first connector portion 618 provided to each end of the frame 616 and/or cushion 617. Each first connector portion 618 is provided with or to a seal ring 614. Both seal ring and plug are examples of second connector portions that are connected or otherwise provided to the first connector portions 618. As seen in FIG. 110, the left hand side of the mask assembly includes the plug 622 while the right hand side of the mask assembly includes the swivel elbow 612, i.e., the reverse arrangement view shown in FIGS. 108 and 109.

FIG. 110 shows that the cushion 617 includes a plurality of vent apertures 619, each of which is designed to reduce noise. Cross-sections of two possible aperture profiles are shown in FIGS. 110-1 and 110-2. In FIG. 110-2, the end 617*a* displaces any potential noise creating flash (i.e., a molding seam) out of main air path through bore of vent. Stated differently, the molding seam is moved from a position from where it could potentially create noise, to a position where it is less likely to create noise.

FIG. 110A is a partial cross-sectional view showing the interaction between the seal ring 614, first connector portion 618 and the plug 622. In particular, the seal ring 614 may be provided with first and second protrusions 624, 626, respectively. The first protrusion 624 may interact with a groove 618*a* provided in the first connector portion 618, for sealing and/or locking purposes. The second protrusion 626 may interact with a groove 628 provided in the plug 622, the sealing and/or locking purposes. As shown in FIG. 10A, each seal ring 614 includes a groove 630 to receive a respective one of the rings 610 of the yoke 608. In FIG. 110A, the yoke 608 is not shown.

FIG. 110B is an enlarged partial cross-sectional view of the mask assembly 600 on the right hand side of FIG. 110. A first end 612*a* of the swivel elbow 612 is inserted in and received within the first connector portion 618. The first end 612*a* may include an enlarged head portion which prevents inadvertent dislodgment of the swivel elbow 612 from the assembly. The front end 612*a* may include at least one slot 613 to allow the enlarged head portion to reduce its diameter upon insertion by resiliently flexing. Preferably, there are a plurality of such slots, e.g., four slots. The seal ring 614 may include first and second protrusions 624, 626, as described above. In this case, the second protrusion 626 may interact by friction with the outer circumference of the swivel elbow 612, and provide a seal. Moreover, the swivel elbow 612 may be provided with a groove or other structure to receive the second protrusion 626.

FIG. 110B also schematically shows that the swivel elbow 612 and the seal ring 614 may include a swivel stop 631. For example, the swivel stop 631 may be formed as part of the yoke 608.

Alternatively or in addition, as shown in FIG. 111, the swivel elbow 612 may be provided with a ring 633 including a protrusion 634. The seal ring 614 may be modified to include swivel stops 632. Accordingly, the protrusion 634 may rotate along with swivel elbow 612 until the protrusion 634 abuts against the swivel stop 632. Therefore, movement of the air delivery tube 606 can be confined with a predetermined range of movement, e.g., about 220°-300°, and preferably 250°-270°, thus minimizing or avoiding undesirable contact between the air delivery tube and the patient.

FIG. 112 is a partial cross-sectional view of the assembly of the frame, first connector portion 618, yoke 608, seal ring 614 and plug 622. FIG. 112 shows the plug 622 to be inserted in the right hand side of the cushion assembly 604, as shown in FIG. 108.

FIG. 113 shows an alternative embodiment of the invention in which the plug and seal ring are formed of a single integral piece. As shown in FIG. 113, the seal ring 636 includes a flange portion 638 which generally follows along a contour of the yoke 608. This is best shown in the cross-sectional view of FIG. 110 where the seal ring 614 and the yoke 608 are positioned closely adjacent one another.

The seventh main illustrated embodiment may provide for improved decoupling of the air delivery tube 606 and/or swivel elbow 612 from the cushion assembly 604. In addition, this embodiment provides a choice of tube routing, which can be either up or down or on the left or right hand sides of the cushion assembly 604. As such, this embodiment may be perceived as less obtrusive and is significantly lighter. It also includes less parts than previous embodiments and can be easier to manufacture, assemble and clean.

The swivel elbow 612 may be provided with a quick release mechanism (not shown). The swivel elbow 612, as shown in FIG. 110B, is able to fit and snap into the mask frame 616. This construction allows free swiveling within the frame 616, between a range of defined angles, thereby ensuring that the tube does not get into an uncomfortable position with respect to the head and pillow.

The seal ring 614 is structured such that it cooperates with the geometry of the elbow swivel 612. In addition, the seal ring 614 may be connected to the ring 610 of the yoke 608.

The seal ring 614 may be permanently connected to the ring 610, e.g., via co-molding. For example, the swivel stop 631 in FIG. 110B may be formed as part of the ring 610. The first connector portion 618 on each side of the frame 616 may be rotated with respect to the seal ring 614, to thereby position the cushion assembly 604 accordingly. The seal ring 614 seals the swivel elbow 612 preferably with minimum friction. Each seal ring 614 may accommodate either the plug 622 or the swivel elbow 612. The seal ring 614 is large enough for patients to handle, especially patients with reduced manual dexterity.

The plug 622 may be press fit into the seal ring 614. The plug 622 can also be designed to be press fit into the frame. The plug 622 may be made from hard polymer, for example, polypropylene. A recess (not shown) may be provided to remove the plug 622. The plug functions to seal the frame and cushion assembly on the side opposing the air delivery tube. The plug 622 is large enough for patients to handle, even with reduced manual dexterity.

The tubing 606 may be permanently attached to the end of the swivel elbow 612. However, a push-on friction connection may also be suitable. The tube length may be between 200 mm and 400 mm, preferably 250 and 350 mm, for example, or any other length which will not interfere with the patient's face.

As shown in FIGS. 110B and 111, respectively, the yokes 608 and seal ring 614 may be provided with structure to limit the angular or rotational movement of the swivel elbow 612 with respect to the first connector portion 618. Further, the headgear and/or yoke may be provided with a tube retention feature to control the tube position. For example, simple VELCRO® straps may be provided along some portion of the headgear to restrain movement of the air delivery tube.

In another example shown in FIGS. 108A and 108B, a tube retainer 900 includes a first portion 902 to be connected or attached to one of the straps of headgear. For example, the first portion 902 can be in the form of a loop that is attached to a portion 904 of headgear strap shown in FIG. 108. Attachment can be accomplished by threading the headgear strap 904 though the first portion 902 before the headgear strap 904 is threaded through the headgear buckle 906. The retainer 900 includes a second portion 908 provided or attached to the first portion 902. The second portion 908 may be made of a resilient plastic that retains the shape shown in FIG. 108A, with a gap 910 defined between two ends 912 of the second portion 908. The gap 910 is sized to be smaller than the diameter of the air delivery tube 606, so as to reliably hold the tube 606. Alternatively, the second portion 908 can be a VELCRO® loop, with the ends 912 including the mating hooks and loops. As shown in FIGS. 108A and 108B, the second portion may include one or more slots 914 to receive ribs 916 (FIG. 108) of the air delivery tube 606, to thereby prevent axial sliding of the tube 606. With this arrangement, the tube 606 can be reliably held in a position over the patient's head.

FIG. 108C illustrates a plan view of a tube retainer, wherein like reference numbers relate to like parts. In FIG. 108C, exemplary dimensions of the tube retainer are shown. It is to be noted that these dimensions are examples only, and the dimensions can be changed up to about ±20% of the values shown therein.

The nasal assemblies 10, 210, 310, 410, 510, 600 described above and below have several advantages. For example, the nasal assemblies 10, 210, 310, 410, 510 are unobtrusive due to their small overall size and weight. The nasal assemblies 10, 210, 310, 410, 510, 600 provide a high level of comfort due to the minimal force applied to the patient's nose—and contact with the bridge can be eliminated. The nasal assemblies 10, 210, 310, 410, 510, 600 are easy to use and include minimal parts and adjustments, e.g., the inlet conduits can be easily adjusted to extend upwardly over the head of the patient or downwardly below the chin of the patient. The pressurized supply can be easily connected to and disconnected from the connectors without altering the headgear setting. Also, the nasal assemblies 10, 210, 310, 410, 510, 600 allow for greater nozzle range of motion to accommodate a wide range of patients. That is, the nozzles can be rotated with respect to the patient's face by rotating the frame relative to the headgear assembly. Further, strap tension need not be as high as the area of contact with the face is less. The headgear provides stability, e.g., the yokes help maintain the mask assembly's position on the face. The adjustment of the headgear is designed such that the force required to tighten the straps is not applied to the patient's face, e.g., the straps can be pulled in opposite directions above the head to counteract one another. It is relatively easy to find balance between performance and comfort. In addition, the weight, noise level, and/or number of parts of the mask assembly is reduced.

An Appendix including additional drawings and depictions of various aspects of preferred embodiments of the invention is included in U.S. Provisional Application No. 60/529,696, filed Dec. 16, 2003 and incorporated herein by reference in its entirety. To the extent that any drawing in the labeled Figures or the Appendix includes dimensions, those dimensions are exemplary only and may be changed without departing from the scope of the disclosure.

Figure 114:
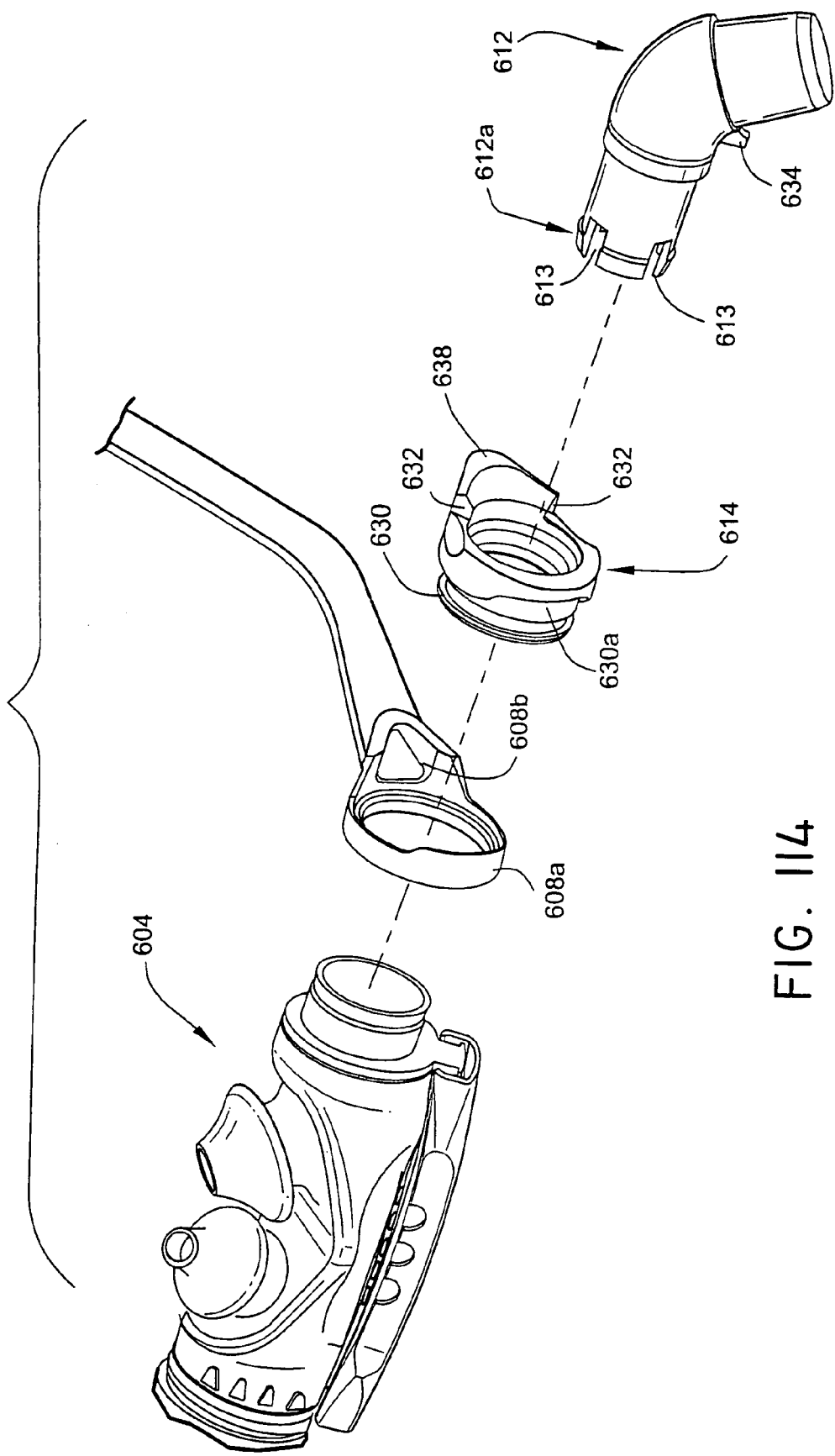
Figure 115:
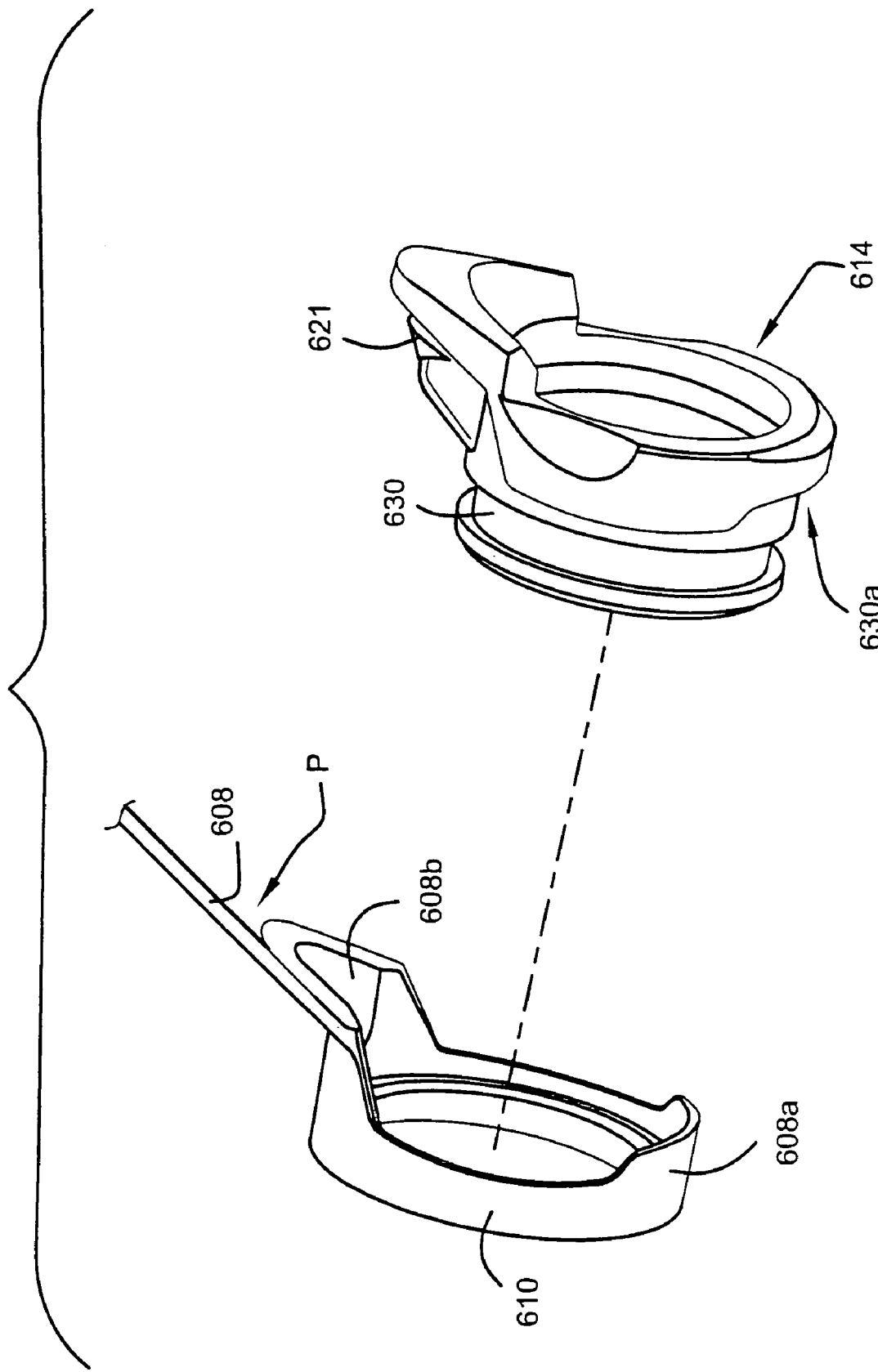

FIG. 114 illustrates an exploded view of another embodiment of the present invention. In this embodiment, the cushion assembly 604 is similar to that shown in FIGS. 108-109, and swivel elbow 612 is as described in relation to FIGS. 108, 110B and 111. Yoke 608 includes a widened portion 608a intended to engage with a corresponding widened portion 630a adjacent or formed as part of groove 630. In addition, yoke 608 includes a recess 608b intended to receive ear 638 of seal ring 614. In a further embodiment, yoke and seal ring may be formed in one piece. Also, the yoke and headgear could be formed of one piece, instead of using stitching. As can be seen in FIG. 115, the yoke 608 and seal ring 614 can be snap fit relative to one another, e.g., via shoulder 621. By this structure, the yoke and ring are prevented from rotating relative to one another. FIG. 115 also shows the general position of yoke flex point P, which allows a good fit with the patient.

Figure 116:
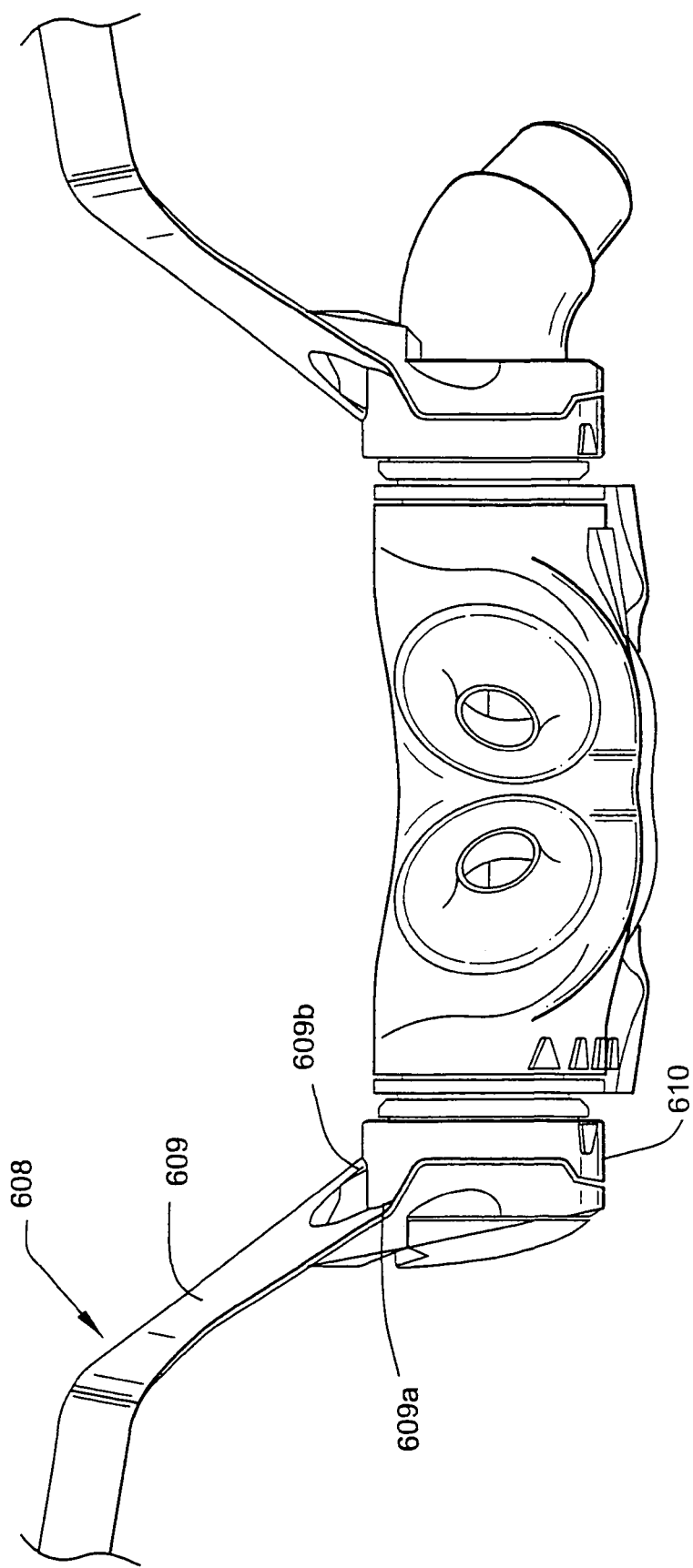
Figure 117:
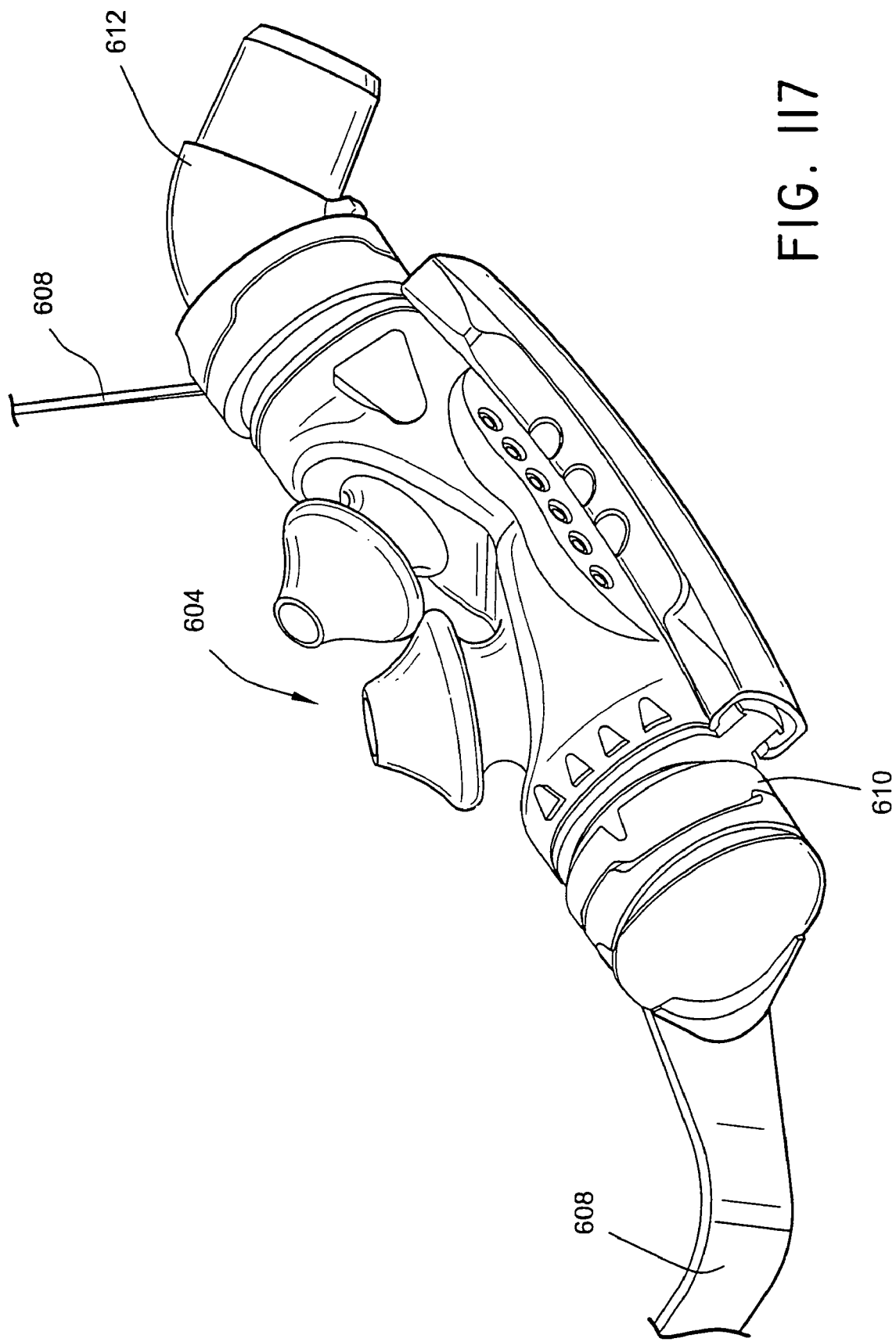
Figure 118:
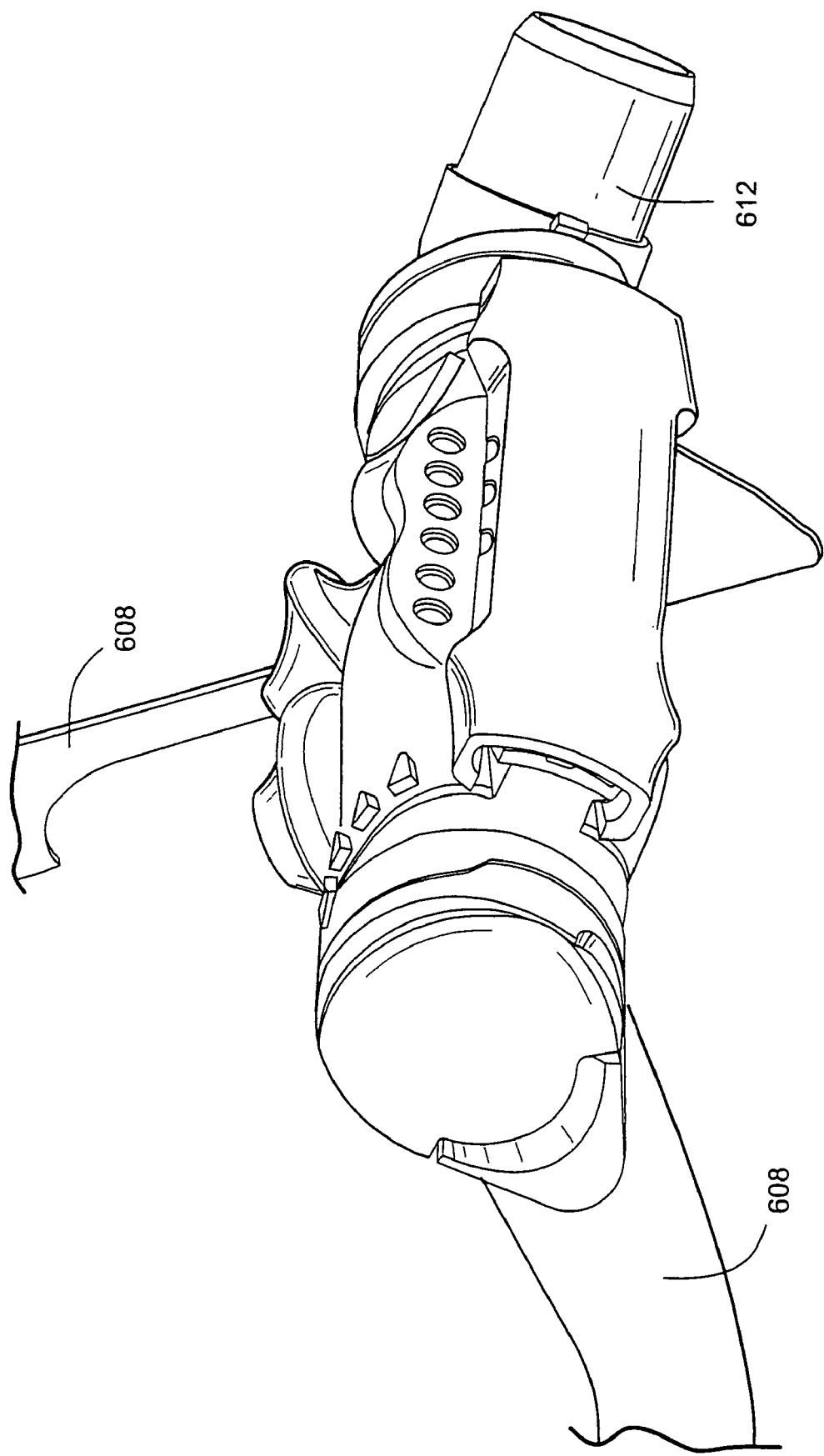

FIGS. 116 to 126 illustrate further views of the embodiment shown in FIGS. 114 and 115. Another aspect of the arrangement is that the ring 610 of the yoke 608 is angularly offset with respect to the main body 609 of the yoke 608. Compare FIG. 116 with FIG. 110, e.g., where the main body 609 in FIG. 116 is twisted. For example, front side 609a in FIG. 116 is positioned laterally outward in comparison to rear side 609b in FIG. 116. This structure helps to bias the bottom portion of the yoke 608 towards the patient's face, so that the yoke more closely follows the contours of the patient's face.

FIGS. 127-130 illustrate a further embodiment of the present invention. This embodiment is similar to that shown and described in FIGS. 114-126. However, there are two main differences. First, the elbow 612 is free to rotate 360° within seal ring 614. As shown in the partial exploded view of FIG. 128, seal ring 614 does not include stops 632 and elbow 612 does not include protrusion 634, as compared to what is shown in FIG. 114.

Figure 129:
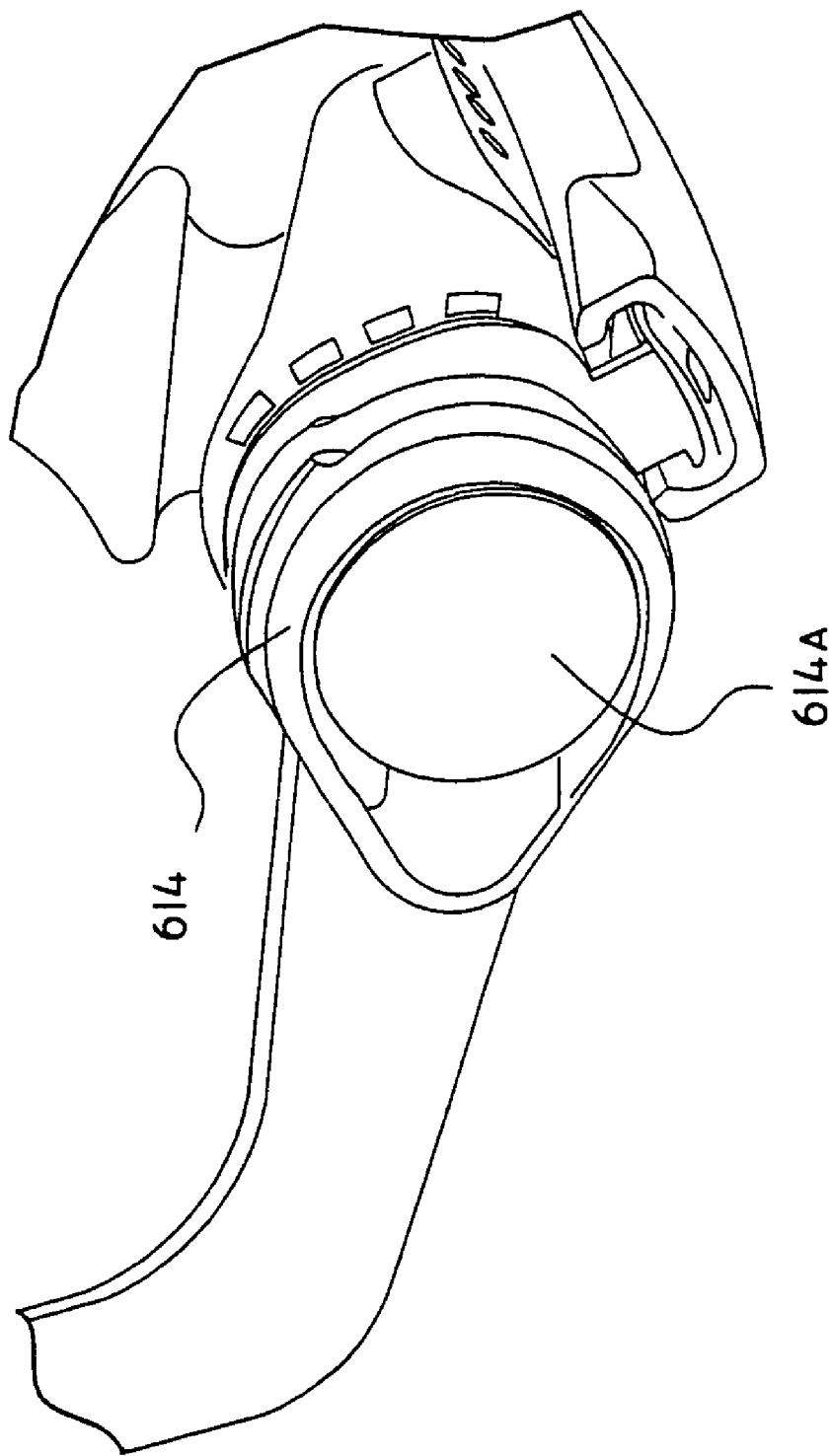
Figure 130:
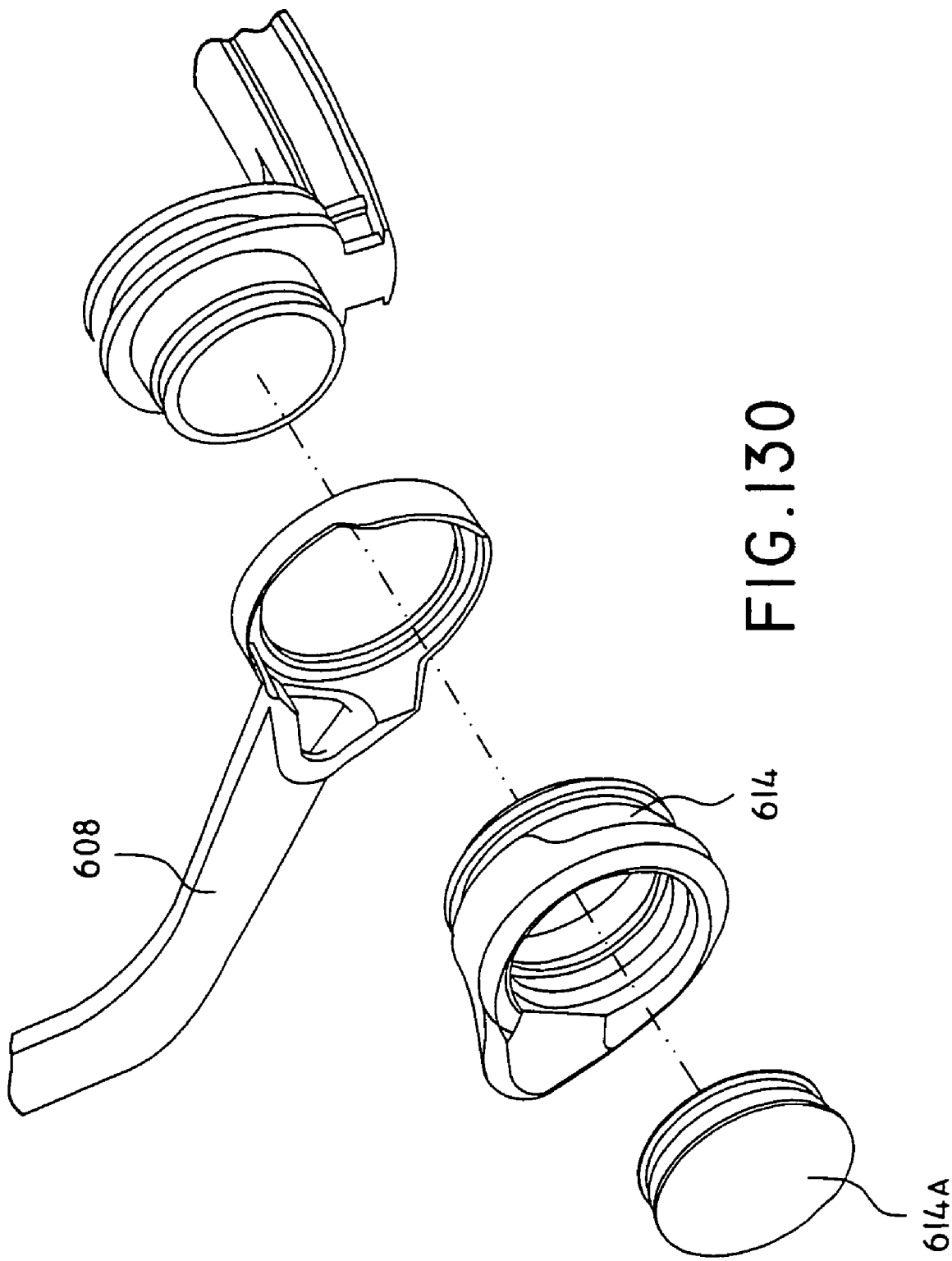

Second, as shown in FIG. 129, seal ring 614 includes a selectively removable and insertable cap 614a. In other words, the plug 622 in FIG. 119 is made in two parts rather than one. The cap 614a may also include a vent, instead of or supplemental to the vent provided on the cushion. FIG. 130 shows a partial exploded view of cap 614a. Because seal rings 614 on both sides of nozzle assembly are identical, the cap 614a and elbow 612 can be removed and swapped, if the patient opts to have the elbow 612 routed over the left or right side. This can be done while the mask assembly is in use on the patient. Also, the elbow 612 can be removed to allow for patient mobility.

FIGS. 131-133 illustrate an elbow 612 according to yet another embodiment. As compared to elbow 612 shown in FIG. 114, elbow 612 in FIGS. 131-133 includes one and preferably a pair of key-shaped apertures 613. The elbow may be made of polypropylene, e.g., "Borealis," or polyester. The shape of the apertures allows for improved retention and removal forces, when the elbow is in place and when it is removed.

Further, the nozzle assembly and/or its associated cushion could be replaced with a nasal mask and/or nasal cushion. See, e.g., FIGS. 134 and 135. FIG. 134 shows an arrangement in which the frame includes opposite apertures or first connector portions (e.g., tubular extensions), each of which is provided with a seal ring as described above. A seal ring 500 is adapted to include a separate or integral plug to close one aperture or first connector portion of the frame, while another seal ring is adapted to engage with the other frame aperture/first connector portion, and to receive the swivel elbow. Of course, the positions of the elbow and plug may be interchanged, depending on patient preference. In FIG. 135, the elbow is provided to the front of the mask frame, like ReMed's VISTA mask, while both apertures/first connector portions are provided with plugged seal rings. Of course, in each embodiment, frame, elbow, and/or seal ring(s) may be provided with appropriate vents to exhaust exhaled gas from the breathing chamber.

It can thus be appreciated that the aspects of the present invention have been fully and effectively accomplished. The foregoing specific embodiments have been provided to illustrate the structural and functional principles of the present invention, and are not intended to be limiting. To the contrary, the present invention is intended to encompass all modifications, alterations, and substitutions within the spirit and scope of the detailed description.

What is claimed is:

1. A cushion having:
    a common base defining a side wall and a central wall, and
    a pair of nozzles provided to the central wall, the nozzles and the common base being formed of a one part silicone piece;
    each nozzle having a first portion in the form of a stalk and a second portion in the form of a head supported by the stalk, the stalk being provided to the central wall and in communication with a respective outlet opening of the central wall, the head being substantially in the form of a truncated hollow cone having a relatively narrow tip portion to enter into the nasal passage of the patient's nose and a relatively wider portion to sealingly engage with an area about the rim of the nostril opening in use;
    each said stalk having a reduced width with respect to the relatively wider portion of the head.

2. The cushion as claimed in claim 1, wherein the central wall has a wall portion that smoothly transitions into a wall portion forming the stalk.

3. The cushion as claimed in claim 1, further comprising an exhalation port including a plurality of orifices for $CO_2$ washout.

4. The cushion as claimed in claim 1, wherein each said stalk has an hour glass shape extending between the central wall and the head.

5. The cushion as claimed in claim 1, wherein the base sidewall includes a lower surface to contact the upper lip of the user in use.

6. The cushion as claimed in claim 5, wherein the lower surface includes a slightly concave shape.

7. The cushion as claimed in claim 1, wherein the cushion is asymmetric about an axis that passes transversely to openings of the nozzles.

8. The cushion as claimed in claim 1, wherein the central wall includes angled halves shaped such that an alar angle between the nozzles ranges from 70-155°.

9. The cushion as claimed in claim 8, wherein the alar angle ranges from about 135-155°.

10. The cushion as claimed in claim 8, wherein the alar angle ranges from about 70-90°.

11. The cushion as claimed in claim 8, wherein an opening of each nozzle is in the form of an ellipse having a major axis and a minor axis.

12. The cushion as claimed in claim 11, wherein the ellipse ratio is about 0.7.

13. The cushion as claimed in claim 11, wherein each head has a longitudinal axis, and the longitudinal axes from the pair of heads converge to define an included angle of about 35°.

14. The cushion as claimed in claim 1, wherein each head defines a sealing zone bounded by a border that extends from an inner side of the base of the head towards an outer side of the head, the border extending to about half the height of the head on the outer side.

15. The cushion as claimed in claim 14, wherein a height of the head of each nozzle is about 9 mm.

16. The cushion as claimed in claim 1, wherein the stalk is configured to act as a spring structure against the patient's nostril.

17. The cushion as claimed in claim 16, wherein, in use, the spring structure is pre-loaded before introducing pressurized gas to provide a sealing force with the user.

18. The cushion as claimed in claim 1, wherein the nozzles are positioned to be near or only in slight contact with the user's nose in use.

19. The cushion as claimed in claim 1, wherein side walls of the stalks and heads are concave.

20. The cushion as claimed in claim 1, wherein a front wall of the base is configured to contact the immediate underside of the user's nose, whereby a resultant force is directed along a line extending from the immediate underside to a rear portion of the user's head, between the eye and the ear of the user in use.

21. The cushion according to claim 1, wherein the central wall is contoured to accommodate a patient's septum.

22. The cushion according to claim 1, wherein the base includes a visual indicator which can be selectively matched with a reference indicator provided adjacent the visual indicator.

23. A cushion having:
    a common base defining a side wall and a central wall, and
    a pair of nozzles provided to the central wall;
    each nozzle having a first portion in the form of a hollow stalk having a first end extending from the central wall and a second end supporting a second portion in the form of a head portion having hollow structure approximating the shape of a truncated cone, whereby pressurized gas may travel from inside the central wall through the stalks and to openings in the head portions for delivery to the patient's nostril openings in use;
    each stalk having only a single concave wall which in cross section extends from the central wall to the head portion.

24. The cushion according to claim 23, wherein the wall is continuously concave from the first end to the second end.

25. A cushion according to claim 23, further comprising an exhalation port including a plurality of orifices for $CO_2$ washout.

26. The cushion according to claim 23, wherein the base and the pair of nozzles comprise a one piece silicone elastomer.

27. The cushion according to claim 23, wherein the base includes a lower surface to contact the upper lip of the user in use.

28. The cushion according to claim 27, wherein the lower surface includes a slightly concave shape.

29. The cushion according to claim 23, wherein the cushion is asymmetric about an axis that passes transversely to openings of the nozzles.

30. The cushion according to claim 23, wherein the central wall has angled halves shaped such that the alar angle between the nozzles ranges from 70-155°.

31. The cushion according to claim 30, wherein the alar angle ranges from about 135-155°.

32. The cushion according to claim 30, wherein the alar angle ranges from about 70-90°.

33. The cushion according to claim 23, wherein the opening of each head portion is in the form of an ellipse having a major axis and a minor axis.

34. The cushion according to claim 33, wherein the ellipse ratio is about 0.7.

35. The cushion according to claim 33, wherein each nozzle has a longitudinal axis, and the longitudinal axes from the pair of nozzles converge to define an included angle of about 35°.

36. The cushion according to claim 23, wherein the stalk is of reduced cross sectional area compared to the head portion.

37. The cushion according to claim 26, wherein the head portion has one portion to seal on the underside of the nostrils and another portion to enter into the nasal passage of the user in use.

38. The cushion according to claim 23, wherein the stalk is configured to act as a spring structure.

39. The cushion according to claim 38, wherein, in use, the spring structure is pre-loaded before introducing pressurized gas to provide a sealing force with the user.

40. The cushion according to claim 23, wherein a front wall of the base is configured to contact the immediate underside of the user's nose, whereby a resultant force is directed along a line extending from the immediate underside to the rear portion of the user's head, between the eye and the ear of the user in use.

41. The cushion according to claim 23, wherein the nozzles are positioned to be near or only in slight contact with the user's nose.

42. The cushion according to claim 23, wherein each head includes a sealing zone defined by a border that extends diagonally across the head.

43. The cushion according to claim 23, wherein the side walls of the head portions are slightly concave.

44. The cushion according to claim 23, wherein the base is contoured to accommodate a patient's septum.

45. The cushion according to claim 23, wherein the base includes a visual indicator.

* * * * *